US009523096B2

(12) United States Patent
Roberts et al.

(10) Patent No.: US 9,523,096 B2
(45) Date of Patent: Dec. 20, 2016

(54) MODIFIED PHOTOSYNTHETIC MICROORGANISMS FOR PRODUCING LIPIDS

(75) Inventors: James Roberts, Seattle, WA (US); Fred Cross, New York, NY (US); Margaret Mary McCormick, Seattle, WA (US); Ernesto Javier Munoz, Seattle, WA (US); Brett K. Kaiser, Seattle, WA (US); Michael Carleton, Kirkland, WA (US)

(73) Assignee: Matrix Genetics, LLC, Seattle, WA (US)

( * ) Notice: Subject to any disclaimer, the term of this patent is extended or adjusted under 35 U.S.C. 154(b) by 695 days.

(21) Appl. No.: 13/995,925

(22) PCT Filed: Dec. 19, 2011

(86) PCT No.: PCT/US2011/065938
§ 371 (c)(1),
(2), (4) Date: Sep. 6, 2013

(87) PCT Pub. No.: WO2012/087982
PCT Pub. Date: Jun. 28, 2012

(65) Prior Publication Data

US 2013/0344549 A1 Dec. 26, 2013

Related U.S. Application Data

(60) Provisional application No. 61/425,179, filed on Dec. 20, 2010.

(51) Int. Cl.

| | |
|---|---|
| ***C12N 1/00*** | (2006.01) |
| ***C12N 1/21*** | (2006.01) |
| ***C12N 15/82*** | (2006.01) |
| ***C07K 14/195*** | (2006.01) |
| ***C12N 9/10*** | (2006.01) |
| ***C12N 9/12*** | (2006.01) |
| ***C12N 9/16*** | (2006.01) |
| ***C12N 9/20*** | (2006.01) |
| ***C12N 9/90*** | (2006.01) |
| ***C12N 9/00*** | (2006.01) |
| ***C12P 7/64*** | (2006.01) |

(52) U.S. Cl.
CPC ............ *C12N 15/82* (2013.01); *C07K 14/195* (2013.01); *C12N 9/1029* (2013.01); *C12N 9/12* (2013.01); *C12N 9/16* (2013.01); *C12N 9/20* (2013.01); *C12N 9/90* (2013.01); *C12N 9/93* (2013.01); *C12P 7/64* (2013.01); *Y02P 20/52* (2015.11)

(58) Field of Classification Search
CPC ................ C12P 7/64; C12N 1/00; C12N 1/21
USPC ...................................................... 435/252.3
See application file for complete search history.

(56) References Cited

U.S. PATENT DOCUMENTS

| | | | | |
|---|---|---|---|---|
| 7,794,969 | B1 | 9/2010 | Reppas et al. | |
| 8,394,614 | B2 * | 3/2013 | Roberts | C12N 1/20 435/170 |
| 8,394,621 | B2 * | 3/2013 | Roberts | C12N 1/20 435/170 |
| 8,835,137 | B2 * | 9/2014 | Roberts | C12N 1/20 435/134 |
| 9,029,120 | B2 * | 5/2015 | Roberts | C12N 1/20 435/252.1 |
| 9,040,264 | B2 * | 5/2015 | Kristof | C07K 14/195 435/134 |
| 2010/0081178 | A1 | 4/2010 | Roberts et al. | |

FOREIGN PATENT DOCUMENTS

| | | |
|---|---|---|
| WO | WO2010033921 | 3/2010 |
| WO | WO2010075440 | 7/2010 |

OTHER PUBLICATIONS

European Office Action mailed Oct. 7, 2015 for European patent application No. 11804900.6, a counterpart foreign application of U.S. Appl. No. 13/995,925, 4 pages.
Hu et al., "Microalgal triacylglycerols as feedstocks for biofuel production: perspectives and advances", The Plant Journal, vol. 54, 2008, pp. 621-639.

(Continued)

*Primary Examiner* — Maryam Monshipouri
(74) *Attorney, Agent, or Firm* — Lee & Hayes, PLLC; Brett Nelson; Benjamin Keim

(57) ABSTRACT

This disclosure describes genetically modified photosynthetic microorganisms, e.g., Cyanobacteria, that overexpress an acyl carrier protein (ACP), an acyl-ACP synthase (Aas), or both, optionally in combination with one or more overexpressed or exogenous lipid biosynthesis proteins, and/or one or more overexpressed or exogenous glycogen breakdown proteins. Exemplary biosynthesis proteins include diacyglycerol acyltransferases, thioesterases, phosphatidate phosphatases, phospholipases, triacylglycerol (TAG) hydrolases, fatty acyl-CoA synthetases, and/or acetyl-CoA carboxylases, including combinations thereof. Also included are photosynthetic microorganisms comprising mutations or deletions in a glycogen biosynthesis or storage pathway, which accumulate a reduced amount of glycogen under reduced nitrogen conditions as compared to a wild type photosynthetic microorganism. The modified photosynthetic microorganisms provided herein are capable of producing increased amounts of lipids such as fatty acids and/or synthesizing triglycerides.

20 Claims, 9 Drawing Sheets

(56) References Cited

OTHER PUBLICATIONS

PCT Search Report mailed Nov. 13, 2012 for PCT application No. PCT/US2011/065938, 13 pages.
Radakovits et al., "Genetic Engineering of Algae for Enhanced Biofuel Production", Eukaryotic Cel, vol. 9, No. 4, Apr. 2010, pp. 486-501.
Australian Office Action mailed May 10, 2016 for Australian patent application No. 2011349463, a counterpart foreign application of U.S. Appl. No. 13/995,925, 3 pages.

* cited by examiner

MODIFIED PHOTOSYNTHETIC MICROORGANISMS FOR PRODUCING LIPIDS

CROSS REFERENCE TO RELATED APPLICATION

This application claims the benefit under 35 U.S.C. §119 (e) of U.S. Provisional Application No. 61/425,179, filed Dec. 20, 2010, which is incorporated by reference in its entirety. This application also claims priority to PCT Patent Application No. PCT/US2011/065938, filed Dec. 19, 2011, which is incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is TARG_020_01WO_ST25.txt. The text file is about 482 KB, was created on Dec. 19, 2011, and is being submitted electronically via EFS-Web.

BACKGROUND

Technical Field

The present invention relates generally to genetically modified photosynthetic microorganisms, e.g., Cyanobacteria, that overexpress an acyl carrier protein (ACP) and/or an acyl-ACP synthetase (Aas), or a fragment or variant thereof, optionally in combination with one or more additional lipid biosynthesis proteins, to produce high levels of lipids such as fatty acids and/or triglycerides. Also included are related methods of using these genetically modified photosynthetic microorganisms as a feedstock, e.g., for producing biofuels and other specialty chemicals.

Description of the Related Art

Triglycerides are neutral polar molecules consisting of glycerol esterified with three fatty acid molecules. Triglycerides are utilized as carbon and energy storage molecules by most eukaryotic organisms, including plants and algae, and by certain prokaryotic organisms, including certain species of *actinomycetes* and members of the genus *Acinetobacter.*

Triglycerides may also be utilized as a feedstock in the production of biofuels and/or various specialty chemicals. For example, triglycerides may be subject to a transesterification reaction, in which an alcohol reacts with triglyceride oils, such as those contained in vegetable oils, animal fats, recycled greases, to produce biodiesels such as fatty acid alkyl esters. Such reactions also produce glycerin as a by-product, which can be purified for use in the pharmaceutical and cosmetic industries Certain organisms can be utilized as a source of triglycerides in the production of biofuels. For example, algae naturally produce triglycerides as energy storage molecules, and certain biofuel-related technologies are presently focused on the use of algae as a feedstock for biofuels. Algae are photosynthetic organisms, and the use of triglyceride-producing organisms such as algae provides the ability to produce biodiesel from sunlight, water, $CO_2$, macronutrients, and micronutrients. Algae, however, cannot be readily genetically manipulated, and produce much less oil (i.e., triglycerides) under culture conditions than in the wild.

Like algae, Cyanobacteria obtain energy from photosynthesis, utilizing chlorophyll A and water to reduce $CO_2$.

Certain Cyanobacteria can produce metabolites, such as carbohydrates, proteins, and fatty acids, from just sunlight, water, $CO_2$, water, and inorganic salts. Unlike algae, Cyanobacteria can be genetically manipulated. For example, *Synechococcus* is a genetically manipulable, oligotrophic Cyanobacterium that thrives in low nutrient level conditions, and in the wild accumulates fatty acids in the form of lipid membranes to about 10% by dry weight. Cyanobacteria such as *Synechococcus*, however, produce no triglyceride energy storage molecules, since Cyanobacteria typically lack the essential enzymes involved in triglyceride synthesis. Instead, *Synechococcus* in the wild typically accumulates glycogen as its primary carbon storage form.

Clearly, therefore, there is a need in the art for modified photosynthetic microorganisms, including Cyanobacteria, capable of producing lipids such as triglycerides and fatty acids, e.g., to be used as feed stock in the production of biofuels and/or various specialty chemicals.

BRIEF SUMMARY

In various embodiments, the present invention provides modified photosynthetic microorganisms, as well as methods of producing and using the same. In certain embodiments, the present invention includes a modified photosynthetic microorganism comprising: (i) one or more introduced polynucleotides encoding an acyl carrier protein (ACP), an acyl-ACP synthetase (Aas), or both, and/or one or more overexpressed acyl carrier protein (ACP) and/or acyl-ACP synthetase (Aas) polypeptides; and (ii) one or both of the following: (a) one or more introduced polynucleotides encoding one or more lipid biosynthesis proteins, and/or overexpressing one or more lipid biosynthesis proteins, and/or (b) reduced expression of one or more genes of a glycogen biosynthesis or storage pathway as compared to a wild-type photosynthetic microorganism, wherein said modified photosynthetic microorganism produces an increased amount of lipid as compared to an unmodified photosynthetic microorganism of the same species. In certain embodiments, the present invention includes a modified photosynthetic microorganism comprising: (i) one or more introduced polynucleotides encoding an acyl carrier protein (ACP), an acyl-ACP synthetase (Aas), or both; and (ii) one or both of the following: (a) one or more introduced polynucleotides encoding one or more lipid biosynthesis proteins, and/or (b) reduced expression of one or more genes of a glycogen biosynthesis or storage pathway as compared to a wild-type photosynthetic microorganism, wherein said modified photosynthetic microorganism produces an increased amount of lipid as compared to an unmodified photosynthetic microorganism of the same species. In certain embodiments, said photosynthetic microorganism is a Cyanobacterium.

In certain embodiments, said one or more lipid biosynthesis proteins are selected from an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, and a phospholipase (PL), including any combination thereof.

Certain embodiments comprise the ACP and the DGAT. Certain embodiments comprise the Aas and the DGAT. Certain embodiments comprise the ACP, the Aas, and the DGAT. Certain embodiments comprise the ACP and the TES. Some embodiments comprise the Aas and the TES. Certain embodiments comprise the ACP, the Aas, and the TES. Certain of the above-noted embodiments further comprise the ACCase. Certain of the above-noted embodiments further comprise the PAP. Certain of the above-noted embodiments further comprise the PL.

Some embodiments comprise the ACP and the ACCase. Certain embodiments comprise the Aas and the ACCase. Certain embodiments comprise the ACP, the Aas, and the ACCase. Certain embodiments comprise the ACP and the PAP. Some embodiments comprise the Aas and the PAP. Certain embodiments comprise the ACP, the Aas, and the PAP. Certain embodiments comprise the ACP and the PL. Certain embodiments comprise the Aas and the PL. Certain embodiments comprise the ACP, the Aas, and the PL. Certain of the above-noted embodiments further comprise the DGAT. Some of the above-noted embodiments further comprise the TES.

Certain embodiments comprise the ACP, the DGAT, and the TAG hydrolase. Certain embodiments comprise the Aas, the DGAT, and the TAG hydrolase. Certain embodiments comprise the ACP, the Aas, the DGAT, and the TAG hydrolase. Particular embodiments comprise the ACP, the DGAT, and the fatty acyl-CoA synthetase. Certain embodiments comprise the Aas, the DGAT, and the fatty acyl-CoA synthetase. Some embodiments comprise the ACP, the Aas, the DGAT, and the fatty acyl-CoA synthetase. Some of the above-noted embodiments further comprise any one or more of the TES, the ACCase, the PAP, or the PL.

In some embodiments, said modified photosynthetic microorganism has reduced expression of one or more genes of a glycogen biosynthesis or storage pathway as compared to a wild-type photosynthetic microorganism. Certain embodiments comprise one or more introduced polynucleotides encoding a protein of a glycogen breakdown pathway. Certain embodiments comprise a full or partial deletion of the one or more genes of a glycogen biosynthesis or storage pathway. In some embodiments, said one or more genes are selected from a glucose-1-phosphate adenyltransferase (glgC) gene and a phosphoglucomutase (pgm) gene.

In particular embodiments, said ACP is a bacterial or a plant ACP. In certain embodiments, said ACP is from *Synechococcus, Spinacia oleracea, Acinetobacter, Streptomyces*, or *Alcanivorax*. In specific embodiments, said ACP has the amino acid sequence of any one of SEQ ID NOS:97, 99, 101, 103, or 105.

In particular embodiments, said Aas is a bacterial Aas. In specific embodiments, said Aas has the amino acid sequence set forth in SEQ ID NO:107. In certain embodiments, said TES is a TesA, a TesB, or a FatB thioesterase. In particular embodiments, said TesA is *E. coli* TesA. In some embodiments, said tesA is a cytoplasmic-localized *E. coli* TesA. In particular embodiments, said cytoplasmic *E. coli* TesA has the amino acid sequence of SEQ ID NO:94 (PldC(*TesA)). In certain embodiments, said TesA is a periplasmic-localized *E. coli* TesA. In specific embodiments, said periplasmic-localized TesA has the amino acid sequence of SEQ ID NO:86 (TesA). In particular embodiments, said TesB is *E. coli* TesB. In certain embodiments, said TesB has the amino acid sequence of SEQ ID NO:92 (TesB). In particular embodiments, said FatB is a C8:0 FatB, a C12:0 FatB, a C14:0 FatB, or a C16:0 FatB. In specific embodiments, said C8:0 FatB is from *Cuphea hookeriana*, said C12:0 FatB is from *Umbellularia californica*, said C14:0 FatB is from *Cinnamomum camphora*, or said C16:0 FatB is from *Cuphea hookeriana.*

In particular embodiments, said DGAT is an *Acinetobacter* DGAT, a *Streptomyces* DGAT, or an *Alcanivorax* DGAT. In certain embodiments, said ACP and said DGAT are derived from the same species.

In particular embodiments, said ACCase is from *Synechococcus*. In certain embodiments, said PAP is selected from Pah1 from *S. cerevisiae*, PgpB from *E. coli*, and PAP from PCC6803.

In certain embodiments, said PL is a phospholipase C (PLC). In certain embodiments, said PL has an amino acid sequence selected from any one of SEQ ID NOs:90 (Vupat1), 109, 111, 113, 115, 117, 119, 121, 123, 125, 127, 129, 131, and 133.

In certain embodiments, said TAG hydrolase has an amino acid sequence selected from any one of SEQ ID NOs:135, 137, 139, and 141. In certain embodiments, said fatty acyl-CoA synthetase has an amino acid sequence selected from any one of SEQ ID NOS:143, 145, 147, and 149.

In certain embodiments, one or more of said one or more introduced polynucleotide is present in one or more expression construct. In certain embodiments, said expression construct is stably integrated into the genome of said modified photosynthetic microorganism. In some embodiments, said expression construct comprises an inducible promoter. In certain embodiments, one or more of the introduced polynucleotides are present in an expression construct comprising a weak promoter under non-induced conditions.

In certain embodiments, one or more of said introduced polynucleotides are codon-optimized for expression in a Cyanobacterium. In some embodiments, said one or more codon-optimized polynucleotides are codon-optimized for expression in a *Synechococcus elongatus*. In particular embodiments, said photosynthetic microorganism is a Cyanobacterium and said Cyanobacterium is a *Synechococcus elongatus*. In specific embodiments, the *Synechococcus elongatus* is strain PCC 7942. In certain embodiments, the Cyanobacterium is a salt tolerant variant of *Synechococcus elongatus* strain PCC 7942. In other embodiments, said photosynthetic microorganism is a Cyanobacterium and said Cyanobacterium is *Synechococcus* sp. PCC 7002. In certain embodiments, said photosynthetic microorganism is a Cyanobacterium and said Cyanobacterium is *Synechocystis* sp. PCC 6803.

Also included are methods of producing a modified photosynthetic microorganism that produces or accumulates an increased amount of lipid as compared to a corresponding wild-type photosynthetic microorganism, comprising (i) introducing one or more polynucleotides encoding an acyl carrier protein (ACP), an acyl-ACP synthetase (Aas), or both, and/or overexpressing one or more acyl carrier protein (ACP) and/or acyl-ACP synthetase (Aas) polypeptides, in the photosynthetic microorganism; and (ii) one or both of the following: (a) introducing one or more polynucleotides encoding one or more lipid biosynthesis proteins, and/or overexpressing one or more lipid biosynthesis proteins in the photosynthetic microorganism, and/or (b) reducing expression of one or more genes of a glycogen biosynthesis or storage pathway as compared to a wild-type photosynthetic microorganism. In certain embodiments, said photosynthetic microorganism is a Cyanobacterium.

In certain embodiments, said one or more lipid biosynthesis proteins is selected from an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, and a phospholipase (PL), including any combination thereof.

Some embodiments combine the ACP and the DGAT. Certain embodiments combine the Aas and the DGAT. Certain embodiments combine the ACP, the Aas, and the DGAT. Certain embodiments combine the ACP and the TES. Certain embodiments combine the Aas and the TES. Certain embodiments combine the ACP, the Aas, and the TES. Certain of the above-noted embodiments further include the ACCase. Certain of the above-noted embodiments further include the PAP. Certain of the above-noted embodiments further include the PL.

Particular embodiments combine the ACP and the ACCase. Certain embodiments combine the Aas and the ACCase. Certain embodiments combine the ACP, the Aas, and the ACCase. Certain embodiments combine the ACP and the PAP. Certain embodiments combine the Aas and the PAP. Certain embodiments combine the ACP, the Aas, and the PAP. Certain embodiments combine the ACP and the PL. Certain embodiments combine the Aas and the PL. Certain embodiments combine the ACP, the Aas, and the PL. Certain of the above-noted embodiments further include the DGAT. Certain of the above-noted embodiments further include the TES.

Certain embodiments combine the ACP, the DGAT, and the TAG hydrolase. Certain embodiments combine the Aas, the DGAT, and the TAG hydrolase. Certain embodiments combine the ACP, the Aas, the DGAT, and the TAG hydrolase. Certain embodiments combine the ACP, the DGAT, and the fatty acyl-CoA synthetase. Certain embodiments combine the Aas, the DGAT, and the fatty acyl-CoA synthetase. Certain embodiments combine the ACP, the Aas, the DGAT, and the fatty acyl-CoA synthetase. Some of the above-noted embodiments further comprise any one or more of the TES, the ACCase, the PAP, or the PL.

Certain embodiments include introducing one or more polynucleotides encoding a protein of a glycogen breakdown pathway. Certain embodiments comprise reducing expression of one or more genes of a glycogen biosynthesis or storage pathway. In particular embodiments, reduced expression is achieved by a full or partial deletion of the one or more genes of a glycogen biosynthesis or storage pathway. In certain embodiments, said one or more genes are selected from a glucose-1-phosphate adenyltransferase (glgC) gene and a phosphoglucomutase (pgm) gene.

In certain embodiments, said ACP is a bacterial or a plant ACP. In certain embodiments, said ACP is from *Synechococcus, Spinacia oleracea, Acinetobacter, Streptomyces*, or *Alcanivorax*. In specific embodiments, said ACP has the amino acid sequence of any one of SEQ ID NOs:97, 99, 101, 103, or 105.

In certain embodiments, said Aas is a bacterial Aas. In particular embodiments, said Aas has the amino acid sequence set forth in SEQ ID NO:107. In certain embodiments, said TES is a TesA, a TesB, or a FatB thioesterase. In certain embodiments, said TesA is *E. coli* TesA. In some embodiments, said TesA is a cytoplasmic-localized *E. coli* TesA. In certain embodiments, said cytoplasmic *E. coli* TesA has the amino acid sequence of SEQ ID NO:94 (PldC(*TesA)). In certain embodiments, said TesA is a periplasmic-localized *E. coli* TesA. In certain embodiments, said periplasmic-localized TesA has the amino acid sequence of SEQ ID NO:86 (TesA). In particular embodiments, said TesB is *E. coli* TesB. In certain embodiments, said TesB has the amino acid sequence of SEQ ID NO:92 (TesB). In certain embodiments, said FatB is a C8:0 FatB, a C12:0 FatB, a C14:0 FatB, or a C16:0 FatB. In specific embodiments, said C8:0 FatB is from *Cuphea hookeriana*, said C12:0 FatB is from *Umbellularia californica*, said C14:0 FatB is from *Cinnamomum camphora*, or said C16:0 FatB is from *Cuphea hookeriana*.

In certain embodiments, said DGAT is an *Acinetobacter* DGAT, a *Streptomyces* DGAT, or an *Alcanivorax* DGAT. In particular embodiments, said DGAT are derived from the same species. In certain embodiments, said ACCase is from *Synechococcus*. In certain embodiments, said PAP is selected from Pah1 from *S. cerevisiae*, PgpB from *E. coli*, and PAP from PCC6803. In some embodiments, said PL is a phospholipase C (PLC). In specific embodiments, said PL has an amino acid sequence selected from any one of SEQ ID NOs:90 (Vupat1), 109, 111, 113, 115, 117, 119, 121, 123, 125, 127, 129, 131, and 133. In certain embodiments, said TAG hydrolase has an amino acid sequence selected from any one of SEQ ID NOs:135, 137, 139, and 141. In certain embodiments, said fatty acyl-CoA synthetase has an amino acid sequence selected from any one of SEQ ID NOs:143, 145, 147, and 149.

Embodiments of the present invention also include modified photosynthetic microorganisms comprising one or more introduced polynucleotides encoding a diacylglycerol transferase (DGAT) and a triacylglycerol (TAG) hydrolase, and optionally an acyl-ACP thioesterase (TES), wherein said modified photosynthetic microorganism produces an increased amount of lipid as compared to an unmodified photosynthetic microorganism of the same species. Related embodiments include modified photosynthetic microorganisms comprising an overexpressed diacylglycerol transferase (DGAT) and an overexpressed triacylglycerol (TAG) hydrolase, and optionally an overexpressed acyl-ACP thioesterase (TES), wherein said modified photosynthetic microorganism produces an increased amount of lipid as compared to an unmodified photosynthetic microorganism of the same species.

Embodiments of the present invention also include modified photosynthetic microorganisms comprising one or more introduced polynucleotides encoding a diacylglycerol transferase (DGAT) and a fatty acyl-CoA synthetase, and optionally an acyl-ACP thioesterase (TES), wherein said modified photosynthetic microorganism produces an increased amount of lipid as compared to an unmodified photosynthetic microorganism of the same species. Related embodiments include modified photosynthetic microorganisms comprising an overexpressed diacylglycerol transferase (DGAT) and an overexpressed fatty acyl-CoA synthetase, and optionally an overexpressed acyl-ACP thioesterase (TES), wherein said modified photosynthetic microorganism produces an increased amount of lipid as compared to an unmodified photosynthetic microorganism of the same species.

Also included are methods for the production of lipids, comprising culturing a modified photosynthetic microorganism described herein, wherein said modified photosynthetic microorganism produces or accumulates an increased amount of lipid as compared to a corresponding wild-type photosynthetic microorganism. In certain embodiments, said culturing comprises inducing expression of one or more of said introduced polynucleotides.

In certain embodiments, said culturing comprises culturing under static growth conditions. In particular embodiments, said inducing occurs under static growth conditions. In certain embodiments, said culturing comprises culturing in media supplemented with bicarbonate. In specific embodiments, the concentration of bicarbonate is selected from about 5, 10, 20, 50, 75, 100, 200, 300, 400, 500, 600, 700, 800, 900, and 1000 mM bicarbonate. In certain embodiments, the bicarbonate is present prior to inducing expressing of the introduced polynucleotide. In certain embodiments, the bicarbonate is present during induction of the introduced polynucleotide. In certain embodiments, said lipid comprises a triglyceride, a free fatty acid, or both.

BRIEF DESCRIPTION OF THE SEVERAL VIEWS OF THE DRAWINGS

As shown in FIG. 1C, C16:0 fatty acids represented the primary fatty acid species that was increased in both the *TesA and the ACP/*TesA strains, likely reflecting the specificity of *TesA.

In FIG. 2A, 5 µg of C18 TAG was used as a reference marker (far left lane). In FIG. 2B, U=uninduced cells and IPTG=cells induced with 1 mM IPTG. As shown in these figures, the induced (IPTG) DGAT/ACP strain produced 1.4-fold and 1.2-fold more total FAMES than the induced ACP only or DGAT only strains, respectively.

As shown in FIG. 3A, induction with IPTG (1 mM) resulted in C16TAG production in an aDGAT strain. This amount was increased in the aDGAT/ACP expressing strain, and even further increased in the ADGAT/Aas/ACP overexpressing strain. FIG. 3B shows transmission electron micrographs (TEM) of PCC 7942 strain ADGAT/Aas/ACP grown in the presence (induced) or absence (uninduced) of IPTG at the indicated timepoints. Asterisk (*) denotes larger lipid bodies.

FIG. 5 shows that expression of C12FatB and C14FatB resulted in increases in FFAs, and induction of DGATs resulted in increased formation of triacylglycerols (TAGs), while induction of both caused an increase in both FFA and the formation of TAGs. Control lanes for TAG and palmitate are shown.

DETAILED DESCRIPTION

Figure 1A:
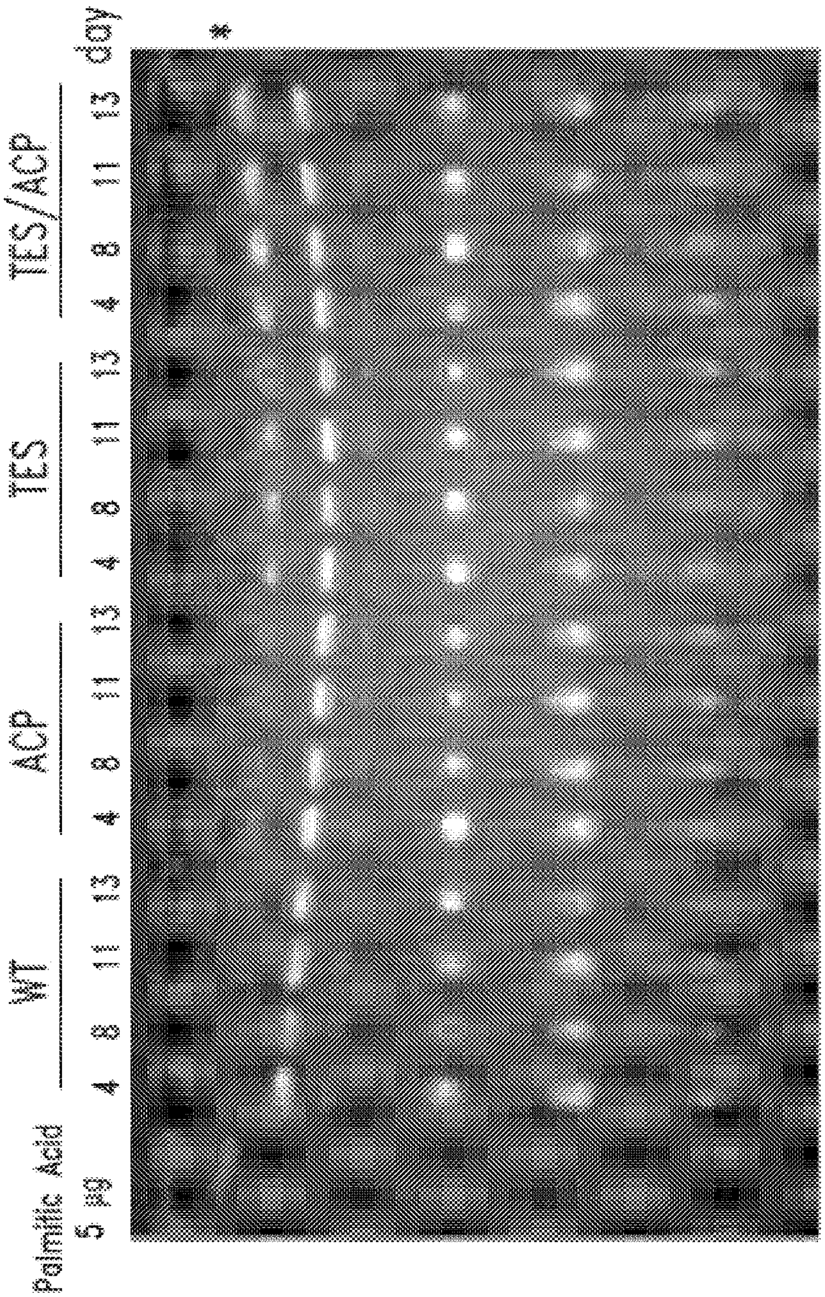
FIGS. 1A-1C show thin layer chromatography (TLC) and gas chromatography (GC) analysis of ACP/*TesA strains grown in continuous culture. As demonstrated by both TLC (1A) and GC (1B and 1C), the ACP, *TesA, and ACP/*TesA strains produced more fatty acids that the wild-type (unmodified) K1 strain (1.3, 1.8, and 2.5-fold more µg FAMES/OD on day 16, respectively). These figures also show that the ACP/*TesA strain produced 1.9-fold more fatty acids than the ACP-only strain, and 1.4-fold more fatty acids than the *TesA only strain.

The present invention is based upon the discovery that photosynthetic microorganisms, e.g., Cyanobacteria, modified to overexpress an acyl carrier protein (ACP) and/or an acyl-ACP synthetase (Aas), or a fragment or variant thereof, optionally in combination with one or more additional lipid biosynthesis proteins, produce increased amounts of lipids, e.g., triglycerides, free fatty acids, and/or wax esters, and often demonstrate an increase in total cellular lipid content, which is advantageous for the production of carbon-based products, including biofuels.

As described in the accompanying Examples, overexpression of acyl carrier protein (ACP) by itself in Cyanobacteria resulted in increased production of free fatty acids relative to an unmodified Cyanobacteria. As also shown in the accompanying Examples, overexpression of the ACP gene in combination with overexpression of either a thioesterase gene or a diacylglycerol transferase (DGAT) gene resulted in increased lipid content compared to controls. For instance, a modified Cyanobacterium overexpressing an ACP from *Synechococcus elongatus* in combination with a mutant form of the lysophospholipase *E. coli* Lysophospholipase L1 (PldC; referred to as *TesA), which localizes to the cytoplasm but retains phospholipase and thioesterase (TES) activities), produced a significantly increased amount of fatty acids compared to the unmodified, ACP only, or *TesA only strains. The ACP/*TesA strain not only displayed no growth defects, but also showed constant production of fatty acids throughout the time course, thus yielding an attractive strain for continuous production of fatty acids. As also shown in the accompanying Examples, a modified Cyanobacterium overexpressing ACP in combination with a diacylglycerol acyltransferase (DGAT), produced a significantly increased amount of lipids compared to the unmodified, ACP only, or DGAT only strains, also yielding strains attractive for biofuel production.

Without wishing to be bound by theory, it is understood that overexpression of the ACP protein further increases the production of fatty acids and/or triacylglycerols in strains that already contain an overexpressed lipid biosynthesis protein such as TesA or DGAT, possibly through mass action (i.e., increasing flux through the fatty acid synthase (FAS) II system), resulting in increased acyl-ACPs, which are substrates of both thioesterases and DGAT; or by deregulating feedback inhibition of Acyl-ACP of FAS II targets. It is likewise understood that independent or concomitant increases in the expression of an acyl-ACP synthetase (Aas) may lead to increased levels in acyl-ACP. Combined with increased expression of other lipid biosynthesis proteins such as TesA or DGAT, endogenous overexpression or exogenous Aas expression can thus be used alone, or in combination with endogenous overexpression or exogenous ACP expression, to further increase the production of lipids such as fatty acids (e.g., free fatty acids) and triglycerides.

The present invention, therefore, relates generally to modified photosynthetic microorganisms, including modified Cyanobacteria, that overexpress one or more ACP proteins and/or one or more Aas proteins, or fragments or variants thereof (e.g., biologically active fragments or variants thereof), alone or in combination with one or more exogenous or overexpressed lipid biosynthesis genes such as DGAT or TesA, as well as methods of producing such modified photosynthetic microorganisms and methods of using them for the production of fatty acids and lipids, e.g., for use in the production of carbon-based products. Examples of lipid biosynthesis proteins that may be overexpressed with ACP and/or Aas include, without limitation, acyl-ACP thioesterases (TES), DGATs, acetyl coenzyme A carboxylases (ACCase), phosphatidic acid phosphatases (PAP; also referred to as phosphatidate phosphatases), lipases, phospholipases (PLs) such as phospholipases A, B, and C (PLA, PLB, PLC), fatty acyl-CoA synthetases, and triacylglycerol (TAG) hydrolases, including any combination thereof.

Separately or in combination with strains having overexpressed lipid biosynthesis proteins, the overexpression of ACP and/or Aas can also be combined with strains having reduced expression of one or more genes of a glycogen biosynthesis or storage pathway as compared to a wild-type photosynthetic microorganism, and/or strains having overexpressed proteins involved in a glycogen breakdown pathway. Certain of these embodiments are detailed elsewhere herein.

The present invention, therefore, relates generally, in part, to modified photosynthetic microorganisms, including modified Cyanobacteria, that overexpress one or more acyl carrier proteins (ACPs) or acyl-ACP synthetases (Aas), or fragments or variants thereof, as well as methods of producing such modified photosynthetic microorganisms and methods of using them for the production of fatty acids and lipids, e.g., for use in the production of carbon-based products. Because the genome of certain photosynthetic microorganisms contain an endogenous or naturally-occurring ACP or Aas, certain embodiments relate to overexpressing endogenous genes without introducing a foreign copy of the gene, such as by stably introducing one or more promoters or other operatively linked regulatory elements into a genomic region surrounding (i.e., upstream or downstream) an endogenous ACP or Aas gene. Such promoters or other regulatory elements (e.g., promoters, enhancers, repressors, ribosome binding sites, transcription termination sites) can be derived from any suitable source; exemplary regulatory elements are described elsewhere herein. In certain aspects, the one or more regulatory elements are all derived from the same species of microorganism being modified. Even though these and related microorganisms are modified by recombinant techniques, they do not necessarily contain any foreign nucleic acid sequences (i.e., sequences from other microorganisms), and thus are not "genetically modified organisms (GMOs)" in the traditional sense of that term. As one example, certain embodiments include the introduction of inducible and/or constitutive promoters, which can be derived from the same or a different genus/species of photosynthetic microorganism relative to the microorganism being modified. ACP and Aas polypeptides can also be overexpressed by recombinantly introducing one or more polynucleotides encoding said polypeptide(s), whether derived from the same or a different genus/species of microorganism relative to the microorganism being modified.

As described above, embodiments of the present invention are useful in combination with the related discovery that photosynthetic microorganisms, including Cyanobacteria such as *Synechococcus*, modified to overexpress a lipase (e.g., a lysophospholipase), or a fragment or variant thereof, produce increased amounts of lipids, e.g., triglycerides, free fatty acids, and/or wax esters, and demonstrate an increase in total cellular lipid content, as described herein and in U.S. Patent Application No. 61/321,337, filed Apr. 6, 2010, titled Modified Photosynthetic Microorganisms for Producing Lipids. For instance, the addition of one or more sequences that encode one or more lipases, e.g., phospholipases or lysophospholipases, which typically have broad substrate specificity (e.g., they have lysophospholipase activity, or both lysophospholipase activity and thioesterase activity), can be used to further increase the production of lipids such as fatty acids.

Embodiments of the present invention are also useful in combination with the related discovery that photosynthetic microorganisms, including Cyanobacteria, such as *Synechococcus*, which do not naturally produce triglycerides, can be genetically modified to synthesize triglycerides, as described herein and in International Patent Application US2009/061936 and U.S. patent application Ser. No. 12/605,204, filed Oct. 23, 2009, titled Modified Photosynthetic Microorganisms for Producing Triglycerides. For instance, the addition of one or more polynucleotide sequences that encode one or more enzymes associated with triglyceride synthesis renders Cyanobacteria capable of converting their naturally-occurring fatty acids into triglyceride energy storage molecules. Examples of enzymes associated with triglyceride synthesis include enzymes having a phosphatidate phosphatase activity and enzymes having a diacylglycerol acyltransferase activity (DGAT). Specifically, phosphatidate phosphatase enzymes catalyze the production of diacylglycerol molecules, an immediate pre-cursor to triglycerides, and DGAT enzymes catalyze the final step of triglyceride synthesis by converting the diacylglycerol precursors to triglycerides.

Aspects of the present invention can also be combined with the discovery that photosynthetic microorganisms such as Cyanobacteria can be genetically modified in other ways to increase the production of fatty acids, as described herein and in International Patent Application US20091061936 and U.S. patent application Ser. No. 12/605,204. Since fatty acids provide the starting material for triglycerides, increasing the production of fatty acids in genetically modified photosynthetic microorganisms may be utilized to increase the production of triglycerides, as described herein and in International Patent Application PCT/US2009/061936. In addition to diverting carbon usage away from glycogen synthesis and towards lipid production, photosynthetic microorganisms of the present invention can also be modified to increase the production of fatty acids by introducing one or more exogenous polynucleotide sequences that encode one or more enzymes associated with fatty acid synthesis. In certain aspects, the exogenous polynucleotide sequence encodes an enzyme that comprises an acyl-CoA carboxylase (ACCase) activity, typically allowing increased ACCase expression, and, thus, increased intracellular ACCase activity. Increased intracellular ACCase activity contributes to the increased production of fatty acids because this enzyme catalyzes the "commitment step" of fatty acid synthesis. Specifically, ACCase catalyzes the production of a fatty acid synthesis precursor molecule, malonyl-CoA. In certain embodiments, the polynucleotide sequence encoding the ACCase is not native the photosynthetic microorganisms's genome.

Aspects of the present invention may also be combined with the discovery that the functional removal of certain genes involved in glycogen synthesis, such as by mutation or deletion, leads to reduced glycogen accumulation and/or storage in photosynthetic microorganisms, such as Cyanobacteria, as described in PCT Application No. US2009/069285 and U.S. patent application Ser. No. 12/645,228. For instance, Cyanobacteria, such as *Synechococcus*, which contain deletions of the glucose-1-phosphate adenylyltransferase gene (glgC), the phosphoglucomutase gene (pgm), and/or the glycogen synthase gene (glgA), individually or in various combinations, may produce and accumulate significantly reduced levels of glycogen as compared to wild-type Cyanobacteria. The reduction of glycogen accumulation may be especially pronounced under stress conditions, including the reduction of nitrogen. Aspects of the present invention may be further combined with the discovery that overexpression of genes or proteins involved in glycogen breakdown in photosynthetic microorganisms, such as Cyanobacteria, also leads to reduced glycogen and/or storage.

A. DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity (e.g., an enzymatic activity) of a reference sequence. The term "reference sequence" refers generally to a nucleic acid coding sequence, or amino acid sequence, to which another sequence is being compared. The term "fragment" encompasses biologically active fragments, which may also be referred to as functional fragments.

The term "biologically active variant", as applied to variants of a reference polynucleotide or polypeptide sequence, refers to a variant that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity (e.g., an enzymatic activity) of a reference sequence. The term "reference sequence" refers generally to a nucleic acid coding sequence, or amino acid sequence, to which another sequence is being compared. The term "variant" encompasses biologically active variants, which may also be referred to as functional variants.

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an activity of a reference polynucleotide or polypeptide. Representative biologically active fragments or variants generally participate in an interaction, e.g., an intra-molecular or an inter-molecular interaction. An inter-molecular interaction can be a specific binding interaction or an enzymatic interaction. Examples of enzymatic interactions or activities include phospholipase activity (e.g., lysophospholipase activity), thioesterase activity, diacylglycerol acyltransferase activity, phosphatidate phosphatase activity, TAG hydrolase activity, and/or acetyl-CoA carboxylase activity, as described herein.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, a "fatty acyl-ACP thioesterase" is an enzyme that catalyzes the cleavage of a fatty acid from an acyl carrier protein (ACP) during lipid synthesis.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

By "increased" or "increasing" is meant the ability of one or more modified photosynthetic microorganisms, e.g., Cyanobacteria, to produce or store a greater amount of a given fatty acid, lipid molecule, or triglyceride as compared to a control photosynthetic microorganism, such as an unmodified Cyanobacteria or a differently modified Cyanobacteria. Also included are increases in total lipids, total fatty acids, total free fatty acids, total intracellular fatty acids, and/or total secreted fatty acids, separately or together. For instance, in certain embodiments, total lipids may increase, with either corresponding increases in all types of lipids, or relative increases in one or more specific types of lipid (e.g., fatty acids, free fatty acids, secreted fatty acids, triglycerides). In certain embodiments, total lipids may increase or they may stay the same (i.e., total lipids are not significantly increased compared to an unmodified microorganism of the same type), and the production or storage of fatty acids (e.g., free fatty acids, secreted fatty acids) may increase relative to other lipids. In particular embodiments, the production or storage of one or more selected types of fatty acids (e.g., secreted fatty acids, free fatty acids, intracellular fatty acids) may increase relative to other types of fatty acids (e.g., secreted fatty acids, free fatty acids, intracellular fatty acids).

An "increased" or "enhanced" amount is typically a "statistically significant" amount, and may include an increase that is about 1.1, 1.2, 1.5, 1.7, 2, 2.5, 3, 3.5, 4, 4.5, 5, 6, 7, 8, 9, 10, 15, 20, 30 or more times (e.g., 100, 500, 1000 times) (including all integers and decimal points in between and above 1, e.g., 1.5, 1.6, 1.7. 1.8, etc.) the amount produced by an unmodified microorganism or a differently modified microorganism, typically of the same species. In particular embodiments, production or storage of total lipids, total triglycerides, total fatty acids, total free fatty acids, total intracellular fatty acids, and/or total secreted fatty acids is increased relative to an unmodified or differently modified microorganism (e.g., for triglycerides, a DGAT-only expressing strain, or a DGAT-expressing strain that does not overexpress an acyl-ACP reductase), as described above, or by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%. In certain embodiments, production or storage of total lipids, total triglycerides, total fatty acids, total free fatty acids, total intracellular fatty acids, and/or total secreted fatty acids is increased by 50% to 200%.

Production of lipids such as fatty acids can be measured according to techniques known in the art, such as Nile Red staining, thin layer chromatography and gas chromatography. Production of triglycerides can be measured, for example, using commercially available enzymatic tests, including colorimetric enzymatic tests using glycerol-3-phosphate-oxidase. Production of free fatty acids can be measured in absolute units such as overall accumulation of FAMES (e.g., OD/ml, μg/ml) or in units that reflect the production of FAMES over time, i.e., the rate of FAMES production (e.g., OD/ml/day, μg/ml/day). For example, certain modified microorganisms described herein may produce at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 μg/mL/day; and/or in the range of at least about 20-30, 20-35, 20-40, 20-45, 20-50, 25-30, 25-35, 25-40, 25-45, 25-50, 30-35, 30-40, 30-45, 30-50, 35-40, 35-45, 35-50, 40-45, or 40-50 μg/mL/day. Production of TAGs can be measured similarly.

In certain instances, by "decreased" or "reduced" is meant the ability of one or more modified photosynthetic microorganisms, e.g., Cyanobacteria, to produce or accumulate a lesser amount (e.g., a statistically significant amount) of a given carbon-based product, such as glycogen, as compared to a control photosynthetic microorganism, such as an unmodified Cyanobacteria or a differently modified Cyanobacteria. Production of glycogen and related molecules can be measured according to techniques known in the art, as exemplified herein (see Example 6; and Suzuki et al., *Biochimica et Biophysica Acta* 1770:763-773, 2007). In certain instances, by "decreased" or "reduced" is meant a lesser level of expression (e.g., a statistically significant amount), by a modified photosynthetic microorganism, e.g., Cyanobacteria, of one or more genes associated with a glycogen biosynthesis or storage pathway, as compared to the level of expression in a control photosynthetic microorganism, such as an unmodified Cyanobacteria or a differently modified Cyanobacteria. In particular embodiments, production or accumulation of a carbon-based product, or expression of one or more genes associated with glycogen biosynthesis or storage is reduced by at least 10%, at least 20%, at least 30%, at least 40%, at least 50%, at least 60%, at least 70%, at least 80%, at least 90%, or 100%. In particular embodiments, production or accumulation of a carbon-based product, or expression of one or more genes associated with glycogen biosynthesis or storage is reduced by 50-100%.

"Stress conditions" refers to any condition that imposes stress upon the Cyanobacteria, including both environmental and physical stresses. Examples of stresses include but not limited to: reduced or increased temperature as compared to standard; nutrient deprivation; reduced or increased light exposure, e.g., intensity or duration, as compared to standard; exposure to reduced or increased nitrogen, iron, sulfur, phosphorus, and/or copper as compared to standard; altered pH, e.g., more or less acidic or basic, as compared to standard; altered salt conditions as compared to standard; exposure to an agent that causes DNA synthesis inhibitor or protein synthesis inhibition; and increased or decreased culture density as compared to standard. Standard growth and culture conditions for various Cyanobacteria are known in the art.

"Reduced nitrogen conditions," or conditions of "nitrogen limitation," refer generally to culture conditions in which a certain fraction or percentage of a standard nitrogen concentration is present in the culture media. Such fractions typically include, but are not limited to, about 1/50, 1/40, 1/30, 1/10, 1/5, 1/4, or about 1/2 the standard nitrogen conditions. Such percentages typically include, but are not limited to, less than about 1%, 2%, 3%, 4%, 5%, 6%, 7%, 8%, 9%, 10%, 15%, 20%, 30%, 40%, or 50% the standard nitrogen conditions. "Standard" nitrogen conditions can be estimated, for example, by the amount of nitrogen present in BG11 media, as exemplified herein and known in the art. For instance, BG11 media usually contains nitrogen in the form of $NaNO_3$ at a concentration of about 1.5 grams/liter (see, e.g., Rippka et al., *J. Gen Microbiol.* 111:1-61, 1979).

By "obtained from" is meant that a sample such as, for example, a polynucleotide or polypeptide is isolated from, or derived from, a particular source, such as a desired organism or a specific tissue within a desired organism. "Obtained from" can also refer to the situation in which a polynucleotide or polypeptide sequence is isolated from, or derived from, a particular organism or tissue within an organism. For example, a polynucleotide sequence encoding an ACP, Aas, diacylglycerol acyltransferase, phosphatidate phosphatase, and/or acetyl-CoA carboxylase enzyme, or any other enzyme described herein, may be isolated from a variety of prokaryotic or eukaryotic organisms, or from particular tissues or cells within certain eukaryotic organism.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the gene from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The recitation "polynucleotide" or "nucleic acid" as used herein designates mRNA, RNA, cRNA, rRNA, cDNA or DNA. These terms typically refer to polymeric form of nucleotides of at least 10 bases in length, either ribonucleotides or deoxynucleotides or a modified form of either type of nucleotide. The term includes single and double stranded forms of DNA and RNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence that encodes a phospholipase (e.g., phospholipase C, lysophospholipase), a diacylglycerol acyltransferase, a phosphatidate phosphatase, and/or an acetyl-CoA carboxylase enzyme. The terms "polynucleotide variant" and "variant" also include naturally-occurring allelic variants and orthologs that encode these enzymes.

With regard to polynucleotides, the term "exogenous" refers to a polynucleotide sequence that does not naturally occur in a wild type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally occurring polynucleotide sequences that may be found in a given wild type cell or organism. For example, certain Cyanobacterial species do not typically contain a DGAT gene, and, therefore, do not comprise an "endogenous" polynucleotide sequence that encodes a DGAT polypeptide. Also, a particular polynucleotide sequence that is isolated from a first organism and transferred to second organism by molecular biological techniques is typically considered an "exogenous" polynucleotide with respect to the second organism.

The recitations "mutation" or "deletion," in relation to the genes of a "glycogen biosynthesis or storage pathway," refer generally to those changes or alterations in a photosynthetic microorganism, e.g., a Cyanobacterium, that render the product of that gene non-functional or having reduced function with respect to the synthesis and/or storage of glycogen. Examples of such changes or alterations include nucleotide substitutions, deletions, or additions to the coding or regulatory sequences of a targeted gene (e.g., glgA, glgC, and pgm), in whole or in part, which disrupt, eliminate, down-regulate, or significantly reduce the expression of the polypeptide encoded by that gene, whether at the level of transcription or translation. Techniques for producing such alterations or changes, such as by recombination with a vector having a selectable marker, are exemplified herein and known in the molecular biological art. In particular embodiments, one or more alleles of a gene, e.g., two or all alleles, may be mutated or deleted within a photosynthetic microorganism. In particular embodiments, modified photosynthetic microorganisms, e.g., Cyanobacteria, of the present invention are merodiploids or partial diploids.

The "deletion" of a targeted gene may also be accomplished by targeting the mRNA of that gene, such as by using various antisense technologies (e.g., antisense oligonucleotides and siRNA) known in the art. Accordingly, targeted genes may be considered "non-functional" when the polypeptide or enzyme encoded by that gene is not expressed by the modified photosynthetic microorganism, or is expressed in negligible amounts, such that the modified photosynthetic microorganism produces or accumulates less glycogen than an unmodified or differently modified photosynthetic microorganism.

In certain aspects, a targeted gene may be rendered "non-functional" by changes or mutations at the nucleotide level that alter the amino acid sequence of the encoded polypeptide, such that a modified polypeptide is expressed, but which has reduced function or activity with respect to glycogen biosynthesis or storage, whether by modifying that polypeptide's active site, its cellular localization, its stability, or other functional features apparent to a person skilled in the art. Such modifications to the coding sequence of a polypeptide involved in glycogen biosynthesis or storage may be accomplished according to known techniques in the art, such as site directed mutagenesis at the genomic level and/or natural selection (i.e., directed evolution) of a given photosynthetic microorganism.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues. Polypeptide variants encompass "biologically active" polypeptide variants.

The present invention contemplates the use in the methods described herein of variants of full-length enzymes having ACP activity, acyl-ACP synthetase activity, lipase activity, phospholipase activity, thioesterase activity, lysophospholipase and thioesterase activities, diacylglycerol acyltransferase activity, phosphatidate phosphatase activity, and/or acetyl-CoA carboxylase activity, polypeptides associated with a glycogen breakdown pathway, truncated fragments of these full-length enzymes and polypeptides, variants of truncated fragments, as well as their related biologically active fragments. Typically, biologically active fragments of a polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken).

Biologically active fragments of a polypeptide/enzyme having a lipase activity, phospholipase activity (e.g., lysophospholipase activity), a thioesterase activity, lysophospholipase and thioesterase activities, an acyl-ACP thioesterase activity, a diacylglycerol acyltransferase activity, a phosphatidate phosphatase activity, a TAG hydrolase activity, and/or an acetyl-CoA carboxylase activity, or polypeptides associated with a glycogen breakdown pathway, include peptides comprising amino acid sequences sufficiently similar to, or derived from, the amino acid sequences of a (putative) full-length reference polypeptide sequence. Typically, biologically active fragments comprise a domain or motif with at least one activity of an ACP polypeptide, acyl-ACP synthetase polypeptide, lipase polypeptide, phospholipase polypeptide, thioesterase polypeptide, diacylglycerol acyltransferase polypeptide, phosphatidate phosphatase polypeptide, TAG hydrolase polypeptide, acetyl-CoA carboxylase polypeptide, or polypeptide associated with a glycogen breakdown pathway, and may include one or more (and in some cases all) of the various active domains. A biologically active fragment of an ACP, acyl-ACP synthetase, lipase, phospholipase, thioesterase, acyl-ACP thioesterase, diacylglycerol acyltransferase, phosphatidate phosphatase, acetyl-CoA carboxylase polypeptide, TAG hydrolase polypeptide, or a polypeptide associated with a glycogen breakdown pathway can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "triglyceride" (triacylglycerol or neutral fat) refers to a fatty acid triester of glycerol. Triglycerides are typically non-polar and water-insoluble.

"Phosphoglycerides" (or glycerophospholipids) are major lipid components of biological membranes, and include, for example, any derivative of sn-glycero-3-phosphoric acid that contains at least one O-acyl, or O-alkyl or O-alk-1'-enyl residue attached to the glycerol moiety and a polar head made of a nitrogenous base, a glycerol, or an inositol unit. Phosphoglycerides can also be characterized as amphipathic lipids formed by esters of acylglycerols with phosphate and another hydroxylated compound.

"Transformation" refers to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a photosynthetic microorganism cell, such as a Cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild type" form of the gene.

B. MODIFIED PHOTOSYNTHETIC MICROORGANISMS

Certain embodiments of the present invention relate to modified photosynthetic microorganisms, including Cyanobacteria, and methods of use thereof, wherein the modified photosynthetic microorganisms comprise one or more overexpressed, exogenous or introduced polynucleotides encoding an acyl carrier protein (ACP) and/or an acyl-ACP synthetase (Aas), or a fragment or variant thereof, optionally in combination with one or more introduced, overexpressed, or exogenous polynucleotides encoding one or more lipid biosynthesis proteins. In particular embodiments, the fragment or variant thereof retains at least 50% of one or more activities of the wild type ACP or Aas protein.

Separately or in combination with the presence of exogenous or overexpressed lipid biosynthesis proteins, ACP and/or Aas encoding polynucleotides may be introduced into or overexpressed in strains of photosynthetic microorganisms having reduced expression of one or more genes of a glycogen biosynthesis or storage pathway, typically as compared to a wild-type photosynthetic microorganism. In some embodiments, a modified photosynthetic microorganism may comprise one or more exogenous, overexpressed, or introduced polynucleotides encoding an ACP and/or an Aas in combination with one or more introduced polynucleotides encoding a protein involved in a glycogen breakdown pathway. These latter embodiments can be combined with those strains having reduced expression of glycogen biosynthesis or storage pathways and/or strains having one or more exogenously or overexpressed lipid biosynthesis proteins.

Examples of lipid biosynthesis proteins that may be overexpressed with ACP and/or Aas include, without limitation, acyl-ACP thioesterases (TES), DGATs, acetyl coenzyme A carboxylases (ACCase), phosphatidic acid phosphatases (PAP; or phosphatidate phosphatases), TAG hydrolases, fatty acyl-CoA synthetases, and phospholipases (PLs) such as phospholipase A, B, or C (PLA, PLB, PLC), including any combination thereof. Certain preferred combinations include, without limitation, modified photosynthetic microorganisms having an exogenous or overexpressed ACP in combination with an exogenous or overexpressed DGAT; an Aas in combination with a DGAT; an ACP and an Aas in combination with a DGAT; an ACP in combination with a TES such as *TesA or a FatB; an Aas in combination with a TES; an ACP and an Aas in combination with a TES; an ACP in combination with a DGAT and a TES; an Aas in combination with a DGAT and a TES; and an ACP and an Aas in combination with a DGAT and a TES.

Also included are combinations that incorporate one or more TAG hydrolases into a TAG-producing strain. For example, certain embodiments include modified photosynthetic microorganisms having an exogenous or overexpressed ACP, Aas, or both, in combination with an exogenous or over-expressed DGAT and a TAG hydrolase, and optionally a TES. Certain embodiments, however, may employ an over-expressed or exogenous DGAT and a TAG hydrolase, and optionally a TES, such as TesA (or *TesA) or any one or more of the FatB sequences, with or without an ACP or Aas. Hence, these and related embodiments may be employed separately from those that require an ACP, an Aas, or both. For instance, certain embodiments may comprise a DGAT and TAG hydrolase, and optionally a TES. Any one of these embodiments can be further combined with one or more additional lipid biosynthesis proteins, such as an ACCase, a PAP, a fatty acyl-CoA synthetase, and/or a PL such as PLC.

Certain combinations incorporate one or more fatty acyl-CoA synthetases (e.g., FadD) into a TAG-producing strain. For instance, certain embodiments include modified photosynthetic microorganisms having an exogenous or overexpressed ACP, Aas, or both, in combination with an exogenous or over-expressed DGAT and fatty acyl-CoA synthetase, and optionally a TES and/or a TAG hydrolase. Certain embodiments, however, may employ an over-expressed or exogenous DGAT and a fatty acyl-CoA synthetase, and optionally a TES, such as TesA (or *TesA) or any one or more of the FatB sequences, with or without an ACP or Aas. Hence, these and related embodiments may be employed separately from those that require an ACP, Aas, or both. For instance, certain embodiments may comprise a DGAT and a fatty acyl-CoA synthetase, and optionally a TES (e.g., TesA, FatB). Any one of these embodiments can be further combined with one or more additional lipid biosynthesis proteins, such as an ACCase, a PAP, a TAG hydrolase, and/or a PL such as PLC.

Any one of these embodiments can also be combined with one or more introduced or overexpressed polynucleotides encoding a protein involved in a glycogen breakdown pathway, and/or with a strain having reduced expression of glycogen biosynthesis or storage pathways (e.g., full or partial deletion of glucose-1-phosphate adenyltransferase (glgC) gene and/or a phosphoglucomutase (pgm) gene). For instance, a specific modified photosynthetic microorganism could comprise an exogenous or overexpressed ACP, Aas, DGAT and PAP, combined with a full or partial deletion of the glgC gene and/or the pgm gene.

Other combinations include, for example, a modified photosynthetic microorganism comprising an exogenous or overexpressed ACP in combination with an exogenous or overexpressed ACCase; an Aas in combination with an ACCase; an ACP and an Aas in combination with an ACCase; an ACP in combination with a PAP; an Aas in combination with a PAP; an ACP and an Aas in combination with a PAP; an ACP in combination with a PL such as PLA, PLB, or PLC; an Aas in combination with a PL; and an ACP and an Aas in combination with a PL. Any one of these embodiments can be combined with each other (e.g., ACP, Aas, ACCase, and PAP), and/or further combined with an exogenous or overexpressed DGAT and/or a TES. Any one of these embodiments can also be combined with one or more introduced polynucleotides encoding a protein involved in a glycogen breakdown pathway, and/or with a strain having reduced expression of glycogen biosynthesis or storage pathways (e.g., full or partial deletion of glucose-1-phosphate adenyltransferase (glgC) gene and/or a phosphoglucomutase (pgm) gene).

ACP and Aas proteins, and fragments and variants thereof, that may be used according to the compositions and methods of the present invention are described in further detail infra. The present invention contemplates the use of naturally-occurring and non-naturally-occurring variants of these ACP, Aas, and lipid (e.g., triglyceride, fatty acid) biosynthesis proteins, as well as variants of their encoding polynucleotides. These enzyme encoding sequences may be derived from any organism (e.g., plants, bacteria) having a suitable sequence, and may also include any man-made variants thereof, such as any optimized coding sequences (i.e., codon-optimized polynucleotides) or optimized polypeptide sequences.

Since fatty acids provide the starting material for triglyceride production, genetically modified photosynthetic microorganisms, e.g., Cyanobacteria, having increased fatty acid production may by utilized to improve the overall production of triglycerides. Accordingly, certain embodiments relate to further modified photosynthetic microorganisms, and methods of use thereof, wherein the modified photosynthetic microorganisms comprise one or more introduced polynucleotides encoding an ACP and/or an Aas polypeptide, and one or more polynucleotides encoding an enzyme associated with fatty acid synthesis and/or triglyceride synthesis. As such, in certain embodiments, the modified photosynthetic microorganisms of the present invention comprise one or more polynucleotides encoding enzymes that comprise an ACP activity and/or an Aas activity, in combination with one or more polynucleotides encoding an enzyme having a DGAT activity, a TES activity, a phosphatidate phosphatase activity (i.e., phosphatidic acid phosphatase activity), a TAG hydrolase activity, an ACCase activity, a fatty acyl-CoA synthetase activity, and/or a lipase or phospholipase activity (e.g., phospholipase C activity, lysophospholipase activity).

Certain embodiments of modified photosynthetic microorganisms of the present invention comprise both: (1) one or more overexpressed or introduced polynucleotides encoding an ACP and/or an Aas, or a fragment or variant thereof; and (2) a further modification such that the modified photosynthetic microorganisms have a reduced level of expression of one or more genes of a glycogen biosynthesis or storage pathway, as compared to the level of expression of the one or more genes in a control photosynthetic microorganism. In certain embodiments, the modified photosynthetic microorganism comprises one or more mutations or deletions in one or more genes of a glycogen biosynthesis or storage pathway. In particular embodiments, said one or more genes include a glucose-1-phosphate adenyltransferase (glgC), a phosphoglucomutase (pgm), and/or a glycogen synthase (glgA) gene. The present invention contemplates the use of any method to reduce expression of the one or more genes in the modified photosynthetic microorganism, including the use of any type of mutation or deletion in the one or more genes associated with glycogen biosynthesis or storage, as long as the modified photosynthetic microorganism, e.g., Cyanobacteria, accumulates a reduced amount of glycogen as compared to a wild type photosynthetic microorganism, e.g., Cyanobacteria (e.g., under reduced nitrogen conditions). These and related embodiments may optionally comprise one or more exogenous or overexpressed lipid biosynthesis proteins.

Certain embodiments of modified photosynthetic microorganisms of the present invention comprise both: (1) one or more overexpressed or introduced polynucleotides encoding an ACP and/or an Aas, or a fragment or variant thereof; and (2) a further modification such that the modified photosynthetic microorganisms have an increased level of expression of one or more polynucleotides encoding one or more enzymes or proteins associated with glycogen breakdown, removal, and/or elimination (e.g., due to the presence of one or more introduced polynucleotides encoding one or more enzymes or proteins associated with glycogen breakdown, removal, and/or elimination, or a functional fragment or variant thereof). In particular embodiments, said one or more polynucleotides encode a glycogen phosphorylase (GlgP), a glycogen debranching enzyme (GlgX), an amylomaltase (MalQ), a phosphoglucomutase (Pgm), a glucokinase (Glk), and/or a phosphoglucose isomerase (Pgi), or a functional fragment or variant thereof. Pgm, Glk, and Pgi are bidirectional enzymes that can promote glycogen synthesis or breakdown depending on conditions. The present invention contemplates the use of any type of polynucleotide encoding a protein or enzyme associated with glycogen breakdown, removal, and/or elimination, as long as the modified photosynthetic microorganism accumulates a reduced amount of glycogen as compared to the wild type photosynthetic microorganism (e.g., under stress conditions). These and related embodiments may optionally comprise one or more exogenous or overexpressed lipid biosynthesis proteins.

Certain embodiments of the present invention also relate to modified photosynthetic microorganisms, e.g., Cyanobacteria, that comprise an introduced polynucleotide encoding an ACP and/or an Aas, or a fragment or variant thereof; and any combination of one or more of the additional modifications described above.

Modified photosynthetic microorganisms of the present invention may be produced using any type of photosynthetic microorganism. These include, but are not limited to photosynthetic bacteria, green algae, and cyanobacteria. The photosynthetic microorganism can be, for example, a naturally photosynthetic microorganism, such as a Cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; eukaryotes, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechococcus* sp., *Synechocystis* sp., and/or *Tolypothrix.*

A modified Cyanobacteria of the present invention may be from any genera or species of Cyanobacteria that is genetically manipulable, i.e., permissible to the introduction and expression of exogenous genetic material. Examples of Cyanobacteria that can be engineered according to the methods of the present invention include, but are not limited to, the genus *Synechocystis, Synechococcus, Thermosynechococcus, Nostoc, Prochlorococcu, Microcystis, Anabaena, Spirulina*, and *Gloeobacter.*

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the present invention.

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Heterocysts may also form under the appropriate environmental conditions (e.g., anoxic) whenever nitrogen is necessary. Heterocyst-forming species are specialized for nitrogen fixation and are able to fix nitrogen gas, which cannot be used by plants, into ammonia ($NH_3$), nitrites ($NO_2^-$), or nitrates ($NO_3^-$), which can be absorbed by plants and converted to protein and nucleic acids.

Many Cyanobacteria also form motile filaments, called hormogonia, which travel away from the main biomass to bud and form new colonies elsewhere. The cells in a hormogonium are often thinner than in the vegetative state, and the cells on either end of the motile chain may be tapered. In order to break away from the parent colony, a hormogonium often must tear apart a weaker cell in a filament, called a necridium.

Each individual Cyanobacterial cell typically has a thick, gelatinous cell wall. Cyanobacteria differ from other gram-negative bacteria in that the quorum sensing molecules autoinducer-2 and acyl-homoserine lactones are absent. They lack flagella, but hormogonia and some unicellular species may move about by gliding along surfaces. In water columns, some Cyanobacteria float by forming gas vesicles, like in archaea.

Cyanobacteria have an elaborate and highly organized system of internal membranes that function in photosynthesis. Photosynthesis in Cyanobacteria generally uses water as an electron donor and produces oxygen as a by-product, though some Cyanobacteria may also use hydrogen sulfide, similar to other photosynthetic bacteria. Carbon dioxide is reduced to form carbohydrates via the Calvin cycle. In most forms, the photosynthetic machinery is embedded into folds of the cell membrane, called thylakoids. Due to their ability to fix nitrogen in aerobic conditions, Cyanobacteria are often found as symbionts with a number of other groups of organisms such as fungi (e.g., lichens), corals, pteridophytes (e.g., *Azolla*), and angiosperms (e.g., *Gunnera*), among others.

Cyanobacteria are the only group of organisms that are able to reduce nitrogen and carbon in aerobic conditions. The water-oxidizing photosynthesis is accomplished by coupling the activity of photosystem (PS) II and I (Z-scheme). In anaerobic conditions, Cyanobacteria are also able to use only PS I (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property; the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes, attached to the thylakoid membrane, act as light harvesting antennae for the photosystems of Cyanobacteria. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

In particular embodiments, the Cyanobacteria may be, e.g., a marine form of Cyanobacteria or a fresh water form of Cyanobacteria. Examples of marine forms of Cyanobacteria include, but are not limited to *Synechococcus* WH8102, *Synechococcus* RCC307, *Synechococcus* NKBG 15041c, and *Trichodesmium*. Examples of fresh water forms of Cyanobacteria include, but are not limited to, *S. elongatus* PCC 7942, *Synechocystis* PCC 6803, *Plectonema boryanum*, and *Anabaena* sp. Exogenous genetic material encoding the desired enzymes or polypeptides may be introduced either transiently, such as in certain self-replicating vectors, or stably, such as by integration (e.g., recombination) into the Cyanobacterium's native genome.

In other embodiments, a genetically modified Cyanobacteria of the present invention may be capable of growing in brackish or salt water. When using a fresh water form of Cyanobacteria, the overall net cost for production of triglycerides will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It consists of liquid waste released from domestic and commercial properties, industry, and/or agriculture and can encompass a wide range of possible contaminants at varying concentrations.

There is a broad distribution of Cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In particular embodiments, the present invention contemplates the use of a Cyanobacteria *S. elongatus* PCC 7942, altered in a way that allows for growth in either waste water or salt/brackish water. A *S. elongatus* PCC 7942 mutant resistant to sodium chloride stress has been described (Bagchi, S. N. et al., Photosynth Res. 2007, 92:87-101), and a genetically modified *S. elongatus* PCC 7942 tolerant of growth in salt water has been described (Waditee, R. et al., PNAS 2002, 99:4109-4114). According to the present invention, a salt water tolerant strain is capable of growing in water or media having a salinity in the range of 0.5% to 4.0% salinity, although it is not necessarily capable of growing in all salinities encompassed by this range. In one embodiment, a salt tolerant strain is capable of growth in water or media having a salinity in the range of 1.0% to 2.0% salinity. In another embodiment, a salt water tolerant strain is capable of growth in water or media having a salinity in the range of 2.0% to 3.0% salinity.

Examples of Cyanobacteria that may be utilized and/or genetically modified according to the methods described herein include, but are not limited to, Chroococcales Cyanobacteria from the genera *Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloecapsa, Gloeothece, Merismopedia, Microcystis, Radiocystis, Rhabdoderma, Snowella, Synychococcus, Synechocystis, Thermosenechococcus*, and *Woronichinia*; Nostacales Cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis*, and *Toypothrix*; Oscillatoriales Cyanobacteria from the genera *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Spirulina, Symploca, Trichodesmium, Tychonema; Pleurocapsales* cyanobacterium from the genera *Chroococcidiopsis, Dermocarpa, Dermocarpella, Myxosarcina, Pleurocapsa, Stanieria, Xenococcus; Prochlorophytes* cyanobacterium from the genera *Prochloron, Prochlorococcus, Prochlorothrix*; and *Stigonematales* cyanobacterium from the genera *Capsosira, Chlorogeopsis, Fischerella, Hapalosiphon, Mastigocladopsis, Nostochopsis, Stigonema, Symphyonema, Symphonemopsis, Umezakia*, and *Westiellopsis*. In certain embodiments, the Cyanobacterium is from the genus *Synechococcus*, including, but not limited to *Synechococcus bigranulatus, Synechococcus elongatus, Synechococcus leopoliensis, Synechococcus lividus, Synechococcus nidulans*, and *Synechococcus rubescens*.

In certain embodiments, the Cyanobacterium is *Anabaena* sp. strain PCC 7120, *Synechocystis* sp. strain PCC 6803, *Nostoc muscorum, Nostoc ellipsosporum*, or *Nostoc* sp. strain PCC 7120. In certain preferred embodiments, the Cyanobacterium is *S. elongatus* sp. strain PCC 7942.

Additional examples of Cyanobacteria that may be utilized in the methods provided herein include, but are not limited to, *Synechococcus* sp. strains WH7803, WH8102, WH8103 (typically genetically modified by conjugation), *Baeocyte*-forming *Chroococcidiopsis* spp. (typically modified by conjugation/electroporation), non-heterocyst-forming filamentous strains *Planktothrix* sp., *Plectonema boryanum* M101 (typically modified by electroporation), and Heterocyst-forming strains *Anabaena* sp. strains ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In certain preferred embodiments, the Cyanobacterium may be *S. elongatus* sp. strain PCC 7942 or *Synechococcus* sp. PCC 7002 (originally known as *Agmenellum quadruplicatum*).

In particular embodiments, the genetically modified, photosynthetic microorganism, e.g., Cyanobacteria, of the present invention may be used to produce triglycerides and/or other carbon-based products from just sunlight, water, air, and minimal nutrients, using routine culture techniques of any reasonably desired scale. In particular embodiments, the present invention contemplates using spontaneous mutants of photosynthetic microorganisms that demonstrate a growth advantage under a defined growth condition. Among other benefits, the ability to produce large amounts of triglycerides from minimal energy and nutrient input makes the modified photosynthetic microorganism, e.g., Cyanobacteria, of the present invention a readily manageable and efficient source of feedstock in the subsequent production of both biofuels, such as biodiesel, as well as specialty chemicals, such as glycerin.

C. METHODS OF PRODUCING MODIFIED PHOTOSYNTHETIC MICROORGANISMS

Embodiments of the present invention also include methods of producing the modified photosynthetic microorganisms, e.g., a Cyanobacterium, of the present invention.

In one embodiment, the present invention comprises a method of modifying a photosynthetic microorganism to produce a modified photosynthetic microorganism that produces an increased amount of lipids, e.g., free fatty acids, as compared to a corresponding wild type photosynthetic microorganism, comprising introducing into said microorganism one or more polynucleotides encoding an ACP and/or an Aas, including active fragments or variants thereof. In a related embodiment, the present invention includes a method of modifying a photosynthetic microorganism to produce a modified photosynthetic microorganism that produces an increased amount of lipids, e.g., free fatty acids, as compared to a corresponding wild type photosynthetic microorganism comprising introducing into said microorganism one or more promoters or other regulatory elements operatively linked to an endogenous ACP or Aas gene. In certain embodiments, the promoters or regulatory elements are introduced into a region surrounding (e.g., upstream or downstream of) a gene encoding an ACP or Aas polypeptide. Regulatory elements can be stably and operatively introduced upstream and/or downstream of the genomic region of the endogenous gene. Examples of regulatory elements include promoters, enhancers, repressors, ribosome binding sites, and transcription termination sites. Such promoters or regulatory elements may be constitutive or inducible. Such promoters or regulatory elements may be derived from the same or a different genus/species relative to the microorganism being modified. In specific embodiments, all of the one or more regulatory elements are derived from the same species of microorganism that is being modified.

The above methods may further comprise a step of selecting for photosynthetic microorganisms in which the one or more desired polynucleotides were successfully introduced, where the polynucleotides were, e.g., present in a vector the expressed a selectable marker, such as an antibiotic resistance gene. As one example, selection and isolation may include the use of antibiotic resistant markers known in the art (e.g., kanamycin, spectinomycin, and streptomycin).

In certain embodiments, methods of the present invention comprise both: (1) introducing into said photosynthetic microorganism one or more polynucleotides encoding an ACP and/or an Aas, or a fragment or variant thereof; or overexpressing an ACP and/or Aas polypeptide, and (2) introducing into said photosynthetic microorganism one or more polynucleotides encoding one or more lipid biosynthesis proteins, e.g., enzymes associated with fatty acid and/or triglyceride biosynthesis, and/or overexpressing one or more lipid biosynthesis proteins. In certain embodiments, the one or more enzymes comprise a thioesterase activity (TES), a diacylglycerol acyltransferase (DGAT) enzymatic activity, an ACCase activity, a phosphatidate phosphatase (i.e., phosphatidic acid phosphatase) enzymatic activity, a TAG hydrolase or lipase activity, a fatty acyl-CoA synthetase activity, and/or a phospholipase activity (e.g., phospholipase C, lysophospholipase), including any combination thereof.

Thus, in one particular embodiment, the present invention includes a method of producing a modified photosynthetic microorganism, e.g., a Cyanobacteria, comprising: (1) introducing into said photosynthetic microorganism one or more polynucleotides encoding an ACP and/or an Aas, or a fragment or variant thereof, and/or overexpressing an ACP and/or Aas polypeptide, or a fragment or variant thereof; and (2) introducing into said photosynthetic microorganism one or more polynucleotides encoding a DGAT, or a fragment or variant thereof and/or overexpressing a DGAT protein. In one particular embodiment, the present invention includes a method of producing a modified photosynthetic microorganism, e.g., a Cyanobacteria, comprising: (1) introducing into said photosynthetic microorganism one or more polynucleotides encoding an ACP and/or an Aas, or a fragment or variant thereof, and/or overexpressing an ACP and/or Aas polypeptide, or a fragment or variant thereof; and (2) introducing into said photosynthetic microorganism one or more polynucleotides encoding a TES, or a fragment or variant thereof, and/or overexpressing a TES protein, or a fragment or variant thereof. These embodiments can also be modified to include introducing one or more polynucleotides encoding an ACCase, a PAP, a TAG hydrolase, a fatty acyl-CoA synthetase, and/or a PL such as PLC, or fragments or variants thereof.

In certain embodiments, the DGAT and/or the TES are derived from a microorganism of the same genus or species as the ACP and/or the Aas, i.e., they are species-specific and/or genus-specific. For instance, the ACP and the DGAT can both be derived from bacteria of the genus *Acinetobacter* or *Streptomyces*. As a further example, the ACP and the TES can both be derived from *E. coli*, or they can both be derived from bacteria of the genus *Acinetobacter* or *Streptomyces*. Likewise, the Aas and the DGAT can both be derived from be derived from bacteria of the genus *Acinetobacter, Streptomyces* or *Rhodococcus*. Also, the Aas and the TES can both be derived from be derived from bacteria of the genus *Acinetobacter, Streptomyces* or *Rhodococcus*. Other combinations of species-specific or genus-specific proteins will be apparent to persons skilled in the art.

In certain embodiments, methods of the present invention comprise both: (1) introducing into said photosynthetic microorganism one or more polynucleotides encoding an ACP and/or an Aas, or a fragment or variant thereof, and/or overexpressing an ACP and/or Aas polypeptide, or a fragment or variant thereof; and (2) modifying the photosynthetic microorganism so that it expresses a reduced amount of one or more genes associated with a glycogen biosynthesis or storage pathway and/or an increased amount of one or more polynucleotides encoding a polypeptide associated with a glycogen breakdown pathway. Thus, in one particular embodiment, the present invention includes a method of producing a modified photosynthetic microorganism, e.g., a Cyanobacteria, comprising: (1) introducing into said photosynthetic microorganism one or more polynucleotides encoding an ACP and/or an Aas, or a fragment or variant thereof, and/or overexpressing an ACP and/or Aas polypeptide, or a fragment or variant thereof; and (2) modifying the photosynthetic microorganism so that it has a reduced level of expression of one or more genes of a glycogen biosynthesis or storage pathway. In particular embodiments, expression or activity is reduced by mutating or deleting a portion or all of said one or more genes. In particular embodiments, expression or activity is reduced by knocking out or knocking down one or more alleles of said one or more genes. In particular embodiments, expression or activity of the one or more genes is reduced by contacting the photosynthetic microorganism with an antisense oligonucleotide or interfering RNA, e.g., an siRNA, that targets said one or more genes. In particular embodiments, a vector that expresses a polynucleotide that hybridizes to said one or more genes, e.g., an antisense oligonucleotide or an siRNA is introduced into said photosynthetic microorganism.

In certain embodiments, methods of the present invention comprise both: (1) introducing into said photosynthetic microorganism one or more polynucleotides encoding an ACP and/or an Aas, or a fragment or variant thereof, and/or overexpressing an ACP and/or Aas polypeptide, or a fragment or variant thereof; (2) introducing into said photosynthetic microorganism one or more polynucleotides encoding one or more lipid biosynthesis proteins (e.g., enzymes associated with fatty acid and/or triglyceride biosynthesis) and/or overexpressing one or more enzymes associated with fatty acid and/or trilyceride biosynthesis; and (3) modifying the photosynthetic microorganism so that it expresses a reduced amount of one or more genes associated with a glycogen biosynthesis or storage pathway and/or an increased amount of one or more polynucleotides encoding a polypeptide associated with a glycogen breakdown pathway.

Photosynthetic microorganisms, e.g., Cyanobacteria, may be genetically modified according to techniques known in the art, e.g., to delete a portion or all of a gene or to introduce a polynucleotide that expresses a functional polypeptide. As noted above, in certain aspects, genetic manipulation in photosynthetic microorganisms, e.g., Cyanobacteria, can be performed by the introduction of non-replicating vectors which contain native photosynthetic microorganism sequences, exogenous genes of interest, and selectable markers or drug resistance genes. Upon introduction into the photosynthetic microorganism, the vectors may be integrated into the photosynthetic microorganism's genome through homologous recombination. In this way, an exogenous gene of interest and the drug resistance gene are stably integrated into the photosynthetic microorganism's genome. Such recombinants cells can then be isolated from non-recombinant cells by drug selection. Cell transformation methods and selectable markers for Cyanobacteria are also well known in the art (see, e.g., Wirth, *Mol Gen Genet.* 216:175-7, 1989; and Koksharova, *Appl Microbiol Biotechnol* 58:123-37, 2002; and THE CYANOBACTERIA: MOLECULAR BIOLOGY, GENETICS, AND EVOLUTION (eds. Antonio Herrera and Enrique Flores) Caister Academic Press, 2008, each of which is incorporated by reference for their description on gene transfer into Cyanobacteria, and other information on Cyanobacteria).

In certain embodiments, an endogenous version of a protein (e.g., ACP, Aas, DGAT, TES, ACCase, TAG hydrolase, fatty acyl-CoA synthetase, PAP, PL), if present, can be overexpressed by introducing a heterologous or other promoter upstream of the endogenous gene encoding that protein, i.e., the naturally-occurring version of that gene. Such promoters may be constitutive or inducible.

Generation of deletions or mutations of any of the one or more genes associated with the biosynthesis or storage of glycogen can be accomplished according to a variety of methods known in the art, including the use of a non-replicating, selectable vector system that is targeted to the upstream and downstream flanking regions of a given gene (e.g., glgC, pgm), and which recombines with the Cyanobacterial genome at those flanking regions to replace the endogenous coding sequence with the vector sequence. Given the presence of a selectable marker in the vector sequence, such as a drug selectable marker, Cyanobacterial cells containing the gene deletion can be readily isolated, identified and characterized. Such selectable vector-based recombination methods need not be limited to targeting upstream and downstream flanking regions, but may also be targeted to internal sequences within a given gene, as long as that gene is rendered "non-functional," as described herein.

The generation of deletions or mutations can also be accomplished using antisense-based technology. For instance, Cyanobacteria have been shown to contain natural regulatory events that rely on antisense regulation, such as a 177-nt ncRNA that is transcribed in antisense to the central portion of an iron-regulated transcript and blocks its accumulation through extensive base pairing (see, e.g., Dühring, et al., *Proc. Natl. Acad. Sci. USA* 103:7054-7058, 2006), as well as a alr1690 mRNA that overlaps with, and is complementary to, the complete furA gene, which acts as an antisense RNA (α-furA RNA) interfering with furA transcript translation (see, e.g., Hernandez et al., *Journal of Molecular Biology* 355:325-334, 2006). Thus, the incorporation of antisense molecules targeted to genes involved in glycogen biosynthesis or storage would be similarly expected to negatively regulate the expression of these genes, rendering them "non-functional," as described herein.

As used herein, antisense molecules encompass both single and double-stranded polynucleotides comprising a strand having a sequence that is complementary to a target coding strand of a gene or mRNA. Thus, antisense molecules include both single-stranded antisense oligonucleotides and double-stranded siRNA molecules.

Photosynthetic microorganisms may be cultured according to techniques known in the art. For example, Cyanobacteria may be cultured or cultivated according to techniques known in the art, such as those described in Acreman et al. (*Journal of Industrial Microbiology and Biotechnology* 13:193-194, 1994), in addition to photobioreactor based techniques, such as those described in Nedbal et al. (*Biotechnol Bioeng.* 100:902-10, 2008). One example of typical laboratory culture conditions for Cyanobacterium is growth in BG-11 medium (ATCC Medium 616) at 30° C. in a vented culture flask with constant agitation and constant illumination at 30-100 μmole photons $m^{-2}$ $sec^{-1}$.

A wide variety of mediums are available for culturing Cyanobacteria, including, for example, Aiba and Ogawa (AO) Medium, Allen and Amon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [BG-11 medium]), ATCC Medium 819 (Blue-green Nitrogen-fixing Medium; ATCC Medium 616 [BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), *Beggiatoa* Medium (ATCC Medium 138), *Beggiatoa* Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (Halophilic cyanobacteria), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erdschreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Spirulina*: ATCC Medium 1679, *Spirulina* (SP) Medium, van Rijn and Cohen (RC) Medium, Walsby's Medium, Yopp Medium, and Z8 Medium, among others.

D. METHODS OF PRODUCING LIPIDS AND FATTY ACIDS

The modified photosynthetic microorganisms of the present invention may be used to produce lipids, fatty acids and triglycerides. Accordingly, the present invention provides methods of producing lipids and fatty acids comprising culturing any of the modified photosynthetic microorganisms of the present invention (described elsewhere herein) under conditions wherein the modified photosynthetic microorganism produces and/or accumulates (e.g., stores, secretes) an increased amount of cellular lipid as compared to a corresponding wild-type photosynthetic microorganism. In one embodiment, the modified photosynthetic microorganism is a Cyanobacterium.

In certain embodiments, the one or more introduced polynucleotides are present in one or more expression constructs. In particular embodiments, the one or more expression constructs comprises one or more inducible promoters. In certain embodiments, the one or more expression constructs are stably integrated into the genome of said modified photosynthetic microorganism. In certain embodiments, the introduced polynucleotide encoding an introduced protein is present in an expression construct comprising a weak promoter under non-induced conditions. In certain embodiments, one or more of the introduced polynucleotides are codon-optimized for expression in a Cyanobacterium, e.g., a *Synechococcus elongatus*.

In particular embodiments, the photosynthetic microorganism is a *Synechococcus elongatus*, such as *Synechococcus elongatus* strain PCC 7942 or a salt tolerant variant of *Synechococcus elongatus* strain PCC 7942.

In particular embodiments, the photosynthetic microorganism is a *Synechococcus* sp. PCC 7002 or a *Synechocystis* sp. PCC 6803.

In particular embodiments, the modified photosynthetic microorganisms are cultured under conditions suitable for inducing expression of the introduced polynucleotide(s), e.g., wherein the introduced polynucleotide(s) comprise an inducible promoter. Conditions and reagents suitable for inducing inducible promoters are known and available in the art. Also included are the use of auto-inductive systems, for example, where a metabolite represses expression of the introduced polynucleotide, and the use of that metabolite by the microorganism over time decreases its concentration and thus its repressive activities, thereby allowing increased expression of the polynucleotide sequence.

In certain embodiments, modified photosynthetic microorganisms, e.g., Cyanobacteria, are grown under conditions favorable for producing lipids, triglycerides and/or fatty acids. In particular embodiments, light intensity is between 100 and 2000 uE/m2/s, or between 200 and 1000 uE/m2/s. In particular embodiments, the pH range of culture media is between 7.0 and 10.0. In certain embodiments, $CO_2$ is injected into the culture apparatus to a level in the range of 1% to 10%. In particular embodiments, the range of $CO_2$ is between 2.5% and 5%. In certain embodiments, nutrient supplementation is performed during the linear phase of growth. Each of these conditions may be desirable for triglyceride production.

In certain embodiments, the modified photosynthetic microorganisms are cultured, at least for some time, under static growth conditions as opposed to shaking conditions. For example, the modified photosynthetic microorganisms may be cultured under static conditions prior to inducing expression of an introduced polynucleotide (e.g., ACP, Aas, DGAT, TES, TAG hydrolase, fatty acyl-CoA synthetase, ACCase, PL, PAP) and/or the modified photosynthetic microorganism may be cultured under static conditions while expression of an introduced polynucleotide is being induced, or during a portion of the time period during which expression on an introduced polynucleotide is being induced. Static growth conditions may be defined, for example, as growth without shaking or growth wherein the cells are shaken at less than or equal to 30 rpm or less than or equal to 50 rpm.

In certain embodiments, the modified photosynthetic microorganisms are cultured, at least for some time, in media supplemented with varying amounts of bicarbonate. For example, the modified photosynthetic microorganisms may be cultured with bicarbonate at 5, 10, 20, 50, 75, 100, 200, 300, 400, 500, 600, 700, 800, 900, 1000 mM bicarbonate prior to inducing expression of an introduced polynucleotide (e.g., ACP, Aas, DGAT, TES, TAG hydrolase, fatty acyl-CoA synthetase, ACCase, PL, PAP) and/or the modified photosynthetic microorganism may be cultured with aforementioned bicarbonate concentrations while expression of an introduced polynucleotide is being induced, or during a portion of the time period during which expression on an introduced polynucleotide is being induced.

E. NUCLEIC ACIDS AND POLYPEPTIDES

Modified photosynthetic microorganisms of the present invention comprise one or more over-expressed, exogenous or introduced nucleic acids that encode an ACP, an Aas, or both, optionally in combination with one or more lipid biosynthesis proteins, e.g., one or more proteins associated with fatty acid or triglyceride biosynthesis, and/or optionally in combination with one or more proteins associated with glycogen breakdown. It is further understood that the compositions and methods of the present invention may be practiced using biologically active fragments and/or variants of any of these or other introduced or overexpressed polypeptides. Also, these modified microorganisms (e.g., those that comprise an ACP, Aas, or both) may optionally further comprise a mutation or deletion in one or more genes associated with glycogen biosynthesis or storage, either alone or in combination with the presence of introduced or over-expressed proteins associated with lipid biosynthesis proteins and/or glycogen breakdown. As will be apparent, modified photosynthetic microorganisms of the present invention may comprise any combination of one or more of the additional modifications noted above, as long as they have an ACP, Aas, or both.

Acyl-Carrier Proteins (ACP), Acyl Carrier Protein Synthases (AcpS) and Acyl-ACP Synthetases (Aas)

Embodiments of the present invention typically include one or more exogenous (e.g., recombinantly introduced) or over-expressed ACP proteins and/or one or more exogenous or over-expressed Aas proteins. These proteins play crucial roles in fatty acid synthesis. Fatty acid synthesis in bacteria, including Cyanobacteria, is carried out by highly conserved enzymes of the type II fatty acid synthase system (FAS II; consisting of about 19 genes) in a sequential, regulated manner. Acyl carrier protein (ACP) plays a central role in this process by carrying all the intermediates as thioesters attached to the terminus of its 4'-phosphopantetheine prosthetic group (ACP-thioesters). Apo-ACP, the product of acp gene, is typically activated by a phosphopantetheinyl transferease (PPT) such as the acyl carrier protein synthase (AcpS) type found in *E. coli* or the Sfp (surfactin type) PTT as characterized in *Bacillus subtilis*. Cyanobacteria posses an Sfp-like PPT, which is understood to act in both primary and secondary metabolism. Embodiments of the present invention therefore include overexpression of PPTs such as AcpS and/or Sfp-type PPTs in combination with overexpression of cognate ACP encoding genes, such as ACP and/or Aas, with or without DGAT.

The ACP-thioesters are substrates for all of the enzymes of the FAS II system. The end product of fatty acid synthesis is a long acyl chain typically consisting of about 14-18 carbons attached to ACP by a thioester bond.

At least three enzymes of the FAS II system in other bacteria can be subject to feedback inhibition by acyl-ACPs: 1) the ACCase complex—a heterotetramer of the AccABCD genes that catalyzes the production of malonyl-coA, the first step in the pathway; 2) the product of the FabH gene (β-ketoacyl-ACP synthase Ill), which catalyzes the condensation of acetyl-CoA with malonyl-ACP; and 3) the product of the Fabl gene (enoyl-ACP reductase), which catalyzes the final elongation step in each round of elongation. Certain lipid biosynthesis proteins such as DGAT and TesA are capable of increasing lipid production in photosynthetic bacteria such as Cyanobacteria, and it has been shown herein that overexpression of ACP in combination with these or other biosynthesis proteins further increases fatty acid and/or triglyceride production in such strains, possibly through mass action (i.e., increasing flux through the FAS II system), resulting in increased acyl-ACPs, which are substrates of both DGAT and thioesterases; and/or by deregulating feedback inhibition of acyl-ACP on FAS II targets.

Acyl-ACP synthetases (Aas) catalyze the ATP-dependent acylation of the thiol of acyl carrier protein (ACP) with fatty acids, including those fatty acids having chain lengths from about C4 to C18. In Cyanobacteria, among other functions, Aas enzymes not only directly incorporate exogenous fatty acids from the culture medium into other lipids, but also play a role in the recycling of acyl chains from lipid membranes. Deletion of Aas in cyanobacteria can lead to secretion of free fatty acids into the culture medium. See, e.g., Kaczmarzyk and Fulda, *Plant Physiology* 152:1598-1610, 2010.

An ACP or an Aas can be derived from a variety of eukaryotic organisms, microorganisms (e.g., bacteria, fungi), or plants. Examples of bacterial Aas enzymes include those derived from *E. coli*, *Acinetobacter*, and *Vibrio* sp. such as *V. harveyi* (see, e.g., Shanklin, *Protein Expression and Purification.* 18:355-360, 2000; Jiang et al., *Biochemistry.* 45:10008-10019, 2006). In certain embodiments, an ACP polynucleotide sequence and its corresponding polypeptide sequence are derived from Cyanobacteria such as *Synechococcus*. In certain embodiments, ACPs can be derived from plants such as spinach. SEQ ID NOS:96-103 provide the nucleotide and polypeptide sequences of exemplary bacterial ACPs from *Synechococcus* and *Acinetobacter*, and SEQ ID NOS:104-105 provide the same for an exemplary plant ACP from *Spinacia oleracea* (spinach). SEQ ID NOS:96 and 97 derive from *Synechococcus elongatus* PCC 7942, and SEQ ID NOS:98-103 derive from *Acinetobacter* sp. ADP1. SEQ ID NOS:106 and 107, respectively, provide the nucleotide and polypeptide sequences of an exemplary Aas from *Synechococcus elongatus* PCC 7942.

In specific embodiments, the ACP or Aas is derived from the same organism as the DGAT or the TES. Accordingly, certain embodiments include ACP and/or Aas sequences from any of the organisms described herein for deriving a DGAT or TES, including, for example, various animals (e.g., mammals, fruit flies, nematodes), plants, parasites, and fungi (e.g., yeast such as *S. cerevisiae* and *Schizosaccharomyces pombe*). Examples of prokaryotic organisms include certain *actinomycetes*, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of *actinomycetes* that have one or more genes encoding an ACP or Aas activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having an ACP or Aas activity include members of the genera *Acinetobacter*, such as *A. calcoaceticus, A. baumanii, A. baylii*, and members of the generua *Alcanivorax*. In certain embodiments, an ACP or Aas gene or enzyme is isolated from *Acinetobacter baylii* sp. ADP1, a gram-negative triglyceride forming prokaryote.

Lipid Biosynthesis Proteins

In various embodiments, modified photosynthetic microorganisms, e.g., Cyanobacteria, of the present invention further comprise one or more exogenous (i.e., introduced) or overexpressed nucleic acids that encode a lipid biosynthesis protein, e.g., a polypeptide having an activity associated with triglyceride biosynthesis or fatty acid biosynthesis, including but not limited to any of those described herein. Specific examples of lipid biosynthesis proteins include thioesterases or acyl-ACP thioesterases (TES) such as TesA or FatB, diacylglycerol acyltransferases (DGAT), acetyl coenzyme A carboxylases (ACCase), phosphatidic acid phosphatases (PAP; or phosphatidate phosphatases), triacylglycerol (TAG) hydrolases or lipases, fatty acyl-CoA synthetases, lipases, and phospholipases (PL) such as phospholipase A, B, or C. Certain of these proteins are described in greater detail below.

In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism. In certain embodiments, the expression of a native or endogenous nucleic acid and its corresponding protein can be increased by introducing a heterologous promoter upstream of the native gene. As noted above, lipid biosynthesis proteins can be involved in triglyceride biosynthesis, fatty acid synthesis, or both.

Triglyceride Biosynthesis.

Triglycerides, or triacylglycerols (TAGs), consist primarily of glycerol esterified with three fatty acids, and yield more energy upon oxidation than either carbohydrates or proteins. Triglycerides provide an important mechanism of energy storage for most eukaryotic organisms. In mammals, TAGs are synthesized and stored in several cell types, including adipocytes and hepatocytes (Bell et al. *Annu. Rev. Biochem.* 49:459-487, 1980) (herein incorporated by reference). In plants, TAG production is mainly important for the generation of seed oils.

In contrast to eukaryotes, the observation of triglyceride production in prokaryotes has been limited to certain *actinomycetes*, such as members of the genera *Mycobacterium, Nocardia, Rhodococcus* and *Streptomyces*, in addition to certain members of the genus *Acinetobacter*. In certain *Actinomycetes* species, triglycerides may accumulate to nearly 80% of the dry cell weight, but accumulate to only about 15% of the dry cell weight in *Acinetobacter*. In general, triglycerides are stored in spherical lipid bodies, with quantities and diameters depending on the respective species, growth stage, and cultivation conditions. For example, cells of *Rhodococcus opacus* and *Streptomyces lividans* contain only few TAGs when cultivated in complex media with a high content of carbon and nitrogen; however, the lipid content and the number of TAG bodies increase drastically when the cells are cultivated in mineral salt medium with a low nitrogen-to-carbon ratio, yielding a maximum in the late stationary growth phase. At this stage, cells can be almost completely filled with lipid bodies exhibiting diameters ranging from 50 to 400 nm. One example is *R. opacus* PD630, in which lipids can reach more than 70% of the total cellular dry weight.

In bacteria, TAG formation typically starts with the docking of a diacylglycerol acyltransferase enzyme to the plasma membrane, followed by formation of small lipid droplets (SLDs). These SLDs are only some nanometers in diameter and remain associated with the membrane-docked enzyme. In this phase of lipid accumulation, SLDs typically form an emulsive, oleogenous layer at the plasma membrane. During prolonged lipid synthesis, SLDs leave the membrane-associated acyltransferase and conglomerate to membrane-bound lipid prebodies. These lipid prebodies reach distinct sizes, e.g., about 200 nm in *A. calcoaceticus* and about 300 nm in *R. opacus*, before they lose contact with the membrane and are released into the cytoplasm. Free and membrane-bound lipid prebodies correspond to the lipid domains occurring in the cytoplasm and at the cell wall, as observed in *M. smegmatis* during fluorescence microscopy and also confirmed in *R. opacus* PD630 and *A. calcoaceticus* ADP1 (see, e.g., Christensen et al., *Mol. Microbiol.* 31:1561-1572, 1999; and Walternann et al., *Mol. Microbiol.* 55:750-763, 2005). Inside the lipid prebodies, SLDs coalesce with each other to form the homogenous lipid core found in mature lipid bodies, which often appear opaque in electron microscopy.

The compositions and structures of bacterial TAGs vary considerably depending on the microorganism and on the carbon source. In addition, unusual acyl moieties, such as phenyldecanoic acid and 4,8,12 trimethyl tridecanoic acid, may also contribute to the structural diversity of bacterial TAGs (see, e.g., Alvarez et al., *Appl Microbiol Biotechnol.* 60:367-76, 2002).

As with eukaryotes, the main function of TAGs in prokaryotes is to serve as a storage compound for energy and carbon. TAGs, however, may provide other functions in prokaryotes. For example, lipid bodies may act as a deposit for toxic or useless fatty acids formed during growth on recalcitrant carbon sources, which must be excluded from the plasma membrane and phospholipid (PL) biosynthesis. Furthermore, many TAG-accumulating bacteria are ubiquitous in soil, and in this habitat, water deficiency causing dehydration is a frequent environmental stress. Storage of evaporation-resistant lipids might be a strategy to maintain a basic water supply, since oxidation of the hydrocarbon chains of the lipids under conditions of dehydration would generate considerable amounts of water. Cyanobacteria such as *Synechococcus*, however, do not produce triglycerides, because these organisms lack the enzymes necessary for triglyceride biosynthesis.

Triglycerides are synthesized from fatty acids and glycerol. As one mechanism of triglyceride (TAG) synthesis, sequential acylation of glycerol-3-phosphate via the "Kennedy Pathway" leads to the formation of phosphatidate. Phosphatidate is then dephosphorylated by the enzyme phosphatidate phosphatase to yield 1,2 diacylglycerol (DAG). Using DAG as a substrate, at least three different classes of enzymes are capable of mediating TAG formation. As one example, an enzyme having diacylglycerol transferase (DGAT) activity catalyzes the acylation of DAG using acyl-CoA as a substrate. Essentially, DGAT enzymes combine acyl-CoA with 1,2 diacylglycerol molecule to form a TAG. As an alternative, Acyl-CoA-independent TAG synthesis may be mediated by a phospholipid:DAG acyltransferase found in yeast and plants, which uses phospholipids as acyl donors for DAG esterification. Third, TAG synthesis in animals and plants may be mediated by a DAG-DAG-transacylase, which uses DAG as both an acyl donor and acceptor, yielding TAG and monoacylglycerol.

Modified photosynthetic microorganisms, e.g., Cyanobacteria, of the present invention may comprise one or more exogenous polynucleotides encoding polypeptides comprising one or more of the polypeptides and enzymes described herein. In particular embodiments, the one or more exogenous polynucleotides encode a diacylglycerol transferase and/or a phosphatidate phosphatase, or a variant or function fragment thereof.

Since wild type Cyanobacteria do not typically encode the enzymes necessary for triglyceride synthesis, such as the enzymes having phosphatidate phosphatase activity and diacylglycerol transferase activity, embodiments of the present invention include genetically modified Cyanobacteria that comprise polynucleotides encoding one or more enzymes having a phosphatidate phosphatase activity and/or one or more enzymes having a diacylglycerol transferase activity.

Moreover, since triglycerides are typically formed from fatty acids, the level of fatty acid biosynthesis in a cell may limit the production of triglycerides. Increasing the level of fatty acid biosynthesis may, therefore, allow increased production of triglycerides. As discussed below, Acetyl-CoA carboxylase catalyzes the commitment step to fatty acid biosynthesis. Thus, certain embodiments of the present invention include Cyanobacterium, and methods of use thereof, comprising polynucleotides that encode one or more enzymes having Acetyl-CoA carboxylase activity to increase fatty acid biosynthesis and lipid production, in addition to one or more enzymes having phosphatidate phosphatase and/or diacylglycerol transferase activity to catalyze triglyceride production. Also included are modified Cyanobacterium that comprise lipases such as phospholipases and/or thioesterases. These and related embodiments are detailed below.

Fatty Acid Biosynthesis.

Fatty acids are a group of negatively charged, linear hydrocarbon chains of various length and various degrees of oxidation states. The negative charge is located at a carboxyl end group and is typically deprotonated at physiological pH values (pK~2-3). The length of the fatty acid 'tail' determines its water solubility (or rather insolubility) and amphipathic characteristics. Fatty acids are components of phospholipids and sphingolipids, which form part of biological membranes, as well as triglycerides, which are primarily used as energy storage molecules inside cells.

Fatty acids are formed from acetyl-CoA and malonyl-CoA precursors. Malonyl-CoA is a carboxylated form of acetyl-CoA, and contains a 3-carbon dicarboxylic acid, malonate, bound to Coenzyme A. Acetyl-CoA carboxylase catalyzes the 2-step reaction by which acetyl-CoA is carboxylated to form malonyl-CoA. In particular, malonate is formed from acetyl-CoA by the addition of $CO_2$ using the biotin cofactor of the enzyme acetyl-CoA carboxylase.

Fatty acid synthase (FAS) carries out the chain elongation steps of fatty acid biosynthesis. FAS is a large multienzyme complex. In mammals, FAS contains two subunits, each containing multiple enzyme activities. In bacteria and plants, individual proteins, which associate into a large complex, catalyze the individual steps of the synthesis scheme. For example, in bacteria and plants, the acyl carrier protein is a smaller, independent protein.

Fatty acid synthesis starts with acetyl-CoA, and the chain grows from the "tail end" so that carbon 1 and the alpha-carbon of the complete fatty acid are added last. The first reaction is the transfer of an acetyl group to a pantothenate group of acyl carrier protein (ACP), a region of the large mammalian fatty acid synthase (FAS) protein. In this reaction, acetyl CoA is added to a cysteine —SH group of the condensing enzyme (CE) domain: acetyl CoA+CE-cys-SH→acetyl-cys-CE+CoASH. Mechanistically, this is a two step process, in which the group is first transferred to the ACP (acyl carrier peptide), and then to the cysteine —SH group of the condensing enzyme domain.

In the second reaction, malonyl CoA is added to the ACP sulfhydryl group: malonyl CoA+ACP-SH→malonyl ACP+CoASH. This —SH group is part of a phosphopantethenic acid prosthetic group of the ACP.

In the third reaction, the acetyl group is transferred to the malonyl group with the release of carbon dioxide: malonyl ACP+acetyl-cys-CE→beta-ketobutyryl-ACP+$CO_2$.

In the fourth reaction, the keto group is reduced to a hydroxyl group by the beta-ketoacyl reductase activity: beta-ketobutyryl-ACP+NADPH+$H^+$→beta-hydroxybutyryl-ACP+$NAD^+$.

In the fifth reaction, the beta-hydroxybutyryl-ACP is dehydrated to form a trans-monounsaturated fatty acyl group by the beta-hydroxyacyl dehydratase activity: beta-hydroxybutyryl-ACP→2-butenoyl-ACP+$H_2O$.

In the sixth reaction, the double bond is reduced by NADPH, yielding a saturated fatty acyl group two carbons longer than the initial one (an acetyl group was converted to a butyryl group in this case): 2-butenoyl-ACP+NADPH+$H^+$→butyryl-ACP+$NADP^+$. The butyryl group is then transferred from the ACP sulfhydryl group to the CE sulfhydryl: butyryl-ACP+CE-cys-SH→ACP-SH+butyryl-cys-CE. This step is catalyzed by the same transferase activity utilized previously for the original acetyl group. The butyryl group is now ready to condense with a new malonyl group (third reaction above) to repeat the process. When the fatty acyl group becomes 16 carbons long, a thioesterase activity hydrolyses it, forming free palmitate: palmitoyl-ACP+$H_2O$→palmitate+ACP-SH. Fatty acid molecules can undergo further modification, such as elongation and/or desaturation.

Modified photosynthetic microorganisms, e.g., Cyanobacteria, may comprise one or more exogenous polynucleotides encoding any of the above polypeptides or enzymes involved in fatty acid synthesis. In particular embodiments, the enzyme is an acetyl-CoA carboxylase or a variant or functional fragment thereof. Certain exemplary lipid biosynthesis proteins are described below.

Thioesterases (TES)

Certain embodiment include one or more exogenous or overexpressed thioesterase enzymes, optionally in combination with at least one of an introduced ACP enzyme, an introduced Aas enzyme, or both. For instance, one embodiment relates to the use an introduced ACP and/or Aas to increase the growth and/or fatty acid production of a free fatty acid producing TES strain, such as a TesA strain or a FatB strain (i.e., a strain having an introduced TesA or FatB). Thioesterases, as referred to herein, exhibit esterase activity (splitting of an ester into acid and alcohol, in the presence of water) specifically at a thiol group. Fatty acids are often attached to cofactor molecules, such as coenzyme A (CoA) and acyl carrier protein (ACP), by thioester linkages during the process of de novo fatty acid synthesis. Certain embodiments employ thioesterases having acyl-ACP thioesterase activity, acyl-CoA thioesterase activity, or both activities. Examples of thioesterases having both activities (i.e., acyl-ACP/acyl-CoA thioesterases) include TesA and related embodiments. In certain embodiments, a selected thioesterase has acyl-ACP thioesterase activity but not acyl-CoA thioesterase activity. Examples of thioesterases having only acyl-ACP thioesterase activity include the FatB thioesterases and related embodiments.

Certain thioesterases have both thioesterase activity and lysophospholipase activity. Specific examples of thioesterases include TesA, TesB, and related embodiments. Certain embodiments may employ periplasmically-localized or cytoplasmically-localized enzymes that thioesterase activity, such as *E. coli* TesA or *E. coli* TesB. For instance, wild type TesA, being localized to the periplasm, is normally used to hydrolyze thioester linkages of fatty acid-ACP (acyl-ACP) or fatty acid-CoA (acyl-CoA) compounds scavenged from the environment. A mutant thioesterase described in the accompanying Examples, PldC (referred to interchangeably as PldC/*TesA or *TesA), is not exported to the periplasm due to deletion of an N-terminal amino acid sequence required for proper transport of TesA from the cytoplasm to the periplasm. This deletion results in a cytoplasmic-localized PldC(*TesA) protein that has access to endogenous acyl-ACP and acyl-CoA intermediates. Other mutations or deletions in the N-terminal region of TesA can be used to achieve the same result, i.e., a cytoplasmic TesA.

Overexpressed PldC(*TesA) results in hydrolysis of acyl groups from endogenous acyl-ACP and acyl-CoA molecules. Cells expressing PldC(*TesA) must channel additional cellular carbon and energy to maintain production of acyl-ACP and acyl-coA molecules, which are required for membrane lipid synthesis. Thus, PldC(*TesA) expression results in a net increase in total cellular lipid content. For instance, PldC(*TesA) expressed alone in *Synechococcus* doubles the total lipid content from 10% of biomass to 20% of biomass, a result that can be further increased by combining *TesA or related molecules with an introduced ACP and/or an introduced Aas. Hence, certain embodiments employ an exogenous or overexpressed cytoplasmic TesA (such as *TesA) in combination with an exogenous or overexpressed ACP, an exogenous or overexpressed Aas, or both.

Certain thioesterases have thioesterase activity only, i.e., they have little or no lysophospholipase activity. Examples of these thioesterases include enzymes of the FatB family. FatB encoded enzymes typically hydrolyze saturated C14-C18 ACPs, preferentially 16:0 ACP, but they can also hydrolyze 18:1 ACP. The production of medium chain (C8-C12) fatty acids in plants or seeds such as those of *Cuphea* spp. often results of FatB enzymes that have chain length specificities for medium chain fatty acyl-ACPs. These medium chain FatB thioesterases are present in many species with medium-chain fatty acids in their oil, including, for example, California bay laurel, coconut, and elm, among others. Hence, FatB sequences may be derived from these and other organisms. Particular examples include plant FatB acyl-ACP thioesterases such as C8, C12, C14, and C16 FatB thioesterases.

Specific examples of FatB thioesterases include the *Cuphea hookeriana* C8/C10 FatB thioesterase, the *Umbellularia californica* C12 FatB1 thioesterase, the *Cinnamomum camphora* C14 FatB1 thioesterase, and the *Cuphea hookeriana* C16 FatB1 thioesterase. In specific embodiments, the thioesterase is a *Cuphea hookeriana* C8/C10 FatB, comprising the amino acid sequence of SEQ ID NO:152 (full-length protein) or SEQ ID NO:153 (mature protein without signal sequence). In particular embodiments, the thioesterase is a *Umbellularia californica* C12 FatB1, comprising the amino acid sequence of SEQ ID NO:156 (full-length protein) or SEQ ID NO:157 (mature protein without signal sequence). In certain embodiments, the thioesterase is a *Cinnamomum camphora* C14 FatB1, comprising the amino acid sequence of SEQ ID NO:160 (full-length protein) or SEQ ID NO:161 (mature protein without signal sequence). In particular embodiments, the thioesterase is a *Cuphea hookeriana* C16 FatB1, comprising the amino acid sequence of SEQ ID NO:164 (full-length protein) or SEQ ID NO:165 (mature protein without signal sequence).

Diacylglycerol Acyltransferases (DGATs)

As used herein, a "diacylglycerol acyltransferase" (DGAT) gene of the present invention includes any polynucleotide sequence encoding amino acids, such as protein, polypeptide or peptide, obtainable from any cell source, which demonstrates the ability to catalyze the production of triacylglycerol from 1,2-diacylglycerol and fatty acyl substrates under enzyme reactive conditions, in addition to any naturally-occurring (e.g., allelic variants, orthologs) or non-naturally occurring variants of a diacylglycerol acyltransferase sequence having such ability. DGAT genes of the present invention also include polynucleotide sequences that encode bi-functional proteins, such as those bi-functional proteins that exhibit a DGAT activity as well as a CoA:fatty alcohol acyltransferase activity, i.e., a wax ester synthesis (WS) activity, as often found in many TAG producing bacteria.

Diacylglycerol acyltransferases (DGATs) are members of the O-acyltransferase superfamily, which esterify either sterols or diacyglycerols in an oleoyl-CoA-dependent manner. DGAT in particular esterifies diacylglycerols, which reaction represents the final enzymatic step in the production of triacylglycerols in plants, fungi and mammals. Specifically, DGAT is responsible for transferring an acyl group from acyl-coenzyme-A to the sn-3 position of 1,2-diacylglycerol (DAG) to form triacylglycerol (TAG). DGAT is an integral membrane protein that has been generally described in Harwood (*Biochem. Biophysics. Acta,* 1301:7-56, 1996), Daum et al. (*Yeast* 16:1471-1510, 1998), and Coleman et al. (*Annu. Rev. Nutr.* 20:77-103, 2000) (each of which are herein incorporated by reference).

In plants and fungi, DGAT is associated with the membrane and lipid body fractions. In catalyzing TAGs, DGAT contributes mainly to the storage of carbon used as energy reserves. In animals, however, the role of DGAT is more complex. DGAT not only plays a role in lipoprotein assembly and the regulation of plasma triacylglycerol concentration (Bell, R. M., et al.), but participates as well in the regulation of diacylglycerol levels (Brindley, *Biochemistry of Lipids*, Lipoproteins and Membranes, eds. Vance, D. E. & Vance, J. E. (Elsevier, Amsterdam), 171-203; and Nishizuka, *Science* 258:607-614 (1992) (each of which are herein incorporated by reference)).

In eukaryotes, at least three independent DGAT gene families (DGAT1, DGAT2, and PDAT) have been described that encode proteins with the capacity to form TAG. Yeast contain all three of DGAT1, DGAT2, and PDAT, but the expression levels of these gene families varies during different phases of the life cycle (Dahlqvst, A., et al. *Proc. Natl. Acad. Sci. USA* 97:6487-6492 (2000) (herein incorporated by reference).

In prokaryotes, WS/DGAT from *Acinetobacter calcoaceticus* ADP1 represents the first identified member of a widespread class of bacterial wax ester and TAG biosynthesis enzymes. This enzyme comprises a putative membrane-spanning region but shows no sequence homology to the DGAT1 and DGAT2 families from eukaryotes. Under in vitro conditions, WS/DGAT shows a broad capability of utilizing a large variety of fatty alcohols, and even thiols as acceptors of the acyl moieties of various acyl-CoA thioesters. WS/DGAT acyltransferase enzymes exhibit extraordinarily broad substrate specificity. Genes for homologous acyltransferases have been found in almost all bacteria capable of accumulating neutral lipids, including, for example, *Acinetobacter baylii, A. baumanii*, and *M. avium*, and *M. tuberculosis* CDC1551, in which about 15 functional homologues are present (see, e.g., Daniel et al., *J. Bacteriol.* 186:5017-5030, 2004; and Kalscheuer et al., *J. Biol. Chem.* 287:8075-8082, 2003).

DGAT proteins may utilize a variety of acyl substrates in a host cell, including fatty acyl-CoA and fatty acyl-ACP molecules. In addition, the acyl substrates acted upon by DGAT enzymes may have varying carbon chain lengths and degrees of saturation, although DGAT may demonstrate preferential activity towards certain molecules.

Like other members of the eukaryotic O-acyltransferase superfamily, eukaryotic DGAT polypeptides typically contain a FYxDWWN (SEQ ID NO:13) heptapeptide retention motif, as well as a histidine (or tyrosine)-serine-phenylalanine (H/YSF) tripeptide motif, as described in Zhongmin et al. (*Journal of Lipid Research,* 42:1282-1291, 2001) (herein incorporated by reference). The highly conserved FYxDWWN (SEQ ID NO:13) is believed to be involved in fatty Acyl-CoA binding.

DGAT enzymes utilized according to the present invention may be isolated from any organism, including eukaryotic and prokaryotic organisms. Eukaryotic organisms having a DGAT gene are well-known in the art, and include various animals (e.g., mammals, fruit flies, nematodes), plants, parasites, and fungi (e.g., yeast such as *S. cerevisiae* and *Schizosaccharomyces pombe*). Examples of prokaryotic organisms include certain *actinomycetes*, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of *actinomycetes* that have one or more genes encoding a DGAT activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having a DGAT activity include members of the genera *Acinetobacter*, such as *A. calcoaceticus, A. baumanii, A. baylii*, and members of the generua *Alcanivorax*. In certain embodiments, a DGAT gene or enzyme is isolated from *Acinetobacter baylii* sp. ADP1, a gram-negative triglyceride forming prokaryote, which contains a well-characterized DGAT (AtfA).

In certain embodiments, the modified photosynthetic microorganisms of the present invention may comprise two or more polynucleotides that encode DGAT or a variant or fragment thereof. In particular embodiments, the two or more polynucleotides are identical or express the same DGAT. In certain embodiments, these two or more polynucleotides may be different or may encode two different DGAT polypeptides. For example, in one embodiment, one of the polynucleotides may encode ADGATd, while another polynucleotide may encode ScoDGAT. In particular embodiments, the following DGATs are coexpressed in modified photosynthetic microorganisms, e.g., Cyanobacteria, using one of the following double DGAT strains: ADGATd(NS1)::ADGATd(NS2); ADGATn(NS1)::ADGATn(NS2); ADGATn(NS1)::SDGAT(NS2); SDGAT(NS1)::ADGATn(NS2); SDGAT(NS1)::SDGAT(NS2). For the NS1 vector, pAM2291, EcoRI follows ATG and is part of the open reading frame (ORF). For the NS2 vector, pAM1579, EcoRI follows ATG and is part of the ORF. A DGAT having EcoRI nucleotides following ATG may be cloned in either pAM2291 or pAM1579; such a DGAT is referred to as ADGATd. Other embodiments utilize the vector, pAM2314FTrc3, which is an NS1 vector with Nde/BglII sites, or the vector, pAM1579FTrc3, which is the NS2 vector with Nde/BglII sites. A DGAT without EcoRI nucleotides may be cloned into either of these last two vectors. Such a DGAT is referred to as ADGATn. Modified photosynthetic microorganisms expressing different DGATs express TAGs having different fatty acid compositions. Accordingly, certain embodiments of the present invention contemplate expressing two or more different DGATs, in order to produce TAGs having varied fatty acid compositions.

Acetyl CoA Carboxylases (ACCase)

As used herein, an "acetyl CoA carboxylase" gene of the present invention includes any polynucleotide sequence encoding amino acids, such as protein, polypeptide or peptide, obtainable from any cell source, which demonstrates the ability to catalyze the carboxylation of acetyl-CoA to produce malonyl-CoA under enzyme reactive conditions, and further includes any naturally-occurring or non-naturally occurring variants of an acetyl-CoA carboxylase sequence having such ability.

Acetyl-CoA carboxylase (ACCase) is a biotin-dependent enzyme that catalyses the irreversible carboxylation of acetyl-CoA to produce malonyl-CoA through its two catalytic activities, biotin carboxylase (BC) and carboxyltransferase (CT). The biotin carboxylase (BC) domain catalyzes the first step of the reaction: the carboxylation of the biotin prosthetic group that is covalently linked to the biotin carboxyl carrier protein (BCCP) domain. In the second step of the reaction, the carboxyltransferase (CT) domain catalyzes the transfer of the carboxyl group from (carboxy) biotin to acetyl-CoA. Formation of malonyl-CoA by acetyl-CoA carboxylase (ACCase) represents the commitment step for fatty acid synthesis, because malonyl-CoA has no metabolic role other than serving as a precursor to fatty acids. Because of this reason, acetyl-CoA carboxylase represents a pivotal enzyme in the synthesis of fatty acids.

In most prokaryotes, ACCase is a multi-subunit enzyme, whereas in most eukaryotes it is a large, multi-domain enzyme. In yeast, the crystal structure of the CT domain of yeast ACCase has been determined at 2.7 A resolution (Zhang et al., *Science,* 299:2064-2067 (2003). This structure contains two domains, which share the same backbone fold. This fold belongs to the crotonase/ClpP family of proteins, with a b-b-a superhelix. The CT domain contains many insertions on its surface, which are important for the dimerization of ACCase. The active site of the enzyme is located at the dimer interface.

Although Cyanobacteria, such as *Synechococcus*, express a native ACCase enzyme, these bacteria typically do not produce or accumulate significant amounts of fatty acids. For example, *Synechococcus* in the wild accumulates fatty acids in the form of lipid membranes to a total of about 4% by dry weight.

Given the role of ACCase in the commitment step of fatty acid biosynthesis, embodiments of the present invention include methods of increasing the production of fatty acid biosynthesis, and, thus, lipid production, in Cyanobacteria by introducing one or more polynucleotides that encode an ACCase enzyme that is exogenous to the Cyanobacterium's native genome. Embodiments of the present invention also include a modified Cyanobacterium, and compositions comprising said Cyanobacterium, comprising one or more polynucleotides that encode an ACCase enzyme that is exogenous to the Cyanobacterium's native genome.

A polynucleotide encoding an ACCase enzyme may be isolated or obtained from any organism, such as any prokaryotic or eukaryotic organism that contains an endogenous ACCase gene. Examples of eukaryotic organisms having an ACCase gene are well-known in the art, and include various animals (e.g., mammals, fruit flies, nematodes), plants, parasites, and fungi (e.g., yeast such as *S. cerevisiae* and *Schizosaccharomyces pombe*). In certain embodiments, the ACCase encoding polynucleotide sequences are obtained from *Synechococcus* sp. PCC7002.

Examples of prokaryotic organisms that may be utilized to obtain a polynucleotide encoding an enzyme having ACCase activity include, but are not limited to, *Escherichia coli, Legionella pneumophila, Listeria monocytogenes, Streptococcus pneumoniae, Bacillus subtilis, Ruminococcus obeum* ATCC 29174, marine gamma proteobacterium HTCC2080, *Roseovarius* sp. HTCC2601, *Oceanicola granulosus* HTCC2516, *Bacteroides caccae* ATCC 43185, *Vibrio alginolyticus* 12G01, *Pseudoalteromonas tunicata* D2, *Marinobacter* sp. ELB17, marine gamma proteobacterium HTCC2143, *Roseobacter* sp. SK209-2-6, *Oceanicola batsensis* HTCC2597, *Rhizobium leguminosarum* bv. *trifolii* WSM1325, *Nitrobacter* sp. Nb-311A, *Chloroflexus aggregans* DSM 9485, *Chlorobaculum parvum, Chloroherpeton thalassium, Acinetobacter baumannii, Geobacillus*, and *Stenotrophomonas maltophilia*, among others.

Phosphatidate Phosphatase (PAP)

As used herein, a "phosphatidate phosphatase" or "phosphatidic acid phosphatase" gene of the present invention includes any polynucleotide sequence encoding amino acids, such as protein, polypeptide or peptide, obtainable from any cell source, which demonstrates the ability to catalyze the dephosphorylation of phosphatidate (PtdOH) under enzyme reactive conditions, yielding diacylglycerol (DAG) and inorganic phosphate, and further includes any naturally-occurring or non-naturally occurring variants of a phosphatidate phosphatase sequence having such ability.

Phosphatidate phosphatases (PAP, 3-sn-phosphatidate phosphohydrolase) catalyze the dephosphorylation of phosphatidate (PtdOH), yielding diacylglycerol (DAG) and inorganic phosphate. This enzyme belongs to the family of hydrolases, specifically those acting on phosphoric monoester bonds. The systematic name of this enzyme class is 3-sn-phosphatidate phosphohydrolase. Other names in common use include phosphatic acid phosphatase, acid phosphatidyl phosphatase, and phosphatic acid phosphohydrolase. This enzyme participates in at least 4 metabolic pathways: glycerolipid metabolism, glycerophospholipid metabolism, ether lipid metabolism, and sphingolipid metabolism.

PAP enzymes have roles in both the synthesis of phospholipids and triacylglycerol through its product diacylglycerol, as well as the generation or degradation of lipid-signaling molecules in eukaryotic cells. PAP enzymes are typically classified as either $Mg^{2+}$-dependent (referred to as PAP1 enzymes) or $Mg^{2+}$-independent (PAP2 or lipid phosphate phosphatase (LPP) enzymes) with respect to their cofactor requirement for catalytic activity. In both yeast and mammalian systems, PAP2 enzymes are known to be involved in lipid signaling. By contrast, PAP1 enzymes, such as those found in *Saccharomyces cerevisiae*, play a role in de novo lipid synthesis (Han, et al. *J Biol. Chem.* 281:9210-9218, 2006), thereby revealing that the two types of PAP are responsible for different physiological functions.

In both yeast and higher eukaryotic cells, the PAP reaction is the committed step in the synthesis of the storage lipid triacylglycerol (TAG), which is formed from PtdOH through the intermediate DAG. The reaction product DAG is also used in the synthesis of the membrane phospholipids phosphatidylcholine (PtdCho) and phosphatidylethanolamine. The substrate PtdOH is used for the synthesis of all membrane phospholipids (and the derivative inositol-containing sphingolipids) through the intermediate CDP-DAG. Thus, regulation of PAP activity might govern whether cells make storage lipids and phospholipids through DAG or phospholipids through CDP-DAG. In addition, PAP is involved in the transcriptional regulation of phospholipid synthesis.

PAP1 enzymes have been purified and characterized from the membrane and cytosolic fractions of yeast, including a gene (Pah1, formerly known as Smp2) been identified to encode a PAP1 enzyme in *S. cerevisiae*. The Pah1-encoded PAP1 enzyme is found in the cytosolic and membrane fractions of the cell, and its association with the membrane is peripheral in nature. As expected from the multiple forms of PAP1 that have been purified from yeast, pah1Δ mutants still contain PAP1 activity, indicating the presence of an additional gene or genes encoding enzymes having PAP1 activity.

Analysis of mutants lacking the Pah1-encoded PAP1 has provided evidence that this enzyme generates the DAG used for lipid synthesis. Cells containing the pah1Δ mutation accumulate PtdOH and have reduced amounts of DAG and its acylated derivative TAG. Phospholipid synthesis predominates over the synthesis of TAG in exponentially growing yeast, whereas TAG synthesis predominates over the synthesis of phospholipids in the stationary phase of growth. The effects of the pah1Δ mutation on TAG content are most evident in the stationary phase. For example, stationary phase cells devoid of the Pah1 gene show a reduction of >90% in TAG content. Likewise, the pah1Δ mutation shows the most marked effects on phospholipid composition (e.g. the consequent reduction in PtdCho content) in the exponential phase of growth. The importance of the Pah1-encoded PAP1 enzyme to cell physiology is further emphasized because of its role in the transcriptional regulation of phospholipid synthesis.

The requirement of $Mg^{2+}$ ions as a cofactor for PAP enzymes is correlated with the catalytic motifs that govern the phosphatase reactions of these enzymes. For example, the Pah1-encoded PAP1 enzyme has a DxDxT (SEQ ID NO:30) catalytic motif within a haloacid dehalogenase (HAD)-like domain ("x" is any amino acid). This motif is found in a superfamily of $Mg^{2+}$-dependent phosphatase enzymes, and its first aspartate residue is responsible for binding the phosphate moiety in the phosphatase reaction. By contrast, the DPP1- and LPP1-encoded PAP2 enzymes contain a three-domain lipid phosphatase motif that is localized to the hydrophilic surface of the membrane. This catalytic motif, which comprises the consensus sequences KxxxxxxRP (domain 1) (SEQ ID NO:10), PSGH (domain 2) (SEQ ID NO:11), and SRxxxxxHxxxD (domain 3) (SEQ ID NO:12), is shared by a superfamily of lipid phosphatases that do not require $Mg^{2+}$ ions for activity. The conserved arginine residue in domain 1 and the conserved histidine residues in domains 2 and 3 may be essential for the catalytic activity of PAP2 enzymes. Accordingly, a phosphatidate phosphatase polypeptide may comprise one or more of the above-described catalytic motifs.

A polynucleotide encoding a polypeptide having a phosphatidate phosphatase enzymatic activity may be obtained from any organism having a suitable, endogenous phosphatidate phosphatase gene. Examples of organisms that may be used to obtain a phosphatidate phosphatase encoding polynucleotide sequence include, but are not limited to, *Homo sapiens, Mus musculus, Rattus norvegicus, Bos taurus, Drosophila melanogaster, Arabidopsis thaliana, Magnaporthe grisea, Saccharomyces cerevisiae, Schizosaccharomyces pombe, Cryptococcus neoformans*, and *Bacillus pumilus*, among others. Specific examples of PAP enzymes include Pah1 from *S. cerevisiae*, PgpB from *E. coli*, and PAP from PCC6803.

Lipasese and Phospholipases

In various embodiments, modified photosynthetic microorganisms, e.g., Cyanobacteria, of the present invention further comprise one or more exogenous or introduced nucleic acids that encode a polypeptide having a lipase or phospholipase activity, or a fragment or variant thereof. Lipases, including phospholipases, lysophospholipases, thioesterases, and enzymes having one, two, or all three of these activities, typically catalyze the hydrolysis of ester chemical bonds in lipid substrates. Without wishing to be bound by any one theory, in certain exemplary embodiments the expression of one or more phospholipases can generate fatty acids from membrane lipids, which may then be used by the ACP and/or Aas to make acyl-ACPs. These acyl-ACPs, for example, can then feed into the triglyceride synthesis pathways, thereby increasing triglyceride (TAG) production.

A phospholipase is an enzyme that hydrolyzes phospholipids into fatty acids and other lipophilic substances. There are four major classes, termed A, B, C and D distinguished by what type of reaction they catalyze. Phospholipase A1 cleaves the SN-1 acyl chain, while Phospholipase A2 cleaves the SN-2 acyl chain, releasing arachidonic acid. Phospholipase B cleaves both SN-1 and SN-2 acyl chains, and is also known as a lysophospholipase. Phospholipase C cleaves before the phosphate, releasing diacylglycerol and a phosphate-containing head group. Phospholipases C play a central role in signal transduction, releasing the second messenger, inositol triphosphate. Phospholipase D cleaves after the phosphate, releasing phosphatidic acid and an alcohol. Types C and D are considered phosphodiesterases. In various embodiments of the present invention, one or more phospholipase from any one of these classes may be used, alone or in any combination.

As noted above, phospholipases (PLA1,2) act on phospholipids of different kinds including phosphatidyl glycerol, the major phospholipid in Cyanobacteria, by cleaving the acyl chains off the sn1 or sn2 positions (carbon 1 or 2 on the glycerol backbone); some are selective for sn1 or sn2, others act on both. Lysophospholipases act on lysophospholipids, which can be the product of phospholipases or on lysophosphatidic acid, a normal intermediate of the de novo phosphatidic acid synthesis pathway, e.g., 1-acyl-DAG-3-phosphate.

Merely by way of non-limiting theory, it is understood that in certain embodiments, phospholipases and/or lysophospholipases can cleave off acyl chains from phospholipids or lysophospholipids and thus deregulate the normal recycling of the lipid membranes, including both cell membrane and thylakoid membranes, which then leads to accumulation of free fatty acids (FFAs). In certain embodiments (e.g., TesA strains), these FFAs may accumulate extracellularly. In other embodiments (e.g., ACP and/or Aas over-expressing microorganisms), FFAs can be converted into acyl-ACPs by acyl ACP synthase (Aas) in a strain that also over-expresses ACP. In specific embodiments (e.g., DGAT-containing microorganisms), these acyl-ACPs can then serve as substrates for DGAT to make TAGs.

In other embodiments, phospholipases can be over-expressed to generate lyshophospholipids and acyl chains. The lysophospholipids can then serve as substrates for a lysophospholipase, which cleaves off the remaining acyl chain. In some embodiments, these acyl chains can either accumulate as FFAs, or in other embodiments may serve as substrates of Acyl ACP synthase (Aas) to generate acyl-ACPs, which can then be used by DGAT to make TAGs.

Particular examples of phospholipase C enzymes include those derived from eukaryotes such as mammals and parasites, in addition to those derived from bacteria. Examples include phosphoinositide phospholipase C (EC 3.1.4.11), the main form found in eukaryotes, especially mammals, the zinc-dependent phospholipase C family of bacterial enzymes (EC 3.1.4.3) that includes alpha toxins, phosphatidylinositol diacylglycerol-lyase (EC 4.6.1.13), a related bacterial enzyme, and glycosylphosphatidylinositol diacylglycerol-lyase (EC 4.6.1.14), a trypanosomal enzyme.

In particular embodiments, the present invention contemplates using a lysophospholipase. A lysophospholipase is an enzyme that catalyzes the chemical reaction:

2-lysophosphatidic acid+$H_2O$⇌glycerol-3-phosphate+a carboxylate

Thus, the two substrates of this enzyme are 2-lysophosphatidylcholine and $H_2O$, whereas its two products are glycerophosphocholine and carboxylate.

Lysophospholipase are members of the hydrolase family, specifically those acting on carboxylic ester bonds. Lysophospholipases participate in glycerophospholipid metabolism. Examples of lysophospholipases include, but are not limited to, 2-Lysophosphatidylcholine acylhydrolase, Lecithinase B, Lysolecithinase, Phospholipase B, Lysophosphatidase, Lecitholipase, Phosphatidase B, Lysophosphatidylcholine hydrolase, Lysophospholipase A1, Lysophospholipase L1 (TesA), Lysophopholipase L2, TesB, Lysophospholipase transacylase, Neuropathy target esterase, NTE, NTE-LysoPLA, NTE-lysophospholipase, and Vu Patatin 1 protein. In particular embodiments, lysophospholipases utilized according to the present invention are derived from a bacteria, e.g., *E. coli*, or a plant. Any of these lysophospholipases may be used according to various embodiments of the present invention.

Certain lysophospholipases, such as Lysophospholipase L1 (also referred to as PldC or TesA) are periplasmically-localized or cytoplasmically-localized enzymes that have both lysophospholipase and thioesterase activity, as described above. Hence, certain thioesterases such as TesA can also be characterized as lysophospholipases. A mutant lysophospholipase described herein, PldC(*TesA), is not exported to the periplasm due to deletion of an N-terminal amino acid sequence required for proper transport of TesA from the cytoplasm to the periplasm. This results in a cytoplasmic-localized PldC(*TesA) protein that has access to endogenous acyl-ACP and acyl-CoA intermediates. Over-expressed PldC(*TesA) results in hydrolysis of acyl groups from endogenous acyl-ACP and acyl-CoA molecules. Cells expressing PldC(*TesA) must channel additional cellular carbon and energy to maintain production of acyl-ACP and acyl-coA molecules, which are required for membrane lipid synthesis. Thus, PldC(*TesA) expression results in a net increase in cellular lipid content. As described herein, PldC (*TesA) is expressed in *Synechococcus* lipid content doubles from 10% of biomass to 20% of biomass.

In certain embodiments of the present invention, lysophospholipases utilized according to the present invention have both phospholipase and thioesterase activities. Examples of lysophospholipases that have both activities include, e.g., Lysophospholipase L1 (TesA), such as *E. coli* Lysophospholipase L1, as well as fragments and variants thereof, including those described in the paragraph above. As a phospholipase, certain embodiments may employ TesA variants having only lysophospholipase activity, including variants with reduced or no thioesterase activity.

Additional non-limiting examples of phospholipases include phospholipase A1 (PldA) from *Acinetobacter* sp. ADP1, phospholipase A (PldA) from *E. coli*, phospholipase from *Streptomyces coelicolor* A3(2), phospholipase A2 (PLA2-α) from *Arabidopsis thaliana*; phospholipase A1/triacylglycerol lipase (DAD1; Defective Anther Dehiscence 1) from *Arabidopsis thaliana*, chloroplast DONGLE from *Arabidopsis thaliana*, patatin-like protein from *Arabidopsis thaliana*, and patatin from *Anabaena variabilis* ATCC 29413. Additional non-limiting examples of lysophospholipases include phospholipase B (PIM p) from *Saccharomyces cerevisiae* S288c, phospholipase B (Plb2p) from *Saccharomyces cerevisiae* S288c, ACIAD1057 (tesA homolog) from *Acinetobacter* ADP1, ACIAD1943 lysophospholipase from *Acinetobacter* ADP1, and a lysophospholipase (YP_702320; RHA1_ro02357) from *Rhodococcus*.

Triacylglycerol (TAG) Hydrolases

Certain embodiments relate to the use of exogenous or overexpressed TAG hydrolases (or TAG lipases) to increase production of TAGs in a TAG-producing strain. For instance, specific embodiments may utilize a TAG hydrolase in combination with a DGAT, and optionally a TES. These embodiments may then further utilize an ACP, an Aas, or both, any of the lipid biosynthesis proteins described herein, and/or any of the modifications to glycogen production and storage described herein. Hence, as noted above, TAG hydrolases may be used in TAG-producing strains (e.g., DGAT-expressing strains) with or without an ACP or Aas.

TAG hydrolases are carboxylesterases that are typically specific for insoluble long chain fatty acid TAGs. Carboxylesterases catalyze the chemical reaction:

carboxylic ester+$H_2O$⇌alcohol+carboxylate

Thus, the two substrates of this enzyme are carboxylic ester and $H_2O$, whereas its two products are alcohol and carboxylate. According to one non-limiting theory, it is understood that TAG hydrolase expression (or overexpression) in a TAG producing strain (e.g., DGAT/ACP, DGAT/Aas, DGAT/ACP/Aas) releases acyl chains to not only increase accumulation of free fatty acids (FFA), but also increase the amount of free 1, 2 diacylglycerol (DAG). This free DAG then serves as a substrate for DGAT, and thereby allows increased TAG production, especially in the presence of over-expressed ACP, Aas, or both. Accordingly, certain embodiments employing a TAG hydrolase produce increased amounts of TAG, relative, for example, to a DGAT only-expressing microorganism. In specific embodiments, the TAG hydrolase is specific for TAG and not DAG, i.e., it preferentially acts on TAG relative to DAG.

Non-limiting examples of TAG hydrolases include SDP1 (SUGAR-DEPENDENT1) triacylglycerol lipase from *Arabidopsis thaliana*, ACIAD1335 from *Acinetobacter* sp. ADP1, TG14P from *S. cerevisiae*, and RHA1_ro04722 (YP_704665) TAG lipase from *Rhodococcus*. Additional putative lipases/esterases from *Rhodococcus* include RHA1_ro01602 lipase/esterase (see SEQ ID NOs:166 and 167 for polynucleotide and polypeptide sequence, respectively), and RHA1_ro06856 lipase/esterase (see SEQ ID NOs:168 and 169 for polynucleotide and polypeptide sequence, respectively).

Fatty Acyl-CoA Synthetases

Certain embodiments relate to the use of exogenous or overexpressed fatty acyl-CoA synthetases to increase activation of fatty acids, and thereby increase production of TAGs in a TAG-producing strain. For instance, specific embodiments may utilize a fatty acyl-CoA synthetase in combination with a DGAT, and optionally a TES, such as TesA or any of the FatB sequences. These embodiments may then further utilize an ACP, an Aas, or both, or any of the lipid biosynthesis proteins described herein, and/or any of the modifications to glycogen production and storage described herein. Hence, as noted above, fatty acyl-CoA synthetases may be used in TAG-producing strains (e.g., DGAT-expressing strains) with or without an ACP or Aas.

Fatty acyl-CoA synthetases activate fatty acids for metabolism by catalyzing the formation of fatty acyl-CoA thioesters. Fatty acyl-CoA thioesters can then serve not only as substrates for beta-oxidation, at least in bacteria capable of growing on fatty acids as a sole source of carbon (e.g., *E. coli, Salmonella*), but also as acyl donors in phospholipid biosynthesis. Many fatty acyl-CoA synthetases are characterized by two highly conserved sequence elements, an ATP/AMP binding motif, which is common to enzymes that form an adenylated intermediate, and a fatty acid binding motif.

According to one non-limiting theory, certain embodiments may employ fatty acyl-CoA synthetases to increase activation of free fatty acids, which can then be incorporated into TAGs, mainly by the DGAT-expressing (and thus TAG-producing) photosynthetic microorganisms described herein. Hence, fatty acyl-CoA synthetases can be used in any of the embodiments described herein, such as those that produce increased levels of free fatty acids, where it is desirable to turn free fatty acids into TAGs. For instance, these and related embodiments may be combined with the use of thioesterases such as TesA and/or FatB enzymes (e.g., DGAT/TesA expressing cells; DGAT/FatB expressing cells); TesA can be used increase cleavage of acyl-ACPs and acyl-CoAs, while FatB enzymes can be used to increase cleavage of acyl-ACPs, both of which result in increased accumulation of free fatty acids. As noted above, these free fatty acids can then be activated by fatty acyl-CoA synthetases to generate acyl-CoA thioesters, which can then serve as substrates by DGAT to produce increased levels of TAGs. Fatty acyl-CoA synthetases can also be used in combination with phospholipases (e.g., lysophospholipases) and other lipid biosynthesis proteins to activate the free fatty acids generated by the expression of these biosynthesis proteins.

One exemplary fatty acyl-CoA synthetase includes the FadD gene from *E. coli* (SEQ ID NOS:148 and 149 for nucleotide and polypeptide sequence, respectively), which encodes a fatty acyl-CoA synthetase having substrate specificity for medium and long chain fatty acids. Other exemplary fatty acyl-CoA synthetases include those derived from *S. cerevisiae*; Faa1p can use C12-C16 acyl-chains in vitro (see SEQ ID NOS:142 and 143 for nucleotide and polypeptide sequence, respectively), Faa2p shows a less restricted specificity ranging from C7-C17 (see SEQ ID NOS:144 and 145 for nucleotide and polypeptide sequence, respectively), and Faa3p, together with that of DGAT1, enhances lipid accumulation in the presence of exogenous fatty acids in *S. cerevisiae* (see SEQ ID NO:146 and 147 for nucleotide and polypeptide sequence, respectively). SEQ ID NO:146 is codon-optimized for expression in *S. elongatus* PCC7942.

Glycogen Synthesis, Storage, and Breakdown

In particular embodiments, a modified photosynthetic microorganism further comprises additional modifications, such that it has reduced expression of one or more genes associated with a glycogen synthesis or storage pathway and/or increased expression of one or more polynucleotides that encode a protein associated with a glycogen breakdown pathway, or a functional variant of fragment thereof.

In various embodiments, modified photosynthetic microorganisms, e.g., Cyanobacteria, of the present invention have reduced expression of one or more genes associated with glycogen synthesis and/or storage. In particular embodiments, these modified photosynthetic microorganisms have a mutated or deleted gene associated with glycogen synthesis and/or storage. In particular embodiments, these modified photosynthetic microorganisms comprise a vector that includes a portion of a mutated or deleted gene, e.g., a targeting vector used to generate a knockout or knockdown of one or more alleles of the mutated or deleted gene. In certain embodiments, these modified photosynthetic microorganisms comprise an antisense RNA or siRNA that binds to an mRNA expressed by a gene associated with glycogen synthesis and/or storage.

In certain embodiments, modified photosynthetic microorganisms, e.g., Cyanobacteria, of the present invention comprise one or more exogenous or introduced nucleic acids that encode a polypeptide having an activity associated with a glycogen breakdown or triglyceride or fatty acid biosynthesis, including but not limited to any of those described herein. In particular embodiments, the exogenous nucleic acid does not comprise a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

Glycogen Biosynthesis and Storage

Glycogen is a polysaccharide of glucose, which functions as a means of carbon and energy storage in most cells, including animal and bacterial cells. More specifically, glycogen is a very large branched glucose homopolymer containing about 90% α-1,4-glucosidic linkages and 10% α-1,6 linkages. For bacteria in particular, the biosynthesis and storage of glycogen in the form of α-1,4-polyglucans represents an important strategy to cope with transient starvation conditions in the environment.

Glycogen biosynthesis involves the action of several enzymes. For instance, bacterial glycogen biosynthesis occurs generally through the following general steps: (1) formation of glucose-1-phosphate, catalyzed by phosphoglucomutase (Pgm), followed by (2) ADP-glucose synthesis from ATP and glucose 1-phosphate, catalyzed by glucose-1-phosphate adenylyltransferase (GlgC), followed by (3) transfer of the glucosyl moiety from ADP-glucose to a pre-existing α-1,4 glucan primer, catalyzed by glycogen synthase (GlgA). This latter step of glycogen synthesis typically occurs by utilizing ADP-glucose as the glucosyl donor for elongation of the α-1,4-glucosidic chain.

In bacteria, the main regulatory step in glycogen synthesis takes place at the level of ADP-glucose synthesis, or step (2) above, the reaction catalyzed by glucose-1-phosphate adenylyltransferase (GlgC), also known as ADP-glucose pyrophosphorylase (see, e.g., Ballicora et al., *Microbiology and Molecular Biology Reviews* 6:213-225, 2003). In contrast, the main regulatory step in mammalian glycogen synthesis occurs at the level of glycogen synthase. As shown herein, by altering the regulatory and/or other active components in the glycogen synthesis pathway of photosynthetic microorganisms such as Cyanobacteria, and thereby reducing the biosynthesis and storage of glycogen, the carbon that would have otherwise been stored as glycogen can be utilized by said photosynthetic microorganism to synthesize other carbon-based storage molecules, such as lipids, fatty acids, and triglycerides.

Therefore, certain modified photosynthetic microorganisms, e.g., Cyanobacteria, of the present invention may comprise a mutation, deletion, or any other alteration that disrupts one or more of these steps (i.e., renders the one or more steps "non-functional" with respect to glycogen biosynthesis and/or storage), or alters any one or more of the enzymes directly involved in these steps, or the genes encoding them. As noted above, such modified photosynthetic microorganisms, e.g., Cyanobacteria, are typically capable of producing and/or accumulating an increased amount of lipids, such as fatty acids, as compared to a wild type photosynthetic microorganism. Certain exemplary glycogen biosynthesis genes are described below.

i. Phosphoglucomutase Gene (pgm)

In one embodiment, a modified photosynthetic microorganism, e.g., a Cyanobacteria, expresses a reduced amount of the phosphoglucomutase gene. In particular embodiments, it may comprise a mutation or deletion in the phosphoglucomutase gene, including any of its regulatory elements (e.g., promoters, enhancers, transcription factors, positive or negative regulatory proteins, etc.). Phosphoglucomutase (Pgm), encoded by the gene pgm, catalyzes the reversible transformation of glucose 1-phosphate into glucose 6-phosphate, typically via the enzyme-bound intermediate, glucose 1,6-biphosphate (see, e.g., Lu et al., *Journal of Bacteriology* 176:5847-5851, 1994). Although this reaction is reversible, the formation of glucose-6-phosphate is markedly favored.

However, typically when a large amount of glucose-6-phosphate is present, Pgm catalyzes the phosphorylation of the 1-carbon and the dephosphorylation of the c-carbon, resulting in glucose-1-phosphate. The resulting glucose-1-phosphate is then converted to UDP-glucose by a number of intermediate steps, including the catalytic activity of GlgC, which can then be added to a glycogen storage molecule by the activity of glycogen synthase, described below. Thus, under certain conditions, the Pgm enzyme plays an intermediary role in the biosynthesis and storage of glycogen.

The pgm gene is expressed in a wide variety of organisms, including most, if not all, Cyanobacteria. The pgm gene is also fairly conserved among Cyanobacteria, as can be appreciated upon comparison of SEQ ID NOs:37 (*S. elongatus* PCC 7942), 75 (*Synechocystis* sp. PCC 6803), and 79 (*Synechococcus* sp. WH8102), which provide the polynucleotide sequences of various pgm genes from Cyanobacteria.

Deletion of the pgm gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

ii. Glucose-1-Phosphate Adenylyltransferase (glgC)

In one embodiment, a modified photosynthetic microorganism, e.g., a Cyanobacteria, expresses a reduced amount of a glucose-1-phosphate adenylyltransferase (glgC) gene. In certain embodiments, it may comprise a mutation or deletion in the glgC gene, including any of its regulatory elements. The enzyme encoded by the glgC gene (e.g., EC 2.7.7.27) participates generally in starch, glycogen and sucrose metabolism by catalyzing the following chemical reaction:

ATP+alpha-D-glucose 1-phosphate⇌diphosphate+ADP-glucose

Thus, the two substrates of this enzyme are ATP and alpha-D-glucose 1-phosphate, whereas its two products are diphosphate and ADP-glucose. The glgC-encoded enzyme catalyzes the first committed and rate-limiting step in starch biosynthesis in plants and glycogen biosynthesis in bacteria. It is the enzymatic site for regulation of storage polysaccharide accumulation in plants and bacteria, being allosterically activated or inhibited by metabolites of energy flux.

The enzyme encoded by the glgC gene belongs to a family of transferases, specifically those transferases that transfer phosphorus-containing nucleotide groups (i.e., nucleotidyltransferases). The systematic name of this enzyme class is typically referred to as ATP:alpha-D-glucose-1-phosphate adenylyltransferase. Other names in common use include ADP glucose pyrophosphorylase, glucose 1-phosphate adenylyltransferase, adenosine diphosphate glucose pyrophosphorylase, adenosine diphosphoglucose pyrophosphorylase, ADP-glucose pyrophosphorylase, ADP-glucose synthase, ADP-glucose synthetase, ADPG pyrophosphorylase, and ADP:alpha-D-glucose-1-phosphate adenylyltransferase.

The glgC gene is expressed in a wide variety of plants and bacteria, including most, if not all, Cyanobacteria. The glgC gene is also fairly conserved among Cyanobacteria, as can be appreciated upon comparison of SEQ ID NOs:67 (*S. elongatus* PCC 7942), 59 (*Synechocystis* sp. PCC 6803), 73 (*Synechococcus* sp. PCC 7002), 69 (*Synechococcus* sp. WH8102), 71 (*Synechococcus* sp. RCC 307), 65 (*Trichodesmium erythraeum* IMS 101), 63 (*Anabaena varibilis*), and 61 (*Nostoc* sp. PCC 7120), which describe the polynucleotide sequences of various glgC genes from Cyanobacteria.

Deletion of the glgC gene in Cyanobacteria, such as *Synechococcus*, has been demonstrated herein for the first time to reduce the accumulation of glycogen in said Cyanobacteria, and also to increase the production of other carbon-based products, such as lipids and fatty acids.

iii. Glycogen Synthase (glgA)

In one embodiment, a modified photosynthetic microorganism, e.g., a Cyanobacteria, expresses a reduced amount of a glycogen synthase gene. In particular embodiments, it may comprise a deletion or mutation in the glycogen synthase gene, including any of is regulatory elements. Glycogen synthase (GlgA), also known as UDP-glucose-glycogen glucosyltransferase, is a glycosyltransferase enzyme that catalyses the reaction of UDP-glucose and (1,4-α-D-glucosyl)$_n$ to yield UDP and (1,4-α-D-glucosyl)$_{n+1}$. Glycogen synthase is an α-retaining glucosyltransferase that uses ADP-glucose to incorporate additional glucose monomers onto the growing glycogen polymer. Essentially, GlgA catalyzes the final step of converting excess glucose residues one by one into a polymeric chain for storage as glycogen.

Classically, glycogen synthases, or α-1,4-glucan synthases, have been divided into two families, animal/fungal glycogen synthases and bacterial/plant starch synthases, according to differences in sequence, sugar donor specificity and regulatory mechanisms. However, detailed sequence analysis, predicted secondary structure comparisons, and threading analysis show that these two families are structurally related and that some domains of animal/fungal synthases were acquired to meet the particular regulatory requirements of those cell types.

Crystal structures have been established for certain bacterial glycogen synthases (see, e.g., Buschiazzo et al., *The EMBO Journal* 23, 3196-3205, 2004). These structures show that reported glycogen synthase folds into two Rossmann-fold domains organized as in glycogen phosphorlyase and other glycosyltransferases of the glycosyltransferases superfamily, with a deep fissure between both domains that includes the catalytic center. The core of the N-terminal domain of this glycogen synthase consists of a nine-stranded, predominantly parallel, central β-sheet flanked on both sides by seven α-helices. The C-terminal domain (residues 271-456) shows a similar fold with a six-stranded parallel 8-sheet and nine α-helices. The last α-helix of this domain undergoes a kink at position 457-460, with the final 17 residues of the protein (461-477) crossing over to the N-terminal domain and continuing as α-helix, a typical feature of glycosyltransferase enzymes.

These structures also show that the overall fold and the active site architecture of glycogen synthase are remarkably similar to those of glycogen phosphorylase, the latter playing a central role in the mobilization of carbohydrate reserves, indicating a common catalytic mechanism and comparable substrate-binding properties. In contrast to glycogen phosphorylase, however, glycogen synthase has a much wider catalytic cleft, which is predicted to undergo an important interdomain 'closure' movement during the catalytic cycle.

Crystal structures have been established for certain GlgA enzymes (see, e.g., Jin et al., *EMBO J.* 24:694-704, 2005, incorporated by reference). These studies show that the N-terminal catalytic domain of GlgA resembles a dinucleotide-binding Rossmann fold and the C-terminal domain adopts a left-handed parallel beta helix that is involved in cooperative allosteric regulation and a unique oligomerization. Also, communication between the regulator-binding sites and the active site involves several distinct regions of the enzyme, including the N-terminus, the glucose-1-phosphate-binding site, and the ATP-binding site.

The glgA gene is expressed in a wide variety of cells, including animal, plant, fungal, and bacterial cells, including most, if not all, Cyanobacteria. The glgA gene is also fairly conserved among Cyanobacteria, as can be appreciated upon comparison of SEQ ID NOs:51 (*S. elongatus* PCC 7942), 43 (*Synechocystis* sp. PCC 6803), 57 (*Synechococcus* sp. PCC 7002), 53 (*Snyechococcus* sp. WH8102), 55 (*Synechococcus* sp. RCC 307), 49 (*Trichodesmium erythraeum* IMS 101), 47 (*Anabaena variabilis*), and 45 (*Nostoc* sp. PCC 7120), which describe the polynucleotide sequences of various glgA genes from Cyanobacteria.

Glycogen Breakdown

In certain embodiments, a modified photosynthetic microorganism of the present invention expresses an increased amount of one or more genes associated with a glycogen breakdown pathway. In particular embodiments, said one or more polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. Pgm, Glk, and Pgi are bidirectional enzymes that can promote glycogen synthesis or breakdown depending on conditions.

F. POLYNUCLEOTIDES AND VECTORS

Modified photosynthetic microorganisms, e.g., Cyanobacteria, of the present invention, comprise one or more introduced polynucleotides encoding an ACP, Aas, or both, optionally in combination with one or more introduced polynucleotides encoding a lipid biosynthesis protein, and/or one or more introduced polynucleotides encoding a polypeptide associated with glycogen breakdown, including functional variants and fragments thereof. Accordingly, the present invention utilizes isolated polynucleotides that encode ACPs, Aas proteins, the various lipid biosynthesis proteins, such as diacylglycerol acyltransferase, phosphatidate phosphatase, acetyl-CoA carboxylase, lipases, phospholipases, among others described herein, and the various glycogen breakdown pathway proteins, in addition to nucleotide sequences that encode any functional naturally-occurring variants or fragments (i.e., allelic variants, orthologs, splice variants) or non-naturally occurring variants or fragments of these native enzymes (i.e., optimized by engineering), as well as compositions comprising such polynucleotides, including, e.g., cloning and expression vectors.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a diacylglycerol acyltransferase, a phosphatidate phosphatase, an acetyl-CoA carboxylase, or a portion thereof) or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide. The effect on the enzymatic activity of the encoded polypeptide may generally be assessed as described herein.

In certain embodiments, a modified photosynthetic microorganism comprises one or more polynucleotides encoding one or more acyl carrier proteins (ACP). Exemplary ACP nucleotide sequences include SEQ ID NO:96 from *Synechococcus elongatus* PCC 7942, SEQ ID NOS:98, 100, and 102 from *Acinetobacter* sp. ADP1, and SEQ ID NO:104 from *Spinacia oleracea.*

In certain embodiments, a modified photosynthetic microorganism comprises one or more polynucleotides encoding one or more acyl-ACP synthetase (Aas) enzymes. In certain embodiments, the Aas nucleotide sequence is derived from the Se918 gene of *Synechococcus elongatus*. One exemplary Aas sequence is SEQ ID NO:106 from *Synechococcus elongatus* PCC 7942 0918.

In certain embodiments, a modified photosynthetic microorganism comprises one or more polynucleotides encoding one or more thioesterases (TES) including acyl-ACP thioesterases and/or acyl-CoA thioesterases. In certain embodiments, the polynucleotide sequence of the TES encodes a TesA or TesB polypeptide from *E. coli*, or a cytoplasmic TesA variant (*TesA) having the sequence set forth in SEQ ID NO:94.

In certain embodiments, the polynucleotide sequence of the TES comprises that of the FatB gene, encoding a FatB enzyme, such as a C8, C12, C14, C16, or C18 FatB enzyme. In certain embodiments, the polynucleotide encodes a thioesterase (e.g., FatB thioesterase), having only thioesterase activity and little or no lysophospholipase activity. In specific embodiments, the thioesterase is a FatB acyl-ACP thioesterase, which can hydrolyze acyl-ACP but not acyl-CoA. SEQ ID NO:150 is an exemplary nucleotide sequence of a C8/C10 FatB2 thioesterase derived from *Cuphea hookeriana*, and SEQ ID NO:151 is codon-optimized for expression in Cyanobacteria. SEQ ID NO:154 is an exemplary nucleotide sequence of a C12 FatB1 acyl-ACP thioesterase derived from *Umbellularia californica*, and SEQ ID NO:155 is a codon-optimized version of SEQ ID NO:154 for optimal expression in Cyanobacteria. SEQ ID NO:158 is an exemplary nucleotide sequence of a C14 FatB1 thioesterase derived from *Cinnamomum camphora*, and SEQ:159 is a codon-optimized version of SEQ ID NO:158. SEQ ID NO:162 is an exemplary nucleotide sequence of a C16 FatB1 thioesterase derived from *Cuphea hookeriana*, and SEQ ID NO:163 is a codon-optimized version of SEQ ID NO:162. In certain embodiments, one or more FatB sequences are operably linked to a strong promoter, such as a Ptrc promoter. In other embodiments, one or more FatB sequences are operably linked to a relatively weak promoter, such as an arabinose promoter.

In certain embodiments, a modified photosynthetic microorganism comprises one or more polynucleotides encoding one or more DGAT enzymes. In certain embodiments of the present invention, a polynucleotide encodes a DGAT comprising of consisting of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd (*Acinetobacter baylii* sp.). In certain embodiments of the present invention, a DGAT polynucleotide comprises or consists of a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd. DGATn and DGATd correspond to *Acinetobacter* baylii DGAT and a modified form thereof, which includes two additional amino acid residues immediately following the initiator methionine.

In certain embodiments of the present invention, a polynucleotide encodes a phosphatidate phosphatase (also referred to as a phosphatidic acid phosphatase; PAP) comprising or consisting of a polypeptide sequence set forth in SEQ ID NO:2, or a fragment or variant thereof. In particular embodiments, a phosphatidate phosphatase polynucleotide comprises or consists of a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPAH1), and SEQ ID NO:5 is a codon-optimized for expression in Cyanobacteria sequence that encodes yPAH1. In certain embodiments, the nucleotide sequence of the PAP is derived from the *E. coli* PgpB gene, and/or the PAP gene from *Synechocystis* sp. PCC6803.

In certain embodiments of the present invention, a polynucleotide encodes an acetyl-CoA carboxylase (ACCase)

comprising or consisting of a polypeptide sequence set forth in any of SEQ ID NOs:3, 20, 21, 22, 23, or 28, or a fragment or variant thereof. In particular embodiments, a ACCase polynucleotide comprises or consists of a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *Triticum aestivum* ACCase; and SEQ ID NO:29 encodes this *Triticum aestivum* ACCase.

In certain embodiments of the present invention, a modified photosynthetic microorganism comprises one or more polynucleotides encoding one or more phospholipases, including lysophospholipases, or a fragment or variant thereof. In certain embodiments, the encoded lysophospholipase is Lysophospholipase L1 (TesA), Lysophospholipase L2, TesB, Vu Patatin 1 protein, or a homolog thereof.

In particular embodiments, the encoded phospholipase, e.g., a lysophospholipase, is a bacterial phospholipase, or a fragment or variant thereof, and the polynucleotide comprises a bacterial phospholipase polynucleotide sequence, e.g., a sequence derived from *Escherichia coli, Enterococcus faecalis*, or *Lactobacillus plantarum*. In particular embodiments, the encoded phospholipase is Lysophospholipase L1 (TesA), Lysophospholipase L2, TesB, Vu Patatin 1 protein, or a functional fragment thereof.

In certain embodiments, a lysophospholipase is a bacterial Lysophospholipase L1 (TesA) or TesB, such as an *E. coli* Lysophospholipase L1 encoded by a polynucleotide (pldC) having the wild-type sequence set forth in SEQ ID NO:85, or an *E. coli* TesB encoded by a polynucleotide having the wild-type sequence set forth in SEQ ID NO:91. The polypeptide sequence of *E. coli* Lysophospholipase L1 is provided in SEQ ID NO:86, and the polypeptide sequence of *E. coli* TesB is provided in SEQ ID NO:92. In other embodiments, a lysophospholipase is a Lysophospholipase L2, such as an *E. coli* Lysophospholipase L2 encoded by a polynucleotide (pldB) having the wild-type sequence set forth in SEQ ID NO:87, or a Vu patatin 1 protein encoded by a polynucleotide having the wild-type sequence set forth in SEQ ID NO:89. The polypeptide sequence of *E. coli* Lysophospholipase L2 is provided in SEQ ID NO:88, and the polypeptide sequence of Vu patatin 1 protein is provided in SEQ ID NO:90.

In particular embodiments, the polynucleotide encoding the phospholipase variant is modified such that it encodes a phospholipase that localizes predominantly to the cytoplasm instead of the periplasm. For example, it may encode a phospholipase having a deletion or mutation in a region associated with periplasmic localization. In particular embodiments, the encoded phospholipase variant is derived from Lysophospholipase L1 (TesA). In certain embodiments, the Lysophospholipase L1 (TesA) variant is a bacterial TesA, such as an *E. coli* Lysophospholipase (TesA) variant encoded by a polynucleotide having the sequence set forth in SEQ ID NO:93. The polypeptide sequence of the Lysophospholipase L1 variant is provided in SEQ ID NO:94 (PldC(*TesA)).

Additional examples of phospholipase-encoding polynucleotide sequences include phospholipase A1 (PldA) from *Acinetobacter* sp. ADP1 (SEQ ID NO:108), phospholipase A (PldA) from *E. coli* (SEQ ID NO:110), phospholipase from *Streptomyces coelicolor* A3(2) (SEQ ID NO:112), phospholipase A2 (PLA2-α) from *Arabidopsis thaliana* (SEQ ID NO:114). phospholipase All triacylglycerol lipase (DAD1; Defective Anther Dehiscence 1) from *Arabidopsis thaliana* (SEQ ID NO:116), chloroplast DONGLE from *Arabidopsis thaliana* (SEQ ID NO:118), patatin-like protein from *Arabidopsis thaliana* (SEQ ID NO:120), and patatin from *Anabaena variabilis* ATCC 29413 (SEQ ID NO:122). Additional non-limiting examples of lysophospholipase-encoding polynucleotide sequences include phospholipase B (PIM p) from *Saccharomyces cerevisiae* S288c (SEQ ID NO:124), phospholipase B (Plb2p) from *Saccharomyces cerevisiae* S288c (SEQ ID NO:126), ACIAD1057 (TesA homolog) from *Acinetobacter* ADP1 (SEQ ID NO:128), ACIAD1943 lysophospholipase from *Acinetobacter* ADP1 (SEQ ID NO:130), and a lysophospholipase (YP_702320; RHA1_ro02357) from *Rhodococcus* (SEQ ID NO:132).

Certain embodiments employ one or more TAG hydrolase encoding polynucleotide sequences. Non-limiting examples of TAG hydrolase polynucleotide sequences include SDP1 (SUGAR-DEPENDENT1) triacylglycerol lipase from *Arabidopsis thaliana* (SEQ ID NO:134), ACIAD1335 from *Acinetobacter* sp. ADP1 (SEQ ID NO:136), TG14P from *S. cerevisiae* (SEQ ID NO:138), and RHA1_ro04722 (YP_704665) TAG lipase from *Rhodococcus* (SEQ ID NO:140). Additional polynucleotide sequences for exemplary lipases/esterases include RHA1_ro01602 lipase/esterase from *Rhodococcus* sp. (see SEQ ID NO:166), and the RHA1_ro06856 lipase/esterase (see SEQ ID NO:168) from *Rhodococcus* sp.

Certain embodiments employ one or more fatty acyl-CoA synthetase encoding polynucleotide sequences. One exemplary fatty acyl-CoA synthetase includes the FadD gene from *E. coli* (SEQ ID NO:148) which encodes a fatty acyl-CoA synthetase having substrate specificity for medium and long chain fatty acids. Other exemplary fatty acyl-CoA synthetases include those derived from *S. cerevisiae*; for example, the Faa1p coding sequence is set forth in SEQ ID NO:142, the Faa2p coding sequence is set forth in SEQ ID NO:144, and the Faa3p is set forth in SEQ ID NO:146. SEQ ID NO:146 is codon-optimized for expression in *S. elongatus* PCC7942.

In certain embodiments of the present invention, a modified photosynthetic microorganism comprises one or more polynucleotides encoding one or more polypeptides associated with a glycogen breakdown, or a fragment or variant thereof. In particular embodiments, the one or more polypeptides are glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof. A representative glgP polynucleotide sequence is provided in SEQ ID NO:31, and a representative GlgP polypeptide sequence is provided in SEQ ID NO:32. A representative glgX polynucleotide sequence is provided in SEQ ID NO:33, and a representative GlgX polypeptide sequence is provided in SEQ ID NO:34. A representative malQ polynucleotide sequence is provided in SEQ ID NO:35, and a representative MalQ polypeptide sequence is provide in SEQ ID NO:36. A representative phosphoglucomutase (pgm) polynucleotide sequence is provided in SEQ ID NO:37, and a representative phosphoglucomutase (Pgm) polypeptide sequence is provided in SEQ ID NO:38, with others provided infra (SEQ ID NOs:75-84). A representative glk polynucleotide sequence is provided in SEQ ID NO:39, and a representative Glk polypeptide sequence is provided in SEQ ID NO:40. A representative pgi polynucleotide sequence is provided in SEQ ID NO:41, and a representative Pgi polypeptide sequence is provided in SEQ ID NO:42. In particular embodiments of the present invention, a polynucleotide comprises one of these polynucleotide sequences, or a fragment or variant thereof, or encodes one of these polypeptide sequences, or a fragment or variant thereof.

In certain embodiments, the present invention provides isolated polynucleotides comprising various lengths of contiguous stretches of sequence identical to or complementary to an ACP, an Aas, a thioesterase, a diacylglycerol acyltransferase, a phospholipase (e.g., phospholipase A, B, or C, lysophospholipase), a phosphatidate phosphatase, TAG hydrolase, a fatty acyl-CoA synthetase, or an acetyl-CoA carboxylase, wherein the isolated polynucleotides encode a biologically active, truncated enzyme.

Exemplary nucleotide sequences that encode the proteins and enzymes of the application encompass full-length ACPs, Aas proteins, thioesterases, diacylglycerol acyltransferases, phospholipases (e.g., phospholipase A, B, or C, lysophospholipases), phosphatidate phosphatases, TAG hydrolases, fatty acyl-CoA synthetases, and/or acetyl-CoA carboxylases, as well as portions of the full-length or substantially full-length nucleotide sequences of these genes or their transcripts or DNA copies of these transcripts. Portions of a nucleotide sequence may encode polypeptide portions or segments that retain the biological activity of the reference polypeptide. A portion of a nucleotide sequence that encodes a biologically active fragment of an enzyme provided herein may encode at least about 20, 21, 22, 23, 24, 25, 30, 40, 50, 60, 70, 80, 90, 100, 120, 150, 200, 300, 400, 500, 600, or more contiguous amino acid residues, almost up to the total number of amino acids present in a full-length enzyme. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the nucleotide sequences of the ACPs, Aas proteins, thioesterases, diacylglycerol acyltransferases, phospholipases (e.g., phospholipase A, B, or C, lysophospholipases), phosphatidate phosphatases, TAG hydrolases, fatty acyl-CoA synthetases, and/or acetyl-CoA carboxylases utilized according to methods and compositions provided herein. Nucleic acid variants can be naturally-occurring, such as allelic variants (same locus), homologs (different locus), and orthologs (different organism) or can be non naturally-occurring. Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having an ACP activity, an Aas activity, a thioesterase activity, a diacylglycerol acyltransferase activity, a phospholipase activity, a phosphatidate phosphatase activity, and/or a acetyl-CoA carboxylase activity. Embodiments of the present invention, therefore, encompass Cyanobacteria comprising such naturally occurring polynucleotide variants.

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in Cyanobacteria, such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide, such as a polypeptide having an ACP activity, an Aas activity, a thioesterase activity, a diacylglycerol acyltransferase activity, a lipase or phospholipase activity, a phosphatidate phosphatase activity, a TAG hydrolase activity, a fatty acyl-CoA synthetase activity, and/or an acetyl-CoA carboxylase activity. Generally, variants of a particular reference nucleotide sequence will have at least about 30%, 40% 50%, 55%, 60%, 65%, 70%, generally at least about 75%, 80%, 85%, 90%, 95% or 98% or more sequence identity to that particular nucleotide sequence as determined by sequence alignment programs described elsewhere herein using default parameters.

Known ACP, Aas protein, thioesterase, diacylglycerol acyltransferase, phospholipase, phosphatidate phosphatase, TAG hydrolase, fatty acyl-CoA synthetase, and/or a acetyl-CoA carboxylase nucleotide sequences can be used to isolate corresponding sequences and alleles from other organisms, particularly other microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other reference coding sequences present in a population of cloned genomic DNA fragments or cDNA fragments (i.e., genomic or cDNA libraries) from a chosen organism.

Accordingly, the present invention also contemplates polynucleotides that hybridize to reference ACP, Aas protein, thioesterase, diacylglycerol acyltransferase, phospholipase, phosphatidate phosphatase, TAG hydrolase, fatty acyl-CoA synthetase, and/or a acetyl-CoA carboxylase nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, an ACP, Aas protein, thioesterase, diacylglycerol acyltransferase, phospholipase, phosphatidate phosphatase, TAG hydrolase, fatty acyl-CoA synthetase, and/or acetyl-CoA carboxylase enzyme is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and the skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m$=81.5+16.6 ($\log_{10}$ M)+0.41 (% G+C)−0.63 (% formamide)−(600/length) wherein: M is the concentration of $Na^+$, preferably in the range of 0.01 molar to 0.4 molar; % G+C is the sum of guano sine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5×Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a triglyceride or lipid biosynthesis enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized."

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. In certain embodiments, the polynucleotides of the present invention may be introduced and expressed in Cyanobacterial systems. As such, the present invention contemplates the use of vector and plasmid systems having regulatory sequences (e.g., promoters and enhancers) that are suitable for use in various Cyanobacteria (see, e.g., Koksharova et al. *Applied Microbiol Biotechnol* 58:123-37, 2002). For example, the promiscuous RSF1010 plasmid provides autonomous replication in several Cyanobacteria of the genera *Synechocystis* and *Synechococcus* (see, e.g., Mermet-Bouvier et al., *Curr Microbiol* 26:323-327, 1993). As another example, the pFC1 expression vector is based on the promiscuous plasmid RSF1010. pFC1 harbors the lambda c1857 repressor-encoding gene and pR promoter, followed by the lambda cro ribosome-binding site and ATG translation initiation codon (see, e.g., Mermet-Bouvier et al., *Curr Microbiol* 28:145-148, 1994). The latter is located within the unique NdeI restriction site (CATATG) of pFC1 and can be exposed after cleavage with this enzyme for in-frame fusion with the protein-coding sequence to be expressed.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. Generally, it is well-known that strong *E. coli* promoters work well in Cyanobacteria. Also, when cloning in Cyanobacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. Other vectors containing IPTG inducible promoters, such as pAM1579 and pAM2991trc, may be utilized according to the present invention.

Certain embodiments may employ a temperature inducible system. As one example, an operon with the bacterial phage left-ward promoter ($P_L$) and a temperature sensitive repressor gene C1857 may be employed to produce a temperature inducible system for producing fatty acids and/or triglycerides in Cyanobacteria (see, e.g., U.S. Pat. No. 6,306,639, herein incorporated by reference). It is believed that at a non-permissible temperature (low temperature, 30 degrees Celsius), the repressor binds to the operator sequence, and thus prevents RNA polymerase from initiating transcription at the $P_L$ promoter. Therefore, the expression of encoded gene or genes is repressed. When the cell culture is transferred to a permissible temperature (37-42 degrees Celsius), the repressor cannot bind to the operator. Under these conditions, RNA polymerase can initiate the transcription of the encoded gene or genes.

In Cyanobacterial systems, a number of expression vectors may be selected depending upon the use intended for the expressed polypeptide. When large quantities are needed, vectors which direct high level expression of encoded proteins may be used. For example, overexpression of ACCase enzymes may be utilized to increase fatty acid biosynthesis. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of (3-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST).

Certain embodiments may employ Cyanobacterial promoters or regulatory operons. In certain embodiments, a promoter may comprise an rbcLS operon of *Synechococcus*, as described, for example, in Ronen-Tarazi et al. (*Plant Physiology* 18:1461-1469, 1995), or a cpc operon of *Synechocystis* sp. strain PCC 6714, as described, for example, in Imashimizu et al. (*J. Bacteriol.* 185:6477-80, 2003). In certain embodiments, the tRNApro gene from *Synechococcus* may also be utilized as a promoter, as described in Chungjatupornchai et al. (*Curr Microbiol.* 38:210-216, 1999). Certain embodiments may employ the nirA promoter from *Synechococcus* sp. strain PCC 7942, which is repressed by ammonium and induced by nitrite (see, e.g., Maeda et al., *J. Bacteriol.* 180:4080-4088, 1998; and Qi et al., *Applied and Environmental Microbiology* 71:5678-5684, 2005). The efficiency of expression may be enhanced by the inclusion of enhancers which are appropriate for the particular Cyanobacterial cell system which is used, such as those described in the literature.

In certain embodiments, expression vectors utilized to express an ACP, Aas protein, thioesterase, diacylglycerol acyltransferase, phospholipase, phosphatidate phosphatase, TAG hydrolases, fatty acyl-CoA synthetases, and/or acetyl-CoA carboxylase, or fragment or variant thereof, comprise a weak promoter under non-inducible conditions, e.g., to avoid toxic effects of long-term overexpression of any of these polypeptides. One example of such a vector for use in Cyanobacteria is the pBAD vector system. Expression levels from any given promoter may be determined, e.g., by performing quantitative polymerase chain reaction (qPCR) to determine the amount of transcript or mRNA produced by a promoter, e.g., before and after induction. In certain instances, a weak promoter is defined as a promoter that has a basal level of expression of a gene or transcript of interest, in the absence of inducer, that is ≤2.0% of the expression level produced by the promoter of the rnpB gene in *S. elongatus* PCC7942. In other embodiments, a weak promoter is defined as a promoter that has a basal level of expression of a gene or transcript of interest, in the absence of inducer, that is ≤5.0% of the expression level produced by the promoter of the rnpB gene in *S. elongatus* PCC7942.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983). The presence of a desired polynucleotide, such as an ACP, Aas, diacylglycerol acyltransferase, phosphatidate phosphatase, phospholipase, TAG hydrolase, fatty acyl-CoA synthetase, and/or an acetyl-CoA carboxylase encoding polypeptide, may also be confirmed by PCR.

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Cyanobacterial host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct localization of the encoded polypeptide to a desired site within the cell. Other recombinant constructions may be used to join sequences encoding a polypeptide of interest to nucleotide sequence encoding a polypeptide domain which will direct secretion of the encoded protein.

In particular embodiments of the present invention, a modified photosynthetic microorganism of the present invention has reduced expression of one or more genes selected from glucose-1-phosphate adenyltransferase (glgC), phosphoglucomutase (pgm), and/or glycogen synthase (glgA). In particular embodiments, the modified photosynthetic microorganism comprises a mutation of one or more of these genes. Specific glgC, pgm, and glgA sequences may be mutated or modified, or targeted to reduce expression.

Examples of such glgC polynucleotide sequences are provided in SEQ ID NOs:59 (*Synechocystis* sp. PCC 6803), 61 (*Nostoc* sp. PCC 7120), 63 (*Anabaena variabilis*), 65 (*Trichodesmium erythraeum* IMS 101), 67 (*Synechococcus elongatus* PCC 7942), 69 (*Synechococcus* sp. WH8102), 71 (*Synechococcus* sp. RCC 307), and 73 (*Synechococcus* sp. PCC 7002), which respectively encode GlgC polypeptides having sequences set forth in SEQ ID NOs: 60, 62, 64, 66, 68, 70, 72, and 74.

Examples of such pgm polynucleotide sequences are provided in SEQ ID NOs: 75 (*Synechocystis* sp. PCC 6803), 77 (*Synechococcus elongatus* PCC 7942), 79 (*Synechococcus* sp. WH8102), 81 (*Synechococcus* RCC307), and 83 (*Synechococcus* 7002), which respectively encode Pgm polypeptides having sequences set forth in SEQ ID NOs:76, 78, 80, 82, and 84.

Examples of such glgA polynucleotide sequences are provided in SEQ ID NOs:43 (*Synechocystis* sp. PCC 6803), 45 (*Nostoc* sp. PCC 7120), 47 (*Anabaena variabilis*), 49 (*Trichodesmium erythraeum* IMS 101), 51 (*Synechococcus elongatus* PCC 7942), 53 (*Synechococcus* sp. WH8102), 55 (*Synechococcus* sp. RCC 307), and 57 (*Synechococcus* sp. PCC 7002), which respectively encode GlgA polypeptides having sequences set forth in SEQ ID NOs:44, 46, 48, 50, 52, 54, 56, and 58.

G. POLYPEPTIDES

The present invention contemplates the use of modified photosynthetic microorganisms, e.g., Cyanobacteria, comprising one or more introduced polynucleotides encoding an ACP, an Aas, or both, in combination with one or more proteins associated with lipid biosynthesis and/or glycogen breakdown. Specific embodiments of the present invention contemplate the use of modified photosynthetic microorganisms, e.g., Cyanobacteria, comprising one or more additional introduced polypeptides, including those associated with a glycogen breakdown pathway or having a diacylglycerol acyltransferase activity, a thioesterase activity, a phosphatidate phosphatase activity, a phospholipase activity, a TAG hydrolase activity, a fatty acyl-CoA synthetase activity, and/or an acetyl-CoA carboxylase activity, including truncated, variant and/or modified polypeptides thereof, for increasing lipid production and/or producing triglycerides or free fatty acids in said modified photosynthetic microorganism.

In certain embodiments, an acyl carrier protein (ACP) comprises or consists of the exemplary ACP polypeptide sequences include SEQ ID NO:97 from *Synechococcus elongatus* PCC 7942, SEQ ID NOS:99, 101, and 103 from *Acinetobacter* sp. ADP1, or SEQ ID NO:105 from *Spinacia oleracea*, or a fragment or variant thereof.

In certain embodiments, an acyl-ACP synthetase (Aas) polypeptide comprises the sequence encoded by the Se918 gene of *Synechococcus elongatus*. One exemplary Aas protein is SEQ ID NO:107 from *Synechococcus elongatus* PCC 7942 0918, or a fragment or variant thereof.

In certain embodiments, a modified photosynthetic microorganism comprises one or more polynucleotides encoding one or more thioesterases (TES) including acyl-ACP thioesterases and/or acyl-CoA thioesterases. In certain embodiments, the TES is a TesA or TesB polypeptide from *E. coli*, or a cytoplasmic TesA variant (*TesA) variant having the sequence set forth in SEQ ID NO:94, or a fragment or variant thereof.

In certain embodiments, the TES is a FatB polypeptide, such as a C8, C12, C14, C16, or C18 FatB. In specific embodiments, the thioesterase is a *Cuphea hookeriana* C8/C10 FatB, comprising the amino acid sequence of SEQ ID NO:152 (full-length protein) or SEQ ID NO:153 (mature protein without signal sequence), or a fragment or variant thereof. In particular embodiments, the thioesterase is a *Umbellularia californica* C12 FatB1, comprising the amino acid sequence of SEQ ID NO:156 (full-length protein) or SEQ ID NO:157 (mature protein without signal sequence), or a fragment or variant thereof. In certain embodiments, the thioesterase is a *Cinnamomum camphora* C14 FatB1, comprising the amino acid sequence of SEQ ID NO:160 (full-length protein) or SEQ ID NO:161 (mature protein without signal sequence), or a fragment or variant thereof. In particular embodiments, the thioesterase is a *Cuphea hookeriana* C16 FatB1, comprising the amino acid sequence of SEQ ID NO:164 (full-length protein) or SEQ ID NO:165 (mature protein without signal sequence), or a fragment or variant thereof.

In certain embodiments of the present invention, a DGAT polypeptide comprises or consists of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd. In certain embodiments of the present invention, a DGAT polypeptide is encoded by a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd.

In certain embodiments of the present invention, a phosphatidate phosphatase polypeptide comprises or consists of a polypeptide sequence set forth in SEQ ID NO:2, or a fragment or variant thereof. In particular embodiments, a phosphatidate phosphatase is encoded by a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPah1), and SEQ ID NO:5 is a codon-optimized for expression in Cyanobacteria sequence that encodes yPah1. In certain embodiments, the polypeptide sequence of the PAP is encoded by the *E. coli* PgpB gene, and/or the PAP gene from *Synechocystis* sp. PCC6803.

In certain embodiments of the present invention, an acetyl-CoA carboxylase (ACCase) polypeptide comprises or consists of a polypeptide sequence set forth in any of SEQ ID NOs:3, 20, 21, 22, 23, or 28, or a fragment or variant thereof. In particular embodiments, an ACCase polypeptide is encoded by a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *T. aestivum* ACCase; and SEQ ID NO:29 encodes this *Triticum aestivum* ACCase.

In particular embodiments, the phospholipase is a bacterial phospholipase, e.g., lysophospholipase, or a fragment or variant thereof, e.g., a phospholipase derived from *Escherichia coli, S. cerevisiae, Rhodococcus, Streptomyces* or *Acinetobacter* species.

In particular embodiments, the encoded phospholipase comprises or consists of a Lysophospholipase L1 (TesA), Lysophospholipase L2, TesB, or Vu patatin 1 protein, or a homolog, fragment, or variant thereof. In certain embodiments, the Lysophospholipase L1 (TesA), Lysophospholipase L2, or TesB is a bacterial Lysophospholipase L1 (TesA), Lysophospholipase L2, or TesB, such as an *E. coli* Lysophospholipase L1 (TesA) having the wild-type sequence set forth in SEQ ID NO:86, an *E. coli* Lysophospholipase L2 having the wild-type sequence set forth in SEQ ID NO:88, or an *E. coli* TesB having the wild-type sequence set forth in SEQ ID NO:92. In particular embodiment, the Vu patatin 1 protein has the wild-type sequence set forth in SEQ ID NO:90.

In particular embodiments, the phospholipase is modified such that it localizes predominantly to the cytoplasm instead of the periplasm. For example, the phospholipase may have a deletion or mutation in a region associated with periplasmic localization. In particular embodiments, the phospholipase variant is derived from Lysophospholipase L1 (TesA) or TesB. In certain embodiments, the Lysophospholipase L1 (TesA) or TesB variant is a bacterial Lysophospholipase L1 (TesA) or TesB variant, such as a cytoplasmic *E. coli* Lysophospholipase L1 (PldC(*TesA)) variant having the sequence set forth in SEQ ID NO:94.

Additional examples of phospholipase polypeptide sequences include phospholipase A1 (PldA) from *Acinetobacter* sp. ADP1 (SEQ ID NO:109), phospholipase A (PldA) from *E. coli* (SEQ ID NO:111), phospholipase from *Streptomyces coelicolor* A3(2) (SEQ ID NO:113), phospholipase A2 (PLA2-α) from *Arabidopsis thaliana* (SEQ ID NO:115). phospholipase All triacylglycerol lipase (DAD1; Defective Anther Dehiscence 1) from *Arabidopsis thaliana* (SEQ ID NO:117), chloroplast DONGLE from *Arabidopsis thaliana* (SEQ ID NO:119), patatin-like protein from *Arabidopsis thaliana* (SEQ ID NO:121), and patatin from *Anabaena variabilis* ATCC 29413 (SEQ ID NO:123). Additional non-limiting examples of lysophospholipase polypeptide sequences include phospholipase B (PIM p) from *Saccharomyces cerevisiae* S288c (SEQ ID NO:125), phospholipase B (Plb2p) from *Saccharomyces cerevisiae* S288c (SEQ ID NO:127), ACIAD1057 (TesA homolog) from *Acinetobacter* ADP1 (SEQ ID NO:129), ACIAD1943 lysophospholipase from *Acinetobacter* ADP1 (SEQ ID NO:131), and a lysophospholipase (YP_702320; RHA1_ro02357) from *Rhodococcus* (SEQ ID NO:133).

Certain embodiments employ one or more TAG hydrolase polypeptides. Non-limiting examples of TAG hydrolase polypeptide sequences include SDP1 (SUGAR-DEPENDENT1) triacylglycerol lipase from *Arabidopsis thaliana* (SEQ ID NO:135), ACIAD1335 from *Acinetobacter* sp. ADP1 (SEQ ID NO:137), TG14P from *S. cerevisiae* (SEQ ID NO:139), and RHA1_ro04722 (YP_704665) TAG lipase from *Rhodococcus* (SEQ ID NO:141). Additional polypeptide sequences for exemplary lipases/esterases include RHA1_ro01602 lipase/esterase from *Rhodococcus* sp. (see SEQ ID NO:167), and the RHA1_ro06856 lipase/esterase (see SEQ ID NO:169) from *Rhodococcus* sp.

Certain embodiments employ one or more fatty acyl-CoA synthetase polypeptides. One exemplary fatty acyl-CoA synthetase includes the polypeptide sequence of the FadD gene from *E. coli* (SEQ ID NO:149), a fatty acyl-CoA synthetase having substrate specificity for medium and long chain fatty acids. Other exemplary fatty acyl-CoA synthetases include those derived from *S. cerevisiae*; for example, the Faa1p polypeptide sequence is set forth in SEQ ID NO:143, the Faa2p polypeptide sequence is set forth in SEQ ID NO:145, and the Faa3p polypeptide sequence is set forth in SEQ ID NO:147.

In particular embodiments, said one or more additional polynucleotides encode glycogen phosphorylase (GlgP), glycogen isoamylase (GlgX), glucanotransferase (MalQ), phosphoglucomutase (Pgm), glucokinase (Glk), and/or phosphoglucose isomerase (Pgi), or a functional fragment or variant thereof, including, e.g., those provided in SEQ ID NOs:32, 34, 36, 38, 40 or 41. Examples of additional Pgm polypeptide sequences useful according to the present invention are provided in SEQ ID NOs:76, 78, 80, 82, and 84.

Variant proteins encompassed by the present application are biologically active, that is, they continue to possess the enzymatic activity of a reference polypeptide. Such variants may result from, for example, genetic polymorphism or from human manipulation. Biologically active variants of a reference ACP, Aas, lipase, phospholipase, lysophospholipase, diacylglycerol acyltransferase, phosphatidate phosphatase, TAG hydrolase, fatty acyl-CoA synthetase, and/or acetyl-CoA carboxylase polypeptide, or other polypeptide involved in fatty acid or triglyceride biosynthesis, will have at least 40%, 50%, 60%, 70%, generally at least 75%, 80%, 85%, usually about 90% to 95% or more, and typically about 97% or 98% or more sequence similarity or identity to the amino acid sequence for a reference protein as determined by sequence alignment programs described elsewhere herein using default parameters. A biologically active variant of a reference polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the reference sequences in the Sequence Listing by at least one but by less than 15, 10 or 5 amino acid residues. In other embodiments, it differs from the reference sequences by at least one residue but less than 20%, 15%, 10% or 5% of the residues.

An ACP, Aas, thioesterase, diacylglycerol acyltransferase, lipase, phospholipase, phosphatidate phosphatase, TAG hydrolase, fatty acyl CoA synthetase, and/or acetyl-CoA carboxylase polypeptide may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("*Molecular Biology of the Gene*", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of ACP, Aas, thioesterase, diacylglycerol acyltransferase, lipase, phospholipase, phosphatidate phosphatase, TAG hydrolase, fatty acyl-CoA synthetase, and/or a acetyl-CoA carboxylase polypeptides. Recursive ensemble mutagenesis (REM), a technique which enhances the frequency of functional mutants in the libraries, can be used in combination with the screening assays to identify polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Polypeptide variants may contain conservative amino acid substitutions at various locations along their sequence, as compared to a reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxylcarbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine, |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant polypeptide can readily be determined by assaying its enzymatic activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in an ACP, Aas, thioesterase, diacylglycerol acyltransferase, lipase, phospholipase, phosphatidate phosphatase, TAG hydrolase, fatty acyl-CoA synthetase, and/or a acetyl-CoA carboxylase polypeptide, including other enzymes described herein, is typically replaced with another amino acid residue from the same side chain family. Alternatively, mutations can be introduced randomly along all or part of a coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference polypeptide, results in abolition of an activity of the parent molecule such that less than 20% of the wild-type activity is present. For example, such essential amino acid residues may include those that are conserved in ACP, Aas, thioesterase, diacylglycerol acyltransferase, phospholipase, phosphatidate phosphatase, TAG hydrolase, fatty acyl-CoA synthetase, and/or acetyl-CoA carboxylase polypeptides across different species, including those sequences that are conserved in the enzymatic sites of polypeptides from various sources.

Accordingly, the present invention also contemplates variants of the naturally-occurring ACP, Aas, thioesterase, diacylglycerol acyltransferase, lipase, phospholipase, phosphatidate phosphatase, TAG hydrolase, fatty acyl-CoA synthetase, and/or a acetyl-CoA carboxylase polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference polypeptide sequence. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of a parent or reference polypeptide sequence are contemplated.

In some embodiments, variant polypeptides differ from a reference ACP, Aas, thioesterase, diacylglycerol acyltransferase, lipase, phospholipase, phosphatidate phosphatase, TAG hydrolase, fatty acyl-CoA synthetase, and/or acetyl-CoA carboxylase polypeptide sequence by at least one but by less than 50, 40, 30, 20, 15, 10, 8, 6, 5, 4, 3 or 2 amino acid residue(s). In other embodiments, variant polypeptides differ from a reference by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of an ACP, Aas, lipase, phospholipase, lysophospholipase, glycogen breakdown polypeptides, diacylglycerol acyltransferase, phosphatidate phosphatase, TAG hydrolase, fatty acyl-CoA synthetase, or acetyl-CoA carboxylase reference polypeptide, and retains the enzymatic activity of that reference polypeptide.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of an ACP, Aas, thioesterase, diacylglycerol acyltransferase, phospholipase, phosphatidate phosphatase, and/or acetyl-CoA carboxylase reference polypeptide can be identified by screening combinatorial libraries of mutants of a reference polypeptide. Libraries or fragments e.g., N terminal, C terminal, or internal fragments, of protein coding sequence can be used to generate a variegated population of fragments for screening and subsequent selection of variants of a reference polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of polypeptides.

The present invention also contemplates the use of chimeric or fusion proteins for increasing lipid production and/or producing triglycerides. As used herein, a "chimeric protein" or "fusion protein" includes an ACP, Aas, thioesterase, diacylglycerol acyltransferase, lipase, phospholipase, phosphatidate phosphatase, TAG hydrolase, fatty acyl-CoA synthetase, and/or acetyl-CoA carboxylase reference polypeptide or polypeptide fragment linked to either another reference polypeptide (e.g., to create multiple fragments), to a non-reference polypeptide, or to both. A "non-reference polypeptide" refers to a "heterologous polypeptide" having an amino acid sequence corresponding to a protein which is different from the ACP, Aas, thioesterase, diacylglycerol acyltransferase, phospholipase, phosphatidate phosphatase, and/or acetyl-CoA carboxylase protein sequence, and which is derived from the same or a different organism. The reference polypeptide of the fusion protein can correspond to all or a portion of a biologically active amino acid sequence. In certain embodiments, a fusion protein includes at least one (or two) biologically active portion of an ACP, Aas, thioesterase, diacylglycerol acyltransferase, phospholipase, phosphatidate phosphatase, and/or acetyl-CoA carboxylase protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the enzymatic activity of the polypeptide. For example, in one embodiment, a fusion partner may comprise a sequence that assists in expressing the protein (an expression enhancer) at higher yields than the native recombinant protein. Other fusion partners may be selected so as to increase the solubility or stability of the protein or to enable the protein to be targeted to desired intracellular compartments.

The fusion protein can include a moiety which has a high affinity for a ligand. For example, the fusion protein can be a GST-fusion protein in which the ACP, Aas, thioesterase, diacylglycerol acyltransferase, lipase, phospholipase, phosphatidate phosphatase, TAG hydrolase, fatty acyl-CoA synthetase, and/or acetyl-CoA carboxylase sequences are fused to the C-terminus of the GST sequences. Such fusion proteins can facilitate the purification and/or identification of the resulting polypeptide. Alternatively, the fusion protein can be an ACP, Aas, thioesterase, diacylglycerol acyltransferase, lipase, phospholipase, phosphatidate phosphatase, TAG hydrolase, fatty acyl-CoA synthetase, and/or acetyl-CoA carboxylase protein containing a heterologous signal sequence at its N-terminus. In certain host cells, expression and/or secretion of such proteins can be increased through use of a heterologous signal sequence.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

EXAMPLES

Example 1

Generation of Cyanobacteria Overexpressing Acyl Carrier Protein

The present example demonstrates that increased expression of acyl carrier protein (ACP) in Cyanobacteria results in increased lipid production, alone or when co-expressed with other genes involved in lipid synthesis. As described herein, overexpression of the endogenous acyl carrier protein gene (acp) alone or in combination with overexpression of either: (1) a thioesterase gene; or (2) a diacylglycerol transferase (DGAT) gene resulted in increased lipid content compared to controls. Overexpression of both ACP and thioesterase resulted in increased fatty acid production, and overexpression of both ACP and a diacylglycerol transferase (DGAT) resulted in increased triglyceride production. Without wishing to by bound by any particular theory, it is hypothesized that ACP is a limiting step in lipid production by Cyanobacteria, and additional expression of ACP further increases free fatty acid (FFA) or triglyceride production in strains that overexpress a thioesterase or DGAT, respectively, possibly through mass action (i.e., increasing flux through the FAS II system), resulting in increased acyl-ACPs, which are substrates of both thioesterases and DGAT; or by deregulating feedback inhibition of Acyl-ACP on FAS II targets.

To produce a Cyanobacteria that overexpressed ACP, the acp gene was PCR-amplified from *S. elongatus* genomic DNA and cloned downstream of the IPTG-inducible ptrc promoter on the pNS4_trc3/laclq$^+$_Gm$^r$ plasmid (generating pNS4_trc3/laclq$^+$_Gm$^r$.ACP). In the absence of the IPTG inducer, some low-level basal transcription was often observed. The ACP gene was flanked by neutral site 4 (NS4) sequences, which permitted ACP to be recombined into the neutral site4 (NS4) of the chromosome of *Synechococcus* elongatus PCC 7942, to produce the ACP strain.

TesA overexpression was achieved using a gene (*tesA) cloned downstream of the inducible pBAD promoter and incorporated into the chromosome of *Synechococcus elongatus* PCC 7942. The *tesA gene was produced by ordering a codon-optimized version of the *E. coli* *tesA gene from DNA 2.0 (Menlo Park, Calif.). This codon optimized *tesA lacks the sequence encoding the signal for transport into the periplasm and introduces a new start codon. A fragment of the DNA 2.0 product containing *tesA was cloned into plasmid pTG2086, so *tesA expression was under control of the arabinose-inducible pBAD promoter and was flanked by neutral site 2 sequences, which permited *tesA to be recombined into neutral site 2 (NS2) in the genome of *Synechococcus elongatus* PCC 7942 to produce the TesA strain.

DGAT overexpression was achieved using DGAT-encoding gene from *Acinetobacter baylii* ADP1 ("aDGAT") that was ordered, codon-optimized, from DNA 2.0, cloned downstream of the inducible pTrc promoter pAM2314trc3, and incorporated into neutral site 1 (NS1) in the *Synechococcus elongatus* PCC 7942 chromosome, to produce the aDGAT strain. The codon-optimized DGAT from *Acinetobacter baylii* ADP1 sequence is shown in SEQ ID NO:19.

TesA/ACP and aDGAT/ACP strains were generated by transforming pNS4_trc3/laclq$^+$_Gm$^r$.ACP into the above TesA and aDGAT strains.

Cultures were grown in shaking conditions in 30-40 mL (250 mL Erlenmeyer flasks) of BG11 medium under high light conditions (100-120 μE) at 30° C. to medium density. Cells were subcultured to an optical density ($OD_{750}$) of 0.2 under the same conditions. For the TesA/ACP strain, this was the starting point of a continuous growth culture in which inducer (IPTG for ACP or arabinose for TesA) was never added. For the aDGAT/ACP strain, IPTG was added the following day (at an $OD_{750}$ of 0.4-0.5) to a final concentration of 1 mM. At timepoints indicated in the accompanying figures, the $OD_{750}$ was measured; one OD-equivalents of whole cell culture was collected for analysis of total fatty acids by gas chromatography (GC); and two OD-equivalents of whole cell sample were collected for analysis by TLC of neutral and polar lipids.

Figure 1B:
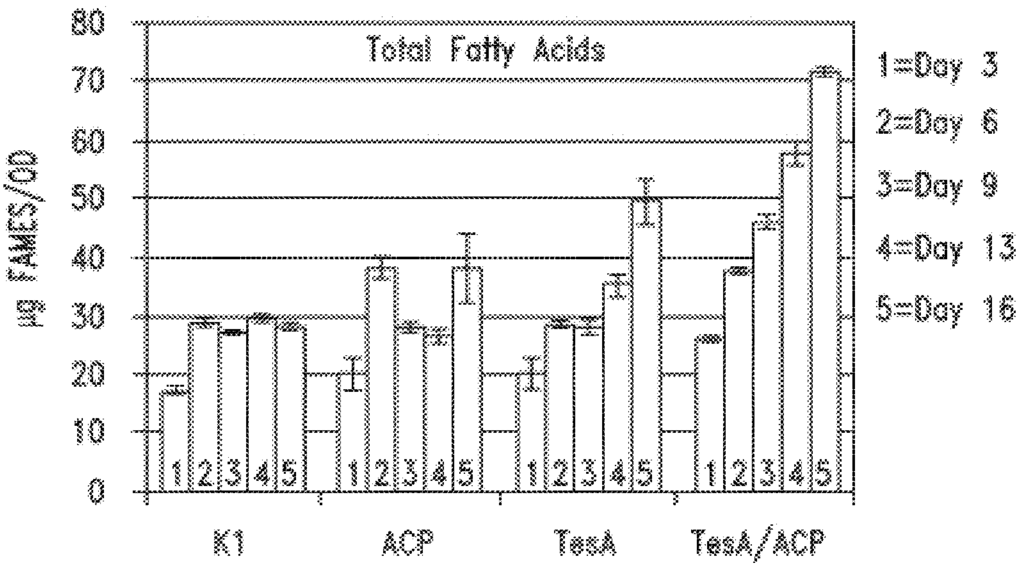
Figure 1C:
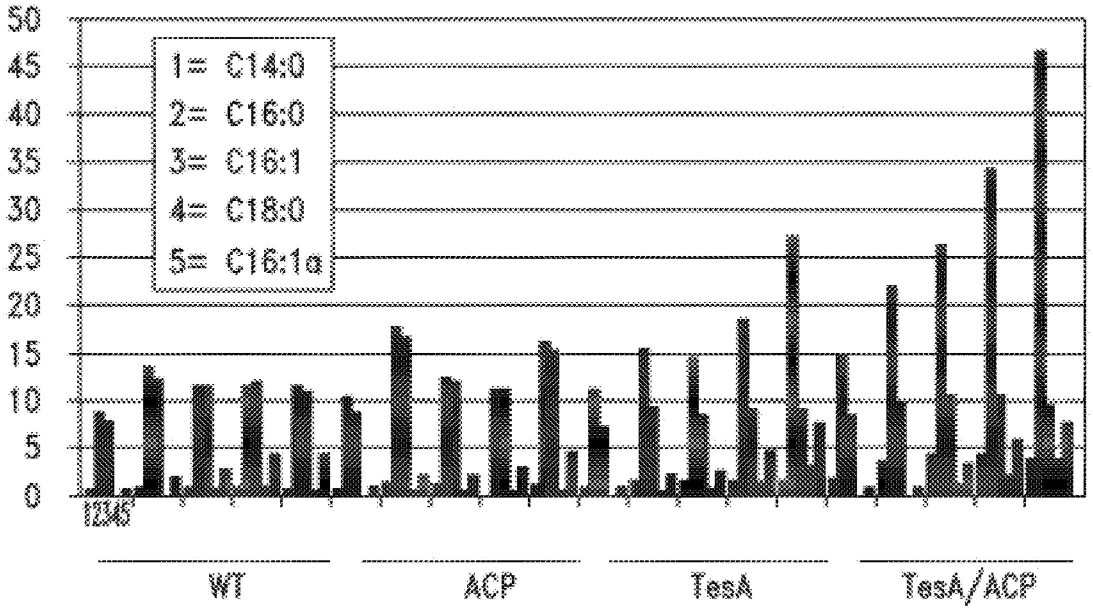

To demonstrate the effect of ACP overexpression, alone or in combination with TesA overexpression, cultures of K1(WT); ACP; TesA; and TesA/ACP strains were diluted back to 0.2 on "day 0" and grown under shaking conditions without adding inducer (IPTG). On days 6, 8, 11 and 13, two $OD_{750}$ equivalents of whole culture was harvested. These samples were then processed for TLC analysis (Bligh and Dyer method) using a polar solvent solution of chloroform: methanol:$H_2O$ at 70:22:3. 0.2 $OD_{750}$ equivalents were loaded on each lane (FIG. 1A). 5 μg of a palmitic acid (FIG. 1A, left lane) was loaded as a reference for free fatty acids (indicate by "*"). On the indicated days, two OD-equivalents of whole cell culture was harvested and analyzed by GC for fatty acid methyl esters (FAMES, μg/OD; FIG. 1B); or for the constituent FAMES (μg/OD), including C14:0; C16:0, C16:1, C18:0 and C18:1 (FIG. 1C).

As demonstrated by both TLC (FIG. 1A) and GC (FIGS. 1B and 1C), the ACP, TesA and TesA/ACP produced more FFAs than the wild type K1 strain (1.3-, 1.8- and 2.5-fold more μg FAMES/OD on day 16, respectively). However, the TesA/ACP strain produced more FFA than either the ACP-only strain (1.9-fold more at day 16) or the TesA-only strain (1.4-fold more at day 16). The primary fatty species that was increased in both the TesA and TesA/ACP strains were unsaturated C16:0 fatty acids (FIG. 1C), likely reflecting the specificity of TesA.

Two further notable aspects of the TesA and TesA/ACP strains were: (1) they did not display growth defects under the conditions described; and (2) their production of free fatty acids (FFAs) was constant throughout the time course. These features make this strain an excellent candidate for continuous production of FFAs.

An interesting aspect of the increased free fatty acid production by the TesA-only and TesA/ACP strains was that the FFAs were produced in the absence of induction with IPTG, indicating that the low levels of basal expression from either promoter, the pBAD (for TesA) and ptrc (for APC) promoters, was sufficient.

Figure 2A:
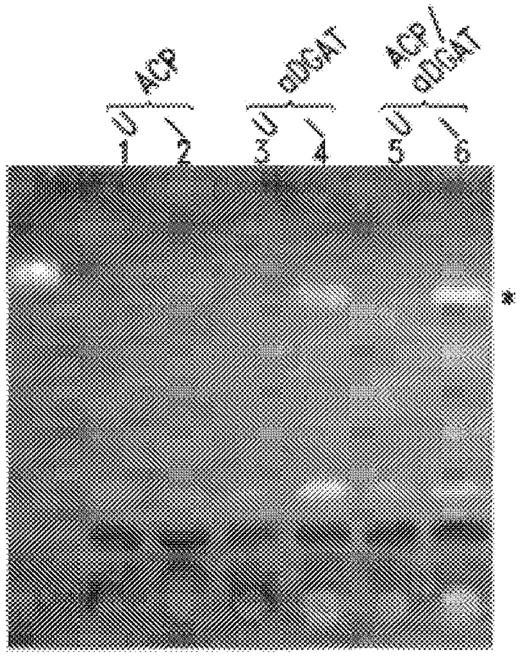
FIGS. 2A-2B show the effect of ACP on DGAT production of triglycerides (TAG) as assessed by TLC (1A) or GC (1B).
Figure 2B:
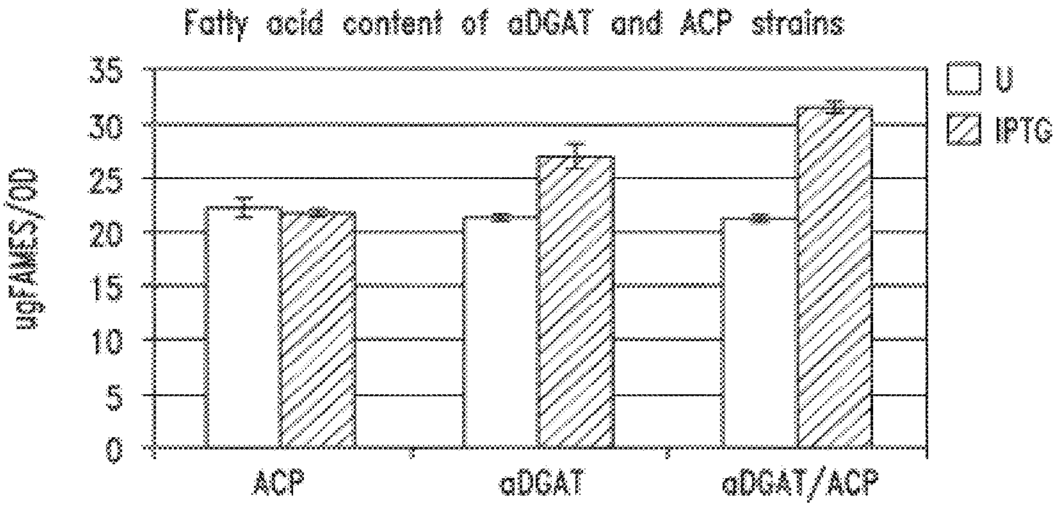

To demonstrate the effect of ACP overexpression in combination with DGAT overexpression, cultures of ACP; aDGAT; and aDGAT/ACP strains were diluted to an $OD_{750}$ of 0.2 the day before induction. The day of induction, IPTG was added to a final concentration of 1 mM (inducing both the ACP and aDGAT transgenes), and at 48 h, samples were taken for analysis by TLC and GC. Separation on TLC plates utilized a non-polar solution of hexane:diethyl ether:acetic acid at 70:30:1. 0.5 OD equivalents of whole cell culture were loaded on each lane (FIG. 2A). 5 μg of C18 TAG was included as a marker (FIG. 2A, far left lane). GC analysis was performed (μg FAMES/OD) on ACP, aDGAT, or aDGAT/ACP strains (FIG. 2B). In FIG. 2B, for each strain examined, data from uninduced cells are shown on the left, and data from cells induced with 1 mM IPTG are shown on the right. The aDGAT/ACP induced samples produced 1.4-fold and 1.2-fold more total FAMES than the ACP or aDGAT strains, respectively.

As shown in FIG. 2, the addition of IPTG (1 mM) resulted in TAG production in an aDGAT strain, and this amount was further increased in an aDGAT/ACP strain.

Example 2

Generation of Cyanobacteria Overexpressing Acyl ACP Synthase

The present example demonstrates that increased expression of acyl ACP synthase (Aas) in Cyanobacteria results in increased lipid production when co-expressed with other genes involved in lipid synthesis. As described herein, overexpression of the endogenous acyl ACP synthase (Aas, a.k.a PCC7942 ORF 0918) in combination with overexpression of (1) a diacyl glycerol transferase gene (DGAT) gene; and (2) an ACP resulted in increased lipid content compared to controls. Overexpression of DGAT, ACP and Aas resulted in higher triglyceride production compared to DGAT alone or ACP and DGAT expressing strains. Without wishing to be bound by any particular theory, it is hypothesized that ACP and/or Aas are limiting steps in lipid production by Cyanobacteria, and additional expression of ACP and Aas further increases triglyceride production in strains that overexpress DGAT possibly through increased acyl-ACPs generated by action of Aas in the presence of increased levels of ACP, or by deregulating feedback inhibition of Acyl-ACP on FAS II targets.

To produce a Cyanobacteria that overexpressed Aas, the Aas gene (PCC7942 ORF 0918) was PCR-amplified from *S.*

*elongatus* genomic DNA and cloned downstream of IPTG-inducible ptrc promoter on the pAM2314FTtrc3$^+$_Sp$^r$/Sm$^r$. The Aas gene was flanked by neutral site 1 (NS1) sequences, which permited aas to be recombined into the neutral site1 (NS1) of the chromosome of *Synechococcus elongatus* PCC 7942 to produce the Aas strain. This construct was also transformed into ADGATn (pNS4trc3) strain to generate ADGATn (pNS4trc3)/Aas (pAM2314FTtrc3), which as then transformed with ACP cloned in pAM1579trc3 (NS2) to generate ADGATn (pNS4trc3)/Aas (pAM2314FTtrc3 (NS1))/ACP(pAM1579trc3(NS2)).

In addition, Aas (pAM2314trc3) was transformed into a strain expressing *TesA (pAM1579ara3) to generate Aas/TesA, expressing Aas from NS1 under the control of the Ptrc promoter and *TesA from NS2 under the control of the Pbad promoter.

Cultures were grown in shaking conditions in 30-40 mL (250 mL Erlenmeyer flasks) of BG11 medium under constant light (100-120 μE) at 30° C. to medium density. Cells were subcultured to an optical density ($OD_{750}$) of 0.2 under the same conditions. For the DGAT/Aas/ACP strain, this was the starting point of a continuous growth culture in which inducer (IPTG) for ACP or arabinose for TesA) was never added. For the aDGAT/ACP strain, IPTG was added the following day (at an $OD_{750}$ of 0.4-0.5) to a final concentration of 1 mM. At timepoints indicated in the accompanying figures, the $OD_{750}$ was measured; one OD-equivalents of whole cell culture was collected for analysis of total fatty acids by gas chromatography (GC); and two OD-equivalents of whole cell sample were collected for analysis by TLC of neutral and polar lipids.

Figure 3A:
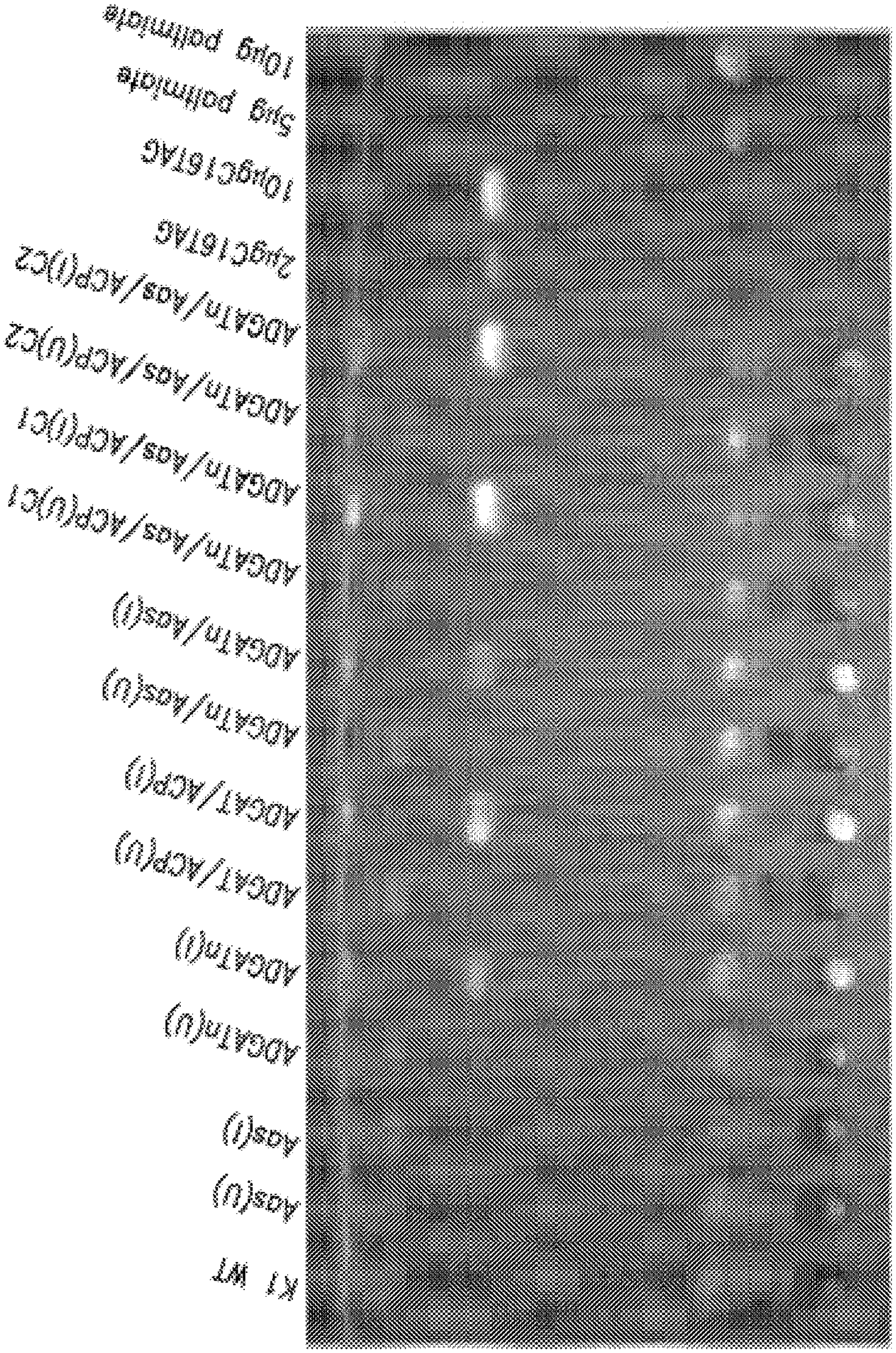
FIGS. 3A-3B show the effect of Aas and ACP overexpression in combination with DGAT overexpression.

To demonstrate the effect of Aas and ACP overexpression in combination with DGAT overexpression, cultures of aDGAT, ADGAT/ACP or ADGAT/Aas/ACP strains were diluted to an $OD_{750}$ of 0.2 the day before induction. The day of induction, IPTG was added to a final concentration of 1 mM and at 24 or 48 h, samples were taken for analysis by TLC. Samples for TEM were obtained and prepared as described below at 24 h. Separation on TLC plates utilized a non-polar solution of hexane:diethyl ether:acetic acid at 75:25:1. 1 OD equivalents of whole cell culture were loaded on each lane (FIG. 3A). 2, 10 μg of C16 TAG was included as a marker (FIG. 3A). As shown in FIG. 3A, the addition of IPTG (1 mM) resulted in TAG production in an aDGAT strain; that amount was further increased in an aDGAT/ACP strain; and, that amount was even further increased in an ADGAT/Aas/ACP overexpressing strain.

Figure 3B:
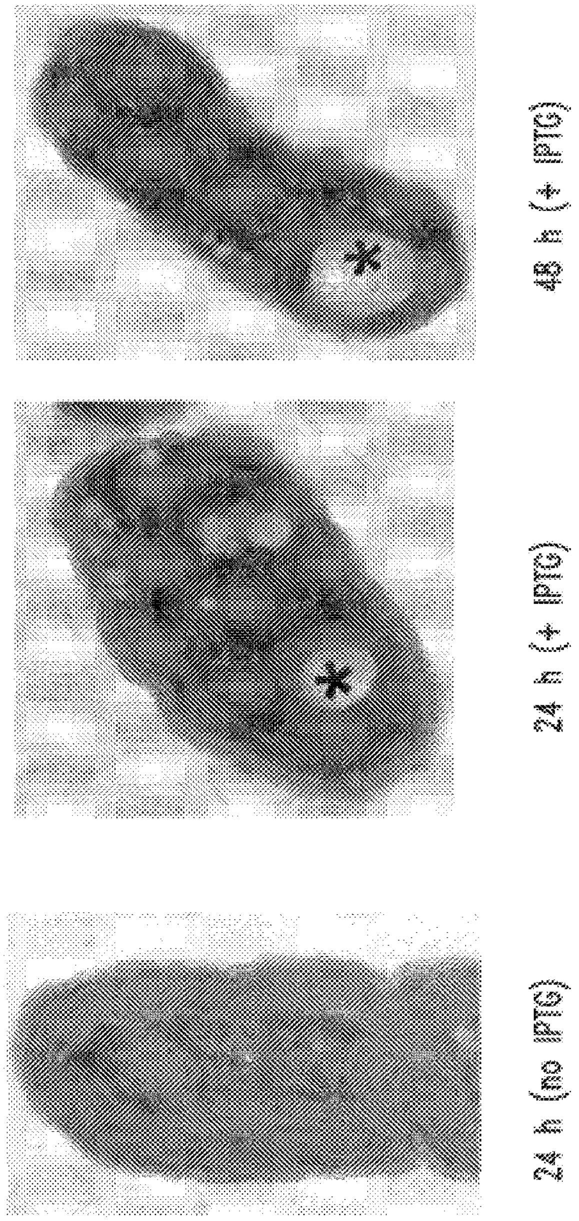
Figure 4A:
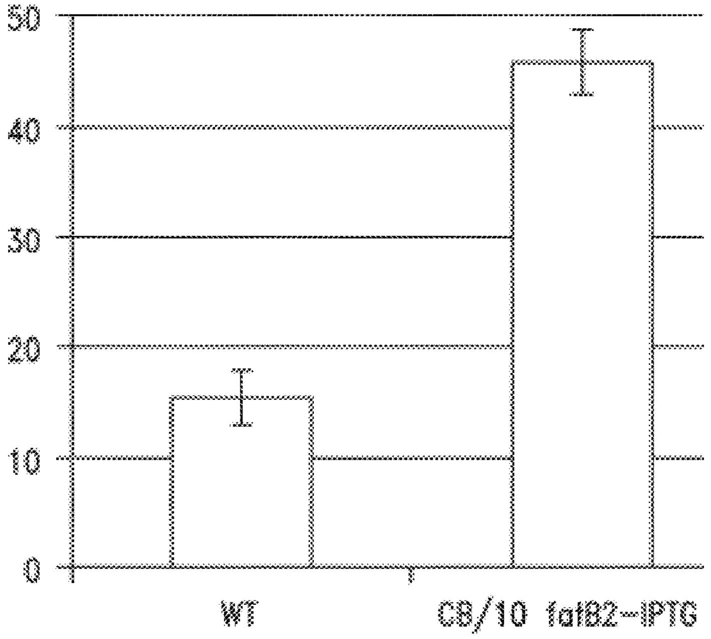
FIGS. 4A-4F show that overexpression of FatB enzymes in Cyanobacteria increases production of fatty acid methyl esters (FAMES) (y-axis for FIGS. 4A-4F is µg FAMES/OD/ml).
Figure 4B:
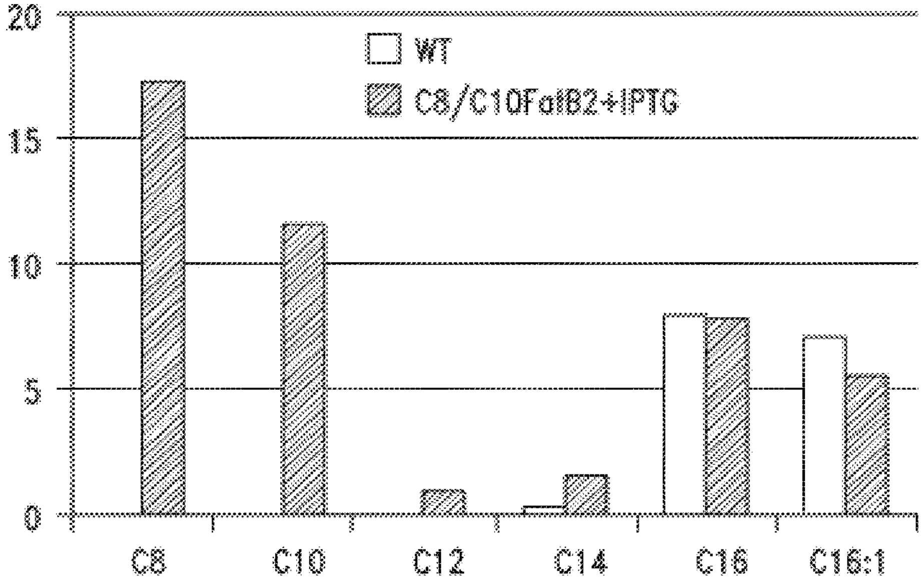
Figure 4C:
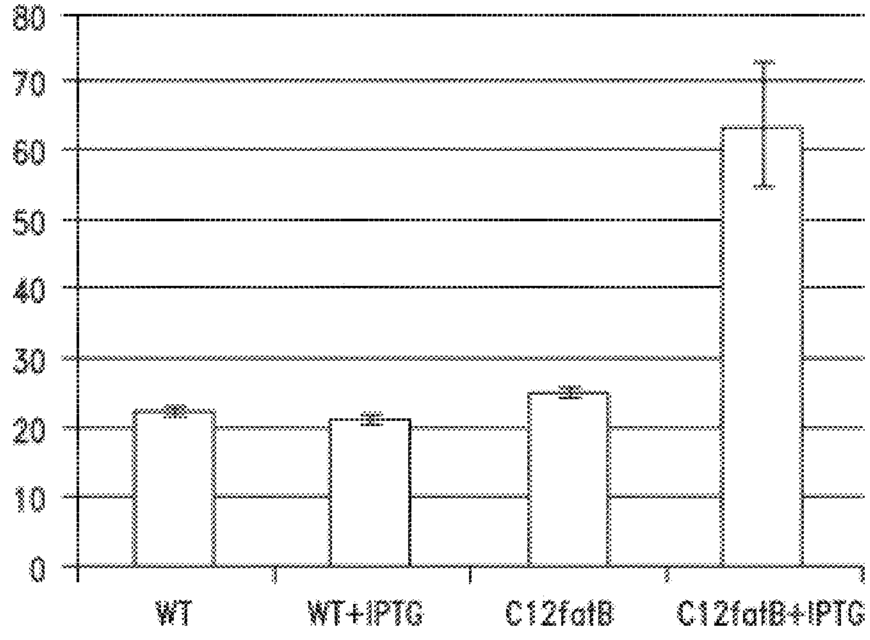
Figure 4D:
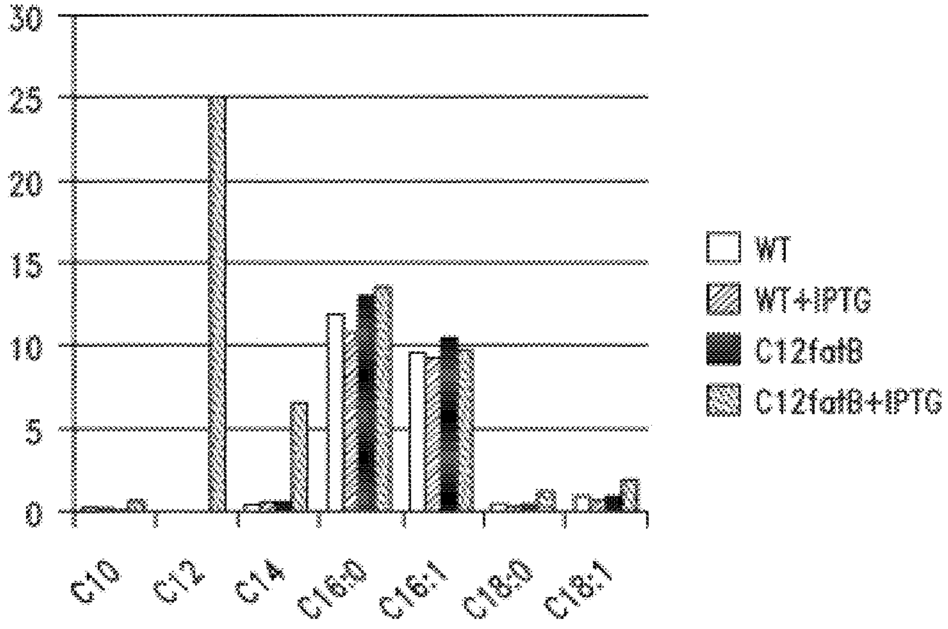
Figure 4E:
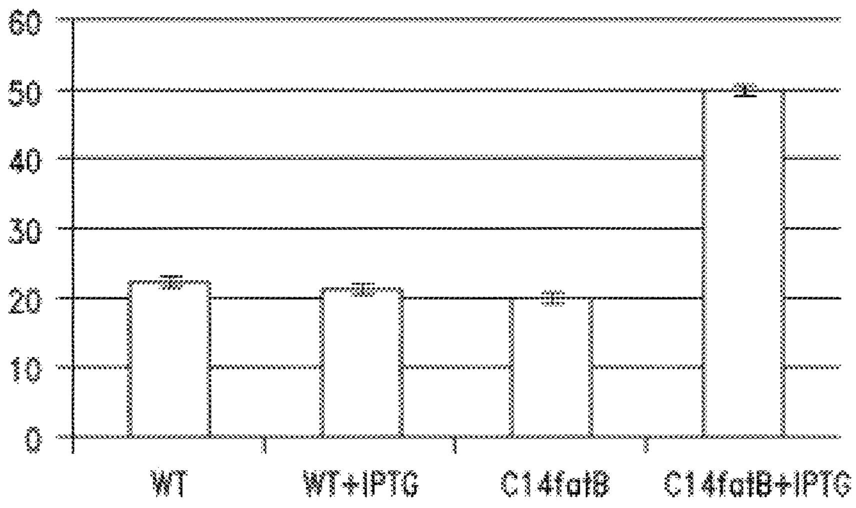
Figure 4F:
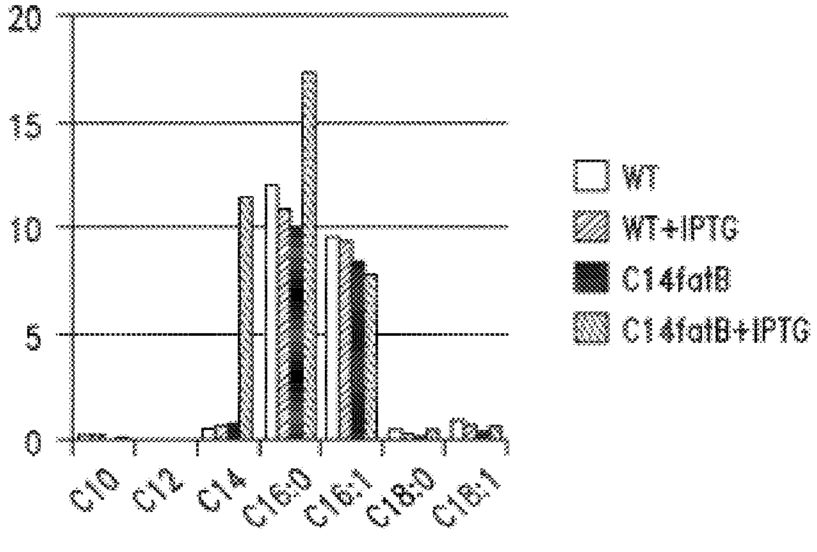

Transmission electron micrographs of PCC 7942 strain ADGAT/Aas/ACP grown in the presence (induced) or absence (uninduced) of IPTG were generated from cultures grown as described above. Induced cultures were sampled and pelleted by centrifugation at 24 and 48 hours post induction along with a 24 hour time-matched, uninduced control. Pellets were embedded in 1% agarose, cut into 2×2 mm segments and fixed in 2% glutaraldehyde followed by post fixation in 1% $OsO_4$. All agarose embedded fixed samples were subjected to stepwise (30%, 50%, 70%, 95%, 100%) dehydration in EtOH. Dehydrated samples were embedded in Spurrs plastic and baked at 60° C. for 24 hours or until plastic polymerization was complete. Thin sections were generated from hardened plastic embedded sample blocks. Sections were post-stained with uranyl acetate and lead citrate prior to imaging by electron microscopy. TEM images are shown in FIG. 3B for uninduced (no IPTG) and induced (+IPTG) at 24 and 48 hours post-induction. Asterisk (*) denotes larger lipid bodies.

Example 3

Generation of Cyanobacteria Expressing FatB Acyl-ACP Thioesterases and Resulting Accumulation of Free Fatty Acids of Specific Chain Lengths Plants contain well-characterized chloroplast localized acyl-ACP thioesterases which use acyl-ACPs as substrates (see, e.g., Jones et al., *Plant Cell.* 7:359-371, 1998). FatB types prefer acyl-ACPs having saturated acyl groups of a variety of lengths. FatAs have been reported to prefer unsaturated acyl groups. These thioesterases can be acyl chain length specific.

Acyl-chain specific fatBs thioesterases were overexpressed to favor the accumulation of FFA of a certain length. In particular, enzymes specific for C8/C10, C12, C14 and C16 acyl-ACP chains were overexpressed in cyanobacteria PCC 7942. In all cases, the genes expressed encoded the mature form of the proteins, predicted to lack the chloroplast signal 5' sequence based on alignments and published data. The sequences were synthesized and codon optimized for *Synechococcus elongatus* PCC 7942 expression using DNA2.0, received in a plasmid, subcloned using established molecular biology techniques into arabinose-inducible vector (pAM2314ara3(NS1)) for C16:0 acyl-ACP thioesterase or into IPTG inducible vectors (pNS3Ptrc) for C8/C10, C12 and C14 FatB acyl-ACP thioesterases and recombined into neutral sites 1 or 3 in the genome of *Synechococcus elongatus* PCC 7942, respectively. The sequence of the preprotein and the mature protein as well as those of the polynucleotides encoding them are shown in SEQ ID NOs:96-111. Colonies were selected from BG11-Cm (For C8/C10, C12 and C14FatBs) or -spec/strep plates for C16FatB, restreaked for isolation and tested by PCR for positive colonies.

As shown in FIGS. 4A-F, overexpression of the codon-optimized mature forms of plant FatBs in PCC7942 resulted in an increase in FFAs (see, e.g., FIGS. 4A, 4C and 4D), the FFAs accumulated were C8 and C10, C12 and C14 primarily in length for strains expressing C8/C10, C12 and C14 FatB expressing strains, respectively.

Figure 5:
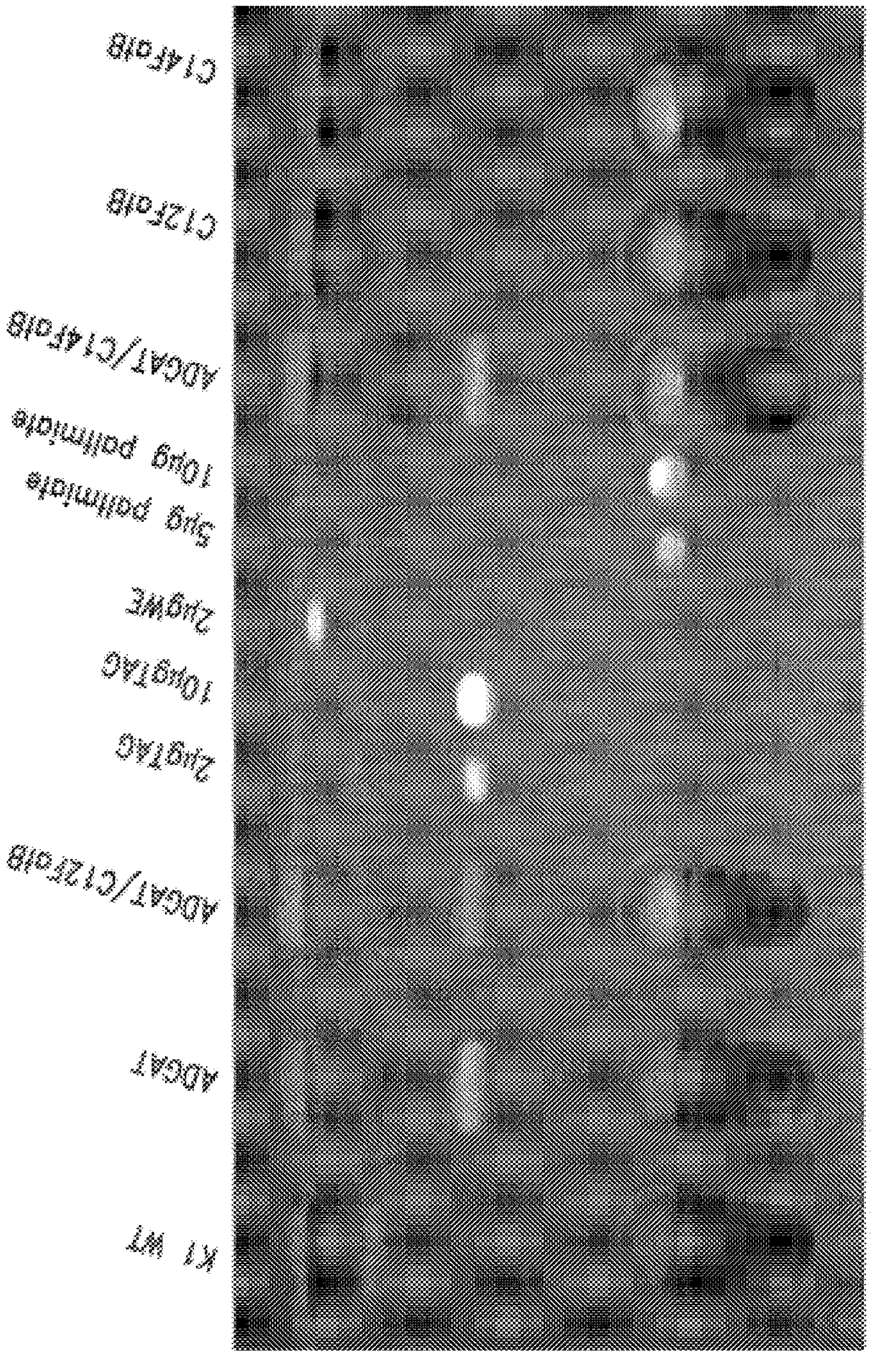

In order to increase acyl-ACP availability for TAG formation, these different acyl-ACP thioesterases were then expressed in DGAT-expressing strains of Cyanobacteria. As shown in FIG. 5, expression of the C12FatB and C14FatB resulted in increases in FFAs, and induction of DGATs resulted in increased formation of triacylglycerols (TAGs), while induction of both caused an increase in both FFA and the formation of TAGs.

Alternative Embodiments

1. A modified photosynthetic microorganism comprising:
(i) one or more introduced polynucleotides encoding an acyl carrier protein (ACP), an acyl-ACP synthetase (Aas), or both, and/or one or more overexpressed ACP or Aas polypeptides, or both; and
(ii) one or both of the following:
(a) one or more introduced polynucleotides encoding one or more lipid biosynthesis proteins and/or one or more overexpressed lipid biosynthesis proteins; and/or (b) reduced expression of one or more genes of a glycogen biosynthesis or storage pathway as compared to a wild-type photosynthetic microorganism, wherein said modified photosynthetic microorganism produces an increased amount of lipid as compared to an unmodified photosynthetic microorganism of the same species.

2. The modified photosynthetic microorganism of embodiment 1, wherein said photosynthetic microorganism is a Cyanobacterium.
3. The modified photosynthetic microorganism of embodiment 1, wherein said one or more lipid biosynthesis proteins are selected from an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, and a phospholipase (PL), including any combination thereof.
4. The modified photosynthetic microorganism of embodiment 3, comprising the ACP and the DGAT.
5. The modified photosynthetic microorganism of embodiment 3, comprising the Aas and the DGAT.
6. The modified photosynthetic microorganism of embodiment 3, comprising the ACP, the Aas, and the DGAT.
7. The modified photosynthetic microorganism of embodiment 3, comprising the ACP and the TES.
8. The modified photosynthetic microorganism of embodiment 3, comprising the Aas and the TES.
9. The modified photosynthetic microorganism of embodiment 3, comprising the ACP, the Aas, and the TES.
10. The modified photosynthetic microorganism of any one of embodiments 4-9, further comprising the ACCase.
11. The modified photosynthetic microorganism of any one of embodiments 4-10, further comprising the PAP.
12. The modified photosynthetic microorganism of any one of embodiments 4-11, further comprising the PL.
13. The modified photosynthetic microorganism of embodiment 3, comprising the ACP and the ACCase.
14. The modified photosynthetic microorganism of embodiment 3, comprising the Aas and the ACCase.
15. The modified photosynthetic microorganism of embodiment 3, comprising the ACP, the Aas, and the ACCase.
16. The modified photosynthetic microorganism of embodiment 3, comprising the ACP and the PAP.
17. The modified photosynthetic microorganism of embodiment 3, comprising the Aas and the PAP.
18. The modified photosynthetic microorganism of embodiment 3, comprising the ACP, the Aas, and the PAP.
19. The modified photosynthetic microorganism of embodiment 3, comprising the ACP and the PL.
20. The modified photosynthetic microorganism of embodiment 3, comprising the Aas and the PL.
21. The modified photosynthetic microorganism of embodiment 3, comprising the ACP, the Aas, and the PL.
22. The modified photosynthetic microorganism of any one of embodiments 16-21, further comprising the DGAT.
23. The modified photosynthetic microorganism of any one of embodiments 16-21, further comprising the TES.
24. The modified photosynthetic microorganism of embodiment 3, comprising the ACP, the DGAT, and the TAG hydrolase.
25. The modified photosynthetic microorganism of embodiment 3, comprising the Aas, the DGAT, and the TAG hydrolase.
26. The modified photosynthetic microorganism of embodiment 3, comprising the ACP, the Aas, the DGAT, and the TAG hydrolase.
27. The modified photosynthetic microorganism of embodiment 3, comprising the ACP, the DGAT, and the fatty acyl-CoA synthetase.
28. The modified photosynthetic microorganism of embodiment 3, comprising the Aas, the DGAT, and the fatty acyl-CoA synthetase.
29. The modified photosynthetic microorganism of embodiment 3, comprising the ACP, the Aas, the DGAT, and the fatty acyl-CoA synthetase.
30. The modified photosynthetic microorganism of any one of embodiments 24-29, further comprising any one or more of the TES, the ACCase, the PAP, or the PL.
31. The modified photosynthetic microorganism of any one of embodiments 1-30, wherein said modified photosynthetic microorganism has reduced expression of one or more genes of a glycogen biosynthesis or storage pathway as compared to a wild-type photosynthetic microorganism.
32. The modified photosynthetic microorganism of any of embodiments 1-31, comprising one or more introduced polynucleotides encoding a protein of a glycogen breakdown pathway.
33. The modified photosynthetic microorganism of embodiment 31, comprising a full or partial deletion of the one or more genes of a glycogen biosynthesis or storage pathway.
34. The modified photosynthetic microorganism of embodiment 33, wherein said one or more genes are selected from a glucose-1-phosphate adenyltransferase (glgC) gene and a phosphoglucomutase (pgm) gene.
35. The modified photosynthetic microorganism of any one of embodiments 1-34, wherein said ACP is a bacterial or a plant ACP.
36. The modified photosynthetic microorganism of embodiment 35, wherein said ACP is from *Synechococcus, Spinacia oleracea, Acinetobacter, Streptomyces*, or *Alcanivorax*.
37. The modified photosynthetic microorganism of embodiment 36, wherein said ACP has the amino acid sequence of any one of SEQ ID NOS:97, 99, 101, 103, or 105.
38. The modified photosynthetic microorganism of any one of embodiments 1-37, wherein said Aas is a bacterial Aas.
39. The modified photosynthetic microorganism of embodiment 38, wherein said Aas has the amino acid sequence set forth in SEQ ID NO:107.
40. The modified photosynthetic microorganism of any one of embodiments 3-39, wherein said TES is a TesA, a TesB, or a FatB thioesterase.
41. The modified photosynthetic microorganism of embodiment 40, wherein said TesA is *E. coli* TesA.
42. The modified photosynthetic microorganism of embodiment 41, wherein said tesA is a cytoplasmic-localized *E. coli* TesA.

43. The modified photosynthetic microorganism of embodiment 42, wherein said cytoplasmic *E. coli* TesA has the amino acid sequence of SEQ ID NO:94 (PldC (*TesA)).
44. The modified photosynthetic microorganism of embodiment 41, wherein said TesA is a periplasmic-localized *E. coli* TesA.
45. The modified photosynthetic microorganism of embodiment 44, wherein said periplasmic-localized TesA has the amino acid sequence of SEQ ID NO:86 (TesA).
46. The modified photosynthetic microorganism of embodiment 40, wherein said TesB is *E. coli* TesB.
47. The modified photosynthetic microorganism of embodiment 46, wherein said TesB has the amino acid sequence of SEQ ID NO:92 (TesB).
48. The modified photosynthetic microorganism of embodiment 40, wherein said FatB is a C8:0 FatB, a C12:0 FatB, a C14:0 FatB, or a C16:0 FatB.
49. The modified photosynthetic microorganism of embodiment 48, wherein said C8:0 FatB is from *Cuphea hookeriana*, said C12:0 FatB is from *Umbellularia californica*, said C14:0 FatB is from *Cinnamomum camphora*, or said C16:0 FatB is from *Cuphea hookeriana.*
50. The modified photosynthetic microorganism of any one of embodiments 3-49, wherein said DGAT is an *Acinetobacter* DGAT, a *Streptomyces* DGAT, or an *Alcanivorax* DGAT.
51. The method of any one of embodiments 3-50, wherein said ACP and said DGAT are derived from the same species.
52. The modified photosynthetic microorganism of any one of embodiments 3-51, wherein said ACCase is from *Synechococcus.*
53. The modified photosynthetic microorganism of any one of embodiments 3-52, wherein said PAP is selected from Pah1 from *S. cerevisiae*, PgpB from *E. coli*, and PAP from PCC6803.
54. The modified photosynthetic microorganism of any one of embodiments 3-53, wherein said PL is a phospholipase C (PLC).
55. The modified photosynthetic microorganism of any one of embodiments 3-54, wherein said PL has an amino acid sequence selected from any one of SEQ ID NOs:90 (Vupat1), 109, 111, 113, 115, 117, 119, 121, 123, 125, 127, 129, 131, and 133.
56. The modified photosynthetic microorganism of any one of embodiments 3-55, wherein said TAG hydrolase has an amino acid sequence selected from any one of SEQ ID NOs:135, 137, 139, and 141.
57. The modified photosynthetic microorganism of any one of embodiments 3-56, wherein said fatty acyl-CoA synthetase has an amino acid sequence selected from any one of SEQ ID NOS:143, 145, 147, and 149.
58. The modified photosynthetic microorganism of any one of embodiments 1-57, wherein one or more of said one or more introduced polynucleotide is present in one or more expression construct.
59. The modified photosynthetic microorganism of embodiment 58, wherein said expression construct is stably integrated into the genome of said modified photosynthetic microorganism.
60. The modified photosynthetic microorganism of embodiment 58 or embodiment 55, wherein said expression construct comprises an inducible promoter.
61. The modified photosynthetic microorganism of any one of embodiments 58-60, wherein one or more of the introduced polynucleotides are present in an expression construct comprising a weak promoter under non-induced conditions.
62. The modified photosynthetic microorganism of any one of embodiments 1-61 wherein one or more of said introduced polynucleotides are codon-optimized for expression in a Cyanobacterium.
63. The modified photosynthetic microorganism of embodiment 62, wherein said one or more codon-optimized polynucleotides are codon-optimized for expression in a *Synechococcus elongatus.*
64. The modified photosynthetic microorganism of any of embodiments 1-63, wherein said photosynthetic microorganism is a Cyanobacterium and said Cyanobacterium is a *Synechococcus elongatus.*
65. The modified Cyanobacterium of embodiment 64, wherein the *Synechococcus elongatus* is strain PCC 7942.
66. The modified Cyanobacterium of embodiment 65, wherein the Cyanobacterium is a salt tolerant variant of *Synechococcus elongatus* strain PCC 7942.
67. The modified photosynthetic microorganism of any of embodiments 1-63, wherein said photosynthetic microorganism is a Cyanobacterium and said Cyanobacterium is *Synechococcus* sp. PCC 7002.
68. The modified photosynthetic microorganism of any of embodiments 1-63, wherein said photosynthetic microorganism is a Cyanobacterium and said Cyanobacterium is *Synechocystis* sp. PCC 6803.
69. A method of producing a modified photosynthetic microorganism that produces or accumulates an increased amount of lipid as compared to a corresponding wild-type photosynthetic microorganism, comprising
(i) introducing one or more polynucleotides encoding an acyl carrier protein (ACP), an acyl-ACP synthetase (Aas), or both, and/or overexpressing an ACP or Aas polypeptide, in the photosynthetic microorganism; and
(ii) one or both of the following:
(a) introducing one or more polynucleotides encoding one or more lipid biosynthesis proteins, and/or overexpressing one or more lipid biosynthesis proteins, in the photosynthetic microorganism, and/or
(b) reducing expression of one or more genes of a glycogen biosynthesis or storage pathway as compared to a wild-type photosynthetic microorganism.
70. The modified photosynthetic microorganism of embodiment 69, wherein said photosynthetic microorganism is a Cyanobacterium.
71. The modified photosynthetic microorganism of embodiment 69, wherein said one or more lipid biosynthesis proteins are selected from an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, and a phospholipase (PL), including any combination thereof.
72. The method of embodiment 71, combining the ACP and the DGAT.
73. The method of embodiment 71, combining the Aas and the DGAT.
74. The method of embodiment 71, combining the ACP, the Aas, and the DGAT.

75. The method of embodiment 71, combining the ACP and the TES.
76. The method of embodiment 71, combining the Aas and the TES.
77. The method of embodiment 71, combining the ACP, the Aas, and the TES.
78. The method of any one of embodiments 72-77, further comprising the ACCase.
79. The method of any one of embodiments 72-78, further comprising the PAP.
80. The method of any one of embodiments 72-79, further comprising the PL.
81. The method of embodiment 71, combining the ACP and the ACCase.
82. The method of embodiment 71, combining the Aas and the ACCase.
83. The method of embodiment 71, combining the ACP, the Aas, and the ACCase.
84. The method of embodiment 71, combining the ACP and the PAP.
85. The method of embodiment 71, combining the Aas and the PAP.
86. The method of embodiment 71, combining the ACP, the Aas, and the PAP.
87. The method of embodiment 71, combining the ACP and the PL.
88. The method of embodiment 71, combining the Aas and the PL.
89. The method of embodiment 71, combining the ACP, the Aas, and the PL.
90. The method of any one of embodiments 81-89, further comprising the DGAT.
91. The method of any one of embodiments 81-90, further comprising the TES.
92. The method of embodiment 71, combining the ACP, the DGAT, and the TAG hydrolase.
93. The method of embodiment 71, combining the Aas, the DGAT, and the TAG hydrolase.
94. The method of embodiment 71, combining the ACP, the Aas, the DGAT, and the TAG hydrolase.
95. The method of embodiment 71, comprising the ACP, the DGAT, and the fatty acyl-CoA synthetase.
96. The method of embodiment 71, comprising the Aas, the DGAT, and the fatty acyl-CoA synthetase.
97. The method of embodiment 71, comprising the ACP, the Aas, the DGAT, and the fatty acyl-CoA synthetase.
98. The method of any one of embodiments 92-97, further comprising any one or more of the TES, the ACCase, the PAP, or the PL.
99. The method of any of embodiments 69-98, comprising introducing one or more polynucleotides encoding a protein of a glycogen breakdown pathway.
100. The method of embodiment 69, wherein (ii)(b) comprises a full or partial deletion of the one or more genes of a glycogen biosynthesis or storage pathway.
101. The method of embodiment 100, wherein said one or more genes are selected from a glucose-1-phosphate adenyltransferase (glgC) gene and a phosphoglucomutase (pgm) gene.
102. The method of any one of embodiments 69-101, wherein said ACP is a bacterial or a plant ACP.
103. The method of embodiment 102, wherein said ACP is from *Synechococcus, Spinacia oleracea, Acinetobacter, Streptomyces*, or *Alcanivorax*.
104. The method of embodiment 102, wherein said ACP has the amino acid sequence of any one of SEQ ID NOs:97, 99, 101, 103, or 105.
105. The method of any one of embodiments 69-104, wherein said Aas is a bacterial Aas.
106. The method of embodiment 105, wherein said Aas has the amino acid sequence set forth in SEQ ID NO:107.
107. The method of any one of embodiments 69-106, wherein said TES is a TesA, a TesB, or a FatB thioesterase.
108. The method of embodiment 107, wherein said TesA is *E. coli* TesA.
109. The method of embodiment 107, wherein said TesA is a cytoplasmic-localized *E. coli* TesA.
110. The method of embodiment 109, wherein said cytoplasmic *E. coli* TesA has the amino acid sequence of SEQ ID NO:94 (PldC(*TesA)).
111. The method of embodiment 110, wherein said TesA is a periplasmic-localized *E. coli* TesA.
112. The method of embodiment 111, wherein said periplasmic-localized TesA has the amino acid sequence of SEQ ID NO:86 (TesA).
113. The method of embodiment 107, wherein said TesB is *E. coli* TesB.
114. The method of embodiment 113, wherein said TesB has the amino acid sequence of SEQ ID NO:92 (TesB).
115. The method of embodiment 107, wherein said FatB is a C8:0 FatB, a C12:0 FatB, a C14:0 FatB, or a C16:0 FatB.
116. The method of embodiment 115, wherein said C8:0 FatB is from *Cuphea hookeriana*, said C12:0 FatB is from *Umbellularia californica*, said C14:0 FatB is from *Cinnamomum camphora*, or said C16:0 FatB is from *Cuphea hookeriana*.
117. The method of any one of embodiments 69-116, wherein said DGAT is an *Acinetobacter* DGAT, a *Streptomyces* DGAT, or an *Alcanivorax* DGAT.
118. The method of any one of embodiments 69-117, wherein said ACP and said DGAT are derived from the same species.
119. The method of any one of embodiments 69-118, wherein said ACCase is from *Synechococcus*.
120. The method of any one of embodiments 69-113, wherein said PAP is selected from Pah1 from *S. cerevisiae*, PgpB from *E. coli*, and PAP from PCC6803.
121. The method of any one of embodiments 69-120, wherein said PL is a phospholipase C (PLC).
122. The method of embodiment 121, wherein said PL has an amino acid sequence selected from any one of SEQ ID NOs:90 (Vupat1), 109, 111, 113, 115, 117, 119, 121, 123, 125, 127, 129, 131, and 133.
123. The method of any one of embodiments 71-122, wherein said TAG hydrolase has an amino acid sequence selected from any one of SEQ ID NOs:135, 137, 139, and 141.
124. The method of any one of embodiments 71-123, wherein said fatty acyl-CoA synthetase has an amino acid sequence selected from any one of SEQ ID NOs: 143, 145, 147, and 149.
125. A modified photosynthetic microorganism comprising one or more introduced polynucleotides encoding a diacylglycerol transferase (DGAT) and a triacylglycerol (TAG) hydrolase, and optionally an acyl-ACP thioesterase (TES), wherein said modified photosynthetic microorganism produces an increased amount of lipid as compared to an unmodified photosynthetic microorganism of the same species.
126. A modified photosynthetic microorganism comprising one or more introduced polynucleotides encoding a diacylglycerol transferase (DGAT) and a fatty acyl-CoA synthetase, and optionally an acyl-ACP thioesterase (TES), wherein said modified photosynthetic microorganism produces an increased amount of lipid as compared to an unmodified photosynthetic microorganism of the same species.

127. A method for the production of lipids, comprising culturing a modified photosynthetic microorganism according to any one of embodiments 1-68 or 125-126, wherein said modified photosynthetic microorganism accumulates an increased amount of lipid as compared to a corresponding wild-type photosynthetic microorganism.

128. The method of embodiment 127, wherein said culturing comprises inducing expression of one or more of said introduced polynucleotides.

129. The method of embodiment 127 or 128, wherein said culturing comprises culturing under static growth conditions.

130. The method of embodiment 128, wherein said inducing occurs under static growth conditions.

131. The method of embodiment 127, wherein said culturing comprises culturing in media supplemented with bicarbonate.

132. The method of embodiment 131, wherein the concentration of bicarbonate is selected from about 5, 10, 20, 50, 75, 100, 200, 300, 400, 500, 600, 700, 800, 900, and 1000 mM bicarbonate.

133. The method of embodiment 131, wherein the bicarbonate is present prior to inducing expressing of the introduced polynucleotide.

134. The method of embodiment 131, wherein the bicarbonate is present during induction of the introduced polynucleotide.

135. The method of embodiment 127, wherein said lipid comprises a triglyceride, a free fatty acid, or both.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A modified Cyanobacterium comprising:

(i) a first modification that increases acyl-ACP synthesis in the modified Cyanobacterium, the first modification comprising an introduced polynucleotide encoding an acyl carrier protein (ACP); and (ii) a second modification that increases a lipid biosynthesis protein in the modified Cyanobacterium, the second modification comprising an introduced polynucleotide encoding a lipid biosynthesis protein, wherein said modified Cyanobacterium produces an increased amount of lipid as compared to a corresponding wild-type Cyanobacterium, a corresponding Cyanobacterium having only the first modification, or a corresponding Cyanobacterium having only the second modification.

2. The modified Cyanobacterium of claim 1, wherein the lipid biosynthesis protein is selected from the group consisting of an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, a phospholipase (PL), and combinations thereof.

3. The modified Cyanobacterium of claim 2, wherein the lipid biosynthesis protein is selected from the group consisting of TES and DGAT.

4. The modified Cyanobacterium of claim 3, wherein the TES is a TesA, a TesB, or a FatB thioesterase, and the DGAT is a prokaryotic DGAT that uses acyl-ACP as a substrate.

5. The modified Cyanobacterium of claim 1, further comprising a third modification that reduces glycogen accumulation in the modified Cyanobacterium, the third modification comprises (i) a full or partial deletion of a gene of a glycogen biosynthesis pathway or a glycogen storage pathway or (ii) reduced expression of a gene of a glycogen biosynthesis pathway or a glycogen storage pathway as compared to the corresponding wild-type Cyanobacterium.

6. The modified Cyanobacterium of claim 5, wherein the gene is selected from a glucose-1-phosphate adenyltransferase (glgC) gene and a phosphoglucomutase (pgm) gene.

7. The modified Cyanobacterium of claim 1, further comprising a third modification that reduces glycogen accumulation in the modified Cyanobacterium, the third modification comprises an introduced polynucleotide encoding a protein of a glycogen breakdown pathway or an overexpressed glycogen breakdown pathway gene.

8. The modified Cyanobacterium of claim 1, wherein said Cyanobacterium is an *Arthrospira*; a *Synechococcus elongatus* sp. PCC 7942; a salt tolerant variant of *Synechococcus elongatus* sp. PCC 7942; a *Synechococcus elongatus* sp. PCC 7002; or a *Synechocystis elongatus* sp. PCC 6803.

9. A method of producing a modified Cyanobacterium that produces or accumulates an increased amount of lipid as compared to a corresponding wild-type Cyanobacterium, comprising (i) making a first modification that increases acyl-ACP synthesis in the modified Cyanobacterium, the first modification comprising introducing a polynucleotide encoding an acyl carrier protein (ACP); and (ii) making a second modification that increases a lipid biosynthesis protein in the modified Cyanobacterium, the second modification comprising introducing a polynucleotide encoding a lipid biosynthesis protein.

10. The method of claim 9, wherein the lipid biosynthesis protein is-selected from the group consisting of an acyl-ACP thioesterase (TES), a diacylglycerol acyltransferase (DGAT), an acetyl coenzyme A carboxylase (ACCase), a phosphatidic acid phosphatase (PAP), a triacylglycerol (TAG) hydrolase, a fatty acyl-CoA synthetase, a phospholipase (PL), and combinations thereof.

11. The method of claim 10, wherein the lipid biosynthesis protein is selected from the group consisting of TES and DGAT, said TES is a TesA, a TesB, or a FatB thioesterase, and said DGAT is a prokaryotic DGAT that uses acyl-ACP as a substrate.

12. The method of claim 9, further comprising making a third modification that reduces glycogen accumulation in the modified Cyanobacterium, the third modification comprising deleting, fully or partially, a gene of a glycogen biosynthesis pathway or a glycogen storage pathway.

13. The method of claim 12, wherein the gene is selected from a glucose-1-phosphate adenyltransferase (glgC) gene and a phosphoglucomutase (pgm) gene.

14. The method of claim 9, further comprising making a third modification that reduces glycogen accumulation in the modified Cyanobacterium, the third modification comprising introducing a polynucleotide encoding a protein of a glycogen breakdown pathway or overexpressing a glycogen breakdown pathway gene.

15. The method of claim 9 wherein said Cyanobacterium is an *Arthrospira*; a *Synechococcus elongatus* sp. PCC 7942; a salt tolerant variant of *Synechococcus elongatus* sp. PCC 7942; a *Synechococcus elongatus* sp. PCC 7002; or a *Synechocystis elongatus* sp. PCC 6803.

16. A method for producing lipids, comprising culturing the modified Cyanobacterium according to claim 1.

17. The method according to claim 16, wherein said lipids comprise a triglyceride, a free fatty acid, or both.

18. The method of claim 9, wherein making the first modification further comprises introducing a polynucleotide encoding an acyl-ACP synthetase (Aas).

19. The modified Cyanobacterium of claim 1, wherein the first modification further comprises an introduced polynucleotide encoding an acyl-ACP synthetase (Aas).

20. The modified Cyanobacterium of claim 19, wherein:

the ACP is a bacterial or a plant ACP, or the Aas is a bacterial Aas.

* * * * *

SEQUENCE LISTING

```
<160> NUMBER OF SEQ ID NOS: 165

<210> SEQ ID NO 1
<211> LENGTH: 458
<212> TYPE: PRT
<213> ORGANISM: Acinetobacter baylii sp.

<400> SEQUENCE: 1

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
```

-continued

```
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455


<210> SEQ ID NO 2
<211> LENGTH: 864
<212> TYPE: PRT
<213> ORGANISM: Saccharomyces cerevisiae

<400> SEQUENCE: 2

Met Glu Phe Gln Tyr Val Gly Arg Ala Leu Gly Ser Val Ser Lys Thr
 1               5                  10                  15

Trp Ser Ser Ile Asn Pro Ala Thr Leu Ser Gly Ala Ile Asp Val Ile
            20                  25                  30

Val Val Glu His Pro Asp Gly Arg Leu Ser Cys Ser Pro Phe His Val
        35                  40                  45

Arg Phe Gly Lys Phe Gln Ile Leu Lys Pro Ser Gln Lys Lys Val Gln
    50                  55                  60

Val Phe Ile Asn Glu Lys Leu Ser Asn Met Pro Met Lys Leu Ser Asp
65                  70                  75                  80

Ser Gly Glu Ala Tyr Phe Val Phe Glu Met Gly Asp Gln Val Thr Asp
                85                  90                  95
```

-continued

```
Val Pro Asp Glu Leu Leu Val Ser Pro Val Met Ser Ala Thr Ser Ser
            100                 105                 110

Pro Pro Gln Ser Pro Glu Thr Ser Ile Leu Glu Gly Gly Thr Glu Gly
        115                 120                 125

Glu Gly Glu Gly Glu Asn Glu Asn Lys Lys Lys Glu Lys Lys Val Leu
    130                 135                 140

Glu Glu Pro Asp Phe Leu Asp Ile Asn Asp Thr Gly Asp Ser Gly Ser
145                 150                 155                 160

Lys Asn Ser Glu Thr Thr Gly Ser Leu Ser Pro Thr Glu Ser Ser Thr
                165                 170                 175

Thr Thr Pro Pro Asp Ser Val Glu Glu Arg Lys Leu Val Glu Gln Arg
            180                 185                 190

Thr Lys Asn Phe Gln Gln Lys Leu Asn Lys Lys Leu Thr Glu Ile His
        195                 200                 205

Ile Pro Ser Lys Leu Asp Asn Asn Gly Asp Leu Leu Leu Asp Thr Glu
    210                 215                 220

Gly Tyr Lys Pro Asn Lys Asn Met Met His Asp Thr Asp Ile Gln Leu
225                 230                 235                 240

Lys Gln Leu Leu Lys Asp Glu Phe Gly Asn Asp Ser Asp Ile Ser Ser
                245                 250                 255

Phe Ile Lys Glu Asp Lys Asn Gly Asn Ile Lys Ile Val Asn Pro Tyr
            260                 265                 270

Glu His Leu Thr Asp Leu Ser Pro Pro Gly Thr Pro Pro Thr Met Ala
        275                 280                 285

Thr Ser Gly Ser Val Leu Gly Leu Asp Ala Met Glu Ser Gly Ser Thr
    290                 295                 300

Leu Asn Ser Leu Ser Ser Ser Pro Ser Gly Ser Asp Thr Glu Asp Glu
305                 310                 315                 320

Thr Ser Phe Ser Lys Glu Gln Ser Ser Lys Ser Glu Lys Thr Ser Lys
                325                 330                 335

Lys Gly Thr Ala Gly Ser Gly Glu Thr Glu Lys Arg Tyr Ile Arg Thr
            340                 345                 350

Ile Arg Leu Thr Asn Asp Gln Leu Lys Cys Leu Asn Leu Thr Tyr Gly
        355                 360                 365

Glu Asn Asp Leu Lys Phe Ser Val Asp His Gly Lys Ala Ile Val Thr
    370                 375                 380

Ser Lys Leu Phe Val Trp Arg Trp Asp Val Pro Ile Val Ile Ser Asp
385                 390                 395                 400

Ile Asp Gly Thr Ile Thr Lys Ser Asp Ala Leu Gly His Val Leu Ala
                405                 410                 415

Met Ile Gly Lys Asp Trp Thr His Leu Gly Val Ala Lys Leu Phe Ser
            420                 425                 430

Glu Ile Ser Arg Asn Gly Tyr Asn Ile Leu Tyr Leu Thr Ala Arg Ser
        435                 440                 445

Ala Gly Gln Ala Asp Ser Thr Arg Ser Tyr Leu Arg Ser Ile Glu Gln
    450                 455                 460

Asn Gly Ser Lys Leu Pro Asn Gly Pro Val Ile Leu Ser Pro Asp Arg
465                 470                 475                 480

Thr Met Ala Ala Leu Arg Arg Glu Val Ile Leu Lys Lys Pro Glu Val
                485                 490                 495

Phe Lys Ile Ala Cys Leu Asn Asp Ile Arg Ser Leu Tyr Phe Glu Asp
            500                 505                 510

Ser Asp Asn Glu Val Asp Thr Glu Glu Lys Ser Thr Pro Phe Phe Ala
```

-continued

```
        515                 520                 525

Gly Phe Gly Asn Arg Ile Thr Asp Ala Leu Ser Tyr Arg Thr Val Gly
    530                 535                 540

Ile Pro Ser Ser Arg Ile Phe Thr Ile Asn Thr Glu Gly Glu Val His
545                 550                 555                 560

Met Glu Leu Leu Glu Leu Ala Gly Tyr Arg Ser Ser Tyr Ile His Ile
                565                 570                 575

Asn Glu Leu Val Asp His Phe Phe Pro Pro Val Ser Leu Asp Ser Val
            580                 585                 590

Asp Leu Arg Thr Asn Thr Ser Met Val Pro Gly Ser Pro Pro Asn Arg
        595                 600                 605

Thr Leu Asp Asn Phe Asp Ser Glu Ile Thr Ser Gly Arg Lys Thr Leu
    610                 615                 620

Phe Arg Gly Asn Gln Glu Glu Lys Phe Thr Asp Val Asn Phe Trp Arg
625                 630                 635                 640

Asp Pro Leu Val Asp Ile Asp Asn Leu Ser Asp Ile Ser Asn Asp Asp
                645                 650                 655

Ser Asp Asn Ile Asp Glu Asp Thr Asp Val Ser Gln Gln Ser Asn Ile
            660                 665                 670

Ser Arg Asn Arg Ala Asn Ser Val Lys Thr Ala Lys Val Thr Lys Ala
        675                 680                 685

Pro Gln Arg Asn Val Ser Gly Ser Thr Asn Asn Asn Glu Val Leu Ala
    690                 695                 700

Ala Ser Ser Asp Val Glu Asn Ala Ser Asp Leu Val Ser Ser His Ser
705                 710                 715                 720

Ser Ser Gly Ser Thr Pro Asn Lys Ser Thr Met Ser Lys Gly Asp Ile
                725                 730                 735

Gly Lys Gln Ile Tyr Leu Glu Leu Gly Ser Pro Leu Ala Ser Pro Lys
            740                 745                 750

Leu Arg Tyr Leu Asp Asp Met Asp Asp Glu Asp Ser Asn Tyr Asn Arg
        755                 760                 765

Thr Lys Ser Arg Arg Ala Ser Ser Ala Ala Ala Thr Ser Ile Asp Lys
    770                 775                 780

Glu Phe Lys Lys Leu Ser Val Ser Lys Ala Gly Ala Pro Thr Arg Ile
785                 790                 795                 800

Val Ser Lys Ile Asn Val Ser Asn Asp Val His Ser Leu Gly Asn Ser
                805                 810                 815

Asp Thr Glu Ser Arg Arg Glu Gln Ser Val Asn Glu Thr Gly Arg Asn
            820                 825                 830

Gln Leu Pro His Asn Ser Met Asp Asp Lys Asp Leu Asp Ser Arg Val
        835                 840                 845

Ser Asp Glu Phe Asp Asp Asp Glu Phe Asp Glu Asp Glu Phe Glu Asp
    850                 855                 860


<210> SEQ ID NO 3
<211> LENGTH: 2235
<212> TYPE: PRT
<213> ORGANISM: Saccharomyces cerevisiae

<400> SEQUENCE: 3

Met Glu Phe Ser Glu Glu Ser Leu Phe Glu Ser Ser Pro Gln Lys Met
 1               5                  10                  15

Glu Tyr Glu Ile Thr Asn Tyr Ser Glu Arg His Thr Glu Leu Pro Gly
            20                  25                  30
```

-continued

```
His Phe Ile Gly Leu Asn Thr Val Asp Lys Leu Glu Glu Ser Pro Leu
        35                  40                  45

Arg Asp Phe Val Lys Ser His Gly Gly His Thr Val Ile Ser Lys Ile
    50                  55                  60

Leu Ile Ala Asn Asn Gly Ile Ala Ala Val Lys Glu Ile Arg Ser Val
65                  70                  75                  80

Arg Lys Trp Ala Tyr Glu Thr Phe Gly Asp Asp Arg Thr Val Gln Phe
                85                  90                  95

Val Ala Met Ala Thr Pro Glu Asp Leu Glu Ala Asn Ala Glu Tyr Ile
            100                 105                 110

Arg Met Ala Asp Gln Tyr Ile Glu Val Pro Gly Gly Thr Asn Asn Asn
        115                 120                 125

Asn Tyr Ala Asn Val Asp Leu Ile Val Asp Ile Ala Glu Arg Ala Asp
    130                 135                 140

Val Asp Ala Val Trp Ala Gly Trp Gly His Ala Ser Glu Asn Pro Leu
145                 150                 155                 160

Leu Pro Glu Lys Leu Ser Gln Ser Lys Arg Lys Val Ile Phe Ile Gly
                165                 170                 175

Pro Pro Gly Asn Ala Met Arg Ser Leu Gly Asp Lys Ile Ser Ser Thr
            180                 185                 190

Ile Val Ala Gln Ser Ala Lys Val Pro Cys Ile Pro Trp Ser Gly Thr
        195                 200                 205

Gly Val Asp Thr Val His Val Asp Glu Lys Thr Gly Leu Val Ser Val
    210                 215                 220

Asp Asp Asp Ile Tyr Gln Lys Gly Cys Cys Thr Ser Pro Glu Asp Gly
225                 230                 235                 240

Leu Gln Lys Ala Lys Arg Ile Gly Phe Pro Val Met Ile Lys Ala Ser
                245                 250                 255

Glu Gly Gly Gly Gly Lys Gly Ile Arg Gln Val Glu Arg Glu Glu Asp
            260                 265                 270

Phe Ile Ala Leu Tyr His Gln Ala Ala Asn Glu Ile Pro Gly Ser Pro
        275                 280                 285

Ile Phe Ile Met Lys Leu Ala Gly Arg Ala Arg His Leu Glu Val Gln
    290                 295                 300

Leu Leu Ala Asp Gln Tyr Gly Thr Asn Ile Ser Leu Phe Gly Arg Asp
305                 310                 315                 320

Cys Ser Val Gln Arg Arg His Gln Lys Ile Ile Glu Glu Ala Pro Val
                325                 330                 335

Thr Ile Ala Lys Ala Glu Thr Phe His Glu Met Glu Lys Ala Ala Val
            340                 345                 350

Arg Leu Gly Lys Leu Val Gly Tyr Val Ser Ala Gly Thr Val Glu Tyr
        355                 360                 365

Leu Tyr Ser His Asp Asp Gly Lys Phe Tyr Phe Leu Glu Leu Asn Pro
    370                 375                 380

Arg Leu Gln Val Glu His Pro Thr Thr Glu Met Val Ser Gly Val Asn
385                 390                 395                 400

Leu Pro Ala Ala Gln Leu Gln Ile Ala Met Gly Ile Pro Met His Arg
                405                 410                 415

Ile Ser Asp Ile Arg Thr Leu Tyr Gly Met Asn Pro His Ser Ala Ser
            420                 425                 430

Glu Ile Asp Phe Glu Phe Lys Thr Gln Asp Ala Thr Lys Lys Gln Arg
        435                 440                 445

Arg Pro Ile Pro Lys Gly His Cys Thr Ala Cys Arg Ile Thr Ser Glu
```

```
    450                 455                 460

Asp Pro Asn Asp Gly Phe Lys Pro Ser Gly Gly Thr Leu His Glu Leu
465                 470                 475                 480

Asn Phe Arg Ser Ser Ser Asn Val Trp Gly Tyr Phe Ser Val Gly Asn
                485                 490                 495

Asn Gly Asn Ile His Ser Phe Ser Asp Ser Gln Phe Gly His Ile Phe
            500                 505                 510

Ala Phe Gly Glu Asn Arg Gln Ala Ser Arg Lys His Met Val Val Ala
        515                 520                 525

Leu Lys Glu Leu Ser Ile Arg Gly Asp Phe Arg Thr Thr Val Glu Tyr
    530                 535                 540

Leu Ile Lys Leu Leu Glu Thr Glu Asp Phe Glu Asp Asn Thr Ile Thr
545                 550                 555                 560

Thr Gly Trp Leu Asp Asp Leu Ile Thr His Lys Met Thr Ala Glu Lys
                565                 570                 575

Pro Asp Pro Thr Leu Ala Val Ile Cys Gly Ala Ala Thr Lys Ala Phe
            580                 585                 590

Leu Ala Ser Glu Glu Ala Arg His Lys Tyr Ile Glu Ser Leu Gln Lys
        595                 600                 605

Gly Gln Val Leu Ser Lys Asp Leu Leu Gln Thr Met Phe Pro Val Asp
    610                 615                 620

Phe Ile His Glu Gly Lys Arg Tyr Lys Phe Thr Val Ala Lys Ser Gly
625                 630                 635                 640

Asn Asp Arg Tyr Thr Leu Phe Ile Asn Gly Ser Lys Cys Asp Ile Ile
                645                 650                 655

Leu Arg Gln Leu Ser Asp Gly Gly Leu Leu Ile Ala Ile Gly Gly Lys
            660                 665                 670

Ser His Thr Ile Tyr Trp Lys Glu Glu Val Ala Ala Thr Arg Leu Ser
        675                 680                 685

Val Asp Ser Met Thr Thr Leu Leu Glu Val Glu Asn Asp Pro Thr Gln
    690                 695                 700

Leu Arg Thr Pro Ser Pro Gly Lys Leu Val Lys Phe Leu Val Glu Asn
705                 710                 715                 720

Gly Glu His Ile Ile Lys Gly Gln Pro Tyr Ala Glu Ile Glu Val Met
                725                 730                 735

Lys Met Gln Met Pro Leu Val Ser Gln Glu Asn Gly Ile Val Gln Leu
            740                 745                 750

Leu Lys Gln Pro Gly Ser Thr Ile Val Ala Gly Asp Ile Met Ala Ile
        755                 760                 765

Met Thr Leu Asp Asp Pro Ser Lys Val Lys His Ala Leu Pro Phe Glu
    770                 775                 780

Gly Met Leu Pro Asp Phe Gly Ser Pro Val Ile Glu Gly Thr Lys Pro
785                 790                 795                 800

Ala Tyr Lys Phe Lys Ser Leu Val Ser Thr Leu Glu Asn Ile Leu Lys
                805                 810                 815

Gly Tyr Asp Asn Gln Val Ile Met Asn Ala Ser Leu Gln Gln Leu Ile
            820                 825                 830

Glu Val Leu Arg Asn Pro Lys Leu Pro Tyr Ser Glu Trp Lys Leu His
        835                 840                 845

Ile Ser Ala Leu His Ser Arg Leu Pro Ala Lys Leu Asp Glu Gln Met
    850                 855                 860

Glu Glu Leu Val Ala Arg Ser Leu Arg Arg Gly Ala Val Phe Pro Ala
865                 870                 875                 880
```

-continued

```
Arg Gln Leu Ser Lys Leu Ile Asp Met Ala Val Lys Asn Pro Glu Tyr
                885                 890                 895

Asn Pro Asp Lys Leu Leu Gly Ala Val Val Glu Pro Leu Ala Asp Ile
            900                 905                 910

Ala His Lys Tyr Ser Asn Gly Leu Glu Ala His Glu His Ser Ile Phe
        915                 920                 925

Val His Phe Leu Glu Glu Tyr Tyr Glu Val Glu Lys Leu Phe Asn Gly
    930                 935                 940

Pro Asn Val Arg Glu Glu Asn Ile Ile Leu Lys Leu Arg Asp Glu Asn
945                 950                 955                 960

Pro Lys Asp Leu Asp Lys Val Ala Leu Thr Val Leu Ser His Ser Lys
                965                 970                 975

Val Ser Ala Lys Asn Asn Leu Ile Leu Ala Ile Leu Lys His Tyr Gln
            980                 985                 990

Pro Leu Cys Lys Leu Ser Ser Lys Val Ser Ala Ile Phe Ser Thr Pro
        995                 1000                1005

Leu Gln His Ile Val Glu Leu Glu Ser Lys Ala Thr Ala Lys Val Ala
    1010                1015                1020

Leu Gln Ala Arg Glu Ile Leu Ile Gln Gly Ala Leu Pro Ser Val Lys
1025                1030                1035                1040

Glu Arg Thr Glu Gln Ile Glu His Ile Leu Lys Ser Ser Val Val Lys
                1045                1050                1055

Val Ala Tyr Gly Ser Ser Asn Pro Lys Arg Ser Glu Pro Asp Leu Asn
            1060                1065                1070

Ile Leu Lys Asp Leu Ile Asp Ser Asn Tyr Val Val Phe Asp Val Leu
        1075                1080                1085

Leu Gln Phe Leu Thr His Gln Asp Pro Val Val Thr Ala Ala Ala Ala
    1090                1095                1100

Gln Val Tyr Ile Arg Arg Ala Tyr Arg Ala Tyr Thr Ile Gly Asp Ile
1105                1110                1115                1120

Arg Val His Glu Gly Val Thr Val Pro Ile Val Glu Trp Lys Phe Gln
                1125                1130                1135

Leu Pro Ser Ala Ala Phe Ser Thr Phe Pro Thr Val Lys Ser Lys Met
            1140                1145                1150

Gly Met Asn Arg Ala Val Ser Val Ser Asp Leu Ser Tyr Val Ala Asn
        1155                1160                1165

Ser Gln Ser Ser Pro Leu Arg Glu Gly Ile Leu Met Ala Val Asp His
    1170                1175                1180

Leu Asp Asp Val Asp Glu Ile Leu Ser Gln Ser Leu Glu Val Ile Pro
1185                1190                1195                1200

Arg His Gln Ser Ser Ser Asn Gly Pro Ala Pro Asp Arg Ser Gly Ser
                1205                1210                1215

Ser Ala Ser Leu Ser Asn Val Ala Asn Val Cys Val Ala Ser Thr Glu
            1220                1225                1230

Gly Phe Glu Ser Glu Glu Glu Ile Leu Val Arg Leu Arg Glu Ile Leu
        1235                1240                1245

Asp Leu Asn Lys Gln Glu Leu Ile Asn Ala Ser Ile Arg Arg Ile Thr
    1250                1255                1260

Phe Met Phe Gly Phe Lys Asp Gly Ser Tyr Pro Lys Tyr Tyr Thr Phe
1265                1270                1275                1280

Asn Gly Pro Asn Tyr Asn Glu Asn Glu Thr Ile Arg His Ile Glu Pro
                1285                1290                1295
```

```
Ala Leu Ala Phe Gln Leu Glu Leu Gly Arg Leu Ser Asn Phe Asn Ile
            1300                1305                1310

Lys Pro Ile Phe Thr Asp Asn Arg Asn Ile His Val Tyr Glu Ala Val
        1315                1320                1325

Ser Lys Thr Ser Pro Leu Asp Lys Arg Phe Phe Thr Arg Gly Ile Ile
    1330                1335                1340

Arg Thr Gly His Ile Arg Asp Asp Ile Ser Ile Gln Glu Tyr Leu Thr
1345                1350                1355                1360

Ser Glu Ala Asn Arg Leu Met Ser Asp Ile Leu Asp Asn Leu Glu Val
                1365                1370                1375

Thr Asp Thr Ser Asn Ser Asp Leu Asn His Ile Phe Ile Asn Phe Ile
            1380                1385                1390

Ala Val Phe Asp Ile Ser Pro Glu Asp Val Glu Ala Ala Phe Gly Gly
        1395                1400                1405

Phe Leu Glu Arg Phe Gly Lys Arg Leu Leu Arg Leu Arg Val Ser Ser
    1410                1415                1420

Ala Glu Ile Arg Ile Ile Ile Lys Asp Pro Gln Thr Gly Ala Pro Val
1425                1430                1435                1440

Pro Leu Arg Ala Leu Ile Asn Asn Val Ser Gly Tyr Val Ile Lys Thr
                1445                1450                1455

Glu Met Tyr Thr Glu Val Lys Asn Ala Lys Gly Glu Trp Val Phe Lys
            1460                1465                1470

Ser Leu Gly Lys Pro Gly Ser Met His Leu Arg Pro Ile Ala Thr Pro
        1475                1480                1485

Tyr Pro Val Lys Glu Trp Leu Gln Pro Lys Arg Tyr Lys Ala His Leu
    1490                1495                1500

Met Gly Thr Thr Tyr Val Tyr Asp Phe Pro Glu Leu Phe Arg Gln Ala
1505                1510                1515                1520

Ser Ser Ser Gln Trp Lys Asn Phe Ser Ala Asp Val Lys Leu Thr Asp
                1525                1530                1535

Asp Phe Phe Ile Ser Asn Glu Leu Ile Glu Asp Glu Asn Gly Glu Leu
            1540                1545                1550

Thr Glu Val Glu Arg Glu Pro Gly Ala Asn Ala Ile Gly Met Val Ala
        1555                1560                1565

Phe Lys Ile Thr Val Lys Thr Pro Glu Tyr Pro Arg Gly Arg Gln Phe
    1570                1575                1580

Val Val Val Ala Asn Asp Ile Thr Phe Lys Ile Gly Ser Phe Gly Pro
1585                1590                1595                1600

Gln Glu Asp Glu Phe Phe Asn Lys Val Thr Glu Tyr Ala Arg Lys Arg
                1605                1610                1615

Gly Ile Pro Arg Ile Tyr Leu Ala Ala Asn Ser Gly Ala Arg Ile Gly
            1620                1625                1630

Met Ala Glu Glu Ile Val Pro Leu Phe Gln Val Ala Trp Asn Asp Ala
        1635                1640                1645

Ala Asn Pro Asp Lys Gly Phe Gln Tyr Leu Tyr Leu Thr Ser Glu Gly
    1650                1655                1660

Met Glu Thr Leu Lys Lys Phe Asp Lys Glu Asn Ser Val Leu Thr Glu
1665                1670                1675                1680

Arg Thr Val Ile Asn Gly Glu Glu Arg Phe Val Ile Lys Thr Ile Ile
                1685                1690                1695

Gly Ser Glu Asp Gly Leu Gly Val Glu Cys Leu Arg Gly Ser Gly Leu
            1700                1705                1710

Ile Ala Gly Ala Thr Ser Arg Ala Tyr His Asp Ile Phe Thr Ile Thr
```

```
        1715                1720                1725

Leu Val Thr Cys Arg Ser Val Gly Ile Gly Ala Tyr Leu Val Arg Leu
    1730                1735                1740

Gly Gln Arg Ala Ile Gln Val Glu Gly Gln Pro Ile Ile Leu Thr Gly
1745                1750                1755                1760

Ala Pro Ala Ile Asn Lys Met Leu Gly Arg Glu Val Tyr Thr Ser Asn
                1765                1770                1775

Leu Gln Leu Gly Gly Thr Gln Ile Met Tyr Asn Asn Gly Val Ser His
            1780                1785                1790

Leu Thr Ala Val Asp Asp Leu Ala Gly Val Glu Lys Ile Val Glu Trp
        1795                1800                1805

Met Ser Tyr Val Pro Ala Lys Arg Asn Met Pro Val Pro Ile Leu Glu
    1810                1815                1820

Thr Lys Asp Thr Trp Asp Arg Pro Val Asp Phe Thr Pro Thr Asn Asp
1825                1830                1835                1840

Glu Thr Tyr Asp Val Arg Trp Met Ile Glu Gly Arg Glu Thr Glu Ser
                1845                1850                1855

Gly Phe Glu Tyr Gly Leu Phe Asp Lys Gly Ser Phe Phe Glu Thr Leu
            1860                1865                1870

Ser Gly Trp Ala Lys Gly Val Val Val Gly Arg Ala Arg Leu Gly Gly
        1875                1880                1885

Ile Pro Leu Gly Val Ile Gly Val Glu Thr Arg Thr Val Glu Asn Leu
    1890                1895                1900

Ile Pro Ala Asp Pro Ala Asn Pro Asn Ser Ala Glu Thr Leu Ile Gln
1905                1910                1915                1920

Glu Pro Gly Gln Val Trp His Pro Asn Ser Ala Phe Lys Thr Ala Gln
                1925                1930                1935

Ala Ile Asn Asp Phe Asn Asn Gly Glu Gln Leu Pro Met Met Ile Leu
            1940                1945                1950

Ala Asn Trp Arg Gly Phe Ser Gly Gly Gln Arg Asp Met Phe Asn Glu
        1955                1960                1965

Val Leu Lys Tyr Gly Ser Phe Ile Val Asp Ala Leu Val Asp Tyr Lys
    1970                1975                1980

Gln Pro Ile Ile Ile Tyr Ile Pro Pro Thr Gly Glu Leu Arg Gly Gly
1985                1990                1995                2000

Ser Trp Val Val Val Asp Pro Thr Ile Asn Ala Asp Gln Met Glu Met
                2005                2010                2015

Tyr Ala Asp Val Asn Ala Arg Ala Gly Val Leu Glu Pro Gln Gly Met
            2020                2025                2030

Val Gly Ile Lys Phe Arg Arg Glu Lys Leu Leu Asp Thr Met Asn Arg
        2035                2040                2045

Leu Asp Asp Lys Tyr Arg Glu Leu Arg Ser Gln Leu Ser Asn Lys Ser
    2050                2055                2060

Leu Ala Pro Glu Val His Gln Gln Ile Ser Lys Gln Leu Ala Asp Arg
2065                2070                2075                2080

Glu Arg Glu Leu Leu Pro Ile Tyr Gly Gln Ile Ser Leu Gln Phe Ala
                2085                2090                2095

Asp Leu His Asp Arg Ser Ser Arg Met Val Ala Lys Gly Val Ile Ser
            2100                2105                2110

Lys Glu Leu Glu Trp Thr Glu Ala Arg Arg Phe Phe Phe Trp Arg Leu
        2115                2120                2125

Arg Arg Arg Leu Asn Glu Glu Tyr Leu Ile Lys Arg Leu Ser His Gln
    2130                2135                2140
```

```
Val Gly Glu Ala Ser Arg Leu Glu Lys Ile Ala Arg Ile Arg Ser Trp
2145                2150                2155                2160

Tyr Pro Ala Ser Val Asp His Glu Asp Asp Arg Gln Val Ala Thr Trp
                2165                2170                2175

Ile Glu Glu Asn Tyr Lys Thr Leu Asp Asp Lys Leu Lys Gly Leu Lys
            2180                2185                2190

Leu Glu Ser Phe Ala Gln Asp Leu Ala Lys Lys Ile Arg Ser Asp His
        2195                2200                2205

Asp Asn Ala Ile Asp Gly Leu Ser Glu Val Ile Lys Met Leu Ser Thr
    2210                2215                2220

Asp Asp Lys Glu Lys Leu Leu Lys Thr Leu Lys
2225                2230                2235


<210> SEQ ID NO 4
<211> LENGTH: 1377
<212> TYPE: DNA
<213> ORGANISM: Artificial Sequence
<220> FEATURE:
<223> OTHER INFORMATION: Codon-optimized Acinetobacter baylii sp. atfA

<400> SEQUENCE: 4

atgcggccct tgcaccccat tgacttcatc tttctgagtt tggagaaacg gcaacagccc     60

atgcatgtcg gtggcttgtt tctcttccaa atccccgata acgccccgga cacctttatt    120

caggatctgg tcaatgatat ccggatctcg aaatcgatcc ccgtgccgcc gtttaataat    180

aaactgaacg gcctcttttg ggacgaagac gaggaatttg atctggatca ccattttcgg    240

cacatcgctt tgccccaccc gggtcggatt cgcgaactcc tgatctatat tagccaagaa    300

cacagcacgt tgttggaccg ggccaaaccg ctctggacgt gcaatatcat cgaaggcatc    360

gaaggcaacc gctttgcgat gtacttcaag attcatcacg cgatggttga cggtgtcgct    420

ggcatgcgcc tgatcgaaaa atcgctgagc catgatgtga ccgaaaagag tatcgtcccc    480

ccctggtgcg tggaaggtaa gcgcgccaag cgcctccgcg aaccgaaaac gggcaagatt    540

aagaaaatca tgagcggtat caagtcgcag ctgcaggcta ccccgaccgt gatccaggag    600

ctgtcgcaaa ccgtgtttaa ggatattggt cggaacccgg atcatgtcag tagtttccaa    660

gctccctgtt cgatcttgaa tcagcgcgtt agcagcagcc gccggttcgc tgctcaaagt    720

tttgatctcg atcggtttcg gaatattgcc aagtcgctga acgtcaccat caatgatgtg    780

gttctcgcgg tttgttcggg tgccctccgc gcgtatctga tgagccataa cagtctcccc    840

agtaagccgc tgattgctat ggttcccgcg tcgattcgga atgacgacag cgatgtgagc    900

aaccggatta ccatgatcct ggctaacctc gcgacccaca aagatgatcc gttgcaacgc    960

ctggagatta tccgccgcag tgtgcagaac agtaaacagc gcttcaaacg gatgaccagt   1020

gatcaaattc tgaattacag cgctgtggtc tatggtcccg ccggcttgaa tattatcagt   1080

ggtatgatgc ccaaacgcca agcgtttaac ttggtgatca gtaatgtgcc gggtccgcgc   1140

gaacccttgt attggaacgg tgctaaactc gatgccctct accccgccag tatcgtgctc   1200

gatggccagg ctctcaatat taccatgacc agctatctcg ataaactcga ggtgggtttg   1260

attgcgtgcc gcaacgcgct gccccgcatg cagaacttgc tgacccacct ggaagaggaa   1320

atccagctct tcgagggcgt gattgcgaag caggaagata ttaaaacggc caactag      1377


<210> SEQ ID NO 5
<211> LENGTH: 2595
<212> TYPE: DNA
```

<213> ORGANISM: Artificial Sequence
<220> FEATURE:
<223> OTHER INFORMATION: Codon-optimized S. cerevisiae phosphatidate phosphatase (PAH1)

<400> SEQUENCE: 5

```
atggaattcc aatatgttgg tcgggctttg ggtagtgtta gtaaaacgtg gtcgagtatc     60

aaccccgcca ccctgagcgg cgctatcgat gtcattgtcg tggaacaccc cgatggccgg    120

ctcagttgta gccccttcca tgtgcgcttt ggtaaattcc agattctgaa acccagccaa    180

aagaaagtcc aggtctttat taacgagaaa ctgtcgaata tgcccatgaa actctcggat    240

agcggcgagg cgtacttcgt ttttgagatg ggtgatcaag tgacggatgt cccggatgaa    300

ctgctcgtct cgccggtcat gagtgccacg agtagtccgc cccaatcgcc ggaaacctcg    360

attctcgaag gcggtaccga aggcgagggc gaaggtgaga atgaaaataa gaaaaaggaa    420

aagaaggtgt tggaggagcc cgactttctg gacattaatg acaccggtga cagcggcagc    480

aagaacagtg agacgacggg ttcgctctcg ccgaccgaaa gtagtacgac gacgccgccc    540

gatagcgtcg aggaacgcaa gttggtcgaa caacggacca agaattttca gcaaaagctg    600

aataagaaac tgaccgaaat ccatattccg agcaaattgg acaataacgg tgatttgctc    660

ctggacaccg agggttataa gccgaataaa aacatgatgc acgacacgga tattcagctg    720

aagcaattgc tcaaggatga gttcggtaac gatagcgata tttcgagctt catcaaagaa    780

gacaagaatg gcaacattaa aatcgtgaac ccctatgagc atttgaccga tttgagtccc    840

ccgggtacgc ccccgaccat ggccacgagt ggcagtgtcc tgggcttgga tgcgatggag    900

agtggttcga cgctgaacag cttgagcagc agcccgagcg gcagtgacac cgaggatgag    960

acgagcttta gcaaggaaca gtcgtcgaag agtgaaaaaa cgtcgaagaa aggcaccgcg   1020

ggttcgggtg aaacggagaa acgctacatc cgcacgatcc ggctcacgaa tgatcagctg   1080

aaatgcctca acttgacgta cggtgaaaat gacttgaaat ttagtgttga ccatggcaaa   1140

gccattgtga ccagcaaatt gtttgtctgg cgctgggacg tccccatcgt tatcagcgac   1200

attgacggta cgattacgaa aagtgatgcg ctgggccacg tcctcgccat gatcggcaaa   1260

gattggaccc atctcggcgt cgctaagctg ttcagtgaga tctcgcgcaa cggttacaat   1320

atcctgtacc tgaccgcgcg ctcggccggt caggctgaca gtacccgctc gtatctccgc   1380

agtattgagc agaacggtag caagctcccg aacggccccg tcattctgag ccccgatcgg   1440

accatggctg ccctgcgccg ggaggtgatt ctgaaaaagc ccgaagtctt taaaatcgct   1500

tgcttgaacg atatccgctc gctctatttc gaagactcgg ataacgaagt ggacacggag   1560

gaaaagagca cgccgttttt cgcgggcttt ggcaatcgga tcaccgatgc gctcagctat   1620

cggacggtcg gcatcccgag tagccgcatc ttcacgatta acacggaagg cgaggtgcac   1680

atggagctgc tcgagctcgc cggttaccgg agtagctata tccatatcaa cgaactggtc   1740

gatcacttct tcccgccggt gagcctggac tcggtcgatc tgcgcacgaa cacgagcatg   1800

gtcccgggca gcccgccgaa ccgcaccctg gataactttg atagcgaaat caccagtggc   1860

cgcaagacgt tgtttcgcgg taatcaggag gaaaaattca cggacgtcaa cttttggcgc   1920

gatccgttgg tggacatcga caacctctcg gatatcagta acgatgattc ggacaatatt   1980

gatgaagaca ccgatgtgag ccaacagtcg aacatcagcc gcaaccgcgc taactcggtc   2040

aagacggcca aggtgaccaa ggctccgcag cggaatgtgt cgggcagtac gaataacaat   2100

gaagttctgg ctgcgagtag tgatgttgaa aatgccagtg acttggttag cagccactcg   2160
```

```
agtagcggct cgacccccaa caagtcgacg atgagtaagg gtgatatcgg caaacaaatc   2220

tatctggaac tgggctcgcc cttggcgagt cccaaactcc ggtatctgga cgatatggat   2280

gatgaggact cgaactataa tcgcaccaag agccgccggg ctagtagcgc cgctgctacc   2340

agcatcgaca aggagtttaa aaagctcagt gtgagtaaag ctggcgctcc cacccgcatc   2400

gttagcaaga tcaacgtgtc gaatgatgtg cacagtttgg gcaacagtga taccgaaagc   2460

cggcgggaac agagcgtcaa tgaaaccggt cgcaatcagt tgccgcacaa tagtatggat   2520

gataaggatt tggattcgcg ggtgagtgac gagttcgatg acgatgagtt tgatgaagat   2580

gagtttgagg attag                                                    2595
```

```
<210> SEQ ID NO 6
<211> LENGTH: 6708
<212> TYPE: DNA
<213> ORGANISM: Artificial Sequence
<220> FEATURE:
<223> OTHER INFORMATION: Codon-optimized S. cerevisiae acetyl Coa
      carboxylase (ACC1)

<400> SEQUENCE: 6
```

```
atggaattct ccgaggaaag tttgttcgaa agcagtccgc agaaaatgga atatgaaatt     60

acgaattatt cggaacgcca cacggagctc cccgggcact tcatcggact caacaccgtg    120

gataagctcg aagaaagtcc cctccgcgat tttgtgaaaa gccacggcgg ccataccgtg    180

atctcgaaga ttctgattgc caataacgga attgccgctg tcaaggagat ccgcagcgtc    240

cggaagtggg cgtacgaaac ttttggcgat gaccgtacag tccagtttgt tgctatggcg    300

actccggaag acttggaggc gaatgcggaa tacattcgaa tggccgatca atacatcgaa    360

gtccccggag gaacgaacaa caacaattat gcgaacgtcg atttgatcgt ggatatcgca    420

gaacgcgcgg acgtggatgc tgtttgggcc ggatggggcc acgcttcgga aaaccctctg    480

ttgccggaaa aactcagcca gtctaaacgg aaagtcattt tcatcggccc tccgggcaac    540

gcaatgcgct cgttgggtga taagatcagc tcgaccattg tggctcagag cgctaaagtc    600

ccatgtattc cctggtcggg taccggcgtg gatacggtcc atgttgatga gaaaactgga    660

ctggtcagcg tcgatgatga tatctaccaa aagggctgtt gcaccagccc ggaagatggc    720

ctgcaaaagg cgaagcgcat cgggttccca gtcatgatca aggcatccga aggcggaggc    780

ggtaagggta tccgccaggt tgagcgtgaa gaagatttta tcgcactgta tcatcaagcg    840

gctaacgaaa tcccgggctc gccaatttc attatgaaac tggctggtcg ggcgcgtcat    900

ctcgaagtgc aactcctcgc tgaccagtac ggtacgaaca tctctttgtt cggtcgggat    960

tgttcggtcc agcgtcgtca ccagaagatc attgaagaag cccctgttac catcgcaaag   1020

gccgagacgt ttcatgagat ggagaaagcg gccgtccgcc tcggcaagct ggtcggttac   1080

gttagcgcag gcaccgtgga atacctctat tcccacgacg atggtaagtt ttactttctc   1140

gaactgaatc ctcgcctgca ggttgaacac ccgaccacag agatggtgtc gggggtcaat   1200

ctgccggctg cgcagttgca gattgcaatg ggcattccga tgcatcgaat cagcgacatc   1260

cgaaccctgt acggcatgaa cccgcacagt gcgagcgaaa tcgactttga gttcaagacc   1320

caagacgcca cgaagaaaca gcgacgccca attccgaagg gccattgcac cgcgtgtcgc   1380

attacctcgg aggaccccaa tgatggtttt aagccctcgg gcggtactct gcacgagctc   1440

aacttccgct cctcctcgaa cgtctggggc tatttcagcg tcggaaataa tggtaacatt   1500

catagttttt ccgattccca atttggccat atcttcgcct ttggcgaaaa ccgacaagct   1560
```

agccgcaaac acatggtcgt ggcgttgaag gagctgagta tccgagggga ctttcgcacg 1620
acggtggaat atctgatcaa actgctcgaa acggaggact ttgaggataa cacaattacc 1680
accggatggt tggacgacct gattacgcac aaaatgaccg ccgagaaacc cgaccccacc 1740
ttggcagtga tttgtggcgc ggcaacgaag gccttttttgg cctctgaaga ggcacgccac 1800
aagtacattg agagtctcca aaagggtcag gtgctgagta aagatctgct gcaaaccatg 1860
tttcctgtcg actttattca tgaggggaaa cgctacaaat tcacggttgc taagtctggt 1920
aatgatcggt acacattgtt tatcaatgga tcgaagtgcg atattatctt gcgacaactc 1980
tccgacggcg gcctcctgat tgctatcggc gggaaaagtc ataccatcta ttggaaagaa 2040
gaggtcgccg ccacccgact gagcgttgat tcgatgacta ctctgctcga agttgaaaac 2100
gatccaacgc aactgcgcac tccctctccg ggtaagctcg tgaagtttct cgtcgagaat 2160
ggcgaacaca ttattaaggg ccagccgtat gcggaaatcg aggtgatgaa gatgcagatg 2220
cccctggtca gccaagagaa cggtattgtg caactgctga aacagcccgg cagcaccatc 2280
gtcgctggcg atatcatggc tatcatgacc ctcgatgatc cttccaaagt caaacatgcc 2340
ctgcccttcg aaggcatgct ccccgatttt ggctcccccg tgattgaggg caccaaacca 2400
gcttacaagt ttaaatcgct ggtttccacc ctcgagaaca tcttgaaggg ctacgataat 2460
caggtcatta tgaatgccag cctccagcag ctcattgagg tcctccgtaa ccccaagctg 2520
ccctacagtg aatggaagct ccacatcagt gcgctccact cgcgactgcc cgcgaagctc 2580
gatgagcaga tggaagagct cgtcgctcgc agcctgcgtc gcggcgcagt ctttccggca 2640
cggcaactgt cgaagctcat cgatatggct gtcaaaaacc ccgaatacaa ccccgataaa 2700
ctcttgggtg ctgtcgttga gccgctcgcc gatatcgcgc acaagtacag taatggcctg 2760
gaggcgcacg aacacagtat ctttgttcac ttcctggaag aatactatga ggttgagaaa 2820
ctgttcaatg ggcctaatgt ccgggaagag aatattatcc tgaagctccg tgatgaaaat 2880
ccgaaagatt tggataaagt cgccttgacg gtgctcagtc atagcaaggt gagtgccaag 2940
aacaatctca tcctggcgat cttgaaacac taccaacctt tgtgcaagct gagttccaag 3000
gtgtcggcta tttttagtac gcccctgcag cacatcgtgg aactcgaaag taaagccacc 3060
gccaaggtgg ctctgcaggc ccgggagatt ctgatccagg gtgctctgcc gagcgtgaaa 3120
gagcggacgg aacaaatcga acacatcctg aagagttcgg tcgtgaaggt tgcatatggc 3180
agcagtaacc ctaaacgctc ggaaccggac ctcaatatcc tgaaggatct gatcgatagt 3240
aattatgttg tttttgatgt cctgctccaa tttctgactc accaagatcc ggttgttact 3300
gcggctgccg cgcaagttta cattcgacgc gcctatcgcg cctacacaat cggcgatatt 3360
cgagtccatg agggcgtgac cgttccaatc gttgaatgga aattccagtt gccatcggcg 3420
gctttttcta cattcccaac agtcaagagt aagatgggca tgaatcgtgc cgtttcggtc 3480
agtgatttgt cctatgtcgc aaactcgcaa tctagtcctc tgcgagaggg catcctgatg 3540
gcagtggatc atttggatga tgtcgatgag atcctctcgc aaagtctcga ggtcattcct 3600
cgccaccaat cgtcgtccaa tggcccagct cccgatcgat ccggttcttc cgccagcttg 3660
tcgaatgtcg ccaacgtctg tgtggcgtcg actgaggggt tcgaaagcga agaagaaatt 3720
ttggtccgct tgcgggaaat tttggacctc aacaagcagg aactgattaa tgcctctatt 3780
cgccgcatta cgtttatgtt cggtttcaag gatggctcgt acccaaaata ctatacgttc 3840
aacggcccga actacaatga gaacgagact atccgacata ttgaacctgc cctcgctttc 3900
caactggaac tggggcggct ctcgaatttc aatattaagc ctatttttac cgacaaccgt 3960

-continued

```
aacatccacg tttacgaggc tgtcagcaaa acaagcccgc tggataagcg attcttcacc   4020

cggggcatta tccgcacagg ccacatccgt gacgatatca gtatccaaga atacctgact   4080

agcgaagcta accgcttgat gagcgacatt ttggataatc tggaagtgac tgatacttcc   4140

aacagcgact tgaatcacat ttttatcaac ttcattgccg tgttcgatat ctcgccggaa   4200

gatgtggaag ccgcgtttgg aggctttctg gaacggtttg gcaaacggct gctgcgcttg   4260

cgggtgtcta gcgcggagat tcggattatc atcaaagatc cgcaaacggg ggctcctgtg   4320

ccactgcgcg cgctgattaa taacgtctcg ggttacgtga tcaagaccga gatgtacaca   4380

gaggttaaaa acgctaaagg cgagtgggtc ttcaagagct tgggcaaacc cggcagcatg   4440

catctccgcc ccatcgccac gccgtatccg gtcaaggagt ggctgcagcc caagcgatac   4500

aaggcgcact tgatggggac gacatatgtt tacgattttc ctgaactgtt ccgtcaagca   4560

agcagctccc agtggaaaaa cttttccgca gatgtgaaat tgactgatga tttcttcatc   4620

tcgaatgagc tcatcgaaga tgagaatggc gagctgaccg aagttgagcg agaacctggt   4680

gccaatgcga ttgggatggt cgcctttaaa atcacggtca aaactcccga gtaccctcgg   4740

ggtcgccagt tcgtcgttgt ggctaacgat atcaccttta agattggatc gtttggcccg   4800

caggaggatg agttctttaa caaggtcact gaatacgccc gaaaacgagg cattccgcgg   4860

atttacttgg cagccaatag cggtgcgcgc atcggcatgg ctgaagaaat cgttccgctg   4920

tttcaggttg cctggaacga cgcggccaac cccgacaagg ggttccagta cttgtatctg   4980

acttccgaag gcatggagac gttgaagaaa tttgataagg agaatagtgt cttgactgag   5040

cggaccgtta ttaacggcga ggagcggttt gtcattaaga ctatcatcgg cagcgaagat   5100

ggcctcggcg tcgaatgttt gcgcgggtcc ggcctgatcg caggggcaac ctcgcgagcc   5160

tatcacgata tctttaccat tactttggtc acgtgtcgtt cggttggcat tggagcatac   5220

ctcgtgcgcc tcggtcagcg cgccatccaa gtggaaggcc aacctatcat tttgactggc   5280

gcgcctgcta tcaataagat gctgggccgt gaagtctaca catcgaacct ccaactgggc   5340

ggtacccaaa ttatgtataa caatggcgtc agccatctga cagccgtcga tgacctggct   5400

ggcgttgaaa agattgttga gtggatgagc tatgtgcccg ccaaacggaa catgccagtc   5460

cccattttgg aaaccaagga tacctgggat cgcccagtgg atttcactcc gactaatgat   5520

gaaacctacg atgtccgctg gatgatcgaa gggcgcgaaa ctgagtcggg cttcgagtac   5580

ggactgtttg ataagggtag tttctttgag actctcagtg gttgggccaa aggcgttgtc   5640

gtcggtcggg cacgtctggg cggcatcccg ctgggagtta ttggtgttga gacacgtacg   5700

gtggaaaatc tgatcccggc tgatccggcc aaccccaata gtgcggaaac gctgattcaa   5760

gagcccgggc aagtgtggca cccgaatagt gcctttaaga cggcgcaggc tattaatgat   5820

tttaacaacg gcgaacaact gcctatgatg attctggcga attggcgggg gtttagtggt   5880

gggcagcgcg acatgttcaa cgaagtgctc aagtacggct ccttcatcgt ggacgccctg   5940

gtcgactata aacaaccaat tatcatctat attcccccta ccggcgagct gcgaggcggt   6000

agctgggtcg tggtggaccc tactattaat gcagatcaaa tggagatgta cgccgacgtg   6060

aatgctcgag cgggcgtgct ggaaccacaa gggatggttg gcatcaaatt ccgccgcgaa   6120

aaactgttgg atactatgaa tcgactggat gataaatatc gcgagctgcg cagccaactg   6180

tcgaacaagt ctctggcccc ggaagtccat caacagattt ctaaacagct ggcagatcgc   6240

gaacgtgaac tcttgccgat ctacggccaa atcagcctcc aatttgccga cctgcatgat   6300
```

-continued

```
cgcagcagcc gcatggttgc gaaaggtgtc atcagcaaag agctcgagtg gacggaagct   6360

cggcggtttt tcttttggcg gctgcgccga cgcctgaatg aagaatactt gattaagcgt   6420

ctgagccacc aggtcggcga ggctagtcgg ttggaaaaga tcgcccgcat tcggagttgg   6480

tatccggcat cggttgacca cgaggacgat cgccaggtcg ctacctggat cgaagagaac   6540

tacaaaacct tggatgataa gctgaaagga ctgaagctgg agtctttcgc ccaagatctc   6600

gccaagaaga tccgtagcga tcatgacaat gcaatcgacg gtttgagcga ggttatcaag   6660

atgttgtcta ccgacgacaa ggagaagctg ctcaaaacgc tgaagtag                6708
```

<210> SEQ ID NO 7
<211> LENGTH: 1376
<212> TYPE: DNA
<213> ORGANISM: Acinetobacter sp.

<400> SEQUENCE: 7

```
atgcgcccat tacatccgat tgattttata ttcctgtcac tagaaaaaag acaacagcct     60

atgcatgtag gtggtttatt tttgtttcag attcctgata acgccccaga cacctttatt    120

caagatctgg tgaatgatat ccggatatca aaatcaatcc ctgttccacc attcaacaat    180

aaactgaatg ggcttttttg ggatgaagat gaagagtttg atttagatca tcattttcgt    240

catattgcac tgcctcatcc tggtcgtatt cgtgaattgc ttatttatat ttcacaagag    300

cacagtacgc tgctagatcg ggcaaagccc ttgtggacct gcaatattat tgaaggaatt    360

gaaggcaatc gttttgccat gtacttcaaa attcaccatg cgatggtcga tggcgttgct    420

ggtatgcggt taattgaaaa atcactctcc catgatgtaa cagaaaaaag tatcgtgcca    480

ccttggtgtg ttgagggaaa acgtgcaaag cgcttaagag aacctaaaac aggtaaaatt    540

aagaaaatca tgtctggtat taagagtcag cttcaggcga cacccacagt cattcaagag    600

ctttctcaga cagtatttaa agatattgga cgtaatcctg atcatgtttc aagctttcag    660

gcgccttgtt ctattttgaa tcagcgtgtg agctcatcgc gacgttttgc agcacagtct    720

tttgacctag atcgttttcg taatattgcc aaatcgttga atgtgaccat taatgatgtt    780

gtactagcgg tatgttctgg tgcattacgt gcgtatttga tgagtcataa tagtttgcct    840

tcaaaaccat taattgccat ggttccagcc tctattcgca atgacgattc agatgtcagc    900

aaccgtatta cgatgattct ggcaaatttg gcaacccaca aagatgatcc tttacaacgt    960

cttgaaatta tccgccgtag tgttcaaaac tcaaagcaac gcttcaaacg tatgaccagc   1020

gatcagattc taaattatag tgctgtcgta tatggccctg caggactcaa cataatttct   1080

ggcatgatgc caaaacgcca agccttcaat ctggttattt ccaatgtgcc tggcccaaga   1140

gagccacttt actggaatgg tgccaaactt gatgcactct acccagcttc aattgtatta   1200

gacggtcaag cattgaatat tacaatgacc agttatttag ataaacttga agttggtttg   1260

attgcatgcc gtaatgcatt gccaagaatg cagaatttac tgacacattt agaagaagaa   1320

attcaactat ttgaaggcgt aattgcaaag caggaagata ttaaaacagc caatta       1376
```

<210> SEQ ID NO 8
<211> LENGTH: 2589
<212> TYPE: DNA
<213> ORGANISM: Artificial Sequence
<220> FEATURE:
<223> OTHER INFORMATION: Synthetic construct Saccharomyces cerevisiae
      clone FLH148377.01X SMP2 gene

<400> SEQUENCE: 8

-continued

```
atgcagtacg taggcagagc tcttgggtct gtgtctaaaa catggtcttc tatcaatccg     60
gctacgctat caggtgctat agatgtcatt gtagtggagc atccagacgg aaggctatca    120
tgttctccct ttcatgtgag gttcggcaaa tttcaaattc taaagccatc tcaaaagaaa    180
gtccaagtgt ttataaatga gaaactgagt aatatgccaa tgaaactgag tgattctgga    240
gaagcctatt tcgttttcga gatgggtgac caggtcactg atgtccctga cgaattgctt    300
gtgtcgcccg tgatgagcgc cacatcaagc ccccctcaat cacctgaaac atccatctta    360
gaaggaggaa ccgagggtga aggtgaaggt gaaaatgaaa ataagaagaa ggaaaagaaa    420
gtgctagagg aaccagattt tttagatatc aatgacactg gagattcagg cagtaaaaat    480
agtgaaacta cagggtcgct ttctcctact gaatcctcta caacgacacc accagattca    540
gttgaagaga ggaagcttgt tgagcagcgt acaaagaact ttcagcaaaa actaaacaaa    600
aaactcactg aaatccatat acccagtaaa cttgataaca atggcgactt actactagac    660
actgaaggtt acaagccaaa caagaatatg atgcatgaca cagacataca actgaagcag    720
ttgttaaagg acgaattcgg taatgattca gatatttcca gttttatcaa ggaggacaaa    780
aatggcaaca tcaagatcgt aaatccttac gagcacctta ctgatttatc tcctccaggt    840
acgcctccaa caatggccac aagcggatca gttttaggct tagatgcaat ggaatcagga    900
agtactttga attcgttatc ttcttcacct tctggttccg atactgagga cgaaacatca    960
tttagcaaag aacaaagcag taaaagtgaa aaaactagca agaaaggaac agcaggggagc   1020
ggtgagaccg agaaaagata catacgaacg ataagattga ctaatgacca gttaaagtgc   1080
ctaaatttaa cttatggtga aaatgatctg aaattttccg tagatcacgg aaaagctatt   1140
gttacgtcaa aattattcgt ttggaggtgg gatgttccaa ttgttatcag tgatattgat   1200
ggcaccatca caaaatcgga cgctttaggc catgttctgg caatgatagg aaaagactgg   1260
acgcacttgg gtgtagccaa gttatttagc gagatctcca ggaatggcta taatatactc   1320
tatctaactg caagaagtgc tggacaagct gattccacga ggagttattt gcgatcaatt   1380
gaacagaatg gcagcaaact accaaatggg cctgtgattt tatcacccga tagaacgatg   1440
gctgcgttaa ggcgggaagt aatactaaaa aaacctgaag tctttaaaat cgcgtgtcta   1500
aacgacataa gatccttgta ttttgaagac agtgataacg aagtggatac agaggaaaaa   1560
tcaacaccat tttttgccgg ctttggtaat aggattactg atgctttatc ttacagaact   1620
gtggggatac ctagttcaag aattttcaca ataaatacag agggtgaggt tcatatggaa   1680
ttattggagt tagcaggtta cagaagctcc tatattcata tcaatgagct tgtcgatcat   1740
ttctttccac cagtcagcct tgatagtgtc gatctaagaa ctaatacttc catggttcct   1800
ggctcccccc ctaatagaac gttggataac tttgactcag aaattacttc aggtcgcaaa   1860
acgctattta gaggcaatca ggaagagaaa ttcacagacg taaatttttg gagagacccg   1920
ttagtcgaca tcgacaactt atcggatatt agcaatgatg attctgataa catcgatgaa   1980
gatactgacg tatcacaaca aagcaacatt agtagaaata gggcaaattc agtcaaaacc   2040
gccaaggtca ctaaagcccc gcaaagaaat gtgagcggca gcacaaataa caacgaagtt   2100
ttagccgctt cgtctgatgt agaaaatgcg tctgacctgg tgagttccca tagtagctca   2160
ggatccacgc ccaataaatc tacaatgtcc aaaggggaca ttggaaaaca aatatatttg   2220
gagctaggtt ctccacttgc atcgccaaaa ctaagatatt tagacgatat ggatgatgaa   2280
gactccaatt acaatagaac taaatcaagg agagcatctt ctgcagccgc gactagtatc   2340
gataaagagt tcaaaaagct ctctgtgtca aaggccggcg ctccaacaag aattgtttca   2400
```

```
aagatcaacg tttcaaatga cgtacattca cttgggaatt cagataccga atcacgaagg   2460

gagcaaagtg ttaatgaaac agggcgcaat cagctacccc acaactcaat ggacgataaa   2520

gatttggatt caagagtaag cgatgaattc gatgacgatg aattcgacga agatgaattc   2580

gaagattag                                                           2589


<210> SEQ ID NO 9
<211> LENGTH: 6702
<212> TYPE: DNA
<213> ORGANISM: Artificial Sequence
<220> FEATURE:
<223> OTHER INFORMATION: Synthetic construct Saccharomyces cerevisiae
      clone FLH148869.01X ACC1

<400> SEQUENCE: 9

atgagcgaag aaagcttatt cgagtcttct ccacagaaga tggagtacga aattacaaac     60

tactcagaaa gacatacaga acttccaggt catttcattg gcctcaatac agtagataaa    120

ctagaggagt ccccgttaag ggactttgtt aagagtcacg gtggtcacac ggtcatatcc    180

aagatcctga tagcaaataa tggtattgcc gccgtgaaag aaattagatc cgtcagaaaa    240

tgggcatacg agacgttcgg cgatgacaga accgtccaat tcgtcgccat ggccacccca    300

gaagatctgg aggccaacgc agaatatatc cgtatggccg atcaatacat tgaagtgcca    360

ggtggtacta ataataacaa ctacgctaac gtagacttga tcgtagacat cgccgaaaga    420

gcagacgtag acgccgtatg ggctggctgg ggtcacgcct ccgagaatcc actattgcct    480

gaaaaattgt cccagtctaa gaggaaagtc atctttattg ggcctccagg taacgccatg    540

aggtctttag gtgataaaat ctcctctacc attgtcgctc aaagtgctaa agtcccatgt    600

attccatggt ctggtaccgg tgttgacacc gttcacgtgg acgagaaaac cggtctggtc    660

tctgtcgacg atgacatcta tcaaaagggt tgttgtacct ctcctgaaga tggtttacaa    720

aaggccaagc gtattggttt tcctgtcatg attaaggcat ccgaaggtgg tggtggtaaa    780

ggtatcagac aagttgaacg tgaagaagat ttcatcgctt tataccacca ggcagccaac    840

gaaattccag gctcccccat tttcatcatg aagttggccg gtagagcgcg tcacttggaa    900

gttcaactgc tagcagatca gtacggtaca aatatttcct tgttcggtag agactgttcc    960

gttcagagac gtcatcaaaa aattatcgaa gaagcaccag ttacaattgc caaggctgaa   1020

acatttcacg agatggaaaa ggctgccgtc agactgggga aactagtcgg ttatgtctct   1080

gccggtaccg tggagtatct atattctcat gatgatggaa aattctactt tttagaattg   1140

aacccaagat tacaagtcga gcatccaaca acggaaatgg tctccggtgt taacttacct   1200

gcagctcaat tacaaatcgc tatgggtatc cctatgcata gaataagtga cattagaact   1260

ttatatggta tgaatcctca ttctgcctca gaaatcgatt tcgaattcaa aactcaagat   1320

gccaccaaga aacaaagaag acctattcca aagggtcatt gtaccgcttg tcgtatcaca   1380

tcagaagatc caaacgatgg attcaagcca tcgggtggta ctttgcatga actaaacttc   1440

cgttcttcct ctaatgtttg ggggttacttc tccgtgggta acaatggtaa tattcactcc   1500

ttttcggact ctcagttcgg ccatattttt gcttttggtg aaaatagaca agcttccagg   1560

aaacacatgg ttgttgccct gaaggaattg tccattaggg gtgatttcag aactactgtg   1620

gaatacttga tcaaactttt ggaaactgaa gatttcgagg ataacactat taccaccggt   1680

tggttggacg atttgattac tcataaaatg accgctgaaa agcctgatcc aactcttgcc   1740

gtcatttgcg gtgccgctac aaaggctttc ttagcatctg aagaagcccg ccacaagtat   1800
```

-continued atcgaatcct tacaaaaggg acaagttcta tctaaagacc tactgcaaac tatgttccct 1860
gtagatttta tccatgaggg taaaagatac aagttcaccg tagctaaatc cggtaatgac 1920
cgttacacat tatttatcaa tggttctaaa tgtgatatca tactgcgtca actatctgat 1980
ggtggtcttt tgattgccat aggcggtaaa tcgcatacca tctattggaa agaagaagtt 2040
gctgctacaa gattatccgt tgactctatg actactttgt tggaagttga aaacgatcca 2100
acccagttgc gtactccatc ccctggtaaa ttggttaaat tcttggtgga aaatggtgaa 2160
cacattatca agggccaacc atatgcagaa attgaagtta tgaaaatgca aatgcctttg 2220
gtttctcaag aaaatggtat cgtccagtta ttaaagcaac ctggttctac cattgttgca 2280
ggtgatatca tggctattat gactcttgac gatccatcca aggtcaagca cgctctacca 2340
tttgaaggta tgctgccaga ttttggttct ccagttatcg aaggaaccaa acctgcctat 2400
aaattcaagt cattagtgtc tactttggaa aacattttga agggttatga caaccaagtt 2460
attatgaacg cttccttgca acaattgata gaggttttga gaaatccaaa actgccttac 2520
tcagaatgga aactacacat ctctgcttta cattcaagat tgcctgctaa gctagatgaa 2580
caaatggaag agttagttgc acgttctttg agacgtggtg ctgttttccc agctagacaa 2640
ttaagtaaat tgattgatat ggccgtgaag aatcctgaat acaaccccga caaattgctg 2700
ggcgccgtcg tggaaccatt ggcggatatt gctcataagt actctaacgg gttagaagcc 2760
catgaacatt ctatatttgt ccatttcttg gaagaatatt acgaagttga aaagttattc 2820
aatggtccaa atgttcgtga ggaaaatatc attctgaaat tgcgtgatga aaaccctaaa 2880
gatctagata aagttgcgct aactgttttg tctcattcga aagtttcagc gaagaataac 2940
ctgatcctag ctatcttgaa acattatcaa ccattgtgca agttatcttc taaagtttct 3000
gccattttct ctactcctct acaacatatt gttgaactag aatctaaggc taccgctaag 3060
gtcgctctac aagcaagaga aattttgatt caaggcgctt taccttcggt caaggaaaga 3120
actgaacaaa ttgaacatat cttaaaatcc tctgttgtga aggttgccta tggctcatcc 3180
aatccaaagc gctctgaacc agatttgaat atcttgaagg acttgatcga ttctaattac 3240
gttgtgttcg atgttttact tcaattccta acccatcaag acccagttgt gactgctgca 3300
gctgctcaag tctatattcg tcgtgcttat cgtgcttaca ccataggaga tattagagtt 3360
cacgaaggtg tcacagttcc aattgttgaa tggaaattcc aactaccttc agctgcgttc 3420
tccacctttc caactgttaa atctaaaatg ggtatgaaca gggctgtttc tgtttcagat 3480
ttgtcatatg ttgcaaacag tcagtcatct ccgttaagag aaggtatttt gatggctgtg 3540
gatcatttag atgatgttga tgaaattttg tcacaaagtt tggaagttat tcctcgtcac 3600
caatcttctt ctaacggacc tgctcctgat cgttctggta gctccgcatc gttgagtaat 3660
gttgctaatg tttgtgttgc ttctacagaa ggtttcgaat ctgaagagga aattttggta 3720
aggttgagag aaattttgga tttgaataag caggaattaa tcaatgcttc tatccgtcgt 3780
atcacattta tgttcggttt taaagatggg tcttatccaa agtattatac ttttaacggt 3840
ccaaattata acgaaaatga aacaattcgt cacattgagc cggctttggc cttccaactg 3900
gaattaggaa gattgtccaa cttcaacatt aaaccaattt tcactgataa tagaaacatc 3960
catgtctacg aagctgttag taagacttct ccattggata agagattctt tacaagaggt 4020
attattagaa cgggtcatat ccgtgatgac atttctattc aagaatatct gacttctgaa 4080
gctaacagat tgatgagtga tatattggat aatttagaag tcaccgacac ttcaaattct 4140

-continued

```
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tctttgggta aacctggatc catgcattta   4440
agacctattg ctactcctta ccctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
gttataaacg gtgaagaaag atttgtcatc aagacaatta ttggttctga agatgggtta   5100
ggtgtcgaat gtctacgtgg atctggttta attgctggtg caacgtcaag ggcttaccac   5160
gatatcttca ctatcacctt agtcacttgt agatccgtcg gtatcggtgc ttatttggtt   5220
cgtttgggtc aaagagctat tcaggtcgaa ggccagccaa ttattttaac tggtgctcct   5280
gcaatcaaca aaatgctggg tagagaagtt tatacttcta acttacaatt gggtggtact   5340
caaatcatgt ataacaacgg tgtttcacat ttgactgctg ttgacgattt agctggtgta   5400
gagaagattg ttgaatggat gtcttatgtt ccagccaagc gtaatatgcc agttcctatc   5460
ttggaaacta aagacacatg ggatagacca gttgatttca ctccaactaa tgatgaaact   5520
tacgatgtaa gatggatgat tgaaggtcgt gagactgaaa gtggatttga atatggtttg   5580
tttgataaag ggtctttctt tgaaactttg tcaggatggg ccaaaggtgt tgtcgttggt   5640
agagcccgtc ttggtggtat tccactgggt gttattggtg ttgaaacaag aactgtcgag   5700
aacttgattc ctgctgatcc agctaatcca aatagtgctg aaacattaat tcaagaacct   5760
ggtcaagttt ggcatccaaa ctccgccttc aagactgctc aagctatcaa tgactttaac   5820
aacggtgaac aattgccaat gatgattttg gccaactgga gaggtttctc tggtggtcaa   5880
cgtgatatgt tcaacgaagt cttgaagtat ggttcgttta ttgttgacgc attggtggat   5940
tacaaacaac caattattat ctatatccca cctaccggtg aactaagagg tggttcatgg   6000
gttgttgtcg atccaactat caacgctgac caaatggaaa tgtatgccga cgtcaacgct   6060
agagctggtg ttttggaacc acaaggtatg gttggtatca agttccgtag agaaaaattg   6120
ctggacacca tgaacagatt ggatgacaag tacagagaat tgagatctca attatccaac   6180
aagagtttgg ctccagaagt acatcagcaa atatccaagc aattagctga tcgtgagaga   6240
gaactattgc caatttacgg acaaatcagt cttcaatttg ctgatttgca cgataggtct   6300
tcacgtatgg tggccaaggg tgttatttct aaggaactgg aatggaccga ggcacgtcgt   6360
ttcttcttct ggagattgag aagaagattg aacgaagaat atttgattaa aaggttgagc   6420
catcaggtag gcgaagcatc aagattagaa aagatcgcaa gaattagatc gtggtaccct   6480
gcttcagtgg accatgaaga tgataggcaa gtcgcaacat ggattgaaga aaactacaaa   6540
```

```
actttggacg ataaactaaa gggtttgaaa ttagagtcat tcgctcaaga cttagctaaa   6600

aagatcagaa gcgaccatga caatgctatt gatggattat ctgaagttat caagatgtta   6660

tctaccgatg ataaagaaaa attgttgaag actttgaaat ag                      6702


<210> SEQ ID NO 10
<211> LENGTH: 9
<212> TYPE: PRT
<213> ORGANISM: Artificial Sequence
<220> FEATURE:
<223> OTHER INFORMATION: Domain 1 lipid phosphatase catalytic motif
<220> FEATURE:
<221> NAME/KEY: VARIANT
<222> LOCATION: 2, 3, 4, 5, 6, 7
<223> OTHER INFORMATION: Xaa = Any Amino Acid

<400> SEQUENCE: 10

Lys Xaa Xaa Xaa Xaa Xaa Xaa Arg Pro
 1               5


<210> SEQ ID NO 11
<211> LENGTH: 4
<212> TYPE: PRT
<213> ORGANISM: Artificial Sequence
<220> FEATURE:
<223> OTHER INFORMATION: Domain 2 lipid phosphatase catalytic motif

<400> SEQUENCE: 11

Pro Ser Gly His
 1


<210> SEQ ID NO 12
<211> LENGTH: 12
<212> TYPE: PRT
<213> ORGANISM: Artificial Sequence
<220> FEATURE:
<223> OTHER INFORMATION: Domain 3 lipid phosphatase catalytic motif
<220> FEATURE:
<221> NAME/KEY: VARIANT
<222> LOCATION: 3, 4, 5, 6, 7, 9, 10, 11
<223> OTHER INFORMATION: Xaa = Any Amino Acid

<400> SEQUENCE: 12

Ser Arg Xaa Xaa Xaa Xaa Xaa His Xaa Xaa Xaa Asp
 1               5                  10


<210> SEQ ID NO 13
<211> LENGTH: 7
<212> TYPE: PRT
<213> ORGANISM: Artificial Sequence
<220> FEATURE:
<223> OTHER INFORMATION: Heptapeptide retention motif
<220> FEATURE:
<221> NAME/KEY: VARIANT
<222> LOCATION: 3
<223> OTHER INFORMATION: Xaa = Any Amino Acid

<400> SEQUENCE: 13

Phe Tyr Xaa Asp Trp Trp Asn
 1               5


<210> SEQ ID NO 14
<211> LENGTH: 446
<212> TYPE: PRT
<213> ORGANISM: Streptomyces coelicolor

<400> SEQUENCE: 14
```

-continued

Met Thr Pro Asp Pro Leu Ala Pro Leu Asp Leu Ala Phe Trp Asn Ile
1 5 10 15

Glu Ser Ala Glu His Pro Met His Leu Gly Ala Leu Gly Val Phe Glu
20 25 30

Ala Asp Ser Pro Thr Ala Gly Ala Leu Ala Ala Asp Leu Leu Ala Ala
35 40 45

Arg Ala Pro Ala Val Pro Gly Leu Arg Met Arg Ile Arg Asp Thr Trp
50 55 60

Gln Pro Pro Met Ala Leu Arg Arg Pro Phe Ala Phe Gly Gly Ala Thr
65 70 75 80

Arg Glu Pro Asp Pro Arg Phe Asp Pro Leu Asp His Val Arg Leu His
85 90 95

Ala Pro Ala Thr Asp Phe His Ala Arg Ala Gly Arg Leu Met Glu Arg
100 105 110

Pro Leu Glu Arg Gly Arg Pro Pro Trp Glu Ala His Val Leu Pro Gly
115 120 125

Ala Asp Gly Gly Ser Phe Ala Val Leu Phe Lys Phe His His Ala Leu
130 135 140

Ala Asp Gly Leu Arg Ala Leu Thr Leu Ala Ala Gly Val Leu Asp Pro
145 150 155 160

Met Asp Leu Pro Ala Pro Arg Pro Arg Pro Glu Gln Pro Pro Arg Gly
165 170 175

Leu Leu Pro Asp Val Arg Ala Leu Pro Asp Arg Leu Arg Gly Ala Leu
180 185 190

Ser Asp Ala Gly Arg Ala Leu Asp Ile Gly Ala Ala Ala Ala Leu Ser
195 200 205

Thr Leu Asp Val Arg Ser Ser Pro Ala Leu Thr Ala Ala Ser Ser Gly
210 215 220

Thr Arg Arg Thr Ala Gly Val Ser Val Asp Leu Asp Asp Val His His
225 230 235 240

Val Arg Lys Thr Thr Gly Gly Thr Val Asn Asp Val Leu Ile Ala Val
245 250 255

Val Ala Gly Ala Leu Arg Arg Trp Leu Asp Glu Arg Gly Asp Gly Ser
260 265 270

Glu Gly Val Ala Pro Arg Ala Leu Ile Pro Val Ser Arg Arg Arg Pro
275 280 285

Arg Ser Ala His Pro Gln Gly Asn Arg Leu Ser Gly Tyr Leu Met Arg
290 295 300

Leu Pro Val Gly Asp Pro Asp Pro Leu Ala Arg Leu Gly Thr Val Arg
305 310 315 320

Ala Ala Met Asp Arg Asn Lys Asp Ala Gly Pro Gly Arg Gly Ala Gly
325 330 335

Ala Val Ala Leu Leu Ala Asp His Val Pro Ala Leu Gly His Arg Leu
340 345 350

Gly Gly Pro Leu Val Ser Gly Ala Ala Arg Leu Trp Phe Asp Leu Leu
355 360 365

Val Thr Ser Val Pro Leu Pro Ser Leu Gly Leu Arg Leu Gly Gly His
370 375 380

Pro Leu Thr Glu Val Tyr Pro Leu Ala Pro Leu Ala Arg Gly His Ser
385 390 395 400

Leu Ala Val Ala Val Ser Thr Tyr Arg Gly Arg Val His Tyr Gly Leu
405 410 415

Leu Ala Asp Ala Lys Ala Val Pro Asp Leu Asp Arg Leu Ala Val Ala

```
            420                 425                 430

Val Ala Glu Glu Val Glu Thr Leu Leu Thr Ala Cys Arg Pro
        435                 440                 445


<210> SEQ ID NO 15
<211> LENGTH: 457
<212> TYPE: PRT
<213> ORGANISM: Alcanivorax borkumensis

<400> SEQUENCE: 15

Met Lys Ala Leu Ser Pro Val Asp Gln Leu Phe Leu Trp Leu Glu Lys
 1               5                  10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350
```

-continued

```
Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445

Glu Leu Glu Ile Gly Ala Gly Ile Lys
    450                 455
```

<210> SEQ ID NO 16
<211> LENGTH: 1341
<212> TYPE: DNA
<213> ORGANISM: Artificial Sequence
<220> FEATURE:
<223> OTHER INFORMATION: Codon-optimized Streptomyces coelicolor DGAT

<400> SEQUENCE: 16

```
atgacgcctg acccgttggc tcccttggac ttggctttct ggaatatcga aagtgccgag     60

cacccgatgc acttgggggc actgggggtc tttgaggcgg atagtccaac cgctggtgca    120

ctcgccgcgg atctcctggc tgcccgcgct cccgcagtgc ccgggctgcg catgcggatt    180

cgcgatacat ggcagccgcc tatggcgctc cgtcgccctt ttgcttttgg cggtgctaca    240

cgcgagcccg acccgcggtt tgatccactc gatcatgtgc ggctccatgc cccagcgacg    300

gatttccacg cacgcgcagg tcggttgatg gagcgccctc tggaacgagg ccgtcctcct    360

tgggaagccc atgtcctgcc aggggctgac ggtggatcgt ttgcggtctt gtttaagttc    420

catcatgccc tggccgacgg tctgcgggcg ctgacgctgg cggcgggcgt gctcgatccg    480

atggatctcc ccgctccacg gccccgccca gagcagcccc cccgtggtct cctgccggat    540

gtccgcgcgc tgccggatcg gctgcgaggg gctctgtctg acgcgggccg cgcgttggac    600

atcggcgccg ccgcagccct cagcaccctg gatgtgcgga gcagtcccgc tctgactgcg    660

gcgtcctcgg gcacgcgacg taccgccggc gtgtccgtgg atctcgacga cgtgcaccat    720

gttcgcaaaa cgacaggcgg taccgttaac gatgttttga tcgccgttgt tgccggggcc    780

ctgcgacgct ggctggatga acgaggcgat gggtcggaag gcgtcgcccc gcgcgccctc    840

attcccgtca gccggcggcg acctcggagc gcacacccgc aaggcaaccg attgagtggc    900

tacctgatgc gcttgccggt cggcgacccg gaccctctcg cacggttggg aaccgtccgt    960

gccgcgatgg atcgaaataa ggatgcgggg cccggccgcg gagctggcgc agttgctctc   1020

ttggcagacc acgttcctgc cctgggccac cgcctgggtg gacccctcgt ctcgggcgct   1080

gctcgactgt ggttcgatct gttggtcacg agcgtcccgt tgccctcttt gggtttgcgc   1140

ctcggtgggc atccgctgac cgaagtgtac ccactggccc ccctggcccg tggccactcc   1200

ttggcggtgg cggtgagcac ttatcgcggt cgggttcatt acggtctcct cgctgatgct   1260

aaagccgttc ctgatctgga tcgtctggca gtggccgtcg ccgaggaggt tgaaaccttg   1320

ctcactgcgt gccgccccta g                                              1341
```

<210> SEQ ID NO 17

<211> LENGTH: 1374
<212> TYPE: DNA
<213> ORGANISM: Artificial Sequence
<220> FEATURE:
<223> OTHER INFORMATION: Codon-optimized Alcanivorax borkumensis DGAT

<400> SEQUENCE: 17

```
atgaaagctt tgagccccgt tgatcagctg tttctgtggt tggaaaaacg gcagcaaccc     60

atgcatgtgg gtgggttgca gctgttctcc tttcccgaag gcgcggggcc gaaatatgtc    120

tcggaactgg cccaacagat gcgcgattat tgtcaccctg tcgccccgtt caaccaacgt    180

ctgacacggc gcctggggca atactactgg acacgtgata agcaatttga cattgaccat    240

cattttcggc acgaggccct gcccaaaccg ggtcggattc gcgagttgct cagcttggtg    300

agtgcggaac actccaactt gttggatcgt gaacgaccca tgtgggaagc gcacctgatc    360

gaaggaatcc gcgggcgcca atttgccttg tattacaaaa ttcatcactc cgtcatggac    420

ggtatctccg ctatgcggat tgcctctaag accttgtcca cggaccccag tgagcgggag    480

atggcccccg cttgggcgtt taatactaag aagcgatcgc gcagcctgcc aagcaatccc    540

gtggatatgg cgagctcgat ggctcgactc actgcaagta tttcgaaaca agctgccacc    600

gtgcccggcc tggcacgaga ggtctacaag gtgacccaaa aagctaaaaa ggatgaaaat    660

tacgttagta ttttccaagc accagacacc atcctcaata atacgattac gggcagtcga    720

cgcttcgccg ctcagtcgtt ccctctcccc cgtctgaagg ttatcgctaa ggcttacaac    780

tgcactatta acacggttgt gctctcgatg tgcggccacg ccctgcgcga atacctcatc    840

agtcaacatg ccctgccgga tgaacccctg atcgcgatgg tccctatgag cctgcgccaa    900

gatgatagca ccggaggcaa ccagatcgga atgattttgg cgaatctggg cacgcatatc    960

tgcgatcctg ccaatcgcct gcgtgtcatc catgatagcg tggaggaggc gaaaagccgt   1020

tttagccaaa tgtctccgga ggagattctg aactttacag cactcactat ggcgccgacc   1080

ggtctgaact tgctcaccgg tttggctccc aaatggcgcg catttaacgt cgttatctct   1140

aacatcccag ggccaaagga accactgtac tggaatgggg cacagctcca gggtgtgtat   1200

ccggtctcca tcgccttgga tcggattgcc ctgaacatta cactgacgtc ttatgttgat   1260

cagatggagt tcggcttgat tgcgtgtcgc cggaccctcc cgtcgatgca acgactcctc   1320

gactatctcg aacagagtat ccgcgaactg gagattggcg cgggcatcaa atag         1374
```

<210> SEQ ID NO 18
<211> LENGTH: 460
<212> TYPE: PRT
<213> ORGANISM: Acinetobacter baylii sp.

<400> SEQUENCE: 18

```
Met Glu Phe Arg Pro Leu His Pro Ile Asp Phe Ile Phe Leu Ser Leu
1               5                   10                  15

Glu Lys Arg Gln Gln Pro Met His Val Gly Gly Leu Phe Leu Phe Gln
            20                  25                  30

Ile Pro Asp Asn Ala Pro Asp Thr Phe Ile Gln Asp Leu Val Asn Asp
        35                  40                  45

Ile Arg Ile Ser Lys Ser Ile Pro Val Pro Pro Phe Asn Asn Lys Leu
    50                  55                  60

Asn Gly Leu Phe Trp Asp Glu Asp Glu Glu Phe Asp Leu Asp His His
65                  70                  75                  80

Phe Arg His Ile Ala Leu Pro His Pro Gly Arg Ile Arg Glu Leu Leu
                85                  90                  95
```

```
Ile Tyr Ile Ser Gln Glu His Ser Thr Leu Leu Asp Arg Ala Lys Pro
            100                 105                 110

Leu Trp Thr Cys Asn Ile Ile Glu Gly Ile Glu Gly Asn Arg Phe Ala
        115                 120                 125

Met Tyr Phe Lys Ile His His Ala Met Val Asp Gly Val Ala Gly Met
    130                 135                 140

Arg Leu Ile Glu Lys Ser Leu Ser His Asp Val Thr Glu Lys Ser Ile
145                 150                 155                 160

Val Pro Pro Trp Cys Val Glu Gly Lys Arg Ala Lys Arg Leu Arg Glu
                165                 170                 175

Pro Lys Thr Gly Lys Ile Lys Lys Ile Met Ser Gly Ile Lys Ser Gln
            180                 185                 190

Leu Gln Ala Thr Pro Thr Val Ile Gln Glu Leu Ser Gln Thr Val Phe
        195                 200                 205

Lys Asp Ile Gly Arg Asn Pro Asp His Val Ser Ser Phe Gln Ala Pro
    210                 215                 220

Cys Ser Ile Leu Asn Gln Arg Val Ser Ser Ser Arg Arg Phe Ala Ala
225                 230                 235                 240

Gln Ser Phe Asp Leu Asp Arg Phe Arg Asn Ile Ala Lys Ser Leu Asn
                245                 250                 255

Val Thr Ile Asn Asp Val Val Leu Ala Val Cys Ser Gly Ala Leu Arg
            260                 265                 270

Ala Tyr Leu Met Ser His Asn Ser Leu Pro Ser Lys Pro Leu Ile Ala
        275                 280                 285

Met Val Pro Ala Ser Ile Arg Asn Asp Asp Ser Asp Val Ser Asn Arg
    290                 295                 300

Ile Thr Met Ile Leu Ala Asn Leu Ala Thr His Lys Asp Asp Pro Leu
305                 310                 315                 320

Gln Arg Leu Glu Ile Ile Arg Arg Ser Val Gln Asn Ser Lys Gln Arg
                325                 330                 335

Phe Lys Arg Met Thr Ser Asp Gln Ile Leu Asn Tyr Ser Ala Val Val
            340                 345                 350

Tyr Gly Pro Ala Gly Leu Asn Ile Ile Ser Gly Met Met Pro Lys Arg
        355                 360                 365

Gln Ala Phe Asn Leu Val Ile Ser Asn Val Pro Gly Pro Arg Glu Pro
    370                 375                 380

Leu Tyr Trp Asn Gly Ala Lys Leu Asp Ala Leu Tyr Pro Ala Ser Ile
385                 390                 395                 400

Val Leu Asp Gly Gln Ala Leu Asn Ile Thr Met Thr Ser Tyr Leu Asp
                405                 410                 415

Lys Leu Glu Val Gly Leu Ile Ala Cys Arg Asn Ala Leu Pro Arg Met
            420                 425                 430

Gln Asn Leu Leu Thr His Leu Glu Glu Glu Ile Gln Leu Phe Glu Gly
        435                 440                 445

Val Ile Ala Lys Gln Glu Asp Ile Lys Thr Ala Asn
    450                 455                 460
```

<210> SEQ ID NO 19
<211> LENGTH: 1383
<212> TYPE: DNA
<213> ORGANISM: Artificial Sequence
<220> FEATURE:
<223> OTHER INFORMATION: Codon-optimized Acinetobacter baylii sp. DGATd

<400> SEQUENCE: 19

```
atggaattcc ggcccttgca ccccattgac ttcatctttc tgagtttgga gaaacggcaa     60
cagcccatgc atgtcggtgg cttgtttctc ttccaaatcc ccgataacgc cccggacacc    120
tttattcagg atctggtcaa tgatatccgg atctcgaaat cgatccccgt gccgccgttt    180
aataataaac tgaacggcct cttttgggac gaagacgagg aatttgatct ggatcaccat    240
tttcggcaca tcgctttgcc ccacccgggt cggattcgcg aactcctgat ctatattagc    300
caagaacaca gcacgttgtt ggaccgggcc aaaccgctct ggacgtgcaa tatcatcgaa    360
ggcatcgaag gcaaccgctt tgcgatgtac ttcaagattc atcacgcgat ggttgacggt    420
gtcgctggca tgcgcctgat cgaaaaatcg ctgagccatg atgtgaccga aaagagtatc    480
gtcccccccct ggtgcgtgga aggtaagcgc gccaagcgcc tccgcgaacc gaaaacgggc    540
aagattaaga aaatcatgag cggtatcaag tcgcagctgc aggctacccc gaccgtgatc    600
caggagctgt cgcaaaccgt gtttaaggat attggtcgga acccggatca tgtcagtagt    660
ttccaagctc cctgttcgat cttgaatcag cgcgttagca gcagccgccg gttcgctgct    720
caaagttttg atctcgatcg gtttcggaat attgccaagt cgctgaacgt caccatcaat    780
gatgtggttc tcgcggtttg ttcgggtgcc ctccgcgcgt atctgatgag ccataacagt    840
ctccccagta agccgctgat tgctatggtt cccgcgtcga ttcggaatga cgacagcgat    900
gtgagcaacc ggattaccat gatcctggct aacctcgcga cccacaaaga tgatccgttg    960
caacgcctgg agattatccg ccgcagtgtg cagaacagta aacagcgctt caaacggatg   1020
accagtgatc aaattctgaa ttacagcgct gtggtctatg gtcccgccgg cttgaatatt   1080
atcagtggta tgatgcccaa acgccaagcg tttaacttgg tgatcagtaa tgtgccgggt   1140
ccgcgcgaac ccttgtattg gaacggtgct aaactcgatg ccctctaccc cgccagtatc   1200
gtgctcgatg gccaggctct caatattacc atgaccagct atctcgataa actcgaggtg   1260
ggtttgattg cgtgccgcaa cgcgctgccc cgcatgcaga acttgctgac ccacctggaa   1320
gaggaaatcc agctcttcga gggcgtgatt gcgaagcagg aagatattaa aacggccaac   1380
tag                                                                  1383

<210> SEQ ID NO 20
<211> LENGTH: 325
<212> TYPE: PRT
<213> ORGANISM: Synechococcus sp. PCC7002

<400> SEQUENCE: 20

Met Pro Lys Thr Glu Arg Arg Thr Phe Leu Leu Asp Phe Glu Lys Pro
1               5                   10                  15

Leu Ser Glu Leu Glu Ser Arg Ile His Gln Ile Arg Asp Leu Ala Ala
            20                  25                  30

Glu Asn Asn Val Asp Val Ser Glu Gln Ile Gln Gln Leu Glu Ala Arg
        35                  40                  45

Ala Asp Gln Leu Arg Glu Glu Ile Phe Ser Thr Leu Thr Pro Ala Gln
    50                  55                  60

Arg Leu Gln Leu Ala Arg His Pro Arg Arg Pro Ser Thr Leu Asp Tyr
65                  70                  75                  80

Val Gln Met Met Ala Asp Glu Trp Phe Glu Leu His Gly Asp Arg Gly
                85                  90                  95

Gly Ser Asp Asp Pro Ala Leu Ile Gly Gly Val Ala Arg Phe Asp Gly
            100                 105                 110

Gln Pro Val Met Met Leu Gly His Gln Lys Gly Arg Asp Thr Lys Asp
```

```
        115                 120                 125

Asn Val Ala Arg Asn Phe Gly Met Pro Ala Pro Gly Gly Tyr Arg Lys
    130                 135                 140

Ala Met Arg Leu Met Asp His Ala Asn Arg Phe Gly Met Pro Ile Leu
145                 150                 155                 160

Thr Phe Ile Asp Thr Pro Gly Ala Trp Ala Gly Leu Glu Ala Glu Lys
                165                 170                 175

Leu Gly Gln Gly Glu Ala Ile Ala Phe Asn Leu Arg Glu Met Phe Ser
            180                 185                 190

Leu Asp Val Pro Ile Ile Cys Thr Val Ile Gly Glu Gly Gly Ser Gly
        195                 200                 205

Gly Ala Leu Gly Ile Gly Val Gly Asp Arg Val Leu Met Leu Lys Asn
    210                 215                 220

Ser Val Tyr Thr Val Ala Thr Pro Glu Ala Cys Ala Ala Ile Leu Trp
225                 230                 235                 240

Lys Asp Ala Gly Lys Ser Glu Gln Ala Ala Ala Ala Leu Lys Ile Thr
                245                 250                 255

Ala Glu Asp Leu Lys Ser Leu Glu Ile Ile Asp Glu Ile Val Pro Glu
            260                 265                 270

Pro Ala Ser Cys Ala His Ala Asp Pro Ile Gly Ala Ala Gln Leu Leu
        275                 280                 285

Lys Ala Ala Ile Gln Asp Asn Leu Gln Ala Leu Leu Lys Leu Thr Pro
    290                 295                 300

Glu Arg Arg Arg Glu Leu Arg Tyr Gln Arg Phe Arg Lys Ile Gly Val
305                 310                 315                 320

Phe Leu Glu Ser Ser
                325


<210> SEQ ID NO 21
<211> LENGTH: 165
<212> TYPE: PRT
<213> ORGANISM: Synechococcus sp. PCC 7002

<400> SEQUENCE: 21

Met Ala Ile Asn Leu Gln Glu Ile Gln Glu Leu Leu Ser Thr Ile Gly
 1               5                  10                  15

Gln Thr Asn Val Thr Glu Phe Glu Leu Lys Thr Asp Asp Phe Glu Leu
            20                  25                  30

Arg Val Ser Lys Gly Thr Val Val Ala Ala Pro Gln Thr Met Val Met
        35                  40                  45

Ser Glu Ala Ile Ala Gln Pro Ala Met Ser Thr Pro Val Val Ser Gln
    50                  55                  60

Ala Thr Ala Thr Pro Glu Ala Ser Gln Ala Glu Thr Pro Ala Pro Ser
65                  70                  75                  80

Val Ser Ile Asp Asp Lys Trp Val Ala Ile Thr Ser Pro Met Val Gly
                85                  90                  95

Thr Phe Tyr Arg Ala Pro Ala Pro Gly Glu Asp Pro Phe Val Ala Val
            100                 105                 110

Gly Asp Arg Val Gly Asn Gly Gln Thr Val Cys Ile Ile Glu Ala Met
        115                 120                 125

Lys Leu Met Asn Glu Ile Glu Ala Glu Val Ser Gly Glu Val Val Lys
    130                 135                 140

Ile Ala Val Glu Asp Gly Glu Pro Ile Glu Phe Gly Gln Thr Leu Met
145                 150                 155                 160
```

Trp Val Asn Pro Thr
165

<210> SEQ ID NO 22
<211> LENGTH: 448
<212> TYPE: PRT
<213> ORGANISM: Synechococcus sp. PCC 7002

<400> SEQUENCE: 22

Met Gln Phe Ser Lys Ile Leu Ile Ala Asn Arg Gly Glu Val Ala Leu
1 5 10 15

Arg Ile Ile His Thr Cys Gln Glu Leu Gly Ile Ala Thr Val Ala Val
20 25 30

His Ser Thr Val Asp Arg Gln Ala Leu His Val Gln Leu Ala Asp Glu
35 40 45

Ser Ile Cys Ile Gly Pro Pro Gln Ser Ser Lys Ser Tyr Leu Asn Ile
50 55 60

Pro Asn Ile Ile Ala Ala Ala Leu Ser Ser Asn Ala Asp Ala Ile His
65 70 75 80

Pro Gly Tyr Gly Phe Leu Ala Glu Asn Ala Lys Phe Ala Glu Ile Cys
85 90 95

Ala Asp His Gln Ile Thr Phe Ile Gly Pro Ser Pro Glu Ala Met Ile
100 105 110

Ala Met Gly Asp Lys Ser Thr Ala Lys Lys Thr Met Gln Ala Ala Lys
115 120 125

Val Pro Thr Val Pro Gly Ser Ala Gly Leu Val Ala Ser Glu Glu Gln
130 135 140

Ala Leu Glu Ile Ala Gln Gln Ile Gly Tyr Pro Val Met Ile Lys Ala
145 150 155 160

Thr Ala Gly Gly Gly Gly Arg Gly Met Arg Leu Val Pro Ser Ala Glu
165 170 175

Glu Leu Pro Arg Leu Tyr Arg Ala Ala Gln Gly Glu Ala Glu Ala Ala
180 185 190

Phe Gly Asn Gly Gly Val Tyr Ile Glu Lys Phe Ile Glu Arg Pro Arg
195 200 205

His Ile Glu Phe Gln Ile Leu Ala Asp Gln Tyr Gly Asn Val Ile His
210 215 220

Leu Gly Glu Arg Asp Cys Ser Ile Gln Arg Arg His Gln Lys Leu Leu
225 230 235 240

Glu Glu Ala Pro Ser Ala Ile Leu Thr Pro Arg Leu Arg Asp Lys Met
245 250 255

Gly Lys Ala Ala Val Lys Ala Ala Lys Ser Ile Asp Tyr Val Gly Ala
260 265 270

Gly Thr Val Glu Phe Leu Val Asp Lys Asn Gly Asp Phe Tyr Phe Met
275 280 285

Glu Met Asn Thr Arg Ile Gln Val Glu His Pro Val Thr Glu Met Val
290 295 300

Thr Gly Leu Asp Leu Ile Ala Glu Gln Ile Lys Val Ala Gln Gly Asp
305 310 315 320

Arg Leu Ser Leu Asn Gln Asn Gln Val Asn Leu Asn Gly His Ala Ile
325 330 335

Glu Cys Arg Ile Asn Ala Glu Asp Pro Asp His Asp Phe Arg Pro Thr
340 345 350

Pro Gly Lys Ile Ser Gly Tyr Leu Pro Pro Gly Gly Pro Gly Val Arg
355 360 365

```
Met Asp Ser His Val Tyr Thr Asp Tyr Glu Ile Ser Pro Tyr Tyr Asp
    370                 375                 380

Ser Leu Ile Gly Lys Leu Ile Val Trp Gly Pro Asp Arg Asp Thr Ala
385                 390                 395                 400

Ile Arg Arg Met Lys Arg Ala Leu Arg Glu Cys Ala Ile Thr Gly Val
                405                 410                 415

Ser Thr Thr Ile Ser Phe His Gln Lys Ile Leu Asn His Pro Ala Phe
            420                 425                 430

Leu Ala Ala Asp Val Asp Thr Asn Phe Ile Gln Gln His Met Leu Pro
        435                 440                 445


<210> SEQ ID NO 23
<211> LENGTH: 319
<212> TYPE: PRT
<213> ORGANISM: Synechococcus sp. PCC 7002

<400> SEQUENCE: 23

Met Ser Leu Phe Asp Trp Phe Ala Ala Asn Arg Gln Asn Ser Glu Thr
 1               5                  10                  15

Gln Leu Gln Pro Gln Gln Glu Arg Glu Ile Ala Asp Gly Leu Trp Thr
            20                  25                  30

Lys Cys Lys Ser Cys Asp Ala Leu Thr Tyr Thr Lys Asp Leu Arg Asn
        35                  40                  45

Asn Gln Met Val Cys Lys Glu Cys Gly Phe His Asn Arg Val Gly Ser
    50                  55                  60

Arg Glu Arg Val Arg Gln Leu Ile Asp Glu Gly Thr Trp Thr Glu Ile
65                  70                  75                  80

Ser Gln Asn Val Ala Pro Thr Asp Pro Leu Lys Phe Arg Asp Lys Lys
                85                  90                  95

Ala Tyr Ser Asp Arg Leu Lys Asp Tyr Gln Glu Lys Thr Asn Leu Thr
            100                 105                 110

Asp Ala Val Ile Thr Gly Thr Gly Leu Ile Asp Gly Leu Pro Leu Ala
        115                 120                 125

Leu Ala Val Met Asp Phe Gly Phe Met Gly Gly Ser Met Gly Ser Val
    130                 135                 140

Val Gly Glu Lys Ile Cys Arg Leu Val Glu His Gly Thr Ala Glu Gly
145                 150                 155                 160

Leu Pro Val Val Val Val Cys Ala Ser Gly Gly Ala Arg Met Gln Glu
                165                 170                 175

Gly Met Leu Ser Leu Met Gln Met Ala Lys Ile Ser Gly Ala Leu Glu
            180                 185                 190

Arg His Arg Thr Lys Lys Leu Leu Tyr Ile Pro Val Leu Thr Asn Pro
        195                 200                 205

Thr Thr Gly Gly Val Thr Ala Ser Phe Ala Met Leu Gly Asp Leu Ile
    210                 215                 220

Leu Ala Glu Pro Lys Ala Thr Ile Gly Phe Ala Gly Arg Arg Val Ile
225                 230                 235                 240

Glu Gln Thr Leu Arg Glu Lys Leu Pro Asp Asp Phe Gln Thr Ser Glu
                245                 250                 255

Tyr Leu Leu Gln His Gly Phe Val Asp Ala Ile Val Pro Arg Thr Glu
            260                 265                 270

Leu Lys Lys Thr Leu Ala Gln Met Ile Ser Leu His Gln Pro Phe His
        275                 280                 285

Pro Ile Leu Pro Glu Leu Gln Leu Ala Pro His Val Glu Lys Glu Lys
```

-continued 290 295 300

Val Tyr Glu Pro Ile Ala Ser Thr Ser Thr Asn Asp Phe Tyr Lys
305 310 315

<210> SEQ ID NO 24
<211> LENGTH: 978
<212> TYPE: DNA
<213> ORGANISM: Synechococcus sp. PCC 7002

<400> SEQUENCE: 24
atgccgaaaa cggagcgccg gacgtttctg cttgattttg aaaaacctct ttcggaatta 60
gaatcacgca tccatcaaat tcgtgatctt gctgcggaga ataatgttga tgtttcagaa 120
cagattcagc agctagaggc gcgggcagac cagctccggg aagaaatttt tagtaccctc 180
accccggccc aacggctgca attggcacgg catccccggc gtcccagcac ccttgattat 240
gttcaaatga tggcggacga atggtttgaa ctccatggcg atcgcggtgg atctgatgat 300
ccggctctca ttggcggggt ggcccgcttc gatggtcaac cggtgatgat gctagggcac 360
caaaaaggac gggatacgaa ggataatgtc gcccgcaatt ttggcatgcc agctcctggg 420
ggctaccgta aggcgatgcg gctgatggac catgccaacc gttttgggat gccgatttta 480
acgtttattg atactcctgg ggcttgggcg ggtttagaag cggaaaagtt gggccaaggg 540
gaggcgatcg cctttaacct ccgggaaatg tttagcctcg atgtgccgat tatttgcacg 600
gtcattggcg aaggcggttc cggtggggcc ttagggattg gcgtgggcga tcgcgtcttg 660
atgttaaaaa attccgttta cacagtggcg accccagagg cttgtgccgc cattctctgg 720
aaagatgccg ggaaatcaga gcaggccgcc gccgccctca agattacagc agaggatctg 780
aaaagccttg agattatcga tgaaattgtc ccagagccag cctcctgcgc ccacgccgat 840
cccattgggg ccgcccaact cctgaaagca gcgatccaag ataacctcca agccttgctg 900
aagctgacgc cagaacgccg ccgtgaattg cgctaccagc ggttccggaa aattggtgtg 960
tttttagaaa gttcctaa 978

<210> SEQ ID NO 25
<211> LENGTH: 498
<212> TYPE: DNA
<213> ORGANISM: Synechococcus sp. PCC 7002

<400> SEQUENCE: 25
atggctatta atttacaaga gatccaagaa cttctatcca ccatcggcca aaccaatgtc 60
accgagtttg aactcaaaac cgatgatttt gaactccgtg tgagcaaagg tactgttgtg 120
gctgctcccc agacgatggt gatgtccgag gcgatcgccc aaccagcaat gtccactccc 180
gttgtttctc aagcaactgc aaccccagaa gcctcccaag cggaaacccc ggctcccagt 240
gtgagcattg atgataagtg ggtcgccatt acctccccca tggtgggaac gttttaccgc 300
gcgccggccc ctggtgaaga tcccttcgtt gccgttggcg atcgcgttgg caatggtcaa 360
accgtttgca tcatcgaagc gatgaaatta atgaatgaga ttgaggcaga agtcagcggt 420
gaagttgtta aaattgccgt tgaagacggt gaacccattg aatttggtca gaccctaatg 480
tgggtcaacc caacctaa 498

<210> SEQ ID NO 26
<211> LENGTH: 1347
<212> TYPE: DNA
<213> ORGANISM: Synechococcus sp. PCC 7002

<400> SEQUENCE: 26

```
atgcagtttt caaagattct catcgccaat cgcggagaag ttgccctacg cattatccac     60
acctgtcagg agctcggcat tgccacagtt gccgtccact ccaccgtaga tcgccaagcc    120
ctccacgttc agctcgccga tgagagcatt tgcattggcc cgccccagag cagcaaaagc    180
tatctcaaca ttcccaatat tatcgctgcg gccctcagca gtaacgccga cgcaatccac    240
ccaggctacg gtttcctcgc tgaaaatgcc aagtttgcag aaatttgtgc cgaccaccaa    300
atcaccttca ttggcccttc cccagaagca atgatcgcca tgggggacaa atccaccgcc    360
aaaaaaacga tgcaggcggc aaaagtccct accgtacccg gtagtgctgg gttggtggcc    420
tccgaagaac aagccctaga aatcgcccaa caaattggct accctgtgat gatcaaagcc    480
acggcgggtg gtggtggccg gggggatgcgc cttgtgccca gcgctgagga gttaccccgt    540
ttgtaccgag cggcccaggg ggaagcagaa gcagcctttg ggaatggcgg cgtttacatc    600
gaaaaattta ttgaacggcc ccgtcacatc gaatttcaga tcctcgcgga tcagtacggc    660
aatgtaattc acctcggcga acgggattgt tcgatccaac ggcggcacca aaaactcctc    720
gaagaagctc ccagcgcgat cctcaccccc agactgcggg acaaaatggg gaaagcggca    780
gtaaaagcgg cgaaatccat tgattatgtc ggggcgggga cggtggaatt cctcgtggat    840
aagaatgggg atttctactt tatggaaatg aatacccgca ttcaggtgga acacccggtc    900
acagagatgg tgacgggact agatctgatc gccgagcaaa ttaaagttgc ccaaggcgat    960
cgcctcagtt tgaatcaaaa tcaagtgaac ttgaatggtc atgccatcga gtgccggatt   1020
aatgccgaag atcccgacca tgatttccga ccgaccccag gcaaaatcag tggctatctt   1080
ccccccggtg gccctggggt acggatggat tcccacgttt acaccgacta tgaaatttct   1140
ccttactacg attctttgat cggtaaatta atcgtttggg gaccagaccg agacaccgcc   1200
attcgccgca tgaagcgggc actccgagaa tgtgccatta ctggagtatc gaccaccatt   1260
agcttccacc aaaagatttt gaatcatccg gctttttttgg cggccgatgt cgatacaaac   1320
tttatccagc agcacatgtt gccctag                                        1347
```

<210> SEQ ID NO 27
<211> LENGTH: 960
<212> TYPE: DNA
<213> ORGANISM: Synechococcus sp. PCC 7002

<400> SEQUENCE: 27

```
atgtctcttt ttgattggtt tgccgcaaat cgccaaaatt ctgaaaccca gctccagccc     60
caacaggagc gcgagattgc cgatggcctc tggacgaaat gcaaatcctg cgatgctctc    120
acctacacta aagacctccg caacaatcaa atggtctgta aagagtgtgg cttccataac    180
cgggtcggca gtcgggaacg ggtacgccaa ttgattgacg aaggcacctg gacagaaatt    240
agtcagaatg tcgcgccgac cgaccccctg aaattccgcg acaaaaaagc ctatagcgat    300
cgcctcaaag attaccaaga gaaaacgaac ctcaccgatg ctgtaatcac tggcacagga    360
ctgattgacg gtttacccct tgctttggca gtgatggact ttggctttat gggcggcagc    420
atgggatccg ttgtcggcga aaaaatttgt cgcctcgtag aacatggcac cgccgaaggt    480
ttacccgtgg tggttgtttg tgcttctggt ggagcaagaa tgcaagaggg catgctcagt    540
ctgatgcaga tggcgaaaat ctctggtgcc ctcgaacgcc atcgcaccaa aaaattactc    600
tacatccctg ttttgactaa tcccaccacc gggggcgtca ccgctagctt tgcgatgttg    660
ggcgatttga ttcttgccga acccaaagca accatcggtt ttgctggacg ccgcgtcatt    720
```

-continued gaacaaacat tgcgcgaaaa acttcctgac gattttcaga catctgaata tttactccaa 780
catgggtttg tggatgcgat tgtgccccgc actgaattga aaaaaaccct cgcccaaatg 840
attagtctcc atcagccctt tcacccgatt ctgccagagc tacaattggc tccccatgtg 900
gaaaaagaaa aagtttacga acccattgcc tctacttcaa ccaacgactt ttacaagtag 960

<210> SEQ ID NO 28
<211> LENGTH: 2311
<212> TYPE: PRT
<213> ORGANISM: Triticum aestivum

<400> SEQUENCE: 28

Met Gly Ser Thr His Leu Pro Ile Val Gly Leu Asn Ala Ser Thr Thr
1 5 10 15

Pro Ser Leu Ser Thr Ile Arg Pro Val Asn Ser Ala Gly Ala Ala Phe
20 25 30

Gln Pro Ser Ala Pro Ser Arg Thr Ser Lys Lys Lys Ser Arg Arg Val
35 40 45

Gln Ser Leu Arg Asp Gly Gly Asp Gly Gly Val Ser Asp Pro Asn Gln
50 55 60

Ser Ile Arg Gln Gly Leu Ala Gly Ile Ile Asp Leu Pro Lys Glu Gly
65 70 75 80

Thr Ser Ala Pro Glu Val Asp Ile Ser His Gly Ser Glu Glu Pro Arg
85 90 95

Gly Ser Tyr Gln Met Asn Gly Ile Leu Asn Glu Ala His Asn Gly Arg
100 105 110

His Ala Ser Leu Ser Lys Val Val Glu Phe Cys Met Ala Leu Gly Gly
115 120 125

Lys Thr Pro Ile His Ser Val Leu Val Ala Asn Asn Gly Arg Ala Ala
130 135 140

Ala Lys Phe Met Arg Ser Val Arg Thr Trp Ala Asn Glu Thr Phe Gly
145 150 155 160

Ser Glu Lys Ala Ile Gln Leu Ile Ala Met Ala Thr Pro Glu Asp Met
165 170 175

Arg Ile Asn Ala Glu His Ile Arg Ile Ala Asp Gln Phe Val Glu Val
180 185 190

Pro Gly Gly Thr Asn Asn Asn Asn Tyr Ala Asn Val Gln Leu Ile Val
195 200 205

Glu Ile Ala Val Arg Thr Gly Val Ser Ala Val Trp Pro Gly Trp Gly
210 215 220

His Ala Ser Glu Asn Pro Glu Leu Pro Asp Ala Leu Asn Ala Asn Gly
225 230 235 240

Ile Val Phe Leu Gly Pro Pro Ser Ser Ser Met Asn Ala Leu Gly Asp
245 250 255

Lys Val Gly Ser Ala Leu Ile Ala Gln Ala Ala Gly Val Pro Thr Leu
260 265 270

Pro Trp Gly Gly Ser Gln Val Glu Ile Pro Leu Glu Val Cys Leu Asp
275 280 285

Ser Ile Pro Ala Glu Met Tyr Arg Lys Ala Cys Val Ser Thr Thr Glu
290 295 300

Glu Ala Leu Ala Ser Cys Gln Met Ile Gly Tyr Pro Ala Met Ile Lys
305 310 315 320

Ala Ser Trp Gly Gly Gly Gly Lys Gly Ile Arg Lys Val Asn Asn Asp
325 330 335

```
Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430

Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Glu Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Val Ser Arg Ala Ala Ala Ile Thr
            580                 585                 590

Asn Met Ser Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Lys
    610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Ile Thr Ser Asn Thr Asp Thr Val Ser Glu Tyr Val
            660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
    690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                725                 730                 735

Gln Leu Asp Gly Asn Ser His Val Ile Tyr Ala Glu Glu Glu Ala Gly
            740                 745                 750
```

-continued

```
Gly Thr Arg Leu Leu Ile Asp Gly Lys Thr Tyr Leu Leu Gln Asn Asp
        755                 760                 765

His Asp Pro Ser Arg Leu Leu Ala Glu Thr Pro Cys Lys Leu Leu Arg
    770                 775                 780

Phe Leu Val Ala Asp Gly Ala His Val Glu Ala Asp Val Pro Tyr Ala
785                 790                 795                 800

Glu Val Glu Val Met Lys Met Cys Met Pro Leu Leu Ser Pro Ala Ala
                805                 810                 815

Gly Val Ile Asn Val Leu Leu Ser Glu Gly Gln Pro Met Gln Ala Gly
            820                 825                 830

Asp Leu Ile Ala Arg Leu Asp Leu Asp Asp Pro Ser Ala Val Lys Arg
        835                 840                 845

Ala Glu Pro Phe Asn Gly Ser Phe Pro Glu Met Ser Leu Pro Ile Ala
    850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
                885                 890                 895

Asp Leu Val Ser Cys Leu Asp Ala Pro Glu Leu Pro Phe Leu Gln Trp
            900                 905                 910

Glu Glu Leu Met Ser Val Leu Ala Thr Arg Leu Pro Arg Leu Leu Lys
        915                 920                 925

Ser Glu Leu Glu Gly Lys Tyr Ser Glu Tyr Lys Leu Asn Val Gly His
    930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Leu Lys Ser Tyr Glu Gly Gly Arg
            980                 985                 990

Glu Ser His Ala His Phe Ile Val Lys Ser Leu Phe Glu Asp Tyr Leu
        995                 1000                1005

Ser Val Glu Glu Leu Phe Ser Asp Gly Ile Gln Ser Asp Val Ile Glu
    1010                1015                1020

Arg Leu Arg Gln Gln His Ser Lys Asp Leu Gln Lys Val Val Asp Ile
1025                1030                1035                1040

Val Leu Ser His Gln Gly Val Arg Asn Lys Thr Lys Leu Ile Leu Thr
                1045                1050                1055

Leu Met Glu Lys Leu Val Tyr Pro Asn Pro Ala Val Tyr Lys Asp Gln
            1060                1065                1070

Leu Thr Arg Phe Ser Ser Leu Asn His Lys Arg Tyr Tyr Lys Leu Ala
        1075                1080                1085

Leu Lys Ala Ser Glu Leu Leu Glu Gln Thr Lys Leu Ser Glu Leu Arg
    1090                1095                1100

Thr Ser Ile Ala Arg Ser Leu Ser Glu Leu Glu Met Phe Thr Glu Glu
1105                1110                1115                1120

Arg Thr Ala Ile Ser Glu Ile Met Gly Asp Leu Val Thr Ala Pro Leu
                1125                1130                1135

Pro Val Glu Asp Ala Leu Val Ser Leu Phe Asp Cys Ser Asp Gln Thr
            1140                1145                1150

Leu Gln Gln Arg Val Ile Glu Thr Tyr Ile Ser Arg Leu Tyr Gln Pro
        1155                1160                1165

His Leu Val Lys Asp Ser Ile Gln Leu Lys Tyr Gln Glu Ser Gly Val
```

-continued

```
    1170                1175                1180

Ile Ala Leu Trp Glu Phe Ala Glu Ala His Ser Glu Lys Arg Leu Gly
1185                1190                1195                1200

Ala Met Val Ile Val Lys Ser Leu Glu Ser Val Ser Ala Ala Ile Gly
                1205                1210                1215

Ala Ala Leu Lys Gly Thr Ser Arg Tyr Ala Ser Ser Glu Gly Asn Ile
            1220                1225                1230

Met His Ile Ala Leu Leu Gly Ala Asp Asn Gln Met His Gly Thr Glu
        1235                1240                1245

Asp Ser Gly Asp Asn Asp Gln Ala Gln Val Arg Ile Asp Lys Leu Ser
    1250                1255                1260

Ala Thr Leu Glu Gln Asn Thr Val Thr Ala Asp Leu Arg Ala Ala Gly
1265                1270                1275                1280

Val Lys Val Ile Ser Cys Ile Val Gln Arg Asp Gly Ala Leu Met Pro
                1285                1290                1295

Met Arg His Thr Phe Leu Leu Ser Asp Glu Lys Leu Cys Tyr Gly Glu
            1300                1305                1310

Glu Pro Val Leu Arg His Val Glu Pro Pro Leu Ser Ala Leu Leu Glu
        1315                1320                1325

Leu Gly Lys Leu Lys Val Lys Gly Tyr Asn Glu Val Lys Tyr Thr Pro
    1330                1335                1340

Ser Arg Asp Arg Gln Trp Asn Ile Tyr Thr Leu Arg Asn Thr Glu Asn
1345                1350                1355                1360

Pro Lys Met Leu His Arg Val Phe Phe Arg Thr Leu Val Arg Gln Pro
                1365                1370                1375

Gly Ala Ser Asn Lys Phe Thr Ser Gly Asn Ile Ser Asp Val Glu Val
            1380                1385                1390

Gly Gly Ala Glu Glu Ser Leu Ser Phe Thr Ser Ser Ser Ile Leu Arg
        1395                1400                1405

Ser Leu Met Thr Ala Ile Glu Glu Leu Glu Leu His Ala Ile Arg Thr
    1410                1415                1420

Gly His Ser His Met Phe Leu Cys Ile Leu Lys Glu Arg Lys Leu Leu
1425                1430                1435                1440

Asp Leu Val Pro Val Ser Gly Asn Lys Val Val Asp Ile Gly Gln Asp
                1445                1450                1455

Glu Ala Thr Ala Cys Leu Leu Leu Lys Glu Met Ala Leu Gln Ile His
            1460                1465                1470

Glu Leu Val Gly Ala Arg Met His His Leu Ser Val Cys Gln Trp Glu
        1475                1480                1485

Val Lys Leu Lys Leu Asp Ser Asp Gly Pro Ala Ser Gly Thr Trp Arg
    1490                1495                1500

Val Val Thr Thr Asn Val Thr Ser His Thr Cys Thr Val Asp Ile Tyr
1505                1510                1515                1520

Arg Glu Val Glu Asp Thr Glu Ser Gln Lys Leu Val Tyr His Ser Ala
                1525                1530                1535

Pro Ser Ser Ser Gly Pro Leu His Gly Val Ala Leu Asn Thr Pro Tyr
            1540                1545                1550

Gln Pro Leu Ser Val Ile Asp Leu Lys Arg Cys Ser Ala Arg Asn Asn
        1555                1560                1565

Arg Thr Thr Tyr Cys Tyr Asp Phe Pro Leu Ala Phe Glu Thr Ala Val
    1570                1575                1580

Gln Lys Ser Trp Ser Asn Ile Ser Ser Asp Asn Asn Arg Cys Tyr Val
1585                1590                1595                1600
```

-continued

Lys Ala Thr Glu Leu Val Phe Ala His Lys Asn Gly Ser Trp Gly Thr
1605 1610 1615

Pro Val Ile Pro Met Glu Arg Pro Ala Gly Leu Asn Asp Ile Gly Met
1620 1625 1630

Val Ala Trp Ile Leu Asp Met Ser Thr Pro Glu Tyr Pro Asn Gly Arg
1635 1640 1645

Gln Ile Val Val Ile Ala Asn Asp Ile Thr Phe Arg Ala Gly Ser Phe
1650 1655 1660

Gly Pro Arg Glu Asp Ala Phe Phe Glu Thr Val Thr Asn Leu Ala Cys
1665 1670 1675 1680

Glu Arg Arg Leu Pro Leu Ile Tyr Leu Ala Ala Asn Ser Gly Ala Arg
1685 1690 1695

Ile Gly Ile Ala Asp Glu Val Lys Ser Cys Phe Arg Val Gly Trp Ser
1700 1705 1710

Asp Asp Gly Ser Pro Glu Arg Gly Phe Gln Tyr Ile Tyr Leu Thr Glu
1715 1720 1725

Glu Asp His Ala Arg Ile Ser Ala Ser Val Ile Ala His Lys Met Gln
1730 1735 1740

Leu Asp Asn Gly Glu Ile Arg Trp Val Ile Asp Ser Val Val Gly Lys
1745 1750 1755 1760

Glu Asp Gly Leu Gly Val Glu Asn Ile His Gly Ser Ala Ala Ile Ala
1765 1770 1775

Ser Ala Tyr Ser Arg Ala Tyr Glu Glu Thr Phe Thr Leu Thr Phe Val
1780 1785 1790

Thr Gly Arg Thr Val Gly Ile Gly Ala Tyr Leu Ala Arg Leu Gly Ile
1795 1800 1805

Arg Cys Ile Gln Arg Thr Asp Gln Pro Ile Ile Leu Thr Gly Phe Ser
1810 1815 1820

Ala Leu Asn Lys Leu Leu Gly Arg Glu Val Tyr Ser Ser His Met Gln
1825 1830 1835 1840

Leu Gly Gly Pro Lys Ile Met Ala Thr Asn Gly Val Val His Leu Thr
1845 1850 1855

Val Ser Asp Asp Leu Glu Gly Val Ser Asn Ile Leu Arg Trp Leu Ser
1860 1865 1870

Tyr Val Pro Ala Asn Ile Gly Gly Pro Leu Pro Ile Thr Lys Ser Leu
1875 1880 1885

Asp Pro Pro Asp Arg Pro Val Ala Tyr Ile Pro Glu Asn Thr Cys Asp
1890 1895 1900

Pro Arg Ala Ala Ile Ser Gly Ile Asp Asp Ser Gln Gly Lys Trp Leu
1905 1910 1915 1920

Gly Gly Met Phe Asp Lys Asp Ser Phe Val Glu Thr Phe Glu Gly Trp
1925 1930 1935

Ala Lys Ser Val Val Thr Gly Arg Ala Lys Leu Gly Gly Ile Pro Val
1940 1945 1950

Gly Val Ile Ala Val Glu Thr Gln Thr Met Met Gln Leu Ile Pro Ala
1955 1960 1965

Asp Pro Gly Gln Leu Asp Ser His Glu Arg Ser Val Pro Arg Ala Gly
1970 1975 1980

Gln Val Trp Phe Pro Asp Ser Ala Thr Lys Thr Ala Gln Ala Met Leu
1985 1990 1995 2000

Asp Phe Asn Arg Glu Gly Leu Pro Leu Phe Ile Leu Ala Asn Trp Arg
2005 2010 2015

-continued

Gly Phe Ser Gly Gly Gln Arg Asp Leu Phe Glu Gly Ile Leu Gln Ala
2020 2025 2030

Gly Ser Thr Ile Val Glu Asn Leu Arg Ala Tyr Asn Gln Pro Ala Phe
2035 2040 2045

Val Tyr Ile Pro Lys Ala Ala Glu Leu Arg Gly Gly Ala Trp Val Val
2050 2055 2060

Ile Asp Ser Lys Ile Asn Pro Asp Arg Ile Glu Phe Tyr Ala Glu Arg
2065 2070 2075 2080

Thr Ala Lys Gly Asn Val Leu Glu Pro Gln Gly Leu Ile Glu Ile Lys
2085 2090 2095

Phe Arg Ser Glu Glu Leu Gln Glu Cys Met Gly Arg Leu Asp Pro Glu
2100 2105 2110

Leu Ile Asn Leu Lys Ala Lys Leu Gln Gly Val Lys His Glu Asn Gly
2115 2120 2125

Ser Leu Pro Glu Ser Glu Ser Leu Gln Lys Ser Ile Glu Ala Arg Lys
2130 2135 2140

Lys Gln Leu Leu Pro Leu Tyr Thr Gln Ile Ala Val Arg Phe Ala Glu
2145 2150 2155 2160

Leu His Asp Thr Ser Leu Arg Met Ala Ala Lys Gly Val Ile Lys Lys
2165 2170 2175

Val Val Asp Trp Glu Asp Ser Arg Ser Phe Phe Tyr Lys Arg Leu Arg
2180 2185 2190

Arg Arg Ile Ser Glu Asp Val Leu Ala Lys Glu Ile Arg Gly Val Ser
2195 2200 2205

Gly Lys Gln Phe Ser His Gln Ser Ala Ile Glu Leu Ile Gln Lys Trp
2210 2215 2220

Tyr Leu Ala Ser Lys Gly Ala Glu Thr Gly Ser Thr Glu Trp Asp Asp
2225 2230 2235 2240

Asp Asp Ala Phe Val Ala Trp Arg Glu Asn Pro Glu Asn Tyr Gln Glu
2245 2250 2255

Tyr Ile Lys Glu Pro Arg Ala Gln Arg Val Ser Gln Leu Leu Ser Asp
2260 2265 2270

Val Ala Asp Ser Ser Pro Asp Leu Glu Ala Leu Pro Gln Gly Leu Ser
2275 2280 2285

Met Leu Leu Glu Lys Met Asp Pro Ala Lys Arg Glu Ile Val Glu Asp
2290 2295 2300

Phe Glu Ile Asn Leu Val Lys
2305 2310

<210> SEQ ID NO 29
<211> LENGTH: 6936
<212> TYPE: DNA
<213> ORGANISM: Triticum aestivum

<400> SEQUENCE: 29
atgggatcca cacatttgcc cattgtcggc cttaatgcct cgacaacacc atcgctatcc 60
actattcgcc cggtaaattc agccggtgct gcattccaac catctgcccc ttctagaacc 120
tccaagaaga aaagtcgtcg tgttcagtca ttaagggatg gaggcgatgg aggcgtgtca 180
gaccctaacc agtctattcg ccaaggtctt gccggcatca ttgacctccc aaaggagggc 240
acatcagctc cggaagtgga tatttcacat gggtccgaag aacccagggg ctcctaccaa 300
atgaatggga tactgaatga agcacataat gggaggcatg cttcgctgtc taaggttgtc 360
gaattttgta tggcattggg cggcaaaaca ccaattcaca gtgtattagt tgcgaacaat 420

-continued

```
ggaagggcag cagctaagtt catgcggagt gtccgaacat gggctaatga aacatttggg    480
tcagagaagg caattcagtt gatagctatg gctactccag aagacatgag gataaatgca    540
gagcacatta gaattgctga tcaatttgtt gaagtacccg gtggaacaaa caataacaac    600
tatgcaaatg tccaactcat agtggagata gcagtgagaa ccggtgtttc tgctgtttgg    660
cctggttggg gccatgcatc tgagaatcct gaacttccag atgcactaaa tgcaaacgga    720
attgtttttc ttgggccacc atcatcatca atgaacgcac taggtgacaa ggttggttca    780
gctctcattg ctcaagcagc aggggttccg actcttcctt ggggtggatc acaggtggaa    840
attccattag aagtttgttt ggactcgata cctgcggaga tgtataggaa agcttgtgtt    900
agtactacgg aggaagcact tgcgagttgt cagatgattg ggtatccagc catgattaaa    960
gcatcatggg gtggtggtgg taaagggatc cgaaaggtta ataacgacga tgatgtcaga   1020
gcactgttta agcaagtgca aggtgaagtt cctggctccc caatatttat catgagactt   1080
gcatctcaga gtcgacatct tgaagttcag ttgctttgtg atcaatatgg caatgtagct   1140
gcgcttcaca gtcgtgactg cagtgtgcaa cggcgacacc aaaagattat tgaggaagga   1200
ccagttactg ttgctcctcg cgagacagtg aaagagctag agcaagcagc aaggaggctt   1260
gctaaggctg tgggttatgt tggtgctgct actgttgaat atctctacag catggagact   1320
ggtgaatact attttctgga acttaatcca cggttgcagg ttgagcatcc agtcaccgag   1380
tggatagctg aagtaaactt gcctgcagct caagttgcag ttggaatggg tataccccctt   1440
tggcaggttc cagagatcag acgtttctat ggaatggaca atggaggagg ctatgacatt   1500
tggagggaaa cagcagctct tgctactcca tttaacttcg atgaagtgga ttctcaatgg   1560
ccaaagggtc attgtgtagc agttaggata accagtgagg atccagatga cggattcaag   1620
cctaccggtg gaaaagtaaa ggagatcagt tttaaaagca agccaaatgt ttgggcctat   1680
ttctctgtta agtccggtgg aggcattcat gaatttgctg attctcagtt tggacatgtt   1740
tttgcatatg gagtgtctag agcagcagca ataaccaaca tgtctcttgc gctaaaagag   1800
attcaaattc gtggagaaat tcattcaaat gttgattaca cagttgatct cttgaatgcc   1860
tcagacttca aagaaaacag gattcatact ggctggctgg ataacagaat agcaatgcga   1920
gtccaagctg agagacctcc gtggtatatt tcagtggttg gaggagctct atataaaaca   1980
ataacgagca acacagacac tgtttctgaa tatgttagct atctcgtcaa gggtcagatt   2040
ccaccgaagc atatatccct tgtccattca actgtttctt tgaatataga ggaaagcaaa   2100
tatacaattg aaactataag gagcggacag ggtagctaca gattgcgaat gaatggatca   2160
gttattgaag caaatgtcca aacattatgt gatggtggac ttttaatgca gttggatgga   2220
aacagccatg taatttatgc tgaagaagag gccggtggta cacggcttct aattgatgga   2280
aagacatact tgttacagaa tgatcacgat ccttcaaggt tattagctga gacaccctgc   2340
aaacttcttc gtttcttggt tgccgatggt gctcatgttg aagctgatgt accatatgcg   2400
gaagttgagg ttatgaagat gtgcatgccc ctcttgtcac ctgctgctgg tgtcattaat   2460
gttttgttgt ctgagggcca gcctatgcag gctggtgatc ttatagcaag acttgatctt   2520
gatgaccctt ctgctgtgaa gagagctgag ccatttaacg gatctttccc agaaatgagc   2580
cttcctattg ctgcttctgg ccaagttcac aaaagatgtg ccacaagctt gaatgctgct   2640
cggatggtcc ttgcaggata tgatcacccg atcaacaaag ttgtacaaga tctggtatcc   2700
tgtctagatg ctcctgagct tcctttccta caatgggaag agcttatgtc tgttttagca   2760
actagacttc caaggcttct taagagcgag ttggagggta aatacagtga atataagtta   2820
```

-continued

```
aatgttggcc atgggaagag caaggatttc ccttccaaga tgctaagaga gataatcgag   2880
gaaaatcttg cacatggttc tgagaaggaa attgctacaa atgagaggct tgttgagcct   2940
cttatgagcc tactgaagtc atatgagggt ggcagagaaa gccatgcaca ctttattgtg   3000
aagtcccttt tcgaggacta tctctcggtt gaggaactat tcagtgatgg cattcagtct   3060
gatgtgattg aacgcctgcg ccaacaacat agtaaagatc tccagaaggt tgtagacatt   3120
gtgttgtctc accagggtgt gagaaacaaa actaagctga tactaacact catggagaaa   3180
ctggtctatc caaaccctgc tgtctacaag gatcagttga ctcgcttttc ctccctcaat   3240
cacaaaagat attataagtt ggcccttaaa gctagcgagc ttcttgaaca aaccaagctt   3300
agtgagctcc gcacaagcat tgcaaggagc ctttcagaac ttgagatgtt tactgaagaa   3360
aggacggcca ttagtgagat catgggagat ttagtgactg ccccactgcc agttgaagat   3420
gcactggttt ctttgtttga ttgtagtgat caaactcttc agcagagggt gatcgagacg   3480
tacatatctc gattatacca gcctcatctt gtcaaggata gtatccagct gaaatatcag   3540
gaatctggtg ttattgcttt atgggaattc gctgaagcgc attcagagaa gagattgggt   3600
gctatggtta ttgtgaagtc gttagaatct gtatcagcag caattggagc tgcactaaag   3660
ggtacatcac gctatgcaag ctctgagggt aacataatgc atattgcttt attgggtgct   3720
gataatcaaa tgcatggaac tgaagacagt ggtgataacg atcaagctca agtcaggata   3780
gacaaacttt ctgcgacact ggaacaaaat actgtcacag ctgatctccg tgctgctggt   3840
gtgaaggtta ttagttgcat tgttcaaagg gatggagcac tcatgcctat gcgccatacc   3900
ttcctcttgt cggatgaaaa gctttgttat ggggaagagc cggttctccg gcatgtggag   3960
cctcctcttt ctgctcttct tgagttgggt aagttgaaag tgaaaggata caatgaggtg   4020
aagtatacac cgtcacgtga tcgtcagtgg aacatataca cacttagaaa tacagagaac   4080
cccaaaatgt tgcacagggt gtttttccga actcttgtca ggcaacccgg tgcttccaac   4140
aaattcacat caggcaacat cagtgatgtt gaagtgggag gagctgagga atctctttca   4200
tttacatcga gcagcatatt aagatcgctg atgactgcta tagaagagtt ggagcttcac   4260
gcgattagga caggtcactc tcatatgttt ttgtgcatat tgaaagagcg aaagcttctt   4320
gatcttgttc ccgtttcagg gaacaaagtt gtggatattg gccaagatga agctactgca   4380
tgcttgcttc tgaaagaaat ggctctacag atacatgaac ttgtgggtgc aaggatgcat   4440
catctttctg tatgccaatg ggaggtgaaa cttaagttgg acagcgatgg gcctgccagt   4500
ggtacctgga gagttgtaac aaccaatgtt actagtcaca cctgcactgt ggatatctac   4560
cgtgaggttg aagatacaga atcacagaaa ctagtatacc actctgctcc atcgtcatct   4620
ggtcctttgc atggcgttgc actgaatact ccatatcagc ctttgagtgt tattgatctg   4680
aaacgttgct ccgctagaaa caacagaact acatactgct atgattttcc gttggcattt   4740
gaaactgcag tgcagaagtc atggtctaac atttctagtg acaataaccg atgttatgtt   4800
aaagcaacgg agctggtgtt tgctcacaag aatgggtcat ggggcactcc tgtaattcct   4860
atggagcgtc ctgctgggct caatgacatt ggtatggtag cttggatctt ggacatgtcc   4920
actcctgaat atcccaatgg caggcagatt gttgtcatcg caaatgatat tacttttaga   4980
gctggatcgt ttggtccaag ggaagatgca ttttttgaaa ctgttaccaa cctagcttgt   5040
gagaggaggc ttcctctcat ctacttggca gcaaactctg gtgctcggat cggcatagca   5100
gatgaagtaa aatcttgctt ccgtgttgga tggtctgatg atggcagccc tgaacgtggg   5160
```

-continued

```
tttcaatata tttatctgac tgaagaagac catgctcgta ttagcgcttc tgttatagcg   5220

cacaagatgc agcttgataa tggtgaaatt aggtgggtta ttgattctgt tgtagggaag   5280

gaggatgggc taggtgtgga gaacatacat ggaagtgctg ctattgccag tgcctattct   5340

agggcctatg aggagacatt tacgcttaca tttgtgactg gaaggactgt tggaatagga   5400

gcatatcttg ctcgacttgg catacggtgc attcagcgta ctgaccagcc cattatccta   5460

actgggtttt ctgccttgaa caagcttctt ggccgggaag tgtacagctc ccacatgcag   5520

ttgggtggcc ccaaaattat ggcgacaaac ggtgttgtcc atctgacagt ttcagatgac   5580

cttgaaggtg tatctaatat attgaggtgg ctcagctatg ttcctgccaa cattggtgga   5640

cctcttccta ttacaaaatc tttggaccca cctgacagac ccgttgctta catccctgag   5700

aatacatgcg atcctcgtgc tgccatcagt ggcattgatg atagccaagg gaaatggttg   5760

gggggcatgt tcgacaaaga cagttttgtg gagacatttg aaggatgggc gaagtcagtt   5820

gttactggca gagcgaaact cggagggatt ccggtgggtg ttatagctgt ggagacacag   5880

actatgatgc agctcatccc tgctgatcca ggccagcttg attcccatga gcgatctgtt   5940

cctcgtgctg ggcaagtctg gtttccagat tcagctacta agacagcgca ggcaatgctg   6000

gacttcaacc gtgaaggatt acctctgttc atccttgcta actggagagg cttctctggt   6060

ggacaaagag atctttttga aggaatcctt caggctgggt caacaattgt tgagaacctt   6120

agggcataca atcagcctgc ctttgtatat atccccaagg ctgcagagct acgtggaggg   6180

gcttgggtcg tgattgatag caagataaat ccagatcgca ttgagttcta tgctgagagg   6240

actgcaaagg gcaatgttct cgaacctcaa gggttgatcg agatcaagtt caggtcagag   6300

gaactccaag agtgcatggg taggcttgat ccagaattga taaatctgaa ggcaaagctc   6360

cagggagtaa agcatgaaaa tggaagtcta cctgagtcag aatcccttca gaagagcata   6420

gaagcccgga agaaacagtt gttgcctttg tatactcaaa ttgcggtacg gttcgctgaa   6480

ttgcatgaca cttcccttag aatggctgct aagggtgtga ttaagaaggt tgtagactgg   6540

gaagattcta ggtcgttctt ctacaagaga ttacggagga ggatatccga ggatgttctt   6600

gcgaaggaaa ttagaggtgt aagtggcaag cagttttctc accaatcggc aatcgagctg   6660

atccagaaat ggtacttggc ctctaaggga gctgaaacag gaagcactga atgggatgat   6720

gacgatgctt ttgttgcctg gagggaaaac cctgaaaact accaggagta tatcaaagaa   6780

cccagggctc aaagggtatc tcagttgctc tcagatgttg cagactccag tccagatcta   6840

gaagccttgc cacagggtct ttctatgcta ctagagaaga tggatcctgc aaagagggaa   6900

attgttgaag actttgaaat aaaccttgta aagtaa                             6936
```

<210> SEQ ID NO 30
<211> LENGTH: 5
<212> TYPE: PRT
<213> ORGANISM: Artificial Sequence
<220> FEATURE:
<223> OTHER INFORMATION: PAP1 enzyme catalytic motif
<220> FEATURE:
<221> NAME/KEY: VARIANT
<222> LOCATION: 2, 4
<223> OTHER INFORMATION: Xaa = Any Amino Acid

<400> SEQUENCE: 30

```
Asp Xaa Asp Xaa Thr
 1               5
```

<210> SEQ ID NO 31

<211> LENGTH: 2535
<212> TYPE: DNA
<213> ORGANISM: Synechococcus elongatus PCC 7942

<400> SEQUENCE: 31

```
atgagtgatt ccaccgccca actcagctac gaccccacca cgagctacct cgagcccagt     60
ggcttggtct gtgaggatga acggacttct gtgactcccg agaccttgaa acgggcttac    120
gaggcccatc tctactacag ccagggcaaa acctcagcga tcgccaccct gcgtgatcac    180
tacatggcac tggcctacat ggtccgcgat cgcctcctgc aacggtggct agcttcactg    240
tcgacctatc aacaacagca cgtcaaagtg gtctgttacc tgtccgctga gtttttgatg    300
ggtcggcacc tcgaaaactg cctgatcaac ctgcatcttc acgaccgcgt tcagcaagtt    360
ttggatgaac tgggtctcga ttttgagcaa ctgctagaga aagaggaaga acccgggcta    420
ggcaacggtg gcctcggtcg cctcgcagct tgtttcctcg actccatggc taccctcgac    480
attcctgccg tcggctatgg cattcgctat gagttcggta tcttccacca agaactccac    540
aacggctggc agatcgaaat ccccgataac tggctgcgct ttggcaaccc ttgggagcta    600
gagcggcgcg aacaggccgt ggaaattaag ttgggcggcc acacggaggc ctaccacgat    660
gcgcgaggcc gctactgcgt ctcttggatc cccgatcgcg tcattcgcgc catcccctac    720
gacacccccg taccgggcta cgacaccaat aacgtcagca tgttgcggct ctggaaggct    780
gagggcacca cggaactcaa ccttgaggct ttcaactcag gcaactacga cgatgcggtt    840
gccgacaaaa tgtcgtcgga aacgatctcg aaggtgctct atcccaacga caacaccccc    900
caagggcggg aactgcggct ggagcagcag tatttcttcg tctcggcttc gctccaagac    960
atcatccgtc gccacttgat gaaccacggt catcttgagc ggctgcatga ggcgatcgca   1020
gtccagctta acgacaccca tcccagcgtg gcggtgccgg agttgatgcg cctcctgatc   1080
gatgagcatc acctgacttg ggacaatgct tggacgatta cacagcgcac cttcgcctac   1140
accaaccaca cgctgctacc tgaagccttg gaacgctggc ccgtgggcat gttccagcgc   1200
actttaccgc gcttgatgga gattatctac gaaatcaact ggcgcttctt ggccaatgtg   1260
cgggcctggt atcccggtga cgacacgaga gctcgccgcc tctccctgat tgaggaagga   1320
gctgagcccc aggtgcgcat ggctcacctc gcctgcgtgg gcagtcatgc catcaacggt   1380
gtggcagccc tgcatacgca actgctcaag caagaaaccc tgcgagattt ctacgagctt   1440
tggcccgaga aattcttcaa catgaccaac ggtgtgacgc cccgccgctg gctgctgcaa   1500
agtaatcctc gcctagccaa cctgatcagc gatcgcattg gcaatgactg gattcatgat   1560
ctcaggcaac tgcgacggct ggaagacagc gtgaacgatc gcgagttttt acagcgctgg   1620
gcagaggtca agcaccaaaa taaggtcgat ctgagccgct acatctacca gcagactcgc   1680
atagaagtcg atccgcactc tctctttgat gtgcaagtca aacggattca cgaatacaaa   1740
cgccagctcc tcgctgtcat gcatatcgtg acgctctaca actggctgaa gcacaatccc   1800
cagctcaacc tggtgccgcg cacttttatc tttgcgggca aagcggcccc gggttactac   1860
cgtgccaagc aaatcgtcaa actgatcaat gcggtcggga gcatcatcaa ccatgatccc   1920
gatgtccaag ggcgactgaa ggtcgtcttc ctacctaact tcaacgtttc cttggggcag   1980
cgcatttatc cagctgccga tttgtcggag caaatctcaa ctgcagggaa agaagcgtcc   2040
ggcaccggca acatgaagtt caccatgaat ggcgcgctga caatcggaac ctacgatggt   2100
gccaacatcg agatccgcga ggaagtcggc cccgaaaact tcttcctgtt tggcctgcga   2160
gccgaagata tcgcccgacg ccaaagtcgg ggctatcgac ctgtggagtt ctggagcagc   2220
```

aatgcggaac tgcgggcagt cctcgatcgc tttagcagtg gtcacttcac accggatcag 2280
cccaacctct tccaagactt ggtcagcgat ctgctgcagc gggatgagta catgttgatg 2340
gcggactatc agtcctacat cgactgccag cgcgaagctg ctgctgccta ccgcgattcc 2400
gatcgctggt ggcggatgtc gctactcaac accgcgagat cgggcaagtt ctcctccgat 2460
cgcacgatcg ctgactacag cgaacagatc tgggaggtca aaccagtccc cgtcagccta 2520
agcactagct tttag 2535

<210> SEQ ID NO 32
<211> LENGTH: 844
<212> TYPE: PRT
<213> ORGANISM: Synechococcus elongatus PCC 7942

<400> SEQUENCE: 32

Met Ser Asp Ser Thr Ala Gln Leu Ser Tyr Asp Pro Thr Thr Ser Tyr
1 5 10 15

Leu Glu Pro Ser Gly Leu Val Cys Glu Asp Glu Arg Thr Ser Val Thr
20 25 30

Pro Glu Thr Leu Lys Arg Ala Tyr Glu Ala His Leu Tyr Tyr Ser Gln
35 40 45

Gly Lys Thr Ser Ala Ile Ala Thr Leu Arg Asp His Tyr Met Ala Leu
50 55 60

Ala Tyr Met Val Arg Asp Arg Leu Leu Gln Arg Trp Leu Ala Ser Leu
65 70 75 80

Ser Thr Tyr Gln Gln Gln His Val Lys Val Val Cys Tyr Leu Ser Ala
85 90 95

Glu Phe Leu Met Gly Arg His Leu Glu Asn Cys Leu Ile Asn Leu His
100 105 110

Leu His Asp Arg Val Gln Gln Val Leu Asp Glu Leu Gly Leu Asp Phe
115 120 125

Glu Gln Leu Leu Glu Lys Glu Glu Glu Pro Gly Leu Gly Asn Gly Gly
130 135 140

Leu Gly Arg Leu Ala Ala Cys Phe Leu Asp Ser Met Ala Thr Leu Asp
145 150 155 160

Ile Pro Ala Val Gly Tyr Gly Ile Arg Tyr Glu Phe Gly Ile Phe His
165 170 175

Gln Glu Leu His Asn Gly Trp Gln Ile Glu Ile Pro Asp Asn Trp Leu
180 185 190

Arg Phe Gly Asn Pro Trp Glu Leu Glu Arg Arg Glu Gln Ala Val Glu
195 200 205

Ile Lys Leu Gly Gly His Thr Glu Ala Tyr His Asp Ala Arg Gly Arg
210 215 220

Tyr Cys Val Ser Trp Ile Pro Asp Arg Val Ile Arg Ala Ile Pro Tyr
225 230 235 240

Asp Thr Pro Val Pro Gly Tyr Asp Thr Asn Asn Val Ser Met Leu Arg
245 250 255

Leu Trp Lys Ala Glu Gly Thr Thr Glu Leu Asn Leu Glu Ala Phe Asn
260 265 270

Ser Gly Asn Tyr Asp Asp Ala Val Ala Asp Lys Met Ser Ser Glu Thr
275 280 285

Ile Ser Lys Val Leu Tyr Pro Asn Asp Asn Thr Pro Gln Gly Arg Glu
290 295 300

Leu Arg Leu Glu Gln Gln Tyr Phe Phe Val Ser Ala Ser Leu Gln Asp

```
305                 310                 315                 320

Ile Ile Arg Arg His Leu Met Asn His Gly His Leu Glu Arg Leu His
                325                 330                 335

Glu Ala Ile Ala Val Gln Leu Asn Asp Thr His Pro Ser Val Ala Val
            340                 345                 350

Pro Glu Leu Met Arg Leu Leu Ile Asp Glu His His Leu Thr Trp Asp
        355                 360                 365

Asn Ala Trp Thr Ile Thr Gln Arg Thr Phe Ala Tyr Thr Asn His Thr
    370                 375                 380

Leu Leu Pro Glu Ala Leu Glu Arg Trp Pro Val Gly Met Phe Gln Arg
385                 390                 395                 400

Thr Leu Pro Arg Leu Met Glu Ile Ile Tyr Glu Ile Asn Trp Arg Phe
                405                 410                 415

Leu Ala Asn Val Arg Ala Trp Tyr Pro Gly Asp Asp Thr Arg Ala Arg
            420                 425                 430

Arg Leu Ser Leu Ile Glu Glu Gly Ala Glu Pro Gln Val Arg Met Ala
        435                 440                 445

His Leu Ala Cys Val Gly Ser His Ala Ile Asn Gly Val Ala Ala Leu
    450                 455                 460

His Thr Gln Leu Leu Lys Gln Glu Thr Leu Arg Asp Phe Tyr Glu Leu
465                 470                 475                 480

Trp Pro Glu Lys Phe Phe Asn Met Thr Asn Gly Val Thr Pro Arg Arg
                485                 490                 495

Trp Leu Leu Gln Ser Asn Pro Arg Leu Ala Asn Leu Ile Ser Asp Arg
            500                 505                 510

Ile Gly Asn Asp Trp Ile His Asp Leu Arg Gln Leu Arg Arg Leu Glu
        515                 520                 525

Asp Ser Val Asn Asp Arg Glu Phe Leu Gln Arg Trp Ala Glu Val Lys
    530                 535                 540

His Gln Asn Lys Val Asp Leu Ser Arg Tyr Ile Tyr Gln Gln Thr Arg
545                 550                 555                 560

Ile Glu Val Asp Pro His Ser Leu Phe Asp Val Gln Val Lys Arg Ile
                565                 570                 575

His Glu Tyr Lys Arg Gln Leu Leu Ala Val Met His Ile Val Thr Leu
            580                 585                 590

Tyr Asn Trp Leu Lys His Asn Pro Gln Leu Asn Leu Val Pro Arg Thr
        595                 600                 605

Phe Ile Phe Ala Gly Lys Ala Ala Pro Gly Tyr Tyr Arg Ala Lys Gln
    610                 615                 620

Ile Val Lys Leu Ile Asn Ala Val Gly Ser Ile Ile Asn His Asp Pro
625                 630                 635                 640

Asp Val Gln Gly Arg Leu Lys Val Val Phe Leu Pro Asn Phe Asn Val
                645                 650                 655

Ser Leu Gly Gln Arg Ile Tyr Pro Ala Ala Asp Leu Ser Glu Gln Ile
            660                 665                 670

Ser Thr Ala Gly Lys Glu Ala Ser Gly Thr Gly Asn Met Lys Phe Thr
        675                 680                 685

Met Asn Gly Ala Leu Thr Ile Gly Thr Tyr Asp Gly Ala Asn Ile Glu
    690                 695                 700

Ile Arg Glu Glu Val Gly Pro Glu Asn Phe Phe Leu Phe Gly Leu Arg
705                 710                 715                 720

Ala Glu Asp Ile Ala Arg Arg Gln Ser Arg Gly Tyr Arg Pro Val Glu
                725                 730                 735
```

Phe Trp Ser Ser Asn Ala Glu Leu Arg Ala Val Leu Asp Arg Phe Ser
740 745 750

Ser Gly His Phe Thr Pro Asp Gln Pro Asn Leu Phe Gln Asp Leu Val
755 760 765

Ser Asp Leu Leu Gln Arg Asp Glu Tyr Met Leu Met Ala Asp Tyr Gln
770 775 780

Ser Tyr Ile Asp Cys Gln Arg Glu Ala Ala Ala Ala Tyr Arg Asp Ser
785 790 795 800

Asp Arg Trp Trp Arg Met Ser Leu Leu Asn Thr Ala Arg Ser Gly Lys
805 810 815

Phe Ser Ser Asp Arg Thr Ile Ala Asp Tyr Ser Glu Gln Ile Trp Glu
820 825 830

Val Lys Pro Val Pro Val Ser Leu Ser Thr Ser Phe
835 840

<210> SEQ ID NO 33
<211> LENGTH: 2085
<212> TYPE: DNA
<213> ORGANISM: Synechococcus elongatus PCC 7942

<400> SEQUENCE: 33
atgactgttt catcccgtcg ccctgaatcg accgtggctg ttgaccccgg ccaaagctat 60
cccctcgggg caaccgtcta tcccaccggc gtcaacttct cgctctacac caagtacgcg 120
acgggcgttg aattactgct gtttgatgac cctgagggtg cccagcctca acggacagtg 180
cgcctcgatc cgcacctcaa tcgcacctct ttctactggc atgtttttat tccgggcatt 240
cgctccggtc aggtttatgc ttaccgcgtc tttggcccct acgcacctga tcgcggcctc 300
tgttttaacc ccaacaaagt gctgctggat ccctacgctc gcggggttgt cggctggcag 360
cactacagtc gcgaagcggc tattaaaccc agtaataact gcgttcaagc cctgcgtagc 420
gtggttgttg accccagcga ctacgactgg gaaggcgatc gccatccacg cacaccctac 480
gctcgcacag taatctatga gctgcatgtt ggcggcttca ccaagcatcc caattccggc 540
gtcgcccctg aaaaacgtgg cacctacgct ggtctaatcg aaaaaattcc ctacctgcaa 600
tccctcggcg tcacggccgt tgagttgctg ccggtgcacc agttcgatcg ccaagatgcc 660
cccttaggac gcgagaacta ctggggctac agcaccatgg ctttttttgc gccccacgca 720
gcctacagct ctcgccatga tccacttggt ccagttgatg agttccgcga cctcgtcaag 780
gcgctccacc aagcagggat tgaggtgatt ctcgacgtgg tgttcaacca cactgctgaa 840
gggaatgaag acggtccaac gctgtctttc aaaggtctag cgaattcaac ctactatctg 900
ctggatgaac aggcgggcta tcgcaactac accggctgcg gcaacaccgt caaagctaac 960
aattcgatcg tgcgatcgct gattctcgat tgcctgcgtt attgggtctc ggaaatgcac 1020
gtcgatggct tccgctttga ccttgcgtcg gtgctgagtc gtgatgccaa tggcaacccc 1080
ctatcggatc cgcccttgct ttgggcgatt gattccgatc cggttttggc cggtacgaag 1140
ctcattgctg aagcttggga cgcagccggc ttatatcagg ttggtacctt tattggcgat 1200
cgctttggga cttggaacgg tcccttccgg gacgatattc ggcgtttttg gcgtggagat 1260
cagggctgta cttacgccct cagtcaacgc ctgctgggta gccccgatgt ctacagcaca 1320
gaccaatggt atgccggacg caccattaac ttcatcacct gccatgacgg ctttacgctg 1380
cgagatctag tcagctatag ccagaagcac aactttgcca atggagagaa caatcgggac 1440
gggaccaatg acaactacag ctggaactac ggcattgaag gcgagaccga tgaccccacg 1500

-continued

```
attctgagct tacgggaacg gcagcagcgc aatttgctcg ccacgttatt cctcgcccag   1560

ggcacaccga tgctgacgat gggcgatgag gtcaaacgca gtcagcaggg taacaataac   1620

gcctactgcc aagacaatga gatcagctgg tttgattggt cgctgtgcga tcgccatgcc   1680

gatttcttgg tgttcagtcg ccgcctgatt gaactttccc agtcgctggt gatgttccaa   1740

cagaacgaac tgctgcagaa cgaaccccat ccgcgtcgtc cctatgccat ctggcatggc   1800

gtcaaactca aacaacccga ttgggcgctg tggtcccaca gtctggccgt cagtctctgc   1860

catcctcgcc agcaggaatg gctttaccta gcctttaatg cttactggga agacctgcgc   1920

ttccagttgc cgaggcctcc tcgcggccgc gtttggtatc gcttgctcga tacttcactg   1980

ccgaatcttg aagcttgtca tctgccggat gaggcaaaac cctgcctacg gcgcgattac   2040

atcgtcccag cgcgatcgct cttactgttg atggctcgtg cttaa                   2085
```

```
<210> SEQ ID NO 34
<211> LENGTH: 694
<212> TYPE: PRT
<213> ORGANISM: Synechococcus elongatus PCC 7942

<400> SEQUENCE: 34

Met Thr Val Ser Ser Arg Arg Pro Glu Ser Thr Val Ala Val Asp Pro
 1               5                  10                  15

Gly Gln Ser Tyr Pro Leu Gly Ala Thr Val Tyr Pro Thr Gly Val Asn
            20                  25                  30

Phe Ser Leu Tyr Thr Lys Tyr Ala Thr Gly Val Glu Leu Leu Leu Phe
        35                  40                  45

Asp Asp Pro Glu Gly Ala Gln Pro Gln Arg Thr Val Arg Leu Asp Pro
    50                  55                  60

His Leu Asn Arg Thr Ser Phe Tyr Trp His Val Phe Ile Pro Gly Ile
65                  70                  75                  80

Arg Ser Gly Gln Val Tyr Ala Tyr Arg Val Phe Gly Pro Tyr Ala Pro
                85                  90                  95

Asp Arg Gly Leu Cys Phe Asn Pro Asn Lys Val Leu Leu Asp Pro Tyr
            100                 105                 110

Ala Arg Gly Val Val Gly Trp Gln His Tyr Ser Arg Glu Ala Ala Ile
        115                 120                 125

Lys Pro Ser Asn Asn Cys Val Gln Ala Leu Arg Ser Val Val Val Asp
    130                 135                 140

Pro Ser Asp Tyr Asp Trp Glu Gly Asp Arg His Pro Arg Thr Pro Tyr
145                 150                 155                 160

Ala Arg Thr Val Ile Tyr Glu Leu His Val Gly Gly Phe Thr Lys His
                165                 170                 175

Pro Asn Ser Gly Val Ala Pro Glu Lys Arg Gly Thr Tyr Ala Gly Leu
            180                 185                 190

Ile Glu Lys Ile Pro Tyr Leu Gln Ser Leu Gly Val Thr Ala Val Glu
        195                 200                 205

Leu Leu Pro Val His Gln Phe Asp Arg Gln Asp Ala Pro Leu Gly Arg
    210                 215                 220

Glu Asn Tyr Trp Gly Tyr Ser Thr Met Ala Phe Phe Ala Pro His Ala
225                 230                 235                 240

Ala Tyr Ser Ser Arg His Asp Pro Leu Gly Pro Val Asp Glu Phe Arg
                245                 250                 255

Asp Leu Val Lys Ala Leu His Gln Ala Gly Ile Glu Val Ile Leu Asp
            260                 265                 270
```

-continued

```
Val Val Phe Asn His Thr Ala Glu Gly Asn Glu Asp Gly Pro Thr Leu
        275                 280                 285

Ser Phe Lys Gly Leu Ala Asn Ser Thr Tyr Tyr Leu Leu Asp Glu Gln
    290                 295                 300

Ala Gly Tyr Arg Asn Tyr Thr Gly Cys Gly Asn Thr Val Lys Ala Asn
305                 310                 315                 320

Asn Ser Ile Val Arg Ser Leu Ile Leu Asp Cys Leu Arg Tyr Trp Val
                325                 330                 335

Ser Glu Met His Val Asp Gly Phe Arg Phe Asp Leu Ala Ser Val Leu
            340                 345                 350

Ser Arg Asp Ala Asn Gly Asn Pro Leu Ser Asp Pro Pro Leu Leu Trp
        355                 360                 365

Ala Ile Asp Ser Asp Pro Val Leu Ala Gly Thr Lys Leu Ile Ala Glu
    370                 375                 380

Ala Trp Asp Ala Ala Gly Leu Tyr Gln Val Gly Thr Phe Ile Gly Asp
385                 390                 395                 400

Arg Phe Gly Thr Trp Asn Gly Pro Phe Arg Asp Asp Ile Arg Arg Phe
                405                 410                 415

Trp Arg Gly Asp Gln Gly Cys Thr Tyr Ala Leu Ser Gln Arg Leu Leu
            420                 425                 430

Gly Ser Pro Asp Val Tyr Ser Thr Asp Gln Trp Tyr Ala Gly Arg Thr
        435                 440                 445

Ile Asn Phe Ile Thr Cys His Asp Gly Phe Thr Leu Arg Asp Leu Val
    450                 455                 460

Ser Tyr Ser Gln Lys His Asn Phe Ala Asn Gly Glu Asn Asn Arg Asp
465                 470                 475                 480

Gly Thr Asn Asp Asn Tyr Ser Trp Asn Tyr Gly Ile Glu Gly Glu Thr
                485                 490                 495

Asp Asp Pro Thr Ile Leu Ser Leu Arg Glu Arg Gln Gln Arg Asn Leu
            500                 505                 510

Leu Ala Thr Leu Phe Leu Ala Gln Gly Thr Pro Met Leu Thr Met Gly
        515                 520                 525

Asp Glu Val Lys Arg Ser Gln Gln Gly Asn Asn Asn Ala Tyr Cys Gln
    530                 535                 540

Asp Asn Glu Ile Ser Trp Phe Asp Trp Ser Leu Cys Asp Arg His Ala
545                 550                 555                 560

Asp Phe Leu Val Phe Ser Arg Arg Leu Ile Glu Leu Ser Gln Ser Leu
                565                 570                 575

Val Met Phe Gln Gln Asn Glu Leu Leu Gln Asn Glu Pro His Pro Arg
            580                 585                 590

Arg Pro Tyr Ala Ile Trp His Gly Val Lys Leu Lys Gln Pro Asp Trp
        595                 600                 605

Ala Leu Trp Ser His Ser Leu Ala Val Ser Leu Cys His Pro Arg Gln
    610                 615                 620

Gln Glu Trp Leu Tyr Leu Ala Phe Asn Ala Tyr Trp Glu Asp Leu Arg
625                 630                 635                 640

Phe Gln Leu Pro Arg Pro Pro Arg Gly Arg Val Trp Tyr Arg Leu Leu
                645                 650                 655

Asp Thr Ser Leu Pro Asn Leu Glu Ala Cys His Leu Pro Asp Glu Ala
            660                 665                 670

Lys Pro Cys Leu Arg Arg Asp Tyr Ile Val Pro Ala Arg Ser Leu Leu
        675                 680                 685
```

Leu Leu Met Ala Arg Ala
690

<210> SEQ ID NO 35
<211> LENGTH: 1500
<212> TYPE: DNA
<213> ORGANISM: Synechococcus elongatus PCC 7942

<400> SEQUENCE: 35
gtgtttacac gagccgccgg cattttgtta catcccactt cgttgccggg gccattcggc 60
agcggcgacc ttggtccggc ctcgcggcag tttcttgact ggttggcaac ggcgggacaa 120
caactgtggc aagtgttgcc ccttgggccg acaggctatg gctattcgcc ttacctctgc 180
tattccgcct tggctggcaa tcccgctctg atcagccctg aactcttggc agaagatggc 240
tggctccaag aatcggactg ggcagactgt cctgcttttc cgagcgatcg cgtcgatttt 300
gccagcgtct tgccctatcg cgatcaactg ctgcgccgtg cctacagcca attcctgcaa 360
agagcggctt ccagcgatcg ccaactcttt caagctttct gtgaacagga agcccattgg 420
ctggatgact acgccctgtt catggcgatt aagctggcta gccaaggtca gccttggaca 480
gaatggccgg aagcgctgcg tcagcggcaa cctcaagcct tggctaaagc ccgcgatcgc 540
tggggcggcg aaattggctt ccagcagttt ctgcagtggc aatttcgcga gcagtggttg 600
gccctgcggg aagaagccca agcccgccat atttcgctga ttggcgatat tccgatctac 660
gtcgctcatg acagtgcgga cgtttgggcc aatcctcagt tctttgccct cgatcctgaa 720
acgggcgcag ttgatcagca ggccggtgtg ccgcctgact atttctccga aaccggccaa 780
ctctggggca atcccgtcta caactgggct gcgctgcagg cggatggcta tcgctggtgg 840
ttgcaacggc tgcaacagct cctcagctta gtggactaca ttcgcatcga ccacttccgc 900
ggtttagagg cgttttggtc ggttcccgct ggtgaagaaa cggcgatcga cggagagtgg 960
gtcaaagccc caggcgctga tctgctgagc acgattcgcc aaaaactggg agcgctaccg 1020
attctggcag aggatctcgg tgtgattacg ccggaggtgg aagcgctgcg cgatcgcttt 1080
gagctgccgg gcatgaagat tctgcagttc gcctttgact ctggggccgg caatgcctat 1140
ctaccgcaca actactgggg tcgtcgctgg gtggcttaca ccggcaccca cgacaatgac 1200
acgaccgtcg gctggttcct gtcccgcaat gacagcgatc gccaaacggt gctggattat 1260
ctgggcgcag agtcgggctg ggaaattgag tggaagctga tccgcttggc ttggagctcg 1320
acggcagatt gggcgatcgc accgctccaa gatgtcttcg ggctggatag cagcgcccgc 1380
atgaatcgac cggggcaagc caccggcaac tgggactggc gcttcagtgc cgactggctg 1440
acgggcgatc gtgcccaacg cctgcggcga ctctcgcagc tctatggacg ctgtagatga 1500

<210> SEQ ID NO 36
<211> LENGTH: 499
<212> TYPE: PRT
<213> ORGANISM: Synechococcus elongatus PCC 7942

<400> SEQUENCE: 36

Met Phe Thr Arg Ala Ala Gly Ile Leu Leu His Pro Thr Ser Leu Pro
1 5 10 15

Gly Pro Phe Gly Ser Gly Asp Leu Gly Pro Ala Ser Arg Gln Phe Leu
20 25 30

Asp Trp Leu Ala Thr Ala Gly Gln Gln Leu Trp Gln Val Leu Pro Leu
35 40 45

Gly Pro Thr Gly Tyr Gly Tyr Ser Pro Tyr Leu Cys Tyr Ser Ala Leu

-continued

```
    50                  55                  60

Ala Gly Asn Pro Ala Leu Ile Ser Pro Glu Leu Leu Ala Glu Asp Gly
65                  70                  75                  80

Trp Leu Gln Glu Ser Asp Trp Ala Asp Cys Pro Ala Phe Pro Ser Asp
                85                  90                  95

Arg Val Asp Phe Ala Ser Val Leu Pro Tyr Arg Asp Gln Leu Leu Arg
            100                 105                 110

Arg Ala Tyr Ser Gln Phe Leu Gln Arg Ala Ala Ser Ser Asp Arg Gln
        115                 120                 125

Leu Phe Gln Ala Phe Cys Glu Gln Glu Ala His Trp Leu Asp Asp Tyr
    130                 135                 140

Ala Leu Phe Met Ala Ile Lys Leu Ala Ser Gln Gly Gln Pro Trp Thr
145                 150                 155                 160

Glu Trp Pro Glu Ala Leu Arg Gln Arg Gln Pro Gln Ala Leu Ala Lys
                165                 170                 175

Ala Arg Asp Arg Trp Gly Gly Glu Ile Gly Phe Gln Gln Phe Leu Gln
            180                 185                 190

Trp Gln Phe Arg Glu Gln Trp Leu Ala Leu Arg Glu Glu Ala Gln Ala
        195                 200                 205

Arg His Ile Ser Leu Ile Gly Asp Ile Pro Ile Tyr Val Ala His Asp
    210                 215                 220

Ser Ala Asp Val Trp Ala Asn Pro Gln Phe Phe Ala Leu Asp Pro Glu
225                 230                 235                 240

Thr Gly Ala Val Asp Gln Gln Ala Gly Val Pro Pro Asp Tyr Phe Ser
                245                 250                 255

Glu Thr Gly Gln Leu Trp Gly Asn Pro Val Tyr Asn Trp Ala Ala Leu
            260                 265                 270

Gln Ala Asp Gly Tyr Arg Trp Trp Leu Gln Arg Leu Gln Gln Leu Leu
        275                 280                 285

Ser Leu Val Asp Tyr Ile Arg Ile Asp His Phe Arg Gly Leu Glu Ala
    290                 295                 300

Phe Trp Ser Val Pro Ala Gly Glu Glu Thr Ala Ile Asp Gly Glu Trp
305                 310                 315                 320

Val Lys Ala Pro Gly Ala Asp Leu Leu Ser Thr Ile Arg Gln Lys Leu
                325                 330                 335

Gly Ala Leu Pro Ile Leu Ala Glu Asp Leu Gly Val Ile Thr Pro Glu
            340                 345                 350

Val Glu Ala Leu Arg Asp Arg Phe Glu Leu Pro Gly Met Lys Ile Leu
        355                 360                 365

Gln Phe Ala Phe Asp Ser Gly Ala Gly Asn Ala Tyr Leu Pro His Asn
    370                 375                 380

Tyr Trp Gly Arg Arg Trp Val Ala Tyr Thr Gly Thr His Asp Asn Asp
385                 390                 395                 400

Thr Thr Val Gly Trp Phe Leu Ser Arg Asn Asp Ser Asp Arg Gln Thr
                405                 410                 415

Val Leu Asp Tyr Leu Gly Ala Glu Ser Gly Trp Glu Ile Glu Trp Lys
            420                 425                 430

Leu Ile Arg Leu Ala Trp Ser Ser Thr Ala Asp Trp Ala Ile Ala Pro
        435                 440                 445

Leu Gln Asp Val Phe Gly Leu Asp Ser Ser Ala Arg Met Asn Arg Pro
    450                 455                 460

Gly Gln Ala Thr Gly Asn Trp Asp Trp Arg Phe Ser Ala Asp Trp Leu
465                 470                 475                 480
```

```
Thr Gly Asp Arg Ala Gln Arg Leu Arg Arg Leu Ser Gln Leu Tyr Gly
                485                 490                 495

Arg Cys Arg
```

<210> SEQ ID NO 37
<211> LENGTH: 1632
<212> TYPE: DNA
<213> ORGANISM: Synechococcus elongatus PCC 7942

<400> SEQUENCE: 37

```
atgaatatcc acactgtcgc gacgcaagcc tttagcgacc aaaagcccgg tacctccggc     60

ctgcgcaagc aagttcctgt cttccaaaaa cggcactatc tcgaaaactt tgtccagtcg    120

atcttcgata gccttgaggg ttatcagggc cagacgttag tgctgggggg tgatggccgc    180

tactacaatc gcacagccat ccaaaccatt ctgaaaatgg cggcggccaa tggttggggc    240

cgcgttttag ttggacaagg cggtattctc tccacgccag cagtctccaa cctaatccgc    300

cagaacggag ccttcggcgg catcatcctc tcggctagcc acaacccagg gggccctgag    360

ggcgatttcg gcatcaagta caacatcagc aacggtggcc ctgcacccga aaaagtcacc    420

gatgccatct atgcctgcag cctcaaaatt gaggcctacc gcattctcga agccggtgac    480

gttgacctcg atcgactcgg tagtcaacaa ctgggcgaga tgaccgttga ggtgatcgac    540

tcggtcgccg actacagccg cttgatgcaa tccctgtttg acttcgatcg cattcgcgat    600

cgcctgaggg gggggctacg gattgcgatc gactcgatgc atgccgtcac cggtccctac    660

gccaccacga tttttgagaa ggagctaggc gcggcggcag gcactgtttt taatggcaag    720

ccgctggaag actttggcgg gggtcaccca gacccgaatt tggtctacgc ccacgacttg    780

gttgaactgt tgtttggcga tcgcgcccca gattttggcg cggcctccga tggcgatggc    840

gatcgcaaca tgatcttggg caatcacttt tttgtgaccc ctagcgacag cttggcgatt    900

ctcgcagcca atgccagcct agtgccggcc taccgcaatg gactgtctgg gattgcgcga    960

tccatgccca ccagtgcggc ggccgatcgc gtcgcccaag ccctcaacct gccctgctac   1020

gaaaccccaa cgggttggaa gtttttcggc aatctgctcg atgccgatcg cgtcaccctc   1080

tgcggcgaag aaagctttgg cacaggctcc aaccatgtgc gcgagaagga tggcctgtgg   1140

gccgtgctgt tctggctgaa tattctggcg gtgcgcgagc aatccgtggc cgaaattgtc   1200

caagaacact ggcgcaccta cggccgcaac tactactctc gccacgacta cgaaggggtg   1260

gagagcgatc gagccagtac gctggtggac aaactgcgat cgcagctacc cagcctgacc   1320

ggacagaaac tgggagccta caccgttgcc tacgccgacg acttccgcta cgaagatccg   1380

gtcgatggca gcatcagcga acagcagggc attcgtattg gctttgaaga cggctcacgt   1440

atggtcttcc gcttgtctgg tactggtacg gcaggagcca ccctgcgcct ctacctcgag   1500

cgcttcgaag gggacaccac caaacagggt ctcgatcccc aagttgccct ggcagatttg   1560

attgcaatcg ccgatgaagt cgcccagatc acaaccttga cgggcttcga tcaaccgaca   1620

gtgatcacct ga                                                       1632
```

<210> SEQ ID NO 38
<211> LENGTH: 543
<212> TYPE: PRT
<213> ORGANISM: Synechococcus elongatus PCC 7942

<400> SEQUENCE: 38

```
Met Asn Ile His Thr Val Ala Thr Gln Ala Phe Ser Asp Gln Lys Pro
```

-continued

```
1               5                   10                  15

Gly Thr Ser Gly Leu Arg Lys Gln Val Pro Val Phe Gln Lys Arg His
            20                  25                  30

Tyr Leu Glu Asn Phe Val Gln Ser Ile Phe Asp Ser Leu Glu Gly Tyr
        35                  40                  45

Gln Gly Gln Thr Leu Val Leu Gly Gly Asp Gly Arg Tyr Tyr Asn Arg
    50                  55                  60

Thr Ala Ile Gln Thr Ile Leu Lys Met Ala Ala Ala Asn Gly Trp Gly
65                  70                  75                  80

Arg Val Leu Val Gly Gln Gly Gly Ile Leu Ser Thr Pro Ala Val Ser
                85                  90                  95

Asn Leu Ile Arg Gln Asn Gly Ala Phe Gly Gly Ile Ile Leu Ser Ala
            100                 105                 110

Ser His Asn Pro Gly Gly Pro Glu Gly Asp Phe Gly Ile Lys Tyr Asn
        115                 120                 125

Ile Ser Asn Gly Gly Pro Ala Pro Glu Lys Val Thr Asp Ala Ile Tyr
    130                 135                 140

Ala Cys Ser Leu Lys Ile Glu Ala Tyr Arg Ile Leu Glu Ala Gly Asp
145                 150                 155                 160

Val Asp Leu Asp Arg Leu Gly Ser Gln Gln Leu Gly Glu Met Thr Val
                165                 170                 175

Glu Val Ile Asp Ser Val Ala Asp Tyr Ser Arg Leu Met Gln Ser Leu
            180                 185                 190

Phe Asp Phe Asp Arg Ile Arg Asp Arg Leu Arg Gly Gly Leu Arg Ile
        195                 200                 205

Ala Ile Asp Ser Met His Ala Val Thr Gly Pro Tyr Ala Thr Thr Ile
    210                 215                 220

Phe Glu Lys Glu Leu Gly Ala Ala Ala Gly Thr Val Phe Asn Gly Lys
225                 230                 235                 240

Pro Leu Glu Asp Phe Gly Gly Gly His Pro Asp Pro Asn Leu Val Tyr
                245                 250                 255

Ala His Asp Leu Val Glu Leu Leu Phe Gly Asp Arg Ala Pro Asp Phe
            260                 265                 270

Gly Ala Ala Ser Asp Gly Asp Gly Asp Arg Asn Met Ile Leu Gly Asn
        275                 280                 285

His Phe Phe Val Thr Pro Ser Asp Ser Leu Ala Ile Leu Ala Ala Asn
    290                 295                 300

Ala Ser Leu Val Pro Ala Tyr Arg Asn Gly Leu Ser Gly Ile Ala Arg
305                 310                 315                 320

Ser Met Pro Thr Ser Ala Ala Ala Asp Arg Val Ala Gln Ala Leu Asn
                325                 330                 335

Leu Pro Cys Tyr Glu Thr Pro Thr Gly Trp Lys Phe Phe Gly Asn Leu
            340                 345                 350

Leu Asp Ala Asp Arg Val Thr Leu Cys Gly Glu Glu Ser Phe Gly Thr
        355                 360                 365

Gly Ser Asn His Val Arg Glu Lys Asp Gly Leu Trp Ala Val Leu Phe
    370                 375                 380

Trp Leu Asn Ile Leu Ala Val Arg Glu Gln Ser Val Ala Glu Ile Val
385                 390                 395                 400

Gln Glu His Trp Arg Thr Tyr Gly Arg Asn Tyr Tyr Ser Arg His Asp
                405                 410                 415

Tyr Glu Gly Val Glu Ser Asp Arg Ala Ser Thr Leu Val Asp Lys Leu
            420                 425                 430
```

```
Arg Ser Gln Leu Pro Ser Leu Thr Gly Gln Lys Leu Gly Ala Tyr Thr
        435                 440                 445

Val Ala Tyr Ala Asp Asp Phe Arg Tyr Glu Asp Pro Val Asp Gly Ser
    450                 455                 460

Ile Ser Glu Gln Gln Gly Ile Arg Ile Gly Phe Glu Asp Gly Ser Arg
465                 470                 475                 480

Met Val Phe Arg Leu Ser Gly Thr Gly Thr Ala Gly Ala Thr Leu Arg
                485                 490                 495

Leu Tyr Leu Glu Arg Phe Glu Gly Asp Thr Thr Lys Gln Gly Leu Asp
            500                 505                 510

Pro Gln Val Ala Leu Ala Asp Leu Ile Ala Ile Ala Asp Glu Val Ala
        515                 520                 525

Gln Ile Thr Thr Leu Thr Gly Phe Asp Gln Pro Thr Val Ile Thr
    530                 535                 540
```

<210> SEQ ID NO 39
<211> LENGTH: 1038
<212> TYPE: DNA
<213> ORGANISM: Synechococcus elongatus PCC 7942

<400> SEQUENCE: 39

```
atgaccttgc tattggccgg ggatatcggc ggaaccaaaa cgaatttaat gttggcgatc      60

gcctctgatt gcgatcgttt agaaccgctc catcaggcca gttttgccag tgcggcctac     120

cctgatttag tgccgatggt gcaggagttt ttggctgccg caccctccgc cgaggtgcga     180

tcgccagttg tggcttgttt tggcattgcc ggccccgttg tccatggaac cgcgaagctg     240

acgaacctgc cttggcagct ctctgaagcg cggctggcga aggaattggg cattgcgcag     300

gtggcgttga tcaatgattt tgctgcgatc gcctacggcc tacccggctt gaccgccgaa     360

gatcaagtcg ttgtgcaagt cggtgaagcc gatccggcgg ctccgatcgc cattctgggg     420

gcaggaactg gcttgggcga aggcttcatc attcccacag cccaaggccg ccaagtgttt     480

ggcagcgaag gttctcacgc tgactttgcg ccgcaaaccg aactggagtc cgagttactg     540

cattttctac gcaattttta cgcaatcgag catatctcgg tcgagcgagt ggtctccggc     600

caagggattg cagccatcta cgccttcctg cgcgatcgcc atcccgacca agaaaatcca     660

gcccttgggg cgattgcctc ggcttggcaa acgggcggcg accaagcccc tgatctggca     720

gcagccgtat cccaagcagc cttgagcgat cgcgatccgc tggccctaca agccatgcag     780

atatttgtca gtgcttacgg ggcggaagcc ggcaacctcg cgttgaaatt gctctcctac     840

ggcggggtct acgtcgccgg cgggattgcg ggcaaaatcc tgccgctctt gactgatggc     900

acttttctgc aagccttcca agccaaggga cgggtgaagg ggctgctgac gcggatgcct     960

atcacgatcg tcacgaacca cgaagtcggg ctgatcgggg ctggactgcg ggcggctgcg    1020

atcgctactc aaccatga                                                  1038
```

<210> SEQ ID NO 40
<211> LENGTH: 345
<212> TYPE: PRT
<213> ORGANISM: Synechococcus elongatus PCC 7942

<400> SEQUENCE: 40

```
Met Thr Leu Leu Leu Ala Gly Asp Ile Gly Gly Thr Lys Thr Asn Leu
 1               5                  10                  15

Met Leu Ala Ile Ala Ser Asp Cys Asp Arg Leu Glu Pro Leu His Gln
            20                  25                  30
```

```
Ala Ser Phe Ala Ser Ala Ala Tyr Pro Asp Leu Val Pro Met Val Gln
        35                  40                  45

Glu Phe Leu Ala Ala Ala Pro Ser Ala Glu Val Arg Ser Pro Val Val
    50                  55                  60

Ala Cys Phe Gly Ile Ala Gly Pro Val Val His Gly Thr Ala Lys Leu
65                  70                  75                  80

Thr Asn Leu Pro Trp Gln Leu Ser Glu Ala Arg Leu Ala Lys Glu Leu
                85                  90                  95

Gly Ile Ala Gln Val Ala Leu Ile Asn Asp Phe Ala Ala Ile Ala Tyr
            100                 105                 110

Gly Leu Pro Gly Leu Thr Ala Glu Asp Gln Val Val Val Gln Val Gly
        115                 120                 125

Glu Ala Asp Pro Ala Ala Pro Ile Ala Ile Leu Gly Ala Gly Thr Gly
    130                 135                 140

Leu Gly Glu Gly Phe Ile Ile Pro Thr Ala Gln Gly Arg Gln Val Phe
145                 150                 155                 160

Gly Ser Glu Gly Ser His Ala Asp Phe Ala Pro Gln Thr Glu Leu Glu
                165                 170                 175

Ser Glu Leu Leu His Phe Leu Arg Asn Phe Tyr Ala Ile Glu His Ile
            180                 185                 190

Ser Val Glu Arg Val Val Ser Gly Gln Gly Ile Ala Ala Ile Tyr Ala
        195                 200                 205

Phe Leu Arg Asp Arg His Pro Asp Gln Glu Asn Pro Ala Leu Gly Ala
    210                 215                 220

Ile Ala Ser Ala Trp Gln Thr Gly Gly Asp Gln Ala Pro Asp Leu Ala
225                 230                 235                 240

Ala Ala Val Ser Gln Ala Ala Leu Ser Asp Arg Asp Pro Leu Ala Leu
                245                 250                 255

Gln Ala Met Gln Ile Phe Val Ser Ala Tyr Gly Ala Glu Ala Gly Asn
            260                 265                 270

Leu Ala Leu Lys Leu Leu Ser Tyr Gly Gly Val Tyr Val Ala Gly Gly
        275                 280                 285

Ile Ala Gly Lys Ile Leu Pro Leu Leu Thr Asp Gly Thr Phe Leu Gln
    290                 295                 300

Ala Phe Gln Ala Lys Gly Arg Val Lys Gly Leu Leu Thr Arg Met Pro
305                 310                 315                 320

Ile Thr Ile Val Thr Asn His Glu Val Gly Leu Ile Gly Ala Gly Leu
                325                 330                 335

Arg Ala Ala Ala Ile Ala Thr Gln Pro
            340                 345
```

<210> SEQ ID NO 41
<211> LENGTH: 1587
<212> TYPE: DNA
<213> ORGANISM: Synechococcus elongatus PCC 7942

<400> SEQUENCE: 41

```
atgaccgccc agcagctctg gcaacgctac ctcgattggc tctactacga tccctcgctg      60

gagttttacc tcgacatcag ccgcatggga ttcgatgacg ctttcgttac tagcatgcag     120

cccaagttcc agcacgcctt tgcggcgatg gcagagctcg aggccggagc gatcgccaac     180

cccgatgaac agcggatggt cggccactac tggctgcgcg atcctgagct ggcacccaca     240

ccggagctgc agacccaaat tcgcgacacg ctggccgcga tccaagactt cgccctcaaa     300
```

-continued

```
gtacacagtg gcgtgttgcg gccacccacc ggctcccgct tcaccgacat tctctcaatt    360

ggcattggcg ggtcggccct agggccgcag tttgtctcag aagccctccg gcctcaagcg    420

gcactgctcc agattcactt ctttgacaac accgatccag ctggcttcga tcgcgtttta    480

gctgatctcg gcgatcgcct tgcttccacc ttagtaatcg ttatttccaa atctggcggc    540

actcccgaaa cccgcaacgg catgctggag gttcagtccg cctttgccca gcgagggatt    600

gcctttgcgc cccaagctgt cgccgtcaca ggggtgggga gccatctcga tcatgtagcg    660

atcacagaaa gatggctggc ccgtttcccc atggaagact gggtgggcgg ccgcacctct    720

gaactatctg cagtcggtct actctcggca gccctactgg gcatcgacat caccgccatg    780

ctggccgggg cgcggcaaat ggacgccctg acccgccatt ccgatttgcg acaaaatccg    840

gcagcgctct tggctttgag ctggtactgg gccggcaatg ggcaaggcaa aaaagacatg    900

gtcatcctgc cctacaagga cagcctgctg ctgtttagcc gctatctgca gcagttgatc    960

atggagtcac tgggcaagga gcgcgatctg ctcggcaagg tagttcacca aggcatcgcc   1020

gtttacggca acaaaggctc gaccgatcaa catgcctacg tccagcaact gcgcgagggc   1080

attcctaact tctttgccac gtttatcgag gtgctcgaag accgacaggg gccgtcgcca   1140

gtcgtggagc ctggcatcac cagtggcgac tatctcagcg ggctgcttca aggcacccgc   1200

gcggcgcttt acgaaaatgg gcgtgagtcg atcacgatta cggtgccgcg cgttgatgca   1260

caacaggtgg gggccttgat cgcgctgtat gaacgggcgg tgggactcta tgccagcttg   1320

gttggcatca atgcctatca ccagccgggg gtggaagccg gcaaaaaggc tgctgccggt   1380

gttctcgaga tccagcgcca gattgtggag ttgctccaac agggacaacc actctcgatc   1440

gcagcgatcg cagacgattt aggtcagagt gagcagattg aaacgatcta caaaatcctg   1500

cgccatctcg aagccaatca acgcggcgtt cagttaaccg gcgatcgcca taatcccctc   1560

agtctgattg cgagttggca acgataa                                      1587
```

```
<210> SEQ ID NO 42
<211> LENGTH: 528
<212> TYPE: PRT
<213> ORGANISM: Synechococcus elongatus PCC 7942

<400> SEQUENCE: 42

Met Thr Ala Gln Gln Leu Trp Gln Arg Tyr Leu Asp Trp Leu Tyr Tyr
1               5                   10                  15

Asp Pro Ser Leu Glu Phe Tyr Leu Asp Ile Ser Arg Met Gly Phe Asp
            20                  25                  30

Asp Ala Phe Val Thr Ser Met Gln Pro Lys Phe Gln His Ala Phe Ala
        35                  40                  45

Ala Met Ala Glu Leu Glu Ala Gly Ala Ile Ala Asn Pro Asp Glu Gln
    50                  55                  60

Arg Met Val Gly His Tyr Trp Leu Arg Asp Pro Glu Leu Ala Pro Thr
65                  70                  75                  80

Pro Glu Leu Gln Thr Gln Ile Arg Asp Thr Leu Ala Ala Ile Gln Asp
                85                  90                  95

Phe Ala Leu Lys Val His Ser Gly Val Leu Arg Pro Pro Thr Gly Ser
            100                 105                 110

Arg Phe Thr Asp Ile Leu Ser Ile Gly Ile Gly Gly Ser Ala Leu Gly
        115                 120                 125

Pro Gln Phe Val Ser Glu Ala Leu Arg Pro Gln Ala Ala Leu Leu Gln
    130                 135                 140
```

-continued

```
Ile His Phe Phe Asp Asn Thr Asp Pro Ala Gly Phe Asp Arg Val Leu
145                 150                 155                 160

Ala Asp Leu Gly Asp Arg Leu Ala Ser Thr Leu Val Ile Val Ile Ser
                165                 170                 175

Lys Ser Gly Gly Thr Pro Glu Thr Arg Asn Gly Met Leu Glu Val Gln
            180                 185                 190

Ser Ala Phe Ala Gln Arg Gly Ile Ala Phe Ala Pro Gln Ala Val Ala
        195                 200                 205

Val Thr Gly Val Gly Ser His Leu Asp His Val Ala Ile Thr Glu Arg
    210                 215                 220

Trp Leu Ala Arg Phe Pro Met Glu Asp Trp Val Gly Gly Arg Thr Ser
225                 230                 235                 240

Glu Leu Ser Ala Val Gly Leu Leu Ser Ala Ala Leu Leu Gly Ile Asp
                245                 250                 255

Ile Thr Ala Met Leu Ala Gly Ala Arg Gln Met Asp Ala Leu Thr Arg
            260                 265                 270

His Ser Asp Leu Arg Gln Asn Pro Ala Ala Leu Leu Ala Leu Ser Trp
        275                 280                 285

Tyr Trp Ala Gly Asn Gly Gln Gly Lys Lys Asp Met Val Ile Leu Pro
    290                 295                 300

Tyr Lys Asp Ser Leu Leu Leu Phe Ser Arg Tyr Leu Gln Gln Leu Ile
305                 310                 315                 320

Met Glu Ser Leu Gly Lys Glu Arg Asp Leu Leu Gly Lys Val Val His
                325                 330                 335

Gln Gly Ile Ala Val Tyr Gly Asn Lys Gly Ser Thr Asp Gln His Ala
            340                 345                 350

Tyr Val Gln Gln Leu Arg Glu Gly Ile Pro Asn Phe Phe Ala Thr Phe
        355                 360                 365

Ile Glu Val Leu Glu Asp Arg Gln Gly Pro Ser Pro Val Val Glu Pro
    370                 375                 380

Gly Ile Thr Ser Gly Asp Tyr Leu Ser Gly Leu Leu Gln Gly Thr Arg
385                 390                 395                 400

Ala Ala Leu Tyr Glu Asn Gly Arg Glu Ser Ile Thr Ile Thr Val Pro
                405                 410                 415

Arg Val Asp Ala Gln Gln Val Gly Ala Leu Ile Ala Leu Tyr Glu Arg
            420                 425                 430

Ala Val Gly Leu Tyr Ala Ser Leu Val Gly Ile Asn Ala Tyr His Gln
        435                 440                 445

Pro Gly Val Glu Ala Gly Lys Lys Ala Ala Ala Gly Val Leu Glu Ile
    450                 455                 460

Gln Arg Gln Ile Val Glu Leu Leu Gln Gln Gly Gln Pro Leu Ser Ile
465                 470                 475                 480

Ala Ala Ile Ala Asp Asp Leu Gly Gln Ser Glu Gln Ile Glu Thr Ile
                485                 490                 495

Tyr Lys Ile Leu Arg His Leu Glu Ala Asn Gln Arg Gly Val Gln Leu
            500                 505                 510

Thr Gly Asp Arg His Asn Pro Leu Ser Leu Ile Ala Ser Trp Gln Arg
        515                 520                 525
```

<210> SEQ ID NO 43
<211> LENGTH: 1434
<212> TYPE: DNA
<213> ORGANISM: Synechocystis sp. PCC 6803

<400> SEQUENCE: 43

```
atgaagattt tatttgtggc ggcggaagta tccccccctag caaaggtagg tggcatgggg      60
gatgtggtgg gttccctgcc taaagttctg catcagttgg gccatgatgt ccgtgtcttc     120
atgccctact acggtttcat cggcgacaag attgatgtgc ccaaggagcc ggtctggaaa     180
ggggaagcca tgttccagca gtttgctgtt taccagtcct atctaccgga caccaaaatt     240
cctctctact tgttcggcca tccagctttc gactcccgaa ggatctatgg cggagatgac     300
gaggcgtggc ggttcacttt tttttctaac ggggcagctg aatttgcctg gaaccattgg     360
aagccggaaa ttatccattg ccatgattgg cacactggca tgatccctgt ttggatgcat     420
cagtccccag acatcgccac cgttttcacc atccataatc ttgcttacca agggccctgg     480
cggggcttgc ttgaaactat gacttggtgt ccttggtaca tgcagggaga caatgtgatg     540
gcggcggcga ttcaatttgc caatcgggtg actaccgttt ctcccaccta tgcccaacag     600
atccaaaccc cggcctatgg ggaaaagctg gaagggttat tgtcctacct gagtggtaat     660
ttagtcggta ttctcaacgg tattgatacg gagatttaca acccggcgga agaccgcttt     720
atcagcaatg ttttcgatgc ggacagtttg gacaagcggg tgaaaaataa aattgccatc     780
caggaggaaa cggggttaga aattaatcgt aatgccatgg tggtgggtat agtggctcgc     840
ttggtggaac aaaaggggat tgatttggtg attcagatcc ttgaccgctt catgtcctac     900
accgattccc agttaattat cctcggcact ggcgatcgcc attacgaaac ccaactttgg     960
cagatggctt cccgatttcc tgggcggatg gcggtgcaat tactccacaa cgatgccctt    1020
tcccgtcgag tctatgccgg ggcggatgtg tttttaatgc cttctcgctt tgagccctgt    1080
gggctgagtc aattgatggc catgcgttat ggctgtatcc ccattgtgcg gcggacaggg    1140
ggtttggtgg atacggtatc cttctacgat cctatcaatg aagccggcac cggctattgc    1200
tttgaccgtt atgaacccct ggattgcttt acggccatgg tgcgggcctg ggagggtttc    1260
cgtttcaagg cagattggca aaaattacag caacgggcca tgcgggcaga ctttagttgg    1320
taccgttccg ccggggaata tatcaaagtt tataagggcg tggtggggaa accggaggaa    1380
ttaagcccca tggaagagga aaaaatcgct gagttaactg cttcctatcg ctaa          1434
```

<210> SEQ ID NO 44
<211> LENGTH: 477
<212> TYPE: PRT
<213> ORGANISM: Synechocystis sp. PCC 6803

<400> SEQUENCE: 44

```
Met Lys Ile Leu Phe Val Ala Ala Glu Val Ser Pro Leu Ala Lys Val
 1               5                  10                  15

Gly Gly Met Gly Asp Val Val Gly Ser Leu Pro Lys Val Leu His Gln
            20                  25                  30

Leu Gly His Asp Val Arg Val Phe Met Pro Tyr Tyr Gly Phe Ile Gly
        35                  40                  45

Asp Lys Ile Asp Val Pro Lys Glu Pro Val Trp Lys Gly Glu Ala Met
    50                  55                  60

Phe Gln Gln Phe Ala Val Tyr Gln Ser Tyr Leu Pro Asp Thr Lys Ile
65                  70                  75                  80

Pro Leu Tyr Leu Phe Gly His Pro Ala Phe Asp Ser Arg Arg Ile Tyr
                85                  90                  95

Gly Gly Asp Asp Glu Ala Trp Arg Phe Thr Phe Phe Ser Asn Gly Ala
            100                 105                 110

Ala Glu Phe Ala Trp Asn His Trp Lys Pro Glu Ile Ile His Cys His
```

-continued

```
        115                 120                 125

Asp Trp His Thr Gly Met Ile Pro Val Trp Met His Gln Ser Pro Asp
    130                 135                 140

Ile Ala Thr Val Phe Thr Ile His Asn Leu Ala Tyr Gln Gly Pro Trp
145                 150                 155                 160

Arg Gly Leu Leu Glu Thr Met Thr Trp Cys Pro Trp Tyr Met Gln Gly
                165                 170                 175

Asp Asn Val Met Ala Ala Ala Ile Gln Phe Ala Asn Arg Val Thr Thr
            180                 185                 190

Val Ser Pro Thr Tyr Ala Gln Gln Ile Gln Thr Pro Ala Tyr Gly Glu
        195                 200                 205

Lys Leu Glu Gly Leu Leu Ser Tyr Leu Ser Gly Asn Leu Val Gly Ile
    210                 215                 220

Leu Asn Gly Ile Asp Thr Glu Ile Tyr Asn Pro Ala Glu Asp Arg Phe
225                 230                 235                 240

Ile Ser Asn Val Phe Asp Ala Asp Ser Leu Asp Lys Arg Val Lys Asn
                245                 250                 255

Lys Ile Ala Ile Gln Glu Glu Thr Gly Leu Glu Ile Asn Arg Asn Ala
            260                 265                 270

Met Val Val Gly Ile Val Ala Arg Leu Val Glu Gln Lys Gly Ile Asp
        275                 280                 285

Leu Val Ile Gln Ile Leu Asp Arg Phe Met Ser Tyr Thr Asp Ser Gln
    290                 295                 300

Leu Ile Ile Leu Gly Thr Gly Asp Arg His Tyr Glu Thr Gln Leu Trp
305                 310                 315                 320

Gln Met Ala Ser Arg Phe Pro Gly Arg Met Ala Val Gln Leu Leu His
                325                 330                 335

Asn Asp Ala Leu Ser Arg Arg Val Tyr Ala Gly Ala Asp Val Phe Leu
            340                 345                 350

Met Pro Ser Arg Phe Glu Pro Cys Gly Leu Ser Gln Leu Met Ala Met
        355                 360                 365

Arg Tyr Gly Cys Ile Pro Ile Val Arg Arg Thr Gly Gly Leu Val Asp
    370                 375                 380

Thr Val Ser Phe Tyr Asp Pro Ile Asn Glu Ala Gly Thr Gly Tyr Cys
385                 390                 395                 400

Phe Asp Arg Tyr Glu Pro Leu Asp Cys Phe Thr Ala Met Val Arg Ala
                405                 410                 415

Trp Glu Gly Phe Arg Phe Lys Ala Asp Trp Gln Lys Leu Gln Gln Arg
            420                 425                 430

Ala Met Arg Ala Asp Phe Ser Trp Tyr Arg Ser Ala Gly Glu Tyr Ile
        435                 440                 445

Lys Val Tyr Lys Gly Val Val Gly Lys Pro Glu Glu Leu Ser Pro Met
    450                 455                 460

Glu Glu Glu Lys Ile Ala Glu Leu Thr Ala Ser Tyr Arg
465                 470                 475


<210> SEQ ID NO 45
<211> LENGTH: 1419
<212> TYPE: DNA
<213> ORGANISM: Nostoc sp. PCC 7120

<400> SEQUENCE: 45

atgcggattc tatttgtggc agcagaagca gcacccattg caaaagtagg agggatgggt      60

gatgttgtcg gtgcattacc taaggtcttg agaaaaatgg ggcatgatgt acgtatcttc     120
```

```
ttgccctatt acggcttttt gccagacaaa atggagattc ccaaagatcc aatatggaag    180
ggatacgcca tgtttcagga ctttacagtt cacgaagcag ttctgcctgg tactgatgtt    240
cccttgtatt tatttggaca tccagccttt accccccggc ggatttattc gggagatgat    300
gaagactggc gcttcacctt gttttccaat ggtgcggctg agttttgctg gaattactgg    360
aaacccgaca ttattcactg tcatgattgg cacacgggca tgattcctgt gtggatgaac    420
caatcaccag atatcaccac agtcttcact atccacaatc tggcttacca agggccttgg    480
cgttggtatt tagataaaat tacttggtgt ccttggtata tgcagggaca caacacaatg    540
gcggcggctg tccagtttgc ggacagggta aatacagttt ctcccacata cgccgagcaa    600
atcaagaccc cggcttacgg tgagaaaata gaaggtttgc tgtctttcat cagtggtaaa    660
ttatctggga ttgttaacgg tatagatacg gaagtttacg acccagctaa tgataaatat    720
attgctcaaa cgttcactgc cgatacttta gataaacgca aagccaacaa aattgcttta    780
caagaagaag taggattaga agttaacagc aatgcctttt taattggcat ggtgacaagg    840
ttagtcgagc agaagggctt agatttagtc atccaaatgc tcgatcgctt tatggcttat    900
actgatgctc agttcgtctt gttgggaaca ggcgatcgct actacgaaac ccaaatgtgg    960
caattagcat cccgctaccc cggtcgtatg gctacttacc tcctgtataa cgatgcccta   1020
tctcgccgca tctacgctgg tactgatgcc tttttgatgc ccagtcgctt tgaaccatgc   1080
ggtattagtc aaatgatggc tttacgctac ggttccattc ccatcgtccg ccgcactgga   1140
ggcttggttg acaccgtatc ccaccacgac cccatcaacg aagcaggtac aggctactgc   1200
ttcgaccgct acgaacccct cgacttattt acctgcatga ttcgcgcctg ggaaggcttc   1260
cgctacaaac cacaatggca agaactacaa aaacgcggta tgagtcaaga cttcagctgg   1320
tacaaatccg ctaaggaata cgacaaactc tatcgctcaa tgtacggttt gccagaccca   1380
gaagagacac agccggagtt aattctgaca aatcagtag                          1419
```

<210> SEQ ID NO 46
<211> LENGTH: 472
<212> TYPE: PRT
<213> ORGANISM: Nostoc sp. PCC 7120

<400> SEQUENCE: 46

```
Met Arg Ile Leu Phe Val Ala Ala Glu Ala Ala Pro Ile Ala Lys Val
1               5                   10                  15

Gly Gly Met Gly Asp Val Val Gly Ala Leu Pro Lys Val Leu Arg Lys
            20                  25                  30

Met Gly His Asp Val Arg Ile Phe Leu Pro Tyr Tyr Gly Phe Leu Pro
        35                  40                  45

Asp Lys Met Glu Ile Pro Lys Asp Pro Ile Trp Lys Gly Tyr Ala Met
    50                  55                  60

Phe Gln Asp Phe Thr Val His Glu Ala Val Leu Pro Gly Thr Asp Val
65                  70                  75                  80

Pro Leu Tyr Leu Phe Gly His Pro Ala Phe Thr Pro Arg Arg Ile Tyr
                85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Asp Ile Ile His Cys His
        115                 120                 125

Asp Trp His Thr Gly Met Ile Pro Val Trp Met Asn Gln Ser Pro Asp
    130                 135                 140
```

-continued

Ile Thr Thr Val Phe Thr Ile His Asn Leu Ala Tyr Gln Gly Pro Trp
145 150 155 160

Arg Trp Tyr Leu Asp Lys Ile Thr Trp Cys Pro Trp Tyr Met Gln Gly
165 170 175

His Asn Thr Met Ala Ala Ala Val Gln Phe Ala Asp Arg Val Asn Thr
180 185 190

Val Ser Pro Thr Tyr Ala Glu Gln Ile Lys Thr Pro Ala Tyr Gly Glu
195 200 205

Lys Ile Glu Gly Leu Leu Ser Phe Ile Ser Gly Lys Leu Ser Gly Ile
210 215 220

Val Asn Gly Ile Asp Thr Glu Val Tyr Asp Pro Ala Asn Asp Lys Tyr
225 230 235 240

Ile Ala Gln Thr Phe Thr Ala Asp Thr Leu Asp Lys Arg Lys Ala Asn
245 250 255

Lys Ile Ala Leu Gln Glu Glu Val Gly Leu Glu Val Asn Ser Asn Ala
260 265 270

Phe Leu Ile Gly Met Val Thr Arg Leu Val Glu Gln Lys Gly Leu Asp
275 280 285

Leu Val Ile Gln Met Leu Asp Arg Phe Met Ala Tyr Thr Asp Ala Gln
290 295 300

Phe Val Leu Leu Gly Thr Gly Asp Arg Tyr Tyr Glu Thr Gln Met Trp
305 310 315 320

Gln Leu Ala Ser Arg Tyr Pro Gly Arg Met Ala Thr Tyr Leu Leu Tyr
325 330 335

Asn Asp Ala Leu Ser Arg Arg Ile Tyr Ala Gly Thr Asp Ala Phe Leu
340 345 350

Met Pro Ser Arg Phe Glu Pro Cys Gly Ile Ser Gln Met Met Ala Leu
355 360 365

Arg Tyr Gly Ser Ile Pro Ile Val Arg Arg Thr Gly Gly Leu Val Asp
370 375 380

Thr Val Ser His His Asp Pro Ile Asn Glu Ala Gly Thr Gly Tyr Cys
385 390 395 400

Phe Asp Arg Tyr Glu Pro Leu Asp Leu Phe Thr Cys Met Ile Arg Ala
405 410 415

Trp Glu Gly Phe Arg Tyr Lys Pro Gln Trp Gln Glu Leu Gln Lys Arg
420 425 430

Gly Met Ser Gln Asp Phe Ser Trp Tyr Lys Ser Ala Lys Glu Tyr Asp
435 440 445

Lys Leu Tyr Arg Ser Met Tyr Gly Leu Pro Asp Pro Glu Glu Thr Gln
450 455 460

Pro Glu Leu Ile Leu Thr Asn Gln
465 470

<210> SEQ ID NO 47
<211> LENGTH: 1419
<212> TYPE: DNA
<213> ORGANISM: Anabaena variabilis

<400> SEQUENCE: 47
atgcggattc tatttgtggc agcagaagca gcacccatcg caaaagtagg agggatgggt 60
gatgttgtcg gtgcattacc taaggtcttg agaaaaatgg ggcatgatgt gcgtatcttc 120
ttgccctatt acggcttttt gccagacaaa atggaaattc ccaaagatcc aatctggaag 180
ggatacgcca tgtttcagga ctttacagtt cacgaagcag ttctgcctgg tactgatgtt 240

```
cccttgtatt tatttggaca tccagccttc aaccccggc gaatttattc gggagatgat      300

gaagactggc ggttcacctt gttttccaat ggtgcggcgg aattttgttg gaattactgg      360

aaaccagaaa ttattcactg tcacgattgg cacacaggca tgattcctgt gtggatgaac      420

caatcaccag atatccacca gtcttcact atccacaacc tagcttacca agggccttgg      480

cgttggtatc tagataaaat tacttggtgt ccttggtata tgcagggaca caacacaatg      540

gcggcggctg tccagtttgc tgacagagta aataccgttt ctcctacata cgccgagcaa      600

atcaagaccc cggcttacgg tgagaaaata aaggcttgc tgtctttcat cagtggtaaa       660

ttatctggga ttgttaacgg tatagatacg aagtttatg acccagctaa tgataaattt       720

attgctcaaa cttttactgc tgatacttta gataaacgca aagccaacaa aattgcttta      780

caagaagaag tagggttaga agttaacagc aatgcctttt taattggcat ggtgacaagg      840

ttagtcgagc agaagggttt agatttagtc atccaaatgc tcgatcgctt tatggcttat      900

actgatgctc agttcgtctt gttaggaaca ggcgatcgct actacgaaac tcaaatgtgg      960

caattagcat cccgctaccc cggacgtatg gccacctatc tcctatacaa tgatgcccta     1020

tcccgccgca tctacgccgg ttctgatgcc ttttaatgc ccagccgctt tgaaccatgc     1080

ggtattagcc agatgatggc tttacgctac ggttccatcc ccatcgttcg ccgcactggg     1140

ggtttagttg acaccgtatc ccaccacgac cccgtaaacg aagccggtac aggctactgc     1200

tttgaccgct acgaaccct agacttattc acctgcatga ttcgcgcctg ggaaggcttc     1260

cgctacaaac cccaatggca agaactacaa aagcgtggta tgagtcaaga cttcagctgg     1320

tacaaatccg ctaaggaata cgacagactc tatcgctcaa atacggtttt gccagaagca     1380

gaagagacac agccagagtt aattctggca aatcagtag                            1419

<210> SEQ ID NO 48
<211> LENGTH: 472
<212> TYPE: PRT
<213> ORGANISM: Anabaena variabilis

<400> SEQUENCE: 48

Met Arg Ile Leu Phe Val Ala Ala Glu Ala Ala Pro Ile Ala Lys Val
 1               5                   10                  15

Gly Gly Met Gly Asp Val Val Gly Ala Leu Pro Lys Val Leu Arg Lys
                20                  25                  30

Met Gly His Asp Val Arg Ile Phe Leu Pro Tyr Tyr Gly Phe Leu Pro
            35                  40                  45

Asp Lys Met Glu Ile Pro Lys Asp Pro Ile Trp Lys Gly Tyr Ala Met
        50                  55                  60

Phe Gln Asp Phe Thr Val His Glu Ala Val Leu Pro Gly Thr Asp Val
 65                  70                  75                  80

Pro Leu Tyr Leu Phe Gly His Pro Ala Phe Asn Pro Arg Arg Ile Tyr
                85                  90                  95

Ser Gly Asp Asp Glu Asp Trp Arg Phe Thr Leu Phe Ser Asn Gly Ala
            100                 105                 110

Ala Glu Phe Cys Trp Asn Tyr Trp Lys Pro Glu Ile Ile His Cys His
        115                 120                 125

Asp Trp His Thr Gly Met Ile Pro Val Trp Met Asn Gln Ser Pro Asp
    130                 135                 140

Ile Thr Thr Val Phe Thr Ile His Asn Leu Ala Tyr Gln Gly Pro Trp
145                 150                 155                 160
```

-continued

```
Arg Trp Tyr Leu Asp Lys Ile Thr Trp Cys Pro Trp Tyr Met Gln Gly
                165                 170                 175

His Asn Thr Met Ala Ala Ala Val Gln Phe Ala Asp Arg Val Asn Thr
            180                 185                 190

Val Ser Pro Thr Tyr Ala Glu Gln Ile Lys Thr Pro Ala Tyr Gly Glu
        195                 200                 205

Lys Ile Glu Gly Leu Leu Ser Phe Ile Ser Gly Lys Leu Ser Gly Ile
    210                 215                 220

Val Asn Gly Ile Asp Thr Glu Val Tyr Asp Pro Ala Asn Asp Lys Phe
225                 230                 235                 240

Ile Ala Gln Thr Phe Thr Ala Asp Thr Leu Asp Lys Arg Lys Ala Asn
                245                 250                 255

Lys Ile Ala Leu Gln Glu Glu Val Gly Leu Glu Val Asn Ser Asn Ala
            260                 265                 270

Phe Leu Ile Gly Met Val Thr Arg Leu Val Glu Gln Lys Gly Leu Asp
        275                 280                 285

Leu Val Ile Gln Met Leu Asp Arg Phe Met Ala Tyr Thr Asp Ala Gln
    290                 295                 300

Phe Val Leu Leu Gly Thr Gly Asp Arg Tyr Tyr Glu Thr Gln Met Trp
305                 310                 315                 320

Gln Leu Ala Ser Arg Tyr Pro Gly Arg Met Ala Thr Tyr Leu Leu Tyr
                325                 330                 335

Asn Asp Ala Leu Ser Arg Arg Ile Tyr Ala Gly Ser Asp Ala Phe Leu
            340                 345                 350

Met Pro Ser Arg Phe Glu Pro Cys Gly Ile Ser Gln Met Met Ala Leu
        355                 360                 365

Arg Tyr Gly Ser Ile Pro Ile Val Arg Arg Thr Gly Gly Leu Val Asp
    370                 375                 380

Thr Val Ser His His Asp Pro Val Asn Glu Ala Gly Thr Gly Tyr Cys
385                 390                 395                 400

Phe Asp Arg Tyr Glu Pro Leu Asp Leu Phe Thr Cys Met Ile Arg Ala
                405                 410                 415

Trp Glu Gly Phe Arg Tyr Lys Pro Gln Trp Gln Glu Leu Gln Lys Arg
            420                 425                 430

Gly Met Ser Gln Asp Phe Ser Trp Tyr Lys Ser Ala Lys Glu Tyr Asp
        435                 440                 445

Arg Leu Tyr Arg Ser Ile Tyr Gly Leu Pro Glu Ala Glu Glu Thr Gln
    450                 455                 460

Pro Glu Leu Ile Leu Ala Asn Gln
465                 470
```

<210> SEQ ID NO 49
<211> LENGTH: 1383
<212> TYPE: DNA
<213> ORGANISM: Trichodesmium erythraeum IMS 101

<400> SEQUENCE: 49

```
atgcgaattt tatttgtgtc tgctgaagcg actcctttag caaaagttgg tggtatggca      60

gatgtagtgg gtgccttacc caaagtacta cggaaaatgg gtcacgatgt tcgtatcttc     120

atgccttatt atggcttttt aggcgacaag atggaagttc ctgaggaacc tatctgggaa     180

ggaacggcca tgtatcaaaa ctttaagatt tatgagacgg tactaccaaa aagtgacgtg     240

ccattgtacc tatttggtca cccggctttt tggccacgtc atatttacta tggagatgat     300

gaggactgga gattcactct atttgctaat ggggcggccg agttttgctg gaatggctgg     360
```

```
aaaccagaga tagttcattg taatgactgg cacactggca tgattccagt ttggatgcac    420

gaaactccag acattaaaac cgtatttact attcataacc tagcttatca aggaccttgg    480

cgctggtact tggaaagaat tacttggtgt ccttggtaca tggaagggca taatacaatg    540

gcagcagcag ttcagtttgc agatcgggta actactgttt ctccaaccta tgctagtcag    600

atccaaacac ctgcctacgg agaaaatcta gatggtttaa tgtcttttat tacggggaaa    660

ctacacggta tcctcaatgg tattgatatg aacttttata atccagctaa tgacagatat    720

attcctcaaa cttatgatgt caataccctg gaaaaacggg ttgacaataa aattgctctt    780

caagaagaag taggttttga agttaacaaa aatagctttc tcatgggaat ggtctcccga    840

ctggtagaac aaaaaggact tgatttaatg ctgcaagtct tagatcggtt tatggcttat    900

actgatactc agtttatttt gttgggtaca ggcgatcgct tctatgaaac ccaaatgtgg    960

caaatagcaa gtcgttatcc tggtcggatg agtgtccaac ttttacataa tgatgccctt   1020

tcccgacgaa tatatgcagg tactgatgct ttcttaatgc ccagtcgatt tgagccttgt   1080

ggtattagtc agttattggc aatgcgttat ggtagtatac ctattgtccg tcgcacaggt   1140

gggttagttg atactgtctc tttctatgat cctattaata atgtaggtac tggctattct   1200

tttgatcgct atgaaccact agacctgctt actgcaatgg tccgagccta tgaaggtttc   1260

cggttcaaag atcaatggca ggagttacag aagcgtggca tgagagagaa ctttagctgg   1320

gataagtcag ctcaaggtta tatcaaaatg tacaaatcaa tgctcggatt acctgaagaa   1380

taa                                                                 1383
```

<210> SEQ ID NO 50
<211> LENGTH: 460
<212> TYPE: PRT
<213> ORGANISM: Trichodesmium erythraeum IMS 101

<400> SEQUENCE: 50

```
Met Arg Ile Leu Phe Val Ser Ala Glu Ala Thr Pro Leu Ala Lys Val
 1               5                  10                  15

Gly Gly Met Ala Asp Val Val Gly Ala Leu Pro Lys Val Leu Arg Lys
            20                  25                  30

Met Gly His Asp Val Arg Ile Phe Met Pro Tyr Tyr Gly Phe Leu Gly
        35                  40                  45

Asp Lys Met Glu Val Pro Glu Glu Pro Ile Trp Glu Gly Thr Ala Met
    50                  55                  60

Tyr Gln Asn Phe Lys Ile Tyr Glu Thr Val Leu Pro Lys Ser Asp Val
65                  70                  75                  80

Pro Leu Tyr Leu Phe Gly His Pro Ala Phe Trp Pro Arg His Ile Tyr
                85                  90                  95

Tyr Gly Asp Asp Glu Asp Trp Arg Phe Thr Leu Phe Ala Asn Gly Ala
            100                 105                 110

Ala Glu Phe Cys Trp Asn Gly Trp Lys Pro Glu Ile Val His Cys Asn
        115                 120                 125

Asp Trp His Thr Gly Met Ile Pro Val Trp Met His Glu Thr Pro Asp
    130                 135                 140

Ile Lys Thr Val Phe Thr Ile His Asn Leu Ala Tyr Gln Gly Pro Trp
145                 150                 155                 160

Arg Trp Tyr Leu Glu Arg Ile Thr Trp Cys Pro Trp Tyr Met Glu Gly
                165                 170                 175

His Asn Thr Met Ala Ala Ala Val Gln Phe Ala Asp Arg Val Thr Thr
```

-continued

```
            180                 185                 190

Val Ser Pro Thr Tyr Ala Ser Gln Ile Gln Thr Pro Ala Tyr Gly Glu
        195                 200                 205

Asn Leu Asp Gly Leu Met Ser Phe Ile Thr Gly Lys Leu His Gly Ile
    210                 215                 220

Leu Asn Gly Ile Asp Met Asn Phe Tyr Asn Pro Ala Asn Asp Arg Tyr
225                 230                 235                 240

Ile Pro Gln Thr Tyr Asp Val Asn Thr Leu Glu Lys Arg Val Asp Asn
                245                 250                 255

Lys Ile Ala Leu Gln Glu Glu Val Gly Phe Glu Val Asn Lys Asn Ser
            260                 265                 270

Phe Leu Met Gly Met Val Ser Arg Leu Val Glu Gln Lys Gly Leu Asp
        275                 280                 285

Leu Met Leu Gln Val Leu Asp Arg Phe Met Ala Tyr Thr Asp Thr Gln
    290                 295                 300

Phe Ile Leu Leu Gly Thr Gly Asp Arg Phe Tyr Glu Thr Gln Met Trp
305                 310                 315                 320

Gln Ile Ala Ser Arg Tyr Pro Gly Arg Met Ser Val Gln Leu Leu His
                325                 330                 335

Asn Asp Ala Leu Ser Arg Arg Ile Tyr Ala Gly Thr Asp Ala Phe Leu
            340                 345                 350

Met Pro Ser Arg Phe Glu Pro Cys Gly Ile Ser Gln Leu Leu Ala Met
        355                 360                 365

Arg Tyr Gly Ser Ile Pro Ile Val Arg Arg Thr Gly Gly Leu Val Asp
    370                 375                 380

Thr Val Ser Phe Tyr Asp Pro Ile Asn Asn Val Gly Thr Gly Tyr Ser
385                 390                 395                 400

Phe Asp Arg Tyr Glu Pro Leu Asp Leu Leu Thr Ala Met Val Arg Ala
                405                 410                 415

Tyr Glu Gly Phe Arg Phe Lys Asp Gln Trp Gln Glu Leu Gln Lys Arg
            420                 425                 430

Gly Met Arg Glu Asn Phe Ser Trp Asp Lys Ser Ala Gln Gly Tyr Ile
        435                 440                 445

Lys Met Tyr Lys Ser Met Leu Gly Leu Pro Glu Glu
    450                 455                 460
```

<210> SEQ ID NO 51
<211> LENGTH: 1398
<212> TYPE: DNA
<213> ORGANISM: Synechococcus elongatus PCC 7942

<400> SEQUENCE: 51

```
atgcggattc tgttcgtggc tgccgaatgt gctcccttcg ccaaagtggg aggcatggga      60

gatgtggttg gttccctgcc caaagtgctg aaagctctgg gccatgatgt ccgaatcttc     120

atgccgtact acggctttct gaacagtaag ctcgatattc ccgctgaacc gatctggtgg     180

ggctacgcga tgtttaatca cttcgcggtt tacgaaacgc agctgcccgg ttcagatgtg     240

ccgctctact taatggggca tccagctttt gatccgcatc gcatctactc aggagaagac     300

gaagactggc gcttcacgtt ttttgccaat ggggctgctg aattttcttg gaactactgg     360

aaaccacaag tcattcactg ccacgattgg cacactggga tgattccggt ttggatgcac     420

cagtccccgg atatctcgac tgtcttcacc attcataact tggcctacca agggccgtgg     480

cgctggaagc tcgagaaaat cacctggtgc ccttggtaca tgcagggcga cagcaccatg     540
```

-continued gcggcggcct tgctctatgc cgatcgcgtc aacacggtat cgcccaccta tgcccagcag 600
attcaaacac cgacctacgg tgaaaagctg gagggtcttc tctcatttat cagtggcaag 660
ctaagcggca tccttaacgg gattgatgtt gatagctaca accctgcaac ggatacgcgg 720
attgtggcca actacgatcg cgacactctt gataaacgac tgaacaataa gctggcgctc 780
caaaaggaga tggggcttga ggtcaatccc gatcgcttcc tgattggctt tgtggctcgt 840
ctagtcgagc agaagggcat tgacttgctg ctgcaaattc ttgatcgctt tctgtcttac 900
agcgatgccc aatttgttgt cttaggaacg ggcgagcgct actacgaaac ccagctctgg 960
gagttggcga cccgctatcc gggccggatg tccacttatc tgatgtacga cgaggggctg 1020
tcgcgacgca tttatgccgg tagcgacgcc ttcttggtgc cctctcgttt tgaaccttgc 1080
ggtatcacgc aaatgctggc actgcgctac ggcagtgtgc cgattgtgcg ccgtacgggg 1140
gggttggtcg atacggtctt ccaccacgat ccgcgtcatg ccgagggcaa tggctattgc 1200
ttcgatcgct acgagccgct ggacctctat acctgtctgg tgcgggcttg ggagagttac 1260
cagtaccagc cccaatggca aaagctacag caacggggta tggccgttga tctgagctgg 1320
aaacaatcgg cgatcgccta cgaacagctc tacgctgaag cgattgggct accgatcgat 1380
gtcttacagg aggcctag 1398

<210> SEQ ID NO 52
<211> LENGTH: 465
<212> TYPE: PRT
<213> ORGANISM: Synechococcus elongatus PCC 7942

<400> SEQUENCE: 52

Met Arg Ile Leu Phe Val Ala Ala Glu Cys Ala Pro Phe Ala Lys Val
1 5 10 15

Gly Gly Met Gly Asp Val Val Gly Ser Leu Pro Lys Val Leu Lys Ala
20 25 30

Leu Gly His Asp Val Arg Ile Phe Met Pro Tyr Tyr Gly Phe Leu Asn
35 40 45

Ser Lys Leu Asp Ile Pro Ala Glu Pro Ile Trp Trp Gly Tyr Ala Met
50 55 60

Phe Asn His Phe Ala Val Tyr Glu Thr Gln Leu Pro Gly Ser Asp Val
65 70 75 80

Pro Leu Tyr Leu Met Gly His Pro Ala Phe Asp Pro His Arg Ile Tyr
85 90 95

Ser Gly Glu Asp Glu Asp Trp Arg Phe Thr Phe Phe Ala Asn Gly Ala
100 105 110

Ala Glu Phe Ser Trp Asn Tyr Trp Lys Pro Gln Val Ile His Cys His
115 120 125

Asp Trp His Thr Gly Met Ile Pro Val Trp Met His Gln Ser Pro Asp
130 135 140

Ile Ser Thr Val Phe Thr Ile His Asn Leu Ala Tyr Gln Gly Pro Trp
145 150 155 160

Arg Trp Lys Leu Glu Lys Ile Thr Trp Cys Pro Trp Tyr Met Gln Gly
165 170 175

Asp Ser Thr Met Ala Ala Ala Leu Leu Tyr Ala Asp Arg Val Asn Thr
180 185 190

Val Ser Pro Thr Tyr Ala Gln Gln Ile Gln Thr Pro Thr Tyr Gly Glu
195 200 205

Lys Leu Glu Gly Leu Leu Ser Phe Ile Ser Gly Lys Leu Ser Gly Ile
210 215 220

```
Leu Asn Gly Ile Asp Val Asp Ser Tyr Asn Pro Ala Thr Asp Thr Arg
225                 230                 235                 240

Ile Val Ala Asn Tyr Asp Arg Asp Thr Leu Asp Lys Arg Leu Asn Asn
                245                 250                 255

Lys Leu Ala Leu Gln Lys Glu Met Gly Leu Glu Val Asn Pro Asp Arg
            260                 265                 270

Phe Leu Ile Gly Phe Val Ala Arg Leu Val Glu Gln Lys Gly Ile Asp
        275                 280                 285

Leu Leu Leu Gln Ile Leu Asp Arg Phe Leu Ser Tyr Ser Asp Ala Gln
    290                 295                 300

Phe Val Val Leu Gly Thr Gly Glu Arg Tyr Tyr Glu Thr Gln Leu Trp
305                 310                 315                 320

Glu Leu Ala Thr Arg Tyr Pro Gly Arg Met Ser Thr Tyr Leu Met Tyr
                325                 330                 335

Asp Glu Gly Leu Ser Arg Arg Ile Tyr Ala Gly Ser Asp Ala Phe Leu
            340                 345                 350

Val Pro Ser Arg Phe Glu Pro Cys Gly Ile Thr Gln Met Leu Ala Leu
        355                 360                 365

Arg Tyr Gly Ser Val Pro Ile Val Arg Arg Thr Gly Gly Leu Val Asp
    370                 375                 380

Thr Val Phe His His Asp Pro Arg His Ala Glu Gly Asn Gly Tyr Cys
385                 390                 395                 400

Phe Asp Arg Tyr Glu Pro Leu Asp Leu Tyr Thr Cys Leu Val Arg Ala
                405                 410                 415

Trp Glu Ser Tyr Gln Tyr Gln Pro Gln Trp Gln Lys Leu Gln Gln Arg
            420                 425                 430

Gly Met Ala Val Asp Leu Ser Trp Lys Gln Ser Ala Ile Ala Tyr Glu
        435                 440                 445

Gln Leu Tyr Ala Glu Ala Ile Gly Leu Pro Ile Asp Val Leu Gln Glu
    450                 455                 460

Ala
465


<210> SEQ ID NO 53
<211> LENGTH: 1542
<212> TYPE: DNA
<213> ORGANISM: Synechococcus sp. WH8102

<400> SEQUENCE: 53

atgcgcatcc tcttcgctgc cgcggaatgc gccccgatga tcaaggtcgg tggcatgggg      60

gatgtggtgg gatcgctgcc tccggctctg gccaagcttg gccacgacgt gcggctgatc     120

atgccgggct actccaagct ctggaccaag ctgacgatct cggacgaacc catctggcgc     180

gcccagacga tgggtacgga attcgcggtt tacgagacga agcatccagg caatgggatg     240

accatctacc tggtgggaca tccggtgttc gatcccgagc ggatctatgg cggtgaagat     300

gaggactggc gcttcacctt ctttgccagt gccgccgctg aattcgcctg gaatgtctgg     360

aagccgaatg ttcttcactg ccacgactgg cacaccggca tgattccggt ctggatgcac     420

caggacccgg agatcagcac ggtcttcacc atccacaacc tcaagtacca gggcccctgg     480

cgttggaagc tggatcgcat cacctggtgc ccctggtaca tgcagggaga tcacaccatg     540

gcggcggcac ttctgtacgc cgaccgggtc aacgccgtct cccccaccta cgccgaggaa     600

atccgtacgg cggagtacgg cgaaaagctg gatggtttgc tcaatttcgt ctccggcaag     660
```

-continued

```
ctgcgcggca tcctcaatgg cattgacctc gaggcctgga acccccagac cgatggggct     720

ctgccggcca ccttcagcgc cgacgacctc tccggtaaag cggtctgcaa gcgggtgttg     780

caggagcgca tgggtcttga ggtgcgtgac gacgcctttg tcctcggcat ggtcagccga     840

ctcgtcgatc agaagggcgt cgatctgctt ctgcaggtgg cggaccgttt gctcgcctac     900

accgacacgc agatcgtggt gctcggcacc ggtgaccgtg gcctggaatc cggcctgtgg     960

cagctggcct cccgccatgc cggccgttgc gccgtcttcc tcacctacga cgacgacctc    1020

tcccgactga tctatgccgg cagtgacgcc ttcctgatgc ccagtcgctt cgagccctgc    1080

ggcatcagcc agctgtacgc catgcgttac ggctccgttc ctgtggtgcg caaggtgggc    1140

ggcctggtgg acaccgttcc tccccacagt ccagctgatg ccagcgggac cggcttctgc    1200

ttcgatcgtt ttgagccggt cgacttctac accgcattgg tgcgtgcctg ggaggcctac    1260

cgccatcgcg acagctggca ggagttgcag aagcgcggca tgcagcagga ctacagctgg    1320

gaccgttcgg ccatcgatta cgacgtcatg taccgcgatg tctgcggtct gaaggaaccc    1380

accoctgatg ccgcgatggt ggaacagttc tcccagggac aggctgcgga tccctcccgc    1440

ccagaggatg atgcgatcaa tgctgctccc gaggcggtca ccgcgccgtc cggccccagc    1500

cgcaaccccc ttaatcgtct cttcggccgc agggccgact ga                       1542


<210> SEQ ID NO 54
<211> LENGTH: 513
<212> TYPE: PRT
<213> ORGANISM: Synechococcus sp. WH8102

<400> SEQUENCE: 54

Met Arg Ile Leu Phe Ala Ala Ala Glu Cys Ala Pro Met Ile Lys Val
1               5                   10                  15

Gly Gly Met Gly Asp Val Val Gly Ser Leu Pro Pro Ala Leu Ala Lys
            20                  25                  30

Leu Gly His Asp Val Arg Leu Ile Met Pro Gly Tyr Ser Lys Leu Trp
        35                  40                  45

Thr Lys Leu Thr Ile Ser Asp Glu Pro Ile Trp Arg Ala Gln Thr Met
    50                  55                  60

Gly Thr Glu Phe Ala Val Tyr Glu Thr Lys His Pro Gly Asn Gly Met
65                  70                  75                  80

Thr Ile Tyr Leu Val Gly His Pro Val Phe Asp Pro Glu Arg Ile Tyr
                85                  90                  95

Gly Gly Glu Asp Glu Asp Trp Arg Phe Thr Phe Phe Ala Ser Ala Ala
            100                 105                 110

Ala Glu Phe Ala Trp Asn Val Trp Lys Pro Asn Val Leu His Cys His
        115                 120                 125

Asp Trp His Thr Gly Met Ile Pro Val Trp Met His Gln Asp Pro Glu
    130                 135                 140

Ile Ser Thr Val Phe Thr Ile His Asn Leu Lys Tyr Gln Gly Pro Trp
145                 150                 155                 160

Arg Trp Lys Leu Asp Arg Ile Thr Trp Cys Pro Trp Tyr Met Gln Gly
                165                 170                 175

Asp His Thr Met Ala Ala Ala Leu Leu Tyr Ala Asp Arg Val Asn Ala
            180                 185                 190

Val Ser Pro Thr Tyr Ala Glu Glu Ile Arg Thr Ala Glu Tyr Gly Glu
        195                 200                 205

Lys Leu Asp Gly Leu Leu Asn Phe Val Ser Gly Lys Leu Arg Gly Ile
    210                 215                 220
```

```
Leu Asn Gly Ile Asp Leu Glu Ala Trp Asn Pro Gln Thr Asp Gly Ala
225                 230                 235                 240

Leu Pro Ala Thr Phe Ser Ala Asp Asp Leu Ser Gly Lys Ala Val Cys
                245                 250                 255

Lys Arg Val Leu Gln Glu Arg Met Gly Leu Glu Val Arg Asp Asp Ala
            260                 265                 270

Phe Val Leu Gly Met Val Ser Arg Leu Val Asp Gln Lys Gly Val Asp
        275                 280                 285

Leu Leu Leu Gln Val Ala Asp Arg Leu Leu Ala Tyr Thr Asp Thr Gln
    290                 295                 300

Ile Val Val Leu Gly Thr Gly Asp Arg Gly Leu Glu Ser Gly Leu Trp
305                 310                 315                 320

Gln Leu Ala Ser Arg His Ala Gly Arg Cys Ala Val Phe Leu Thr Tyr
                325                 330                 335

Asp Asp Asp Leu Ser Arg Leu Ile Tyr Ala Gly Ser Asp Ala Phe Leu
            340                 345                 350

Met Pro Ser Arg Phe Glu Pro Cys Gly Ile Ser Gln Leu Tyr Ala Met
        355                 360                 365

Arg Tyr Gly Ser Val Pro Val Val Arg Lys Val Gly Gly Leu Val Asp
    370                 375                 380

Thr Val Pro Pro His Ser Pro Ala Asp Ala Ser Gly Thr Gly Phe Cys
385                 390                 395                 400

Phe Asp Arg Phe Glu Pro Val Asp Phe Tyr Thr Ala Leu Val Arg Ala
                405                 410                 415

Trp Glu Ala Tyr Arg His Arg Asp Ser Trp Gln Glu Leu Gln Lys Arg
            420                 425                 430

Gly Met Gln Gln Asp Tyr Ser Trp Asp Arg Ser Ala Ile Asp Tyr Asp
        435                 440                 445

Val Met Tyr Arg Asp Val Cys Gly Leu Lys Glu Pro Thr Pro Asp Ala
    450                 455                 460

Ala Met Val Glu Gln Phe Ser Gln Gly Gln Ala Ala Asp Pro Ser Arg
465                 470                 475                 480

Pro Glu Asp Asp Ala Ile Asn Ala Ala Pro Glu Ala Val Thr Ala Pro
                485                 490                 495

Ser Gly Pro Ser Arg Asn Pro Leu Asn Arg Leu Phe Gly Arg Arg Ala
            500                 505                 510

Asp


<210> SEQ ID NO 55
<211> LENGTH: 1524
<212> TYPE: DNA
<213> ORGANISM: Synechococcus sp RCC 307

<400> SEQUENCE: 55

atgcgcatcc tctttgctgc ggccgaatgc gcaccgatgg tgaaagtcgg cggcatggga      60

gatgtggtgg gatctctgcc tccagccctc gctgagttgg gtcacgacgt gcgcgtgatc     120

atgcccggct acggcaagct ctggtcccag cttgatgtgc ccagcgagcc gatctggcgt     180

gcccaaacca tgggcaccga ttttgctgtc tatgagaccc gtcaccccaa gaccgggctc     240

acgatctatt tggtgggcca tccggttttt gatggtgagc gcatctatgg aggtgaagac     300

gaggactggc gcttcacctt cttcgctagc gccacctccg aatttgcctg gaacgcttgg     360

aagccccagg tgctgcattg ccatgactgg cacaccggca tgattccggt gtggatgcac     420
```

-continued

```
caagaccccg agatcagcac ggtcttcacc atccacaacc tcaaatatca aggtccctgg    480

cgctggaagc tcgagcgcat gacctggtgc ccctggtaca tgcagggcga ccacaccatg    540

gcggcagcct tgctgtatgc cgaccgcgtc aatgcggttt cacccaccta cgcccaagag    600

atccgcacgc cggaatacgg cgaacaactg gaggggttgc tgaactacat cagcggcaag    660

ctgcgaggca tcctcaatgg catcgatgtg gaggcttgga atcccgccac tgattcgcgg    720

attccggcca cctacagcac tgctgacctc agtggcaaag ccgtctgcaa gcgggctctg    780

caagagcgca tggggcttca ggtgaacccc gacacctttg tgatcggttt ggtgagccgt    840

ttggtggacc aaaaaggcgt cgacctgctg ctgcaggttg ccgaacgctt ccttgcctac    900

accgatacgc agatcgttgt gttgggcacc ggggatcgcc atttggaatc gggcctgtgg    960

caaatggcga gtcagcacag cggccgcttc gcttccttcc tcacctacga cgatgatctc   1020

tcccggctga tctacgccgg cagtgatgcc ttcttgatgc cctcgcgctt tgagccctgc   1080

ggcatcagcc agttgctctc gatgcgctac ggcaccatcc cggtggtgcg ccgcgtcggt   1140

ggactggtcg acaccgtgcc tccctatgtt cccgccaccc aagagggcaa tggcttctgc   1200

ttcgaccgct atgaagcgat cgacctttac accgccttgg tgcgcgcctg ggaggcctac   1260

cgccatcaag acagctggca gcaattgatg aagcgggtga tgcaggttga tttcagctgg   1320

gctcgttccg ccttggaata cgaccgcatg tatcgcgatg tttgcggaat gaaggagccc   1380

acgccggaag ccgatgcggt ggcggccttc tccattcccc agccgcctga acagcaggcc   1440

gcacgtgctg ccgctgaagc cgctgacccc aacccccaac ggcgctttaa tccccttgga   1500

ttgctgcgcc gaaacggcgg ttga                                          1524
```

<210> SEQ ID NO 56
<211> LENGTH: 507
<212> TYPE: PRT
<213> ORGANISM: Synechococcus sp RCC 307

<400> SEQUENCE: 56

```
Met Arg Ile Leu Phe Ala Ala Ala Glu Cys Ala Pro Met Val Lys Val
 1               5                  10                  15

Gly Gly Met Gly Asp Val Val Gly Ser Leu Pro Pro Ala Leu Ala Glu
            20                  25                  30

Leu Gly His Asp Val Arg Val Ile Met Pro Gly Tyr Gly Lys Leu Trp
        35                  40                  45

Ser Gln Leu Asp Val Pro Ser Glu Pro Ile Trp Arg Ala Gln Thr Met
    50                  55                  60

Gly Thr Asp Phe Ala Val Tyr Glu Thr Arg His Pro Lys Thr Gly Leu
65                  70                  75                  80

Thr Ile Tyr Leu Val Gly His Pro Val Phe Asp Gly Glu Arg Ile Tyr
                85                  90                  95

Gly Gly Glu Asp Glu Asp Trp Arg Phe Thr Phe Phe Ala Ser Ala Thr
            100                 105                 110

Ser Glu Phe Ala Trp Asn Ala Trp Lys Pro Gln Val Leu His Cys His
        115                 120                 125

Asp Trp His Thr Gly Met Ile Pro Val Trp Met His Gln Asp Pro Glu
    130                 135                 140

Ile Ser Thr Val Phe Thr Ile His Asn Leu Lys Tyr Gln Gly Pro Trp
145                 150                 155                 160

Arg Trp Lys Leu Glu Arg Met Thr Trp Cys Pro Trp Tyr Met Gln Gly
                165                 170                 175
```

-continued

```
Asp His Thr Met Ala Ala Ala Leu Leu Tyr Ala Asp Arg Val Asn Ala
            180                 185                 190

Val Ser Pro Thr Tyr Ala Gln Glu Ile Arg Thr Pro Glu Tyr Gly Glu
        195                 200                 205

Gln Leu Glu Gly Leu Leu Asn Tyr Ile Ser Gly Lys Leu Arg Gly Ile
    210                 215                 220

Leu Asn Gly Ile Asp Val Glu Ala Trp Asn Pro Ala Thr Asp Ser Arg
225                 230                 235                 240

Ile Pro Ala Thr Tyr Ser Thr Ala Asp Leu Ser Gly Lys Ala Val Cys
                245                 250                 255

Lys Arg Ala Leu Gln Glu Arg Met Gly Leu Gln Val Asn Pro Asp Thr
            260                 265                 270

Phe Val Ile Gly Leu Val Ser Arg Leu Val Asp Gln Lys Gly Val Asp
        275                 280                 285

Leu Leu Leu Gln Val Ala Glu Arg Phe Leu Ala Tyr Thr Asp Thr Gln
    290                 295                 300

Ile Val Val Leu Gly Thr Gly Asp Arg His Leu Glu Ser Gly Leu Trp
305                 310                 315                 320

Gln Met Ala Ser Gln His Ser Gly Arg Phe Ala Ser Phe Leu Thr Tyr
                325                 330                 335

Asp Asp Asp Leu Ser Arg Leu Ile Tyr Ala Gly Ser Asp Ala Phe Leu
            340                 345                 350

Met Pro Ser Arg Phe Glu Pro Cys Gly Ile Ser Gln Leu Leu Ser Met
        355                 360                 365

Arg Tyr Gly Thr Ile Pro Val Val Arg Arg Val Gly Gly Leu Val Asp
    370                 375                 380

Thr Val Pro Pro Tyr Val Pro Ala Thr Gln Glu Gly Asn Gly Phe Cys
385                 390                 395                 400

Phe Asp Arg Tyr Glu Ala Ile Asp Leu Tyr Thr Ala Leu Val Arg Ala
                405                 410                 415

Trp Glu Ala Tyr Arg His Gln Asp Ser Trp Gln Gln Leu Met Lys Arg
            420                 425                 430

Val Met Gln Val Asp Phe Ser Trp Ala Arg Ser Ala Leu Glu Tyr Asp
        435                 440                 445

Arg Met Tyr Arg Asp Val Cys Gly Met Lys Glu Pro Thr Pro Glu Ala
    450                 455                 460

Asp Ala Val Ala Ala Phe Ser Ile Pro Gln Pro Pro Glu Gln Gln Ala
465                 470                 475                 480

Ala Arg Ala Ala Ala Glu Ala Ala Asp Pro Asn Pro Gln Arg Arg Phe
                485                 490                 495

Asn Pro Leu Gly Leu Leu Arg Arg Asn Gly Gly
            500                 505
```

<210> SEQ ID NO 57
<211> LENGTH: 1437
<212> TYPE: DNA
<213> ORGANISM: Synechococcus sp. PCC 7002

<400> SEQUENCE: 57

```
atgcgtattt tgtttgtttc tgccgaggct gctcccatcg ctaaagctgg aggcatggga      60

gatgtggtgg gatcactgcc taaagtttta cggcagttag gacatgacgc gagaattttc     120

ttaccctatt acggctttct caacgacaaa ctcgacatcc ctgcagaacc cgtttggtgg     180

ggcagtgcga tgttcaatac ttttgccgtt tatgaaactg tgttgcccaa caccgatgtc     240
```

-continued

```
ccccttatc tgtttggcca tcccgccttt gatggacggc atatttatgg tgggcaggat    300

gaattttggc gctttacctt ttttgccaat ggggccgctg aatttatgtg gaaccactgg    360

aaaccccaga tcgcccactg tcacgactgg cacacgggca tgattccggt atggatgcac    420

caatcgccgg atatcagtac ggtgtttacg atccacaact tagcctacca agggccttgg    480

cggggtttcc tggagcgcaa tacttggtgt ccctggtata tggatggtga taacgtgatg    540

gcttcggcgc tgatgtttgc cgatcaggtg aacaccgtat ctcccaccta tgcccaacaa    600

atccaaacca aagtctatgg tgaaaaatta gagggtttgt tgtcttggat cagtggcaaa    660

agtcgcggca tcgtgaatgg tattgacgta gaactttata atccttctaa cgatcaagcc    720

ctggtgaagc aattttctac gactaatctt gaggatcggg ccgccaacaa agtgattatc    780

caagaagaaa cggggctaga ggtcaactcc aaggcttttt tgatggcgat ggtcacccgc    840

ttagtggaac aaaagggcat tgatctgctg ctaaatatcc tggagcagtt tatggcatac    900

actgacgccc agctcattat cctcggcact ggcgatcgcc actacgaaac ccaactctgg    960

cagactgcct accgctttaa ggggcggatg tccgtgcaac tgctctataa tgatgccctc   1020

tcccgccgga tttacgctgg atccgatgtc tttttgatgc cgtcacgctt tgagccctgt   1080

ggcattagtc aaatgatggc gatgcgctac ggttctgtac cgattgtgcg gcgcaccggg   1140

ggtttggtgg atacggtctc tttccatgat ccgattcacc aaaccgggac aggctttagt   1200

tttgaccgct acgaaccgct ggatatgtac acctgcatgg tgcgggcttg ggaaagtttc   1260

cgctacaaaa aagactgggc tgaactacaa agacgaggca tgagccatga ctttagttgg   1320

tacaaatctg ccggggaata tctcaagatg taccgccaaa gcattaaaga agctccggaa   1380

ttaacgaccg atgaagccga aaaaatcacc tatttagtga aaaaacacgc catttaa      1437
```

<210> SEQ ID NO 58
<211> LENGTH: 478
<212> TYPE: PRT
<213> ORGANISM: Synechococcus sp. PCC 7002

<400> SEQUENCE: 58

```
Met Arg Ile Leu Phe Val Ser Ala Glu Ala Ala Pro Ile Ala Lys Ala
 1               5                  10                  15

Gly Gly Met Gly Asp Val Val Gly Ser Leu Pro Lys Val Leu Arg Gln
            20                  25                  30

Leu Gly His Asp Ala Arg Ile Phe Leu Pro Tyr Tyr Gly Phe Leu Asn
        35                  40                  45

Asp Lys Leu Asp Ile Pro Ala Glu Pro Val Trp Trp Gly Ser Ala Met
    50                  55                  60

Phe Asn Thr Phe Ala Val Tyr Glu Thr Val Leu Pro Asn Thr Asp Val
65                  70                  75                  80

Pro Leu Tyr Leu Phe Gly His Pro Ala Phe Asp Gly Arg His Ile Tyr
                85                  90                  95

Gly Gly Gln Asp Glu Phe Trp Arg Phe Thr Phe Phe Ala Asn Gly Ala
            100                 105                 110

Ala Glu Phe Met Trp Asn His Trp Lys Pro Gln Ile Ala His Cys His
        115                 120                 125

Asp Trp His Thr Gly Met Ile Pro Val Trp Met His Gln Ser Pro Asp
    130                 135                 140

Ile Ser Thr Val Phe Thr Ile His Asn Leu Ala Tyr Gln Gly Pro Trp
145                 150                 155                 160

Arg Gly Phe Leu Glu Arg Asn Thr Trp Cys Pro Trp Tyr Met Asp Gly
```

```
                165                 170                 175

Asp Asn Val Met Ala Ser Ala Leu Met Phe Ala Asp Gln Val Asn Thr
            180                 185                 190

Val Ser Pro Thr Tyr Ala Gln Gln Ile Gln Thr Lys Val Tyr Gly Glu
        195                 200                 205

Lys Leu Glu Gly Leu Leu Ser Trp Ile Ser Gly Lys Ser Arg Gly Ile
    210                 215                 220

Val Asn Gly Ile Asp Val Glu Leu Tyr Asn Pro Ser Asn Asp Gln Ala
225                 230                 235                 240

Leu Val Lys Gln Phe Ser Thr Thr Asn Leu Glu Asp Arg Ala Ala Asn
                245                 250                 255

Lys Val Ile Ile Gln Glu Glu Thr Gly Leu Glu Val Asn Ser Lys Ala
            260                 265                 270

Phe Leu Met Ala Met Val Thr Arg Leu Val Glu Gln Lys Gly Ile Asp
        275                 280                 285

Leu Leu Leu Asn Ile Leu Glu Gln Phe Met Ala Tyr Thr Asp Ala Gln
    290                 295                 300

Leu Ile Ile Leu Gly Thr Gly Asp Arg His Tyr Glu Thr Gln Leu Trp
305                 310                 315                 320

Gln Thr Ala Tyr Arg Phe Lys Gly Arg Met Ser Val Gln Leu Leu Tyr
                325                 330                 335

Asn Asp Ala Leu Ser Arg Arg Ile Tyr Ala Gly Ser Asp Val Phe Leu
            340                 345                 350

Met Pro Ser Arg Phe Glu Pro Cys Gly Ile Ser Gln Met Met Ala Met
        355                 360                 365

Arg Tyr Gly Ser Val Pro Ile Val Arg Arg Thr Gly Gly Leu Val Asp
    370                 375                 380

Thr Val Ser Phe His Asp Pro Ile His Gln Thr Gly Thr Gly Phe Ser
385                 390                 395                 400

Phe Asp Arg Tyr Glu Pro Leu Asp Met Tyr Thr Cys Met Val Arg Ala
                405                 410                 415

Trp Glu Ser Phe Arg Tyr Lys Lys Asp Trp Ala Glu Leu Gln Arg Arg
            420                 425                 430

Gly Met Ser His Asp Phe Ser Trp Tyr Lys Ser Ala Gly Glu Tyr Leu
        435                 440                 445

Lys Met Tyr Arg Gln Ser Ile Lys Glu Ala Pro Glu Leu Thr Thr Asp
    450                 455                 460

Glu Ala Glu Lys Ile Thr Tyr Leu Val Lys Lys His Ala Ile
465                 470                 475
```

<210> SEQ ID NO 59
<211> LENGTH: 1320
<212> TYPE: DNA
<213> ORGANISM: Synechocystis sp. PCC 6803

<400> SEQUENCE: 59

```
gtgtgttgtt ggcaatcgag aggtctgctt gtgaaacgtg tcttagcgat tatcctgggc      60

ggtggggccg ggacccgcct ctatccttta accaaactca gagccaaacc cgcagttccc     120

ttggccggaa agtatcgcct catcgatatt cccgtcagta attgcatcaa ctcagaaatc     180

gttaaaattt acgtccttac ccagtttaat tccgcctccc ttaaccgtca catcagccgg     240

gcctataatt tttccggctt ccaagaagga tttgtggaag tcctcgccgc ccaacaaacc     300

aaagataatc ctgattggtt tcagggcact gctgatgcgg tacggcaata cctctggttg     360
```

-continued

```
tttagggaat gggacgtaga tgaatatctt attctgtccg gcgaccatct ctaccgcatg    420

gattacgccc aatttgttaa aagacaccgg gaaaccaatg ccgacataac cctttccgtt    480

gtgcccgtgg atgacagaaa ggcacccgag ctgggcttaa tgaaaatcga cgcccagggc    540

agaattactg acttttctga aaagccccag ggggaagccc tccgggccat gcaggtggac    600

accagcgttt tgggcctaag tgcggagaag gctaagctta atccttacat tgcctccatg    660

ggcatttacg ttttcaagaa ggaagtattg cacaacctcc tggaaaaata tgaaggggca    720

acggactttg gcaaagaaat cattcctgat tcagccagtg atcacaatct gcaagcctat    780

ctctttgatg actattggga agacattggt accattgaag ccttctatga ggctaattta    840

gccctgacca aacaacctag tcccgacttt agtttttata acgaaaaagc cccccatctat    900

accaggggtc gttatcttcc ccccaccaaa atgttgaatt ccaccgtgac ggaatccatg    960

atcggggaag gttgcatgat taagcaatgt cgcatccacc actcagtttt aggcattcgc   1020

agtcgcattg aatctgattg caccattgag gatactttgg tgatgggcaa tgatttctac   1080

gaatcttcat cagaacgaga caccctcaaa gcccgggggg aaattgccgc tggcataggt   1140

tccggcacca ctatccgccg agccatcatc gacaaaaatg cccgcatcgg caaaaacgtc   1200

atgattgtca acaaggaaaa tgtccaggag gctaaccggg aagagttagg tttttacatc   1260

cgcaatggca tcgtagtagt gattaaaaat gtcacgatcg ccgacggcac ggtaatctag   1320
```

<210> SEQ ID NO 60
<211> LENGTH: 439
<212> TYPE: PRT
<213> ORGANISM: Synechocystis sp. PCC 6803

<400> SEQUENCE: 60

```
Met Cys Cys Trp Gln Ser Arg Gly Leu Leu Val Lys Arg Val Leu Ala
1               5                   10                  15

Ile Ile Leu Gly Gly Gly Ala Gly Thr Arg Leu Tyr Pro Leu Thr Lys
            20                  25                  30

Leu Arg Ala Lys Pro Ala Val Pro Leu Ala Gly Lys Tyr Arg Leu Ile
        35                  40                  45

Asp Ile Pro Val Ser Asn Cys Ile Asn Ser Glu Ile Val Lys Ile Tyr
    50                  55                  60

Val Leu Thr Gln Phe Asn Ser Ala Ser Leu Asn Arg His Ile Ser Arg
65                  70                  75                  80

Ala Tyr Asn Phe Ser Gly Phe Gln Glu Gly Phe Val Glu Val Leu Ala
                85                  90                  95

Ala Gln Gln Thr Lys Asp Asn Pro Asp Trp Phe Gln Gly Thr Ala Asp
            100                 105                 110

Ala Val Arg Gln Tyr Leu Trp Leu Phe Arg Glu Trp Asp Val Asp Glu
        115                 120                 125

Tyr Leu Ile Leu Ser Gly Asp His Leu Tyr Arg Met Asp Tyr Ala Gln
    130                 135                 140

Phe Val Lys Arg His Arg Glu Thr Asn Ala Asp Ile Thr Leu Ser Val
145                 150                 155                 160

Val Pro Val Asp Asp Arg Lys Ala Pro Glu Leu Gly Leu Met Lys Ile
                165                 170                 175

Asp Ala Gln Gly Arg Ile Thr Asp Phe Ser Glu Lys Pro Gln Gly Glu
            180                 185                 190

Ala Leu Arg Ala Met Gln Val Asp Thr Ser Val Leu Gly Leu Ser Ala
        195                 200                 205
```

-continued

```
Glu Lys Ala Lys Leu Asn Pro Tyr Ile Ala Ser Met Gly Ile Tyr Val
    210                 215                 220

Phe Lys Lys Glu Val Leu His Asn Leu Leu Glu Lys Tyr Glu Gly Ala
225                 230                 235                 240

Thr Asp Phe Gly Lys Glu Ile Ile Pro Asp Ser Ala Ser Asp His Asn
                245                 250                 255

Leu Gln Ala Tyr Leu Phe Asp Asp Tyr Trp Glu Asp Ile Gly Thr Ile
            260                 265                 270

Glu Ala Phe Tyr Glu Ala Asn Leu Ala Leu Thr Lys Gln Pro Ser Pro
        275                 280                 285

Asp Phe Ser Phe Tyr Asn Glu Lys Ala Pro Ile Tyr Thr Arg Gly Arg
    290                 295                 300

Tyr Leu Pro Pro Thr Lys Met Leu Asn Ser Thr Val Thr Glu Ser Met
305                 310                 315                 320

Ile Gly Glu Gly Cys Met Ile Lys Gln Cys Arg Ile His His Ser Val
                325                 330                 335

Leu Gly Ile Arg Ser Arg Ile Glu Ser Asp Cys Thr Ile Glu Asp Thr
            340                 345                 350

Leu Val Met Gly Asn Asp Phe Tyr Glu Ser Ser Ser Glu Arg Asp Thr
        355                 360                 365

Leu Lys Ala Arg Gly Glu Ile Ala Ala Gly Ile Gly Ser Gly Thr Thr
    370                 375                 380

Ile Arg Arg Ala Ile Ile Asp Lys Asn Ala Arg Ile Gly Lys Asn Val
385                 390                 395                 400

Met Ile Val Asn Lys Glu Asn Val Gln Glu Ala Asn Arg Glu Glu Leu
                405                 410                 415

Gly Phe Tyr Ile Arg Asn Gly Ile Val Val Val Ile Lys Asn Val Thr
            420                 425                 430

Ile Ala Asp Gly Thr Val Ile
        435
```

<210> SEQ ID NO 61
<211> LENGTH: 1290
<212> TYPE: DNA
<213> ORGANISM: Nostoc sp. PCC 7120

<400> SEQUENCE: 61

```
gtgaaaaaag tcttagcaat tattcttggt ggtggtgcgg gtactcgcct ttacccacta      60

accaaactcc gcgctaaacc ggcagtacca gtggcaggga aataccgcct aatagatatc     120

cctgtcagta actgcattaa ttcggaaatt tttaaaatct acgtattaac acaatttaac     180

tcagcttctc tcaatcgcca cattgcccgt acctacaact ttagtggttt tagcgagggt     240

tttgtggaag tgctggccgc ccagcagaca ccagagaacc ctaactggtt ccaaggtaca     300

gccgatgctg tacgtcagta tctctggatg ttacaagagt gggacgtaga tgaatttttg     360

atcctgtcgg gggatcacct gtaccggatg gactatcgcc tatttatcca gcgccatcga     420

gaaaccaatg cggatatcac actttccgta attcccattg atgatcgccg cgcctcggat     480

tttggtttaa tgaaaatcga taactctgga cgagtcattg atttcagtga aaaacccaag     540

ggcgaagcct taaccaaaat gcgtgttgat accacggttt taggcttgac accagaacag     600

gcggcatcac agccttacat tgcctcgatg ggatttacg tatttaaaaa agacgttttg      660

atcaagctgt tgaaggaagc tttagaacgt actgatttcg gcaaagaaat tattcctgat     720

gccgccaaag atcacaacgt tcaagcttac ctattcgatg actactggga agatattggg     780
```

-continued

```
acaatcgaag ctttttataa cgccaattta gcgttaactc agcagcccat gccgcccttt    840

agcttctacg atgaagaagc acctatttat acccgcgctc gttacttacc acccacaaaa    900

ctattagatt gccacgttac agaatcaatc attggcgaag gctgtattct gaaaaactgt    960

cgcattcaac actcagtatt gggagtgcga tcgcgtattg aaactggctg catgatcgaa   1020

gaatctttac tcatgggtgc cgacttctac caagcttcag tggaacgcca gtgcagcatc   1080

gataaaggag acatccctgt aggcatcggt ccagatacaa tcattcgccg tgccatcatc   1140

gataaaaatg cccgcatcgg tcacgatgtc aaaattatca ataaagacaa cgtgcaagaa   1200

gccgaccgcg aaagtcaagg atttacatc cgcagtggca ttgtcgtcgt cctcaaaaat   1260

gccgttatta cagatggcac aatcatttag                                    1290


<210> SEQ ID NO 62
<211> LENGTH: 429
<212> TYPE: PRT
<213> ORGANISM: Nostoc sp. PCC 7120

<400> SEQUENCE: 62

Met Lys Lys Val Leu Ala Ile Ile Leu Gly Gly Gly Ala Gly Thr Arg
 1               5                  10                  15

Leu Tyr Pro Leu Thr Lys Leu Arg Ala Lys Pro Ala Val Pro Val Ala
            20                  25                  30

Gly Lys Tyr Arg Leu Ile Asp Ile Pro Val Ser Asn Cys Ile Asn Ser
        35                  40                  45

Glu Ile Phe Lys Ile Tyr Val Leu Thr Gln Phe Asn Ser Ala Ser Leu
    50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
        115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ala Leu Glu Arg Thr Asp Phe Gly Lys Glu Ile Ile Pro Asp
225                 230                 235                 240

Ala Ala Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285
```

```
Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Met Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
        355                 360                 365

Ile Gly Pro Asp Thr Ile Ile Arg Arg Ala Ile Ile Asp Lys Asn Ala
    370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
            420                 425
```

<210> SEQ ID NO 63
<211> LENGTH: 1290
<212> TYPE: DNA
<213> ORGANISM: Anabaena variabilis

<400> SEQUENCE: 63

```
gtgaaaaaag tcttagcaat tattcttggt ggtggtgcgg gtactcgcct ttacccacta     60

accaaactcc gcgctaaacc ggcagtacca gtggcaggga aataccgcct aatagatatc    120

cctgtcagta actgcattaa ttcggaaatt tttaaaatct acgtattaac acaatttaac    180

tcagcttctc tcaatcgcca cattgcccgt acctacaact ttagtggttt tagcgagggt    240

tttgtggaag tgctggccgc ccagcagaca ccagagaacc ctaactggtt ccaaggtaca    300

gccgatgctg tacgtcagta tctctggatg ttacaagagt gggacgtaga tgaatttttg    360

atcctgtcag gagatcacct gtaccggatg gattatcgcc tatttatcca gcgccatcga    420

gaaaccaatg cggatatcac actttccgta attcccattg acgatcgccg cgcctcggat    480

tttggtttaa tgaagatcga taactctgga cgagtcatcg attttagcga aaaacccaaa    540

ggcgaagcct taaccaaaat gcgtgttgat accaccgttt taggcttgac accagaacag    600

gcagcatcac agccttacat cgcctcgatg ggatttacgg tatttaaaaa agatgttttg    660

atcaaactgt tgaaggaatc tttagaacgt actgatttcg gcaaagaaat tattcctgat    720

gcctccaaag atcacaacgt tcaagcttac ttattcgatg actactggga agatattggg    780

acaatcgaag ctttttataa tgctaattta gcattgactc agcagcccat gccgcccttt    840

agcttctacg acgaagaagc accaatttat acccgcgcac gttacttacc acccacaaaa    900

ctattagatt gccacgttac agaatcaatc attggcgaag gctgtattct gaaaaactgt    960

cgcattcaac actcagtatt gggagtgcga tcgcgtattg aaaccggctg cgtcatcgaa   1020

gaatctttac tcatgggtgc cgacttctac caagcttcag tggaacgcca gtgcagcatt   1080

gacaaaggag acatccccgt aggcatcggc ccagatacca ttattcgccg tgccatcatc   1140

gataaaaatg cccgcatcgg tcacgatgtc aaaattatca ataaagacaa cgtgcaggaa   1200

gccgaccgcg aaagtcaagg attttacatc cgcagtggca ttgtcgtcgt tctcaaaaat   1260

gccgtcatta ccgatggcac aataatttag                                    1290
```

<210> SEQ ID NO 64
<211> LENGTH: 429
<212> TYPE: PRT
<213> ORGANISM: Anabaena variabilis

<400> SEQUENCE: 64

```
Met Lys Lys Val Leu Ala Ile Ile Leu Gly Gly Gly Ala Gly Thr Arg
 1               5                  10                  15

Leu Tyr Pro Leu Thr Lys Leu Arg Ala Lys Pro Ala Val Pro Val Ala
            20                  25                  30

Gly Lys Tyr Arg Leu Ile Asp Ile Pro Val Ser Asn Cys Ile Asn Ser
        35                  40                  45

Glu Ile Phe Lys Ile Tyr Val Leu Thr Gln Phe Asn Ser Ala Ser Leu
    50                  55                  60

Asn Arg His Ile Ala Arg Thr Tyr Asn Phe Ser Gly Phe Ser Glu Gly
65                  70                  75                  80

Phe Val Glu Val Leu Ala Ala Gln Gln Thr Pro Glu Asn Pro Asn Trp
                85                  90                  95

Phe Gln Gly Thr Ala Asp Ala Val Arg Gln Tyr Leu Trp Met Leu Gln
            100                 105                 110

Glu Trp Asp Val Asp Glu Phe Leu Ile Leu Ser Gly Asp His Leu Tyr
        115                 120                 125

Arg Met Asp Tyr Arg Leu Phe Ile Gln Arg His Arg Glu Thr Asn Ala
    130                 135                 140

Asp Ile Thr Leu Ser Val Ile Pro Ile Asp Asp Arg Arg Ala Ser Asp
145                 150                 155                 160

Phe Gly Leu Met Lys Ile Asp Asn Ser Gly Arg Val Ile Asp Phe Ser
                165                 170                 175

Glu Lys Pro Lys Gly Glu Ala Leu Thr Lys Met Arg Val Asp Thr Thr
            180                 185                 190

Val Leu Gly Leu Thr Pro Glu Gln Ala Ala Ser Gln Pro Tyr Ile Ala
        195                 200                 205

Ser Met Gly Ile Tyr Val Phe Lys Lys Asp Val Leu Ile Lys Leu Leu
    210                 215                 220

Lys Glu Ser Leu Glu Arg Thr Asp Phe Gly Lys Glu Ile Ile Pro Asp
225                 230                 235                 240

Ala Ser Lys Asp His Asn Val Gln Ala Tyr Leu Phe Asp Asp Tyr Trp
                245                 250                 255

Glu Asp Ile Gly Thr Ile Glu Ala Phe Tyr Asn Ala Asn Leu Ala Leu
            260                 265                 270

Thr Gln Gln Pro Met Pro Pro Phe Ser Phe Tyr Asp Glu Glu Ala Pro
        275                 280                 285

Ile Tyr Thr Arg Ala Arg Tyr Leu Pro Pro Thr Lys Leu Leu Asp Cys
    290                 295                 300

His Val Thr Glu Ser Ile Ile Gly Glu Gly Cys Ile Leu Lys Asn Cys
305                 310                 315                 320

Arg Ile Gln His Ser Val Leu Gly Val Arg Ser Arg Ile Glu Thr Gly
                325                 330                 335

Cys Val Ile Glu Glu Ser Leu Leu Met Gly Ala Asp Phe Tyr Gln Ala
            340                 345                 350

Ser Val Glu Arg Gln Cys Ser Ile Asp Lys Gly Asp Ile Pro Val Gly
        355                 360                 365

Ile Gly Pro Asp Thr Ile Ile Arg Arg Ala Ile Ile Asp Lys Asn Ala
```

-continued

```
            370                 375                 380

Arg Ile Gly His Asp Val Lys Ile Ile Asn Lys Asp Asn Val Gln Glu
385                 390                 395                 400

Ala Asp Arg Glu Ser Gln Gly Phe Tyr Ile Arg Ser Gly Ile Val Val
                405                 410                 415

Val Leu Lys Asn Ala Val Ile Thr Asp Gly Thr Ile Ile
            420                 425


<210> SEQ ID NO 65
<211> LENGTH: 1287
<212> TYPE: DNA
<213> ORGANISM: Trichodesmium erythraeum IMS 101

<400> SEQUENCE: 65

gtgaaaaacg tactaagtat aattctaggc ggtggcgcag gtacccgttt atatccctta      60

acaaaactac gggccaagcc tgcagtgccc ctagcaggaa aatatcgttt aatagatatt     120

cctataagta attgcataaa ctcagaaatc cagaaaattt atgttttgac ccaatttaac     180

tcagcttctc taaaccgcca tatcactcgt acctataact tctcaggttt cagtgatggt     240

tttgtcgaag ttctagcagc tcaacaaact aaagataatc cagagtggtt tcaaggaaca     300

gcagatgctg tccgtaaata tatatggtta ttcaaagagt gggatattga ttattatcta     360

attctctctg gagaccatct ctaccgtatg gactaccgag actttgtcca acgccatatc     420

gacaccaagg cagatatcac cctttctgtc ttgcctattg atgaagcacg ggcctccgag     480

tttggcgtca tgaaaattga taactcaggt cgaattgttg aatttagtga aaaaccgaaa     540

ggtaatgccc ttaaagctat ggcagttgat acttctattt taggagtcag tccagaaata     600

gctacaaaac aaccttatat tgcttctatg ggaatttatg tatttaataa agatgcaatg     660

atcaaactta tagaagattc agaggataca gattttggta aggaaatttt acccaagtcg     720

gctcaatctt ataatcttca agcctaccca ttccaaggtt actgggaaga catcggaacc     780

atcaaatcat tttatgaagc taatttggct ttgactcaac agcctcagcc accctttagc     840

ttttatgatg aacaagcccc tatctatacc cgctctcgtt atttacctcc gagcaaactt     900

ttggactgtg agattacaga gtcaattgtg ggagaaggtt gtattcttaa aaaatgtcgg     960

attgaccatt gtgtcttagg agtgcgatcg cgtatagaag ctaattgtat aattcaagat    1020

tctctgctaa tgggttcaga tttctatgaa tctcctacag aacgtcgata tggcctaaaa    1080

aaaggttctg tacctttggg tattggtgct gaaacgaaaa ttcgtggagc aattattgac    1140

aaaaatgccc gcattggttg taatgtccaa ataatcaata aggacaatgt agaagaagcc    1200

caacgtgagg aggaagggtt tatcattcgc agtggtattg ttgttgtttt gaaaaatgct    1260

actattcccg atggtacagt gatttag                                        1287


<210> SEQ ID NO 66
<211> LENGTH: 428
<212> TYPE: PRT
<213> ORGANISM: Trichodesmium erythraeum IMS 101

<400> SEQUENCE: 66

Met Lys Asn Val Leu Ser Ile Ile Leu Gly Gly Gly Ala Gly Thr Arg
 1               5                  10                  15

Leu Tyr Pro Leu Thr Lys Leu Arg Ala Lys Pro Ala Val Pro Leu Ala
            20                  25                  30

Gly Lys Tyr Arg Leu Ile Asp Ile Pro Ile Ser Asn Cys Ile Asn Ser
        35                  40                  45
```

```
Glu Ile Gln Lys Ile Tyr Val Leu Thr Gln Phe Asn Ser Ala Ser Leu
    50                  55                  60

Asn Arg His Ile Thr Arg Thr Tyr Asn Phe Ser Gly Phe Ser Asp Gly
65                  70                  75                  80

Phe Val Glu Val Leu Ala Ala Gln Gln Thr Lys Asp Asn Pro Glu Trp
                85                  90                  95

Phe Gln Gly Thr Ala Asp Ala Val Arg Lys Tyr Ile Trp Leu Phe Lys
            100                 105                 110

Glu Trp Asp Ile Asp Tyr Tyr Leu Ile Leu Ser Gly Asp His Leu Tyr
        115                 120                 125

Arg Met Asp Tyr Arg Asp Phe Val Gln Arg His Ile Asp Thr Lys Ala
    130                 135                 140

Asp Ile Thr Leu Ser Val Leu Pro Ile Asp Glu Ala Arg Ala Ser Glu
145                 150                 155                 160

Phe Gly Val Met Lys Ile Asp Asn Ser Gly Arg Ile Val Glu Phe Ser
                165                 170                 175

Glu Lys Pro Lys Gly Asn Ala Leu Lys Ala Met Ala Val Asp Thr Ser
            180                 185                 190

Ile Leu Gly Val Ser Pro Glu Ile Ala Thr Lys Gln Pro Tyr Ile Ala
        195                 200                 205

Ser Met Gly Ile Tyr Val Phe Asn Lys Asp Ala Met Ile Lys Leu Ile
    210                 215                 220

Glu Asp Ser Glu Asp Thr Asp Phe Gly Lys Glu Ile Leu Pro Lys Ser
225                 230                 235                 240

Ala Gln Ser Tyr Asn Leu Gln Ala Tyr Pro Phe Gln Gly Tyr Trp Glu
                245                 250                 255

Asp Ile Gly Thr Ile Lys Ser Phe Tyr Glu Ala Asn Leu Ala Leu Thr
            260                 265                 270

Gln Gln Pro Gln Pro Pro Phe Ser Phe Tyr Asp Glu Gln Ala Pro Ile
        275                 280                 285

Tyr Thr Arg Ser Arg Tyr Leu Pro Pro Ser Lys Leu Leu Asp Cys Glu
    290                 295                 300

Ile Thr Glu Ser Ile Val Gly Glu Gly Cys Ile Leu Lys Lys Cys Arg
305                 310                 315                 320

Ile Asp His Cys Val Leu Gly Val Arg Ser Arg Ile Glu Ala Asn Cys
                325                 330                 335

Ile Ile Gln Asp Ser Leu Leu Met Gly Ser Asp Phe Tyr Glu Ser Pro
            340                 345                 350

Thr Glu Arg Arg Tyr Gly Leu Lys Lys Gly Ser Val Pro Leu Gly Ile
        355                 360                 365

Gly Ala Glu Thr Lys Ile Arg Gly Ala Ile Ile Asp Lys Asn Ala Arg
    370                 375                 380

Ile Gly Cys Asn Val Gln Ile Ile Asn Lys Asp Asn Val Glu Glu Ala
385                 390                 395                 400

Gln Arg Glu Glu Glu Gly Phe Ile Ile Arg Ser Gly Ile Val Val Val
                405                 410                 415

Leu Lys Asn Ala Thr Ile Pro Asp Gly Thr Val Ile
            420                 425
```

<210> SEQ ID NO 67
<211> LENGTH: 1293
<212> TYPE: DNA
<213> ORGANISM: Synechococcus elongatus PCC 7942

-continued

<400> SEQUENCE: 67

```
gtgaaaaacg tgctggcgat cattctcggt ggaggcgcag gcagtcgtct ctatccacta     60
accaaacagc gcgccaaacc agcggtcccc ctggcgggca aataccgctt gatcgatatt    120
cccgtcagca attgcatcaa cgctgacatc aacaaaatct atgtgctgac gcagtttaac    180
tctgcctcgc tcaaccgcca cctcagtcag acctacaacc tctccagcgg ctttggcaat    240
ggctttgttg aggtgctagc agctcagatt acgccggaga accccaactg gttccaaggc    300
accgccgatg cggttcgcca gtatctctgg ctaatcaaag agtgggatgt ggatgagtac    360
ctgatcctgt cgggggatca tctctaccgc atggactata gccagttcat tcagcggcac    420
cgagacacca atgccgacat cacactctcg gtcttgccga tcgatgaaaa gcgcgcctct    480
gattttggcc tgatgaagct agatggcagc ggccgggtgg tcgagttcag cgaaaagccc    540
aaaggggatg aactcagggc gatgcaagtc gataccacga tcctcgggct tgaccctgtc    600
gctgctgctg cccagccctt cattgcctcg atgggcatct acgtcttcaa gcgggatgtt    660
ctgatcgatt tgctcagcca tcatcccgag caaaccgact ttggcaagga agtgattccc    720
gctgcagcca cccgctacaa cacccaagcc tttctgttca acgactactg ggaagacatc    780
ggcacgatcg cctcattcta cgaggccaat ctggcgctga ctcagcaacc tagcccaccc    840
ttcagcttct acgacgagca ggcgccgatt tacacccgcg ctcgctacct gccgccaacc    900
aagctgctcg attgccaggt gacccagtcg atcattggcg agggctgcat tctcaagcaa    960
tgcaccgttc agaattccgt cttagggatt cgctcccgca ttgaggccga ctgcgtgatc   1020
caggacgcct tgttgatggg cgctgacttc tacgaaacct cggagctacg gcaccagaat   1080
cgggccaatg gcaaagtgcc gatgggaatc ggcagtggca gcaccatccg tcgcgccatc   1140
gtcgacaaaa atgcccacat tggccagaac gttcagatcg tcaacaaaga ccatgtggaa   1200
gaggccgatc gcgaagatct gggctttatg atccgcagcg gcattgtcgt tgtggtcaaa   1260
ggggcggtta ttcccgacaa cacggtgatc taa                                1293
```

<210> SEQ ID NO 68
<211> LENGTH: 430
<212> TYPE: PRT
<213> ORGANISM: Synechococcus elongatus PCC 7942

<400> SEQUENCE: 68

```
Met Lys Asn Val Leu Ala Ile Ile Leu Gly Gly Gly Ala Gly Ser Arg
1               5                   10                  15

Leu Tyr Pro Leu Thr Lys Gln Arg Ala Lys Pro Ala Val Pro Leu Ala
            20                  25                  30

Gly Lys Tyr Arg Leu Ile Asp Ile Pro Val Ser Asn Cys Ile Asn Ala
        35                  40                  45

Asp Ile Asn Lys Ile Tyr Val Leu Thr Gln Phe Asn Ser Ala Ser Leu
    50                  55                  60

Asn Arg His Leu Ser Gln Thr Tyr Asn Leu Ser Ser Gly Phe Gly Asn
65                  70                  75                  80

Gly Phe Val Glu Val Leu Ala Ala Gln Ile Thr Pro Glu Asn Pro Asn
                85                  90                  95

Trp Phe Gln Gly Thr Ala Asp Ala Val Arg Gln Tyr Leu Trp Leu Ile
            100                 105                 110

Lys Glu Trp Asp Val Asp Glu Tyr Leu Ile Leu Ser Gly Asp His Leu
        115                 120                 125

Tyr Arg Met Asp Tyr Ser Gln Phe Ile Gln Arg His Arg Asp Thr Asn
```

```
    130                 135                 140

Ala Asp Ile Thr Leu Ser Val Leu Pro Ile Asp Glu Lys Arg Ala Ser
145                 150                 155                 160

Asp Phe Gly Leu Met Lys Leu Asp Gly Ser Gly Arg Val Val Glu Phe
                165                 170                 175

Ser Glu Lys Pro Lys Gly Asp Glu Leu Arg Ala Met Gln Val Asp Thr
            180                 185                 190

Thr Ile Leu Gly Leu Asp Pro Val Ala Ala Ala Ala Gln Pro Phe Ile
        195                 200                 205

Ala Ser Met Gly Ile Tyr Val Phe Lys Arg Asp Val Leu Ile Asp Leu
    210                 215                 220

Leu Ser His His Pro Glu Gln Thr Asp Phe Gly Lys Glu Val Ile Pro
225                 230                 235                 240

Ala Ala Ala Thr Arg Tyr Asn Thr Gln Ala Phe Leu Phe Asn Asp Tyr
                245                 250                 255

Trp Glu Asp Ile Gly Thr Ile Ala Ser Phe Tyr Glu Ala Asn Leu Ala
            260                 265                 270

Leu Thr Gln Gln Pro Ser Pro Pro Phe Ser Phe Tyr Asp Glu Gln Ala
        275                 280                 285

Pro Ile Tyr Thr Arg Ala Arg Tyr Leu Pro Pro Thr Lys Leu Leu Asp
    290                 295                 300

Cys Gln Val Thr Gln Ser Ile Ile Gly Glu Gly Cys Ile Leu Lys Gln
305                 310                 315                 320

Cys Thr Val Gln Asn Ser Val Leu Gly Ile Arg Ser Arg Ile Glu Ala
                325                 330                 335

Asp Cys Val Ile Gln Asp Ala Leu Leu Met Gly Ala Asp Phe Tyr Glu
            340                 345                 350

Thr Ser Glu Leu Arg His Gln Asn Arg Ala Asn Gly Lys Val Pro Met
        355                 360                 365

Gly Ile Gly Ser Gly Ser Thr Ile Arg Arg Ala Ile Val Asp Lys Asn
    370                 375                 380

Ala His Ile Gly Gln Asn Val Gln Ile Val Asn Lys Asp His Val Glu
385                 390                 395                 400

Glu Ala Asp Arg Glu Asp Leu Gly Phe Met Ile Arg Ser Gly Ile Val
                405                 410                 415

Val Val Val Lys Gly Ala Val Ile Pro Asp Asn Thr Val Ile
            420                 425                 430


<210> SEQ ID NO 69
<211> LENGTH: 1296
<212> TYPE: DNA
<213> ORGANISM: Synechococcus sp. WH8102

<400> SEQUENCE: 69

atgaagcggg ttttggccat cattctcggc ggcggtgccg ggactcgtct ctacccgctc      60

accaagatgc gcgccaagcc ggccgtcccc ttggccggta agtatcgact gattgatatc     120

cccatcagca actgcatcaa ctcgaacatc aacaagatgt acgtgatgac gcagttcaac     180

agtgcgtctc tcaatcgtca cctcagccag acgttcaacc tgagcgcatc cttcggtcag     240

ggattcgtcg aggtgcttgc tgcccagcag acgcctgaca gtccatcctg gtttgaaggc     300

actgccgacg ctgtgcggaa gtaccagtgg ctgttccagg aatgggatgt cgatgaatac     360

ctgatcctgt ccggtgacca gctgtaccgg atggattaca gcctgttcgt tgaacatcac     420

cgcagcactg gtgctgacct caccgttgca gcccttcctg tggacccgaa acaggccgag     480
```

-continued

```
gcgttcggct tgatgcgcac ggatggtgac ggagacatca aggagttccg cgaaaagccc    540

aagggtgatt ctttgcttga gatggcggtt gacaccagcc gatttggact cagtgcgaat    600

tcggccaagg agcgtcccta cctggcgtcg atggggattt atgtcttcag cagagacact    660

ctgttcgacc tgctcgattc caatcctggt tataaggact tcggcaagga agtcattcct    720

gaggccctca agcgtggcga caagctgaag agctatgtct ttgacgatta ttgggaagat    780

atcggaacga tcggagcgtt ctacgaggcc aacctggcgc tcacccagca acccacaccc    840

cccttcagct tctacgacga gaagttcccg atctacactc gtccccgcta tttacccccg    900

agcaaactgg ttgatgctca gatcaccaat tcgatcgttg gcgaaggctc aattttgaag    960

tcatgcagca ttcatcactg cgttttgggt gttcgcagtc gcattgaaac cgatgtggtg   1020

ctgcaagaca ccttggtgat gggcgctgac ttctttgaat ccagtgatga gcgtgccgtg   1080

cttcgcgagc gtggtggtat tccggtcggg gtgggccaag gtacgactgt gaagcgcgcc   1140

atcctcgata aaaacgctcg catcggatcc aacgtcacca tcgtcaacaa ggatcacgtc   1200

gaggaagctg atcgttccga tcagggcttc tatattcgta atggcattgt tgttgttgtc   1260

aagaacgcca ccatccagga cggaactgtg atctga                             1296


<210> SEQ ID NO 70
<211> LENGTH: 431
<212> TYPE: PRT
<213> ORGANISM: Synechococcus sp. WH8102

<400> SEQUENCE: 70

Met Lys Arg Val Leu Ala Ile Ile Leu Gly Gly Gly Ala Gly Thr Arg
1               5                   10                  15

Leu Tyr Pro Leu Thr Lys Met Arg Ala Lys Pro Ala Val Pro Leu Ala
            20                  25                  30

Gly Lys Tyr Arg Leu Ile Asp Ile Pro Ile Ser Asn Cys Ile Asn Ser
        35                  40                  45

Asn Ile Asn Lys Met Tyr Val Met Thr Gln Phe Asn Ser Ala Ser Leu
    50                  55                  60

Asn Arg His Leu Ser Gln Thr Phe Asn Leu Ser Ala Ser Phe Gly Gln
65                  70                  75                  80

Gly Phe Val Glu Val Leu Ala Ala Gln Gln Thr Pro Asp Ser Pro Ser
                85                  90                  95

Trp Phe Glu Gly Thr Ala Asp Ala Val Arg Lys Tyr Gln Trp Leu Phe
            100                 105                 110

Gln Glu Trp Asp Val Asp Glu Tyr Leu Ile Leu Ser Gly Asp Gln Leu
        115                 120                 125

Tyr Arg Met Asp Tyr Ser Leu Phe Val Glu His His Arg Ser Thr Gly
    130                 135                 140

Ala Asp Leu Thr Val Ala Ala Leu Pro Val Asp Pro Lys Gln Ala Glu
145                 150                 155                 160

Ala Phe Gly Leu Met Arg Thr Asp Gly Asp Gly Asp Ile Lys Glu Phe
                165                 170                 175

Arg Glu Lys Pro Lys Gly Asp Ser Leu Leu Glu Met Ala Val Asp Thr
            180                 185                 190

Ser Arg Phe Gly Leu Ser Ala Asn Ser Ala Lys Glu Arg Pro Tyr Leu
        195                 200                 205

Ala Ser Met Gly Ile Tyr Val Phe Ser Arg Asp Thr Leu Phe Asp Leu
    210                 215                 220
```

-continued

Leu Asp Ser Asn Pro Gly Tyr Lys Asp Phe Gly Lys Glu Val Ile Pro
225 230 235 240

Glu Ala Leu Lys Arg Gly Asp Lys Leu Lys Ser Tyr Val Phe Asp Asp
245 250 255

Tyr Trp Glu Asp Ile Gly Thr Ile Gly Ala Phe Tyr Glu Ala Asn Leu
260 265 270

Ala Leu Thr Gln Gln Pro Thr Pro Pro Phe Ser Phe Tyr Asp Glu Lys
275 280 285

Phe Pro Ile Tyr Thr Arg Pro Arg Tyr Leu Pro Pro Ser Lys Leu Val
290 295 300

Asp Ala Gln Ile Thr Asn Ser Ile Val Gly Glu Gly Ser Ile Leu Lys
305 310 315 320

Ser Cys Ser Ile His His Cys Val Leu Gly Val Arg Ser Arg Ile Glu
325 330 335

Thr Asp Val Val Leu Gln Asp Thr Leu Val Met Gly Ala Asp Phe Phe
340 345 350

Glu Ser Ser Asp Glu Arg Ala Val Leu Arg Glu Arg Gly Gly Ile Pro
355 360 365

Val Gly Val Gly Gln Gly Thr Thr Val Lys Arg Ala Ile Leu Asp Lys
370 375 380

Asn Ala Arg Ile Gly Ser Asn Val Thr Ile Val Asn Lys Asp His Val
385 390 395 400

Glu Glu Ala Asp Arg Ser Asp Gln Gly Phe Tyr Ile Arg Asn Gly Ile
405 410 415

Val Val Val Val Lys Asn Ala Thr Ile Gln Asp Gly Thr Val Ile
420 425 430

<210> SEQ ID NO 71
<211> LENGTH: 1296
<212> TYPE: DNA
<213> ORGANISM: Synechococcus sp. RCC 307

<400> SEQUENCE: 71
atgaaacggg ttctcgcaat cattctcggt ggcggtgcgg gtacgcggct ctatccgctg 60
accaaaatgc gggccaaacc agccgtgccg ctggcgggta agtaccgcct catcgacatc 120
cccgttagca actgcatcaa cagcgggatc aacaagatct atgtgctgac gcagttcaac 180
agcgcatcac tgaatcgcca catcgctcaa accttcaacc tctcctcggg gtttgatcaa 240
gggtttgttg aagttctggc ggcccagcag accccagata gccccagttg gtttgaagga 300
acagccgatg ctgttcgtaa atacgaatgg ctgctgcagg agtgggacat cgacgaagtg 360
ctgatccttt cgggtgacca gctctaccgg atggactatg cccattttgt ggctcagcac 420
cgcgccagcg gcgctgacct caccgtggcc gccctcccgg ttgatcgcga gcaagcccag 480
agctttggct tgatgcacac cggtgcagaa gcctccatca ccaagttccg cgaaaagccc 540
aaaggcgagg cactcgatga gatgtcctgc gataccgcca gcatgggctt gagcgctgag 600
gaagcccatc gccggccgtt cctggcttcc atgggcatct acgtgttcaa gcgggacgtg 660
ctcttccgct tactggctga aaaccccggt gccactgact tcggtaagga gatcatcccc 720
aaggcactcg acgatggctt caaactccgc tcctatctct tcgacgatta ctgggaagac 780
atcggaacca tccgtgcttt ctatgaagcg aatctggcgc tgacgaccca gccgcgtccg 840
cccttctctt tctacgacaa gcgtttcccg atctacacac gtcatcgcta cctgccgccc 900
tccaagcttc aagatgcgca ggtcaccgac tccattgttg gtgaggggtc cattttgaag 960
gcttgcagta ttcaccactg cgtcttgggt gtgcgcagcc gcattgaaga cgaggttgcc 1020
ttgcaagaca ccctggtgat gggcaacgac ttctatgagt ccggcgaaga gcgggccatc 1080
ctgcgggaac gtggtggcat ccccatgggt gtgggccgag gaaccacggt gaaaaaggcc 1140
atcctcgata agaacgtccg catcggcagc aacgtcagca tcatcaacaa agacaacgtt 1200
gaggaagccg accgcgctga gcagggcttc tacatccgtg gcgggattgt ggtgatcacc 1260
aaaaacgctt cgattcccga cgggatggtg atctga 1296

<210> SEQ ID NO 72
<211> LENGTH: 431
<212> TYPE: PRT
<213> ORGANISM: Synechococcus sp. RCC 307

<400> SEQUENCE: 72

Met Lys Arg Val Leu Ala Ile Ile Leu Gly Gly Gly Ala Gly Thr Arg
1 5 10 15

Leu Tyr Pro Leu Thr Lys Met Arg Ala Lys Pro Ala Val Pro Leu Ala
20 25 30

Gly Lys Tyr Arg Leu Ile Asp Ile Pro Val Ser Asn Cys Ile Asn Ser
35 40 45

Gly Ile Asn Lys Ile Tyr Val Leu Thr Gln Phe Asn Ser Ala Ser Leu
50 55 60

Asn Arg His Ile Ala Gln Thr Phe Asn Leu Ser Ser Gly Phe Asp Gln
65 70 75 80

Gly Phe Val Glu Val Leu Ala Ala Gln Gln Thr Pro Asp Ser Pro Ser
85 90 95

Trp Phe Glu Gly Thr Ala Asp Ala Val Arg Lys Tyr Glu Trp Leu Leu
100 105 110

Gln Glu Trp Asp Ile Asp Glu Val Leu Ile Leu Ser Gly Asp Gln Leu
115 120 125

Tyr Arg Met Asp Tyr Ala His Phe Val Ala Gln His Arg Ala Ser Gly
130 135 140

Ala Asp Leu Thr Val Ala Ala Leu Pro Val Asp Arg Glu Gln Ala Gln
145 150 155 160

Ser Phe Gly Leu Met His Thr Gly Ala Glu Ala Ser Ile Thr Lys Phe
165 170 175

Arg Glu Lys Pro Lys Gly Glu Ala Leu Asp Glu Met Ser Cys Asp Thr
180 185 190

Ala Ser Met Gly Leu Ser Ala Glu Glu Ala His Arg Arg Pro Phe Leu
195 200 205

Ala Ser Met Gly Ile Tyr Val Phe Lys Arg Asp Val Leu Phe Arg Leu
210 215 220

Leu Ala Glu Asn Pro Gly Ala Thr Asp Phe Gly Lys Glu Ile Ile Pro
225 230 235 240

Lys Ala Leu Asp Asp Gly Phe Lys Leu Arg Ser Tyr Leu Phe Asp Asp
245 250 255

Tyr Trp Glu Asp Ile Gly Thr Ile Arg Ala Phe Tyr Glu Ala Asn Leu
260 265 270

Ala Leu Thr Thr Gln Pro Arg Pro Pro Phe Ser Phe Tyr Asp Lys Arg
275 280 285

Phe Pro Ile Tyr Thr Arg His Arg Tyr Leu Pro Pro Ser Lys Leu Gln
290 295 300

Asp Ala Gln Val Thr Asp Ser Ile Val Gly Glu Gly Ser Ile Leu Lys
305 310 315 320

Ala Cys Ser Ile His His Cys Val Leu Gly Val Arg Ser Arg Ile Glu
325 330 335

Asp Glu Val Ala Leu Gln Asp Thr Leu Val Met Gly Asn Asp Phe Tyr
340 345 350

Glu Ser Gly Glu Glu Arg Ala Ile Leu Arg Glu Arg Gly Gly Ile Pro
355 360 365

Met Gly Val Gly Arg Gly Thr Thr Val Lys Lys Ala Ile Leu Asp Lys
370 375 380

Asn Val Arg Ile Gly Ser Asn Val Ser Ile Ile Asn Lys Asp Asn Val
385 390 395 400

Glu Glu Ala Asp Arg Ala Glu Gln Gly Phe Tyr Ile Arg Gly Gly Ile
405 410 415

Val Val Ile Thr Lys Asn Ala Ser Ile Pro Asp Gly Met Val Ile
420 425 430

<210> SEQ ID NO 73
<211> LENGTH: 1290
<212> TYPE: DNA
<213> ORGANISM: Synechococcus sp. PCC 7002

<400> SEQUENCE: 73
gtgaaacgag tcctaggaat catacttggc ggcggcgcag gtactcgcct atatccgcta 60
acaaaactca gagctaagcc cgcagtacct ctagcaggca aatatcgtct cattgatatt 120
cctgttagca attgcattaa ttctgaaatt cataaaatct acattttaac ccaatttaat 180
tcagcatctt taaatcgtca cattagtcga acctacaact ttaccggctt caccgaaggc 240
tttaccgaag tactcgcagc ccaacaaact aaagaaaatc ccgattggtt ccaaggcacc 300
gccgacgctg tccgacagta cagttggctt ctagaagact gggatgtcga tgaatacatc 360
attctctccg gtgatcacct ctaccgtatg gattaccgtg aatttatcca gcgccaccgt 420
gacactgggg cagacatcac cctgtctgtg gttcccgtgg gcgaaaaagt agcccccgcc 480
tttgggttga tgaaaattga tgccaatggt cgtgtcgtgg actttagtga aaagcccact 540
ggtgaagccc ttaaggcgat gcaggtggat acccagtcct tgggtctcga tccagagcag 600
gcgaaagaaa agccctacat tgcgtcgatg ggatctacg tctttaagaa acaagtactc 660
ctcgatctac tcaaagaagg caaagataaa accgatttcg ggaaagaaat tattcctgat 720
gcggccaagg actacaacgt tcaggcctat ctctttgatg attattgggc tgacattggg 780
accatcgaag cgttctatga agcaaacctt ggcttgacga agcagccgat cccacccttt 840
agtttctatg acgaaaaggc tcccatctac acccgggcgc gctacttacc gccgacgaag 900
gtgctcaacg ctgacgtgac agaatcgatg atcagcgaag gttgcatcat taaaaactgc 960
cgcattcacc actcagttct tggcattcgc acccgtgtcg aagcggactg cactatcgaa 1020
gatacgatga tcatgggcgc agattattat cagccctatg agaagcgcca ggattgtctc 1080
cgtcgtggca agcctcccat tgggattggt gaagggacaa cgattcgccg ggcgatcatc 1140
gataaaaatg cacgcatcgg taaaaacgtg atgatcgtca ataaggaaaa tgtggaggag 1200
tcaaaccgtg aggagcttgg ctactacatt cgcagcggca ttacagtggt gctaaagaac 1260
gccgttattc ccgacggtac ggtcatttaa 1290

<210> SEQ ID NO 74
<211> LENGTH: 429
<212> TYPE: PRT
<213> ORGANISM: Synechococcus sp. PCC 7002

<400> SEQUENCE: 74

Met Lys Arg Val Leu Gly Ile Ile Leu Gly Gly Gly Ala Gly Thr Arg
1 5 10 15

Leu Tyr Pro Leu Thr Lys Leu Arg Ala Lys Pro Ala Val Pro Leu Ala
20 25 30

Gly Lys Tyr Arg Leu Ile Asp Ile Pro Val Ser Asn Cys Ile Asn Ser
35 40 45

Glu Ile His Lys Ile Tyr Ile Leu Thr Gln Phe Asn Ser Ala Ser Leu
50 55 60

Asn Arg His Ile Ser Arg Thr Tyr Asn Phe Thr Gly Phe Thr Glu Gly
65 70 75 80

Phe Thr Glu Val Leu Ala Ala Gln Gln Thr Lys Glu Asn Pro Asp Trp
85 90 95

Phe Gln Gly Thr Ala Asp Ala Val Arg Gln Tyr Ser Trp Leu Leu Glu
100 105 110

Asp Trp Asp Val Asp Glu Tyr Ile Ile Leu Ser Gly Asp His Leu Tyr
115 120 125

Arg Met Asp Tyr Arg Glu Phe Ile Gln Arg His Arg Asp Thr Gly Ala
130 135 140

Asp Ile Thr Leu Ser Val Val Pro Val Gly Glu Lys Val Ala Pro Ala
145 150 155 160

Phe Gly Leu Met Lys Ile Asp Ala Asn Gly Arg Val Val Asp Phe Ser
165 170 175

Glu Lys Pro Thr Gly Glu Ala Leu Lys Ala Met Gln Val Asp Thr Gln
180 185 190

Ser Leu Gly Leu Asp Pro Glu Gln Ala Lys Glu Lys Pro Tyr Ile Ala
195 200 205

Ser Met Gly Ile Tyr Val Phe Lys Lys Gln Val Leu Leu Asp Leu Leu
210 215 220

Lys Glu Gly Lys Asp Lys Thr Asp Phe Gly Lys Glu Ile Ile Pro Asp
225 230 235 240

Ala Ala Lys Asp Tyr Asn Val Gln Ala Tyr Leu Phe Asp Asp Tyr Trp
245 250 255

Ala Asp Ile Gly Thr Ile Glu Ala Phe Tyr Glu Ala Asn Leu Gly Leu
260 265 270

Thr Lys Gln Pro Ile Pro Pro Phe Ser Phe Tyr Asp Glu Lys Ala Pro
275 280 285

Ile Tyr Thr Arg Ala Arg Tyr Leu Pro Pro Thr Lys Val Leu Asn Ala
290 295 300

Asp Val Thr Glu Ser Met Ile Ser Glu Gly Cys Ile Ile Lys Asn Cys
305 310 315 320

Arg Ile His His Ser Val Leu Gly Ile Arg Thr Arg Val Glu Ala Asp
325 330 335

Cys Thr Ile Glu Asp Thr Met Ile Met Gly Ala Asp Tyr Tyr Gln Pro
340 345 350

Tyr Glu Lys Arg Gln Asp Cys Leu Arg Arg Gly Lys Pro Pro Ile Gly
355 360 365

Ile Gly Glu Gly Thr Thr Ile Arg Arg Ala Ile Ile Asp Lys Asn Ala
370 375 380

Arg Ile Gly Lys Asn Val Met Ile Val Asn Lys Glu Asn Val Glu Glu
385 390 395 400

Ser Asn Arg Glu Glu Leu Gly Tyr Tyr Ile Arg Ser Gly Ile Thr Val 405                 410                 415

Val Leu Lys Asn Ala Val Ile Pro Asp Gly Thr Val Ile
            420                 425

<210> SEQ ID NO 75
<211> LENGTH: 1704
<212> TYPE: DNA
<213> ORGANISM: Synechocystis sp. PCC 6803

<400> SEQUENCE: 75
gtgtctaagc ccctgatcgc cgccctccat tttttacaat ttttgtatat gacaagcaga 60
attaatcccc tcgccggcca gcatcccccc gccgacagcc ttttggatgt ggccaaactt 120
ttagacgact attaccgtca gcaaccggac ccggaaaatc ccgcccagtt agtgagcttt 180
ggtacctctg gccatcgggg ttctgccctc aacggtactt ttaatgaagc ccatattttg 240
gcggtgaccc aggcagtggt ggactatcgc caagcccagg gcattacggg gccccttat 300 atggggatgg atagccatgc tctgtcggaa ccagcccaga aaacggcgtt ggaagtgttg 360
gccgctaacc aagtagaaac ttttttaacc accgccacgg atttaacccg tttcaccccc 420
actccggcgg tatcctacgc cattttgacc cacaaccagg gacgtaaaga aggtttagcg 480
gacggcatta ttattacccc ttcccacaat ccccccactg atggaggctt taaatataat 540 ccccctccg gtggcccggc ggaaccggaa gcgacccaat ggattcagaa ccgggccaat 600
gagttgctga aaaatggcaa taaaacagtt aaacggctgg attacgagca ggcattaaaa 660
gccaccacca cccatgccca tgattttgtc actccctatg tggccggtct ggcggacatc 720
attgacttgg atgtaattcg ttcagcgggc ttgcgcttgg gagttgaccc cctgggggga 780
gccaatgtgg gctattggga acccattgcc gctaaataca atttgaacat cagcttggtt 840
aatcccgggg tagatcccac gtttaaattt atgaccctgg attgggacgg caaaatccgc 900
atggattgtt cttcccccta cgccatggcc agtttggtga aatcaaaga ccattacgac 960 attgcctttg gcaacgacac cgacggcgat cgccatggca ttgtcacccc cagcgtgggt 1020
ttgatgaatc ccaatcattt tctttccgtg gccatttggt atttgtttag tcagcggcaa 1080
cagtggtcag ggctgtcggc gatcggcaaa accctagtca gcagcagcat gattgaccgg 1140
gtgggggcca tgattaatcg ccaagtttac gaagtgcccg tgggctttaa atggtttgtc 1200
agcggtttgc tagatggttc ctttggcttt gggggtgaag aaagtgccgg ggcttcgttt 1260
ttgaaaaaaa atggcaccgt ttggaccacc gacaaagatg gcaccattat ggatttattg 1320
gcggcggaaa tcaccgctaa aaccggcaaa gatcccggcc tccattacca ggatttgacc 1380
gctaagttag gtaatcccat ttaccaacgc attgatgccc ccgccactcc ggcccaaaaa 1440
gaccgcttga aaaaactgtc ccccgatgac gttacagcta cctccttagc tggggatgcc 1500
attactgcta aattaaccaa agcccctggc aaccaagcgg cgatcggtgg gttgaaggtg 1560
accactgcgg aaggttggtt tgcggcccgg ccctccggca cggaaaatgt ttacaaaatc 1620
tatgccgaaa gtttcaaaga cgaagcccat ctccaggcta ttttcacgga ggcggaagcc 1680
attgttacct cggctttggg ctaa 1704

<210> SEQ ID NO 76
<211> LENGTH: 567
<212> TYPE: PRT
<213> ORGANISM: Synechocystis sp. PCC 6803

<400> SEQUENCE: 76

-continued

```
Met Ser Lys Pro Leu Ile Ala Ala Leu His Phe Leu Gln Phe Leu Tyr
1               5                   10                  15

Met Thr Ser Arg Ile Asn Pro Leu Ala Gly Gln His Pro Pro Ala Asp
            20                  25                  30

Ser Leu Leu Asp Val Ala Lys Leu Leu Asp Asp Tyr Tyr Arg Gln Gln
        35                  40                  45

Pro Asp Pro Glu Asn Pro Ala Gln Leu Val Ser Phe Gly Thr Ser Gly
    50                  55                  60

His Arg Gly Ser Ala Leu Asn Gly Thr Phe Asn Glu Ala His Ile Leu
65                  70                  75                  80

Ala Val Thr Gln Ala Val Val Asp Tyr Arg Gln Ala Gln Gly Ile Thr
                85                  90                  95

Gly Pro Leu Tyr Met Gly Met Asp Ser His Ala Leu Ser Glu Pro Ala
            100                 105                 110

Gln Lys Thr Ala Leu Glu Val Leu Ala Ala Asn Gln Val Glu Thr Phe
        115                 120                 125

Leu Thr Thr Ala Thr Asp Leu Thr Arg Phe Thr Pro Thr Pro Ala Val
    130                 135                 140

Ser Tyr Ala Ile Leu Thr His Asn Gln Gly Arg Lys Glu Gly Leu Ala
145                 150                 155                 160

Asp Gly Ile Ile Ile Thr Pro Ser His Asn Pro Pro Thr Asp Gly Gly
                165                 170                 175

Phe Lys Tyr Asn Pro Pro Ser Gly Gly Pro Ala Glu Pro Glu Ala Thr
            180                 185                 190

Gln Trp Ile Gln Asn Arg Ala Asn Glu Leu Leu Lys Asn Gly Asn Lys
        195                 200                 205

Thr Val Lys Arg Leu Asp Tyr Glu Gln Ala Leu Lys Ala Thr Thr Thr
    210                 215                 220

His Ala His Asp Phe Val Thr Pro Tyr Val Ala Gly Leu Ala Asp Ile
225                 230                 235                 240

Ile Asp Leu Asp Val Ile Arg Ser Ala Gly Leu Arg Leu Gly Val Asp
                245                 250                 255

Pro Leu Gly Gly Ala Asn Val Gly Tyr Trp Glu Pro Ile Ala Ala Lys
            260                 265                 270

Tyr Asn Leu Asn Ile Ser Leu Val Asn Pro Gly Val Asp Pro Thr Phe
        275                 280                 285

Lys Phe Met Thr Leu Asp Trp Asp Gly Lys Ile Arg Met Asp Cys Ser
    290                 295                 300

Ser Pro Tyr Ala Met Ala Ser Leu Val Lys Ile Lys Asp His Tyr Asp
305                 310                 315                 320

Ile Ala Phe Gly Asn Asp Thr Asp Gly Asp Arg His Gly Ile Val Thr
                325                 330                 335

Pro Ser Val Gly Leu Met Asn Pro Asn His Phe Leu Ser Val Ala Ile
            340                 345                 350

Trp Tyr Leu Phe Ser Gln Arg Gln Gln Trp Ser Gly Leu Ser Ala Ile
        355                 360                 365

Gly Lys Thr Leu Val Ser Ser Ser Met Ile Asp Arg Val Gly Ala Met
    370                 375                 380

Ile Asn Arg Gln Val Tyr Glu Val Pro Val Gly Phe Lys Trp Phe Val
385                 390                 395                 400

Ser Gly Leu Leu Asp Gly Ser Phe Gly Phe Gly Gly Glu Glu Ser Ala
                405                 410                 415

Gly Ala Ser Phe Leu Lys Lys Asn Gly Thr Val Trp Thr Thr Asp Lys
```

```
            420                 425                 430

Asp Gly Thr Ile Met Asp Leu Leu Ala Ala Glu Ile Thr Ala Lys Thr
        435                 440                 445

Gly Lys Asp Pro Gly Leu His Tyr Gln Asp Leu Thr Ala Lys Leu Gly
    450                 455                 460

Asn Pro Ile Tyr Gln Arg Ile Asp Ala Pro Ala Thr Pro Ala Gln Lys
465                 470                 475                 480

Asp Arg Leu Lys Lys Leu Ser Pro Asp Asp Val Thr Ala Thr Ser Leu
                485                 490                 495

Ala Gly Asp Ala Ile Thr Ala Lys Leu Thr Lys Ala Pro Gly Asn Gln
            500                 505                 510

Ala Ala Ile Gly Gly Leu Lys Val Thr Thr Ala Glu Gly Trp Phe Ala
        515                 520                 525

Ala Arg Pro Ser Gly Thr Glu Asn Val Tyr Lys Ile Tyr Ala Glu Ser
    530                 535                 540

Phe Lys Asp Glu Ala His Leu Gln Ala Ile Phe Thr Glu Ala Glu Ala
545                 550                 555                 560

Ile Val Thr Ser Ala Leu Gly
                565


<210> SEQ ID NO 77
<211> LENGTH: 1632
<212> TYPE: DNA
<213> ORGANISM: Synechococcus elongatus PCC 7942

<400> SEQUENCE: 77

atgaatatcc acactgtcgc gacgcaagcc tttagcgacc aaaagcccgg tacctccggc     60

ctgcgcaagc aagttcctgt cttccaaaaa cggcactatc tcgaaaactt tgtccagtcg    120

atcttcgata gccttgaggg ttatcagggc cagacgttag tgctgggggg tgatggccgc    180

tactacaatc gcacagccat ccaaaccatt ctgaaaatgg cggcggccaa tggttggggc    240

cgcgttttag ttggacaagg cggtattctc tccacgccag cagtctccaa cctaatccgc    300

cagaacggag ccttcggcgg catcatcctc tcggctagcc acaacccagg gggccctgag    360

ggcgatttcg gcatcaagta caacatcagc aacggtggcc ctgcacccga aaaagtcacc    420

gatgccatct atgcctgcag cctcaaaatt gaggcctacc gcattctcga agccggtgac    480

gttgacctcg atcgactcgg tagtcaacaa ctgggcgaga tgaccgttga ggtgatcgac    540

tcggtcgccg actacagccg cttgatgcaa tccctgtttg acttcgatcg cattcgcgat    600

cgcctgaggg gggggctacg gattgcgatc gactcgatgc atgccgtcac cggtccctac    660

gccaccacga tttttgagaa ggagctaggc gcggcggcag gcactgtttt taatggcaag    720

ccgctggaag actttggcgg gggtcaccca gacccgaatt tggtctacgc ccacgacttg    780

gttgaactgt tgtttggcga tcgcgcccca gattttggcg cggcctccga tggcgatggc    840

gatcgcaaca tgatcttggg caatcacttt tttgtgaccc ctagcgacag cttggcgatt    900

ctcgcagcca atgccagcct agtgccggcc taccgcaatg gactgtctgg gattgcgcga    960

tccatgccca ccagtgcggc ggccgatcgc gtcgcccaag ccctcaacct gccctgctac   1020

gaaaccccaa cgggttggaa gtttttcggc aatctgctcg atgccgatcg cgtcaccctc   1080

tgcggcgaag aaagctttgg cacaggctcc aaccatgtgc gcgagaagga tggcctgtgg   1140

gccgtgctgt tctggctgaa tattctggcg gtgcgcgagc aatccgtggc cgaaattgtc   1200

caagaacact ggcgcaccta cggccgcaac tactactctc gccacgacta cgaaggggtg   1260
```

```
gagagcgatc gagccagtac gctggtggac aaactgcgat cgcagctacc cagcctgacc   1320

ggacagaaac tgggagccta caccgttgcc tacgccgacg acttccgcta cgaagatccg   1380

gtcgatggca gcatcagcga acagcagggc attcgtattg gctttgaaga cggctcacgt   1440

atggtcttcc gcttgtctgg tactggtacg gcaggagcca ccctgcgcct ctacctcgag   1500

cgcttcgaag gggacaccac caaacagggt ctcgatcccc aagttgccct ggcagatttg   1560

attgcaatcg ccgatgaagt cgcccagatc acaaccttga cgggcttcga tcaaccgaca   1620

gtgatcacct ga                                                       1632
```

```
<210> SEQ ID NO 78
<211> LENGTH: 543
<212> TYPE: PRT
<213> ORGANISM: Synechococcus elongatus PCC 7942

<400> SEQUENCE: 78

Met Asn Ile His Thr Val Ala Thr Gln Ala Phe Ser Asp Gln Lys Pro
 1               5                  10                  15

Gly Thr Ser Gly Leu Arg Lys Gln Val Pro Val Phe Gln Lys Arg His
            20                  25                  30

Tyr Leu Glu Asn Phe Val Gln Ser Ile Phe Asp Ser Leu Glu Gly Tyr
        35                  40                  45

Gln Gly Gln Thr Leu Val Leu Gly Gly Asp Gly Arg Tyr Tyr Asn Arg
    50                  55                  60

Thr Ala Ile Gln Thr Ile Leu Lys Met Ala Ala Ala Asn Gly Trp Gly
65                  70                  75                  80

Arg Val Leu Val Gly Gln Gly Gly Ile Leu Ser Thr Pro Ala Val Ser
                85                  90                  95

Asn Leu Ile Arg Gln Asn Gly Ala Phe Gly Gly Ile Ile Leu Ser Ala
            100                 105                 110

Ser His Asn Pro Gly Gly Pro Glu Gly Asp Phe Gly Ile Lys Tyr Asn
        115                 120                 125

Ile Ser Asn Gly Gly Pro Ala Pro Glu Lys Val Thr Asp Ala Ile Tyr
    130                 135                 140

Ala Cys Ser Leu Lys Ile Glu Ala Tyr Arg Ile Leu Glu Ala Gly Asp
145                 150                 155                 160

Val Asp Leu Asp Arg Leu Gly Ser Gln Gln Leu Gly Glu Met Thr Val
                165                 170                 175

Glu Val Ile Asp Ser Val Ala Asp Tyr Ser Arg Leu Met Gln Ser Leu
            180                 185                 190

Phe Asp Phe Asp Arg Ile Arg Asp Arg Leu Arg Gly Gly Leu Arg Ile
        195                 200                 205

Ala Ile Asp Ser Met His Ala Val Thr Gly Pro Tyr Ala Thr Thr Ile
    210                 215                 220

Phe Glu Lys Glu Leu Gly Ala Ala Ala Gly Thr Val Phe Asn Gly Lys
225                 230                 235                 240

Pro Leu Glu Asp Phe Gly Gly Gly His Pro Asp Pro Asn Leu Val Tyr
                245                 250                 255

Ala His Asp Leu Val Glu Leu Leu Phe Gly Asp Arg Ala Pro Asp Phe
            260                 265                 270

Gly Ala Ala Ser Asp Gly Asp Gly Asp Arg Asn Met Ile Leu Gly Asn
        275                 280                 285

His Phe Phe Val Thr Pro Ser Asp Ser Leu Ala Ile Leu Ala Ala Asn
    290                 295                 300
```

-continued

Ala Ser Leu Val Pro Ala Tyr Arg Asn Gly Leu Ser Gly Ile Ala Arg
305 310 315 320

Ser Met Pro Thr Ser Ala Ala Ala Asp Arg Val Ala Gln Ala Leu Asn
325 330 335

Leu Pro Cys Tyr Glu Thr Pro Thr Gly Trp Lys Phe Phe Gly Asn Leu
340 345 350

Leu Asp Ala Asp Arg Val Thr Leu Cys Gly Glu Glu Ser Phe Gly Thr
355 360 365

Gly Ser Asn His Val Arg Glu Lys Asp Gly Leu Trp Ala Val Leu Phe
370 375 380

Trp Leu Asn Ile Leu Ala Val Arg Glu Gln Ser Val Ala Glu Ile Val
385 390 395 400

Gln Glu His Trp Arg Thr Tyr Gly Arg Asn Tyr Tyr Ser Arg His Asp
405 410 415

Tyr Glu Gly Val Glu Ser Asp Arg Ala Ser Thr Leu Val Asp Lys Leu
420 425 430

Arg Ser Gln Leu Pro Ser Leu Thr Gly Gln Lys Leu Gly Ala Tyr Thr
435 440 445

Val Ala Tyr Ala Asp Asp Phe Arg Tyr Glu Asp Pro Val Asp Gly Ser
450 455 460

Ile Ser Glu Gln Gln Gly Ile Arg Ile Gly Phe Glu Asp Gly Ser Arg
465 470 475 480

Met Val Phe Arg Leu Ser Gly Thr Gly Thr Ala Gly Ala Thr Leu Arg
485 490 495

Leu Tyr Leu Glu Arg Phe Glu Gly Asp Thr Thr Lys Gln Gly Leu Asp
500 505 510

Pro Gln Val Ala Leu Ala Asp Leu Ile Ala Ile Ala Asp Glu Val Ala
515 520 525

Gln Ile Thr Thr Leu Thr Gly Phe Asp Gln Pro Thr Val Ile Thr
530 535 540

<210> SEQ ID NO 79
<211> LENGTH: 1659
<212> TYPE: DNA
<213> ORGANISM: Synechococcus sp. WH8102

<400> SEQUENCE: 79
atgaccacct cggcccccgc ggaaccgacc ctgcgcctgg tgcgcctgga cgcacctttc 60
acggatcaga aacccggcac atccggtttg cgcaaaagca gccagcagtt cgagcaagcg 120
aactatctgg agagctttgt ggaagccgta ttccgcacct tgcccggtgt tcaagggggc 180
acgctggtgt tgggaggtga cggccgttac ggcaaccgcc gtgccatcga cgtgatcctg 240
cgcatgggcg cggcccacgg cctcagcaag gtgatcgtca ccaccggcgg catcctctcc 300
accccggcgg cctcgaacct gattcgccag cgtcaggcca tcggcggcat catcctctcg 360
gcaagccaca accctggcgg ccccaatgga gacttcggcg tcaaggtgaa tggcgccaac 420
ggtggcccga ccccggcctc gttcaccgat gcggtgttcg agtgcaccaa gaccttggag 480
caatacacga tcgttgatgc cgcggccatc gccatcgata cccccggcag ctacagcatc 540
ggcgccatgc aggtggaggt gatcgacggc gtcgacgact tcgtggctct gatgcaacag 600
ctgttcgact ttgatcggat ccgggagctg atccgcagcg acttcccgct ggcgtttgat 660
gcgatgcatg cggtcactgg cccctacgcc actcgcctgt tggaagagat cctcggcgct 720
cctgccggca gcgtccgcaa cggcgttcct ctggaggact tcggcggcgg ccaccccgac 780

-continued

```
cccaacctca cctacgccca cgagctggcc gaacttctgc tcgacgggga ggagttccgc    840

ttcggggccg cctgcgacgg cgatggtgac cgcaacatga tcctggggca gcactgcttc    900

gtaaacccca gcgacagcct ggcggtgctc acagccaacg ccacggtggc accggcctat    960

gccgatggtt tggctggcgt ggcccgctcg atgcccacca gctctgccgt ggatgtggtg   1020

gccaaggaac tgggcatcga ctgctacgag acccccaccg gctggaagtt cttcggcaat   1080

ctgctggatg ccggcaaaat cacgctctgc ggtgaagaga gcttcggcac cggcagcaac   1140

cacgtgcgtg aaaaggatgg cctctgggct gttctgttct ggctgcagat cctggccgag   1200

cgccgctgca gcgtcgccga gatcatggct gagcattgga agcgcttcgg ccgccactac   1260

tactctcgcc acgactacga agccgtcgcc agcgacgcag cccatgggct gttccaccgc   1320

ctcgagggca tgctccctgg tctggtgggg cagagcttcg ctggccgcag cgtcagcgca   1380

gccgacaact tcagctacac cgatcccgtt gatggctctg tgaccaaggg ccagggcctg   1440

cgcatcctgc tggaggatgg cagccgcgtg atggtgcgcc tctcgggcac cggcaccaag   1500

ggcgccacga tccgcgtcta tctggagagt tatgtaccga gcagcggtga tctcaaccag   1560

gatccccagg tcgctctggc cgacatgatc agcgccatca atgaactggc ggagatcaag   1620

cagcgcaccg gcatggatcg gcccaccgtg atcacctga                          1659


<210> SEQ ID NO 80
<211> LENGTH: 552
<212> TYPE: PRT
<213> ORGANISM: Synechococcus sp. WH8102

<400> SEQUENCE: 80

Met Thr Thr Ser Ala Pro Ala Glu Pro Thr Leu Arg Leu Val Arg Leu
 1               5                  10                  15

Asp Ala Pro Phe Thr Asp Gln Lys Pro Gly Thr Ser Gly Leu Arg Lys
            20                  25                  30

Ser Ser Gln Gln Phe Glu Gln Ala Asn Tyr Leu Glu Ser Phe Val Glu
        35                  40                  45

Ala Val Phe Arg Thr Leu Pro Gly Val Gln Gly Gly Thr Leu Val Leu
    50                  55                  60

Gly Gly Asp Gly Arg Tyr Gly Asn Arg Arg Ala Ile Asp Val Ile Leu
65                  70                  75                  80

Arg Met Gly Ala Ala His Gly Leu Ser Lys Val Ile Val Thr Thr Gly
                85                  90                  95

Gly Ile Leu Ser Thr Pro Ala Ala Ser Asn Leu Ile Arg Gln Arg Gln
            100                 105                 110

Ala Ile Gly Gly Ile Ile Leu Ser Ala Ser His Asn Pro Gly Gly Pro
        115                 120                 125

Asn Gly Asp Phe Gly Val Lys Val Asn Gly Ala Asn Gly Gly Pro Thr
    130                 135                 140

Pro Ala Ser Phe Thr Asp Ala Val Phe Glu Cys Thr Lys Thr Leu Glu
145                 150                 155                 160

Gln Tyr Thr Ile Val Asp Ala Ala Ala Ile Ala Ile Asp Thr Pro Gly
                165                 170                 175

Ser Tyr Ser Ile Gly Ala Met Gln Val Glu Val Ile Asp Gly Val Asp
            180                 185                 190

Asp Phe Val Ala Leu Met Gln Gln Leu Phe Asp Phe Asp Arg Ile Arg
        195                 200                 205

Glu Leu Ile Arg Ser Asp Phe Pro Leu Ala Phe Asp Ala Met His Ala
    210                 215                 220
```

Val Thr Gly Pro Tyr Ala Thr Arg Leu Leu Glu Glu Ile Leu Gly Ala
225 230 235 240

Pro Ala Gly Ser Val Arg Asn Gly Val Pro Leu Glu Asp Phe Gly Gly
245 250 255

Gly His Pro Asp Pro Asn Leu Thr Tyr Ala His Glu Leu Ala Glu Leu
260 265 270

Leu Leu Asp Gly Glu Glu Phe Arg Phe Gly Ala Ala Cys Asp Gly Asp
275 280 285

Gly Asp Arg Asn Met Ile Leu Gly Gln His Cys Phe Val Asn Pro Ser
290 295 300

Asp Ser Leu Ala Val Leu Thr Ala Asn Ala Thr Val Ala Pro Ala Tyr
305 310 315 320

Ala Asp Gly Leu Ala Gly Val Ala Arg Ser Met Pro Thr Ser Ser Ala
325 330 335

Val Asp Val Val Ala Lys Glu Leu Gly Ile Asp Cys Tyr Glu Thr Pro
340 345 350

Thr Gly Trp Lys Phe Phe Gly Asn Leu Leu Asp Ala Gly Lys Ile Thr
355 360 365

Leu Cys Gly Glu Glu Ser Phe Gly Thr Gly Ser Asn His Val Arg Glu
370 375 380

Lys Asp Gly Leu Trp Ala Val Leu Phe Trp Leu Gln Ile Leu Ala Glu
385 390 395 400

Arg Arg Cys Ser Val Ala Glu Ile Met Ala Glu His Trp Lys Arg Phe
405 410 415

Gly Arg His Tyr Tyr Ser Arg His Asp Tyr Glu Ala Val Ala Ser Asp
420 425 430

Ala Ala His Gly Leu Phe His Arg Leu Glu Gly Met Leu Pro Gly Leu
435 440 445

Val Gly Gln Ser Phe Ala Gly Arg Ser Val Ser Ala Ala Asp Asn Phe
450 455 460

Ser Tyr Thr Asp Pro Val Asp Gly Ser Val Thr Lys Gly Gln Gly Leu
465 470 475 480

Arg Ile Leu Leu Glu Asp Gly Ser Arg Val Met Val Arg Leu Ser Gly
485 490 495

Thr Gly Thr Lys Gly Ala Thr Ile Arg Val Tyr Leu Glu Ser Tyr Val
500 505 510

Pro Ser Ser Gly Asp Leu Asn Gln Asp Pro Gln Val Ala Leu Ala Asp
515 520 525

Met Ile Ser Ala Ile Asn Glu Leu Ala Glu Ile Lys Gln Arg Thr Gly
530 535 540

Met Asp Arg Pro Thr Val Ile Thr
545 550

<210> SEQ ID NO 81
<211> LENGTH: 1662
<212> TYPE: DNA
<213> ORGANISM: Synechococcus sp. RCC 307

<400> SEQUENCE: 81
gtgacgcttt cctcacccag cactgagttc tccgtgcagc agatcaagct gccagaagcg 60
tttcaagacc agaagcctgg cacctcggga ctgcgcaaga gcacccaaca atttgaacag 120
cctcattacc tcgaaagttt tatcgaggcg atcttccgca ccctccctgg tgtgcaaggc 180
gggaccttgg tggtgggcgg tgatggccgc tacggcaacc gccgcgccat cgatgtcatc 240

```
acccggatgg cggcagccca tggactgggg cggattgtgc tgaccaccgg cggcatcctc    300

tccacccctg ccgcttccaa cttgatccgc caacgccagg ccattggcgg catcatcctc    360

tcggccagcc acaaccctgg agggcccaaa ggcgactttg gcgtcaaggt caatggcgcc    420

aacggcggcc ctgcccctga atctcttacc gatgccatct acgcctgcag ccagcagctc    480

gatggctacc gcatcgcaag tggaaccgca ctgcccctcg acgccccagc cgagcatcaa    540

atcggtgcgt tgaacgtgga ggtgatcgac ggcgtcgacg actacctgca actgatgcag    600

cacttgttcg acttcgatct gatcagcgat ttgctcaagg gctcatggcc aatggccttt    660

gacgccatgc atgccgtcac tggtccctac gccagcaaac tctttgagca gctcctagga    720

gccccaagcg ggaccgtgcg caacgggcgc tgcctcgaag actttggtgg cggccatccc    780

gatcccaacc tcacctacgc caaagagctg gcgacgctgc tgctggatgg tgatgactat    840

cgctttggcg cggcctgtga tggcgatggc gaccgcaaca tgattttggg gcagcgctgc    900

tttgtgaacc ccagcgacag cctcgctgtc ttaacggcga acgccacctt ggtgaagggc    960

tatgcctccg gcctggccgg cgttgctcgc tcgatgccca ccagtgccgc agtggatgtg   1020

gtggccaagc agctggggat caattgcttt gagaccccca ccggttggaa atttttcggc   1080

aacctgctcg atgccggacg catcaccctt tgcggggaag agagctttgg aacaggcagt   1140

gatcacatcc gcgaaaaaga tggcctctgg gctgtgttgt tttggctctc gatcctggcc   1200

aagcgccaat gctctgttgc ggaggtgatg cagcagcact ggagcaccta cgggcgtcat   1260

tactactcgc gccatgacta cgaaggtgtc gaaaccgatc gggcccatgg gctctacaac   1320

ggcctgcgcg atcggcttgg cgagctgact ggaaccagct ttgccgatag ccgcatcgcc   1380

aatgctgacg acttcgccta cagcgacccc gtcgatggct cactgaccca gaagcaaggc   1440

ctacgtctgc tcctggagga cggcagccgc atcatcctgc ggctctcggg aaccggcacc   1500

aaaggagcca cgctgcggct ctatctcgag cgctatgtcg ccactggcgg caacctcgat   1560

caaaatcccc agcaagcctt agccggcatg attgcggccg ccgatgccct cgccggcatc   1620

cggtcaacca ccggcatgga tgtccccacg gtgatcacct ga                       1662
```

<210> SEQ ID NO 82
<211> LENGTH: 553
<212> TYPE: PRT
<213> ORGANISM: Synechococcus sp. RCC 307

<400> SEQUENCE: 82

```
Met Thr Leu Ser Ser Pro Ser Thr Glu Phe Ser Val Gln Gln Ile Lys
1               5                   10                  15

Leu Pro Glu Ala Phe Gln Asp Gln Lys Pro Gly Thr Ser Gly Leu Arg
            20                  25                  30

Lys Ser Thr Gln Gln Phe Glu Gln Pro His Tyr Leu Glu Ser Phe Ile
        35                  40                  45

Glu Ala Ile Phe Arg Thr Leu Pro Gly Val Gln Gly Gly Thr Leu Val
    50                  55                  60

Val Gly Gly Asp Gly Arg Tyr Gly Asn Arg Arg Ala Ile Asp Val Ile
65                  70                  75                  80

Thr Arg Met Ala Ala Ala His Gly Leu Gly Arg Ile Val Leu Thr Thr
                85                  90                  95

Gly Gly Ile Leu Ser Thr Pro Ala Ala Ser Asn Leu Ile Arg Gln Arg
            100                 105                 110

Gln Ala Ile Gly Gly Ile Ile Leu Ser Ala Ser His Asn Pro Gly Gly
```

```
        115                 120                 125

Pro Lys Gly Asp Phe Gly Val Lys Val Asn Gly Ala Asn Gly Gly Pro
    130                 135                 140

Ala Pro Glu Ser Leu Thr Asp Ala Ile Tyr Ala Cys Ser Gln Gln Leu
145                 150                 155                 160

Asp Gly Tyr Arg Ile Ala Ser Gly Thr Ala Leu Pro Leu Asp Ala Pro
                165                 170                 175

Ala Glu His Gln Ile Gly Ala Leu Asn Val Glu Val Ile Asp Gly Val
            180                 185                 190

Asp Asp Tyr Leu Gln Leu Met Gln His Leu Phe Asp Phe Asp Leu Ile
        195                 200                 205

Ser Asp Leu Leu Lys Gly Ser Trp Pro Met Ala Phe Asp Ala Met His
    210                 215                 220

Ala Val Thr Gly Pro Tyr Ala Ser Lys Leu Phe Glu Gln Leu Leu Gly
225                 230                 235                 240

Ala Pro Ser Gly Thr Val Arg Asn Gly Arg Cys Leu Glu Asp Phe Gly
                245                 250                 255

Gly Gly His Pro Asp Pro Asn Leu Thr Tyr Ala Lys Glu Leu Ala Thr
            260                 265                 270

Leu Leu Leu Asp Gly Asp Asp Tyr Arg Phe Gly Ala Ala Cys Asp Gly
        275                 280                 285

Asp Gly Asp Arg Asn Met Ile Leu Gly Gln Arg Cys Phe Val Asn Pro
    290                 295                 300

Ser Asp Ser Leu Ala Val Leu Thr Ala Asn Ala Thr Leu Val Lys Gly
305                 310                 315                 320

Tyr Ala Ser Gly Leu Ala Gly Val Ala Arg Ser Met Pro Thr Ser Ala
                325                 330                 335

Ala Val Asp Val Val Ala Lys Gln Leu Gly Ile Asn Cys Phe Glu Thr
            340                 345                 350

Pro Thr Gly Trp Lys Phe Phe Gly Asn Leu Leu Asp Ala Gly Arg Ile
        355                 360                 365

Thr Leu Cys Gly Glu Glu Ser Phe Gly Thr Gly Ser Asp His Ile Arg
    370                 375                 380

Glu Lys Asp Gly Leu Trp Ala Val Leu Phe Trp Leu Ser Ile Leu Ala
385                 390                 395                 400

Lys Arg Gln Cys Ser Val Ala Glu Val Met Gln Gln His Trp Ser Thr
                405                 410                 415

Tyr Gly Arg His Tyr Tyr Ser Arg His Asp Tyr Glu Gly Val Glu Thr
            420                 425                 430

Asp Arg Ala His Gly Leu Tyr Asn Gly Leu Arg Asp Arg Leu Gly Glu
        435                 440                 445

Leu Thr Gly Thr Ser Phe Ala Asp Ser Arg Ile Ala Asn Ala Asp Asp
    450                 455                 460

Phe Ala Tyr Ser Asp Pro Val Asp Gly Ser Leu Thr Gln Lys Gln Gly
465                 470                 475                 480

Leu Arg Leu Leu Leu Glu Asp Gly Ser Arg Ile Ile Leu Arg Leu Ser
                485                 490                 495

Gly Thr Gly Thr Lys Gly Ala Thr Leu Arg Leu Tyr Leu Glu Arg Tyr
            500                 505                 510

Val Ala Thr Gly Gly Asn Leu Asp Gln Asn Pro Gln Gln Ala Leu Ala
        515                 520                 525

Gly Met Ile Ala Ala Ala Asp Ala Leu Ala Gly Ile Arg Ser Thr Thr
    530                 535                 540
```

```
Gly Met Asp Val Pro Thr Val Ile Thr
545                 550

<210> SEQ ID NO 83
<211> LENGTH: 1467
<212> TYPE: DNA
<213> ORGANISM: Synechococcus sp PCC 7002

<400> SEQUENCE: 83

gtgttggcgt ttgggaatca acagccgatt cggttcggca cagacggttg gcgtggcatt     60

attgcggcgg attttacctt tgaacgggtg caacgggtgg cgatcgccac agcccatgtt    120

ttaaaagaaa atttcgcaaa ccaagccatt gataacacga taatcgtcgg ctacgaccgg    180

cggtttctcg cagatgaatt tgcccttgct gccgccgaag cgatccaggg ggaaggattt    240

cacgtacttc tagccaatag ttttgcgcca accccagccc tgagctatgc cgcccaccac    300

cacaaggctc tgggggcgat cgccttaacg gccagccata atccagcggg ttatttagga    360

ttaaaagtga aaggggcttt cggcggctcg gtttccgaag aaattacggc tcagattgaa    420

gcgcgactgg aagccgggat tgatcctcaa cattcaacga cgggccgttt agattatttt    480

gatccctggc aggactattg cgccggatta cagcaactgg ttgatttaga aaaaattcgc    540

caggcgatcg ccgctggtcg tctccaggtc tttgccgatg taatgtatgg cgcagcggcg    600

ggcggtttga cccaactgct caatgcggcg atccaagaaa tccattgtga accagatcct    660

ttgttcggcg gccgcccacc agagccttta gaaaaacatt tgtctcaact gcaacgcacc    720

attcgcgccg cccataatca agatttagag gcaattcagg tgggatttgt ctttgatggt    780

gatggcgatc gcattgctgc tgtggctggg gatggtgagt ttctcagttc ccaaaagcta    840

atcccgattt tgctggccca tttgtcccaa aatcgccaat atcaagggga agtggtaaaa    900

actgtcagcg gctctgattt aatccccgt ttgagcgaat actacggttt gccagtcttt    960

gaaacaccca tcggctacaa atacattgcc gaacgaatgc aacagaccca ggtgcttctt   1020

ggtggcgaag aatccggcgg cattggctac ggccaccaca ttcccgaacg ggatgcgctg   1080

ctggcggcat tgtatctcct agaggcgatc gccatttttg atcaagacct cggcgagatt   1140

taccagagtc ttcaaagcaa agctaatttt tatggcgcct acgaccgcat tgatttacat   1200

ttgcgggatt tctccagccg cgatcgccta ttaaaaatcc tcgcgacaaa tccccccaag   1260

gcgatctcca accatgacgt aattcacagc gaccccaaag atggctataa attccgcctt   1320

gctgatcaaa gttggttgct gattcgcttc agtggtaccg agcctgtact gcggttatat   1380

agtgaagcgg tcaatcctaa agccgtacaa gaaatcctcg cctgggcgca aacctgggct   1440

gaggctgccg accaagccga aggttag                                       1467

<210> SEQ ID NO 84
<211> LENGTH: 488
<212> TYPE: PRT
<213> ORGANISM: Synechococcus sp PCC 7002

<400> SEQUENCE: 84

Met Leu Ala Phe Gly Asn Gln Gln Pro Ile Arg Phe Gly Thr Asp Gly
 1               5                  10                  15

Trp Arg Gly Ile Ile Ala Ala Asp Phe Thr Phe Glu Arg Val Gln Arg
            20                  25                  30

Val Ala Ile Ala Thr Ala His Val Leu Lys Glu Asn Phe Ala Asn Gln
        35                  40                  45
```

-continued

```
Ala Ile Asp Asn Thr Ile Ile Val Gly Tyr Asp Arg Arg Phe Leu Ala
    50                  55                  60

Asp Glu Phe Ala Leu Ala Ala Ala Glu Ala Ile Gln Gly Glu Gly Phe
65                  70                  75                  80

His Val Leu Leu Ala Asn Ser Phe Ala Pro Thr Pro Ala Leu Ser Tyr
                85                  90                  95

Ala Ala His His His Lys Ala Leu Gly Ala Ile Ala Leu Thr Ala Ser
            100                 105                 110

His Asn Pro Ala Gly Tyr Leu Gly Leu Lys Val Lys Gly Ala Phe Gly
        115                 120                 125

Gly Ser Val Ser Glu Glu Ile Thr Ala Gln Ile Glu Ala Arg Leu Glu
    130                 135                 140

Ala Gly Ile Asp Pro Gln His Ser Thr Thr Gly Arg Leu Asp Tyr Phe
145                 150                 155                 160

Asp Pro Trp Gln Asp Tyr Cys Ala Gly Leu Gln Gln Leu Val Asp Leu
                165                 170                 175

Glu Lys Ile Arg Gln Ala Ile Ala Ala Gly Arg Leu Gln Val Phe Ala
            180                 185                 190

Asp Val Met Tyr Gly Ala Ala Ala Gly Gly Leu Thr Gln Leu Leu Asn
        195                 200                 205

Ala Ala Ile Gln Glu Ile His Cys Glu Pro Asp Pro Leu Phe Gly Gly
    210                 215                 220

Arg Pro Pro Glu Pro Leu Glu Lys His Leu Ser Gln Leu Gln Arg Thr
225                 230                 235                 240

Ile Arg Ala Ala His Asn Gln Asp Leu Glu Ala Ile Gln Val Gly Phe
                245                 250                 255

Val Phe Asp Gly Asp Gly Asp Arg Ile Ala Ala Val Ala Gly Asp Gly
            260                 265                 270

Glu Phe Leu Ser Ser Gln Lys Leu Ile Pro Ile Leu Leu Ala His Leu
        275                 280                 285

Ser Gln Asn Arg Gln Tyr Gln Gly Glu Val Val Lys Thr Val Ser Gly
    290                 295                 300

Ser Asp Leu Ile Pro Arg Leu Ser Glu Tyr Tyr Gly Leu Pro Val Phe
305                 310                 315                 320

Glu Thr Pro Ile Gly Tyr Lys Tyr Ile Ala Glu Arg Met Gln Gln Thr
                325                 330                 335

Gln Val Leu Leu Gly Gly Glu Glu Ser Gly Gly Ile Gly Tyr Gly His
            340                 345                 350

His Ile Pro Glu Arg Asp Ala Leu Leu Ala Ala Leu Tyr Leu Leu Glu
        355                 360                 365

Ala Ile Ala Ile Phe Asp Gln Asp Leu Gly Glu Ile Tyr Gln Ser Leu
    370                 375                 380

Gln Ser Lys Ala Asn Phe Tyr Gly Ala Tyr Asp Arg Ile Asp Leu His
385                 390                 395                 400

Leu Arg Asp Phe Ser Ser Arg Asp Arg Leu Leu Lys Ile Leu Ala Thr
                405                 410                 415

Asn Pro Pro Lys Ala Ile Ser Asn His Asp Val Ile His Ser Asp Pro
            420                 425                 430

Lys Asp Gly Tyr Lys Phe Arg Leu Ala Asp Gln Ser Trp Leu Leu Ile
        435                 440                 445

Arg Phe Ser Gly Thr Glu Pro Val Leu Arg Leu Tyr Ser Glu Ala Val
    450                 455                 460

Asn Pro Lys Ala Val Gln Glu Ile Leu Ala Trp Ala Gln Thr Trp Ala
```

Glu Ala Ala Asp Gln Ala Glu Gly
            485

<210> SEQ ID NO 85
<211> LENGTH: 627
<212> TYPE: DNA
<213> ORGANISM: Escherichia coli

<400> SEQUENCE: 85
atgatgaact tcaacaatgt tttccgctgg catttgccct tcctgttcct ggtcctgtta      60
accttccgtg ccgccgcagc ggacacgtta ttgattctgg gtgatagcct gagcgccggg     120
tatcgaatgt ctgccagcgc ggcctggcct gccttgttga atgataagtg gcagagtaaa     180
acgtcggtag ttaatgccag catcagcggc gacacctcgc aacaaggact ggcgcgcctt     240
ccggctctgc tgaaacagca tcagccgcgt tgggtgctgg ttgaactggg cggcaatgac     300
ggtttgcgtg gttttcagcc acagcaaacc gagcaaacgc tgcgccagat tttgcaggat     360
gtcaaagccg ccaacgctga accattgtta atgcaaatac gtctgcctgc aaactatggt     420
cgccgttata atgaagcctt tagcgccatt taccccaaac tcgccaaaga gtttgatgtt     480
ccgctgctgc ccttttttat ggaagaggtc tacctcaagc cacaatggat gcaggatgac     540
ggtattcatc ccaaccgcga cgcccagccg tttattgccg actggatggc gaagcagttg     600
cagcctttag taaatcatga ctcataa                                         627

<210> SEQ ID NO 86
<211> LENGTH: 208
<212> TYPE: PRT
<213> ORGANISM: Escherichia coli

<400> SEQUENCE: 86

Met Met Asn Phe Asn Asn Val Phe Arg Trp His Leu Pro Phe Leu Phe
 1               5                  10                  15

Leu Val Leu Leu Thr Phe Arg Ala Ala Ala Ala Asp Thr Leu Leu Ile
             20                  25                  30

Leu Gly Asp Ser Leu Ser Ala Gly Tyr Arg Met Ser Ala Ser Ala Ala
         35                  40                  45

Trp Pro Ala Leu Leu Asn Asp Lys Trp Gln Ser Lys Thr Ser Val Val
     50                  55                  60

Asn Ala Ser Ile Ser Gly Asp Thr Ser Gln Gln Gly Leu Ala Arg Leu
 65                  70                  75                  80

Pro Ala Leu Leu Lys Gln His Gln Pro Arg Trp Val Leu Val Glu Leu
                 85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
195 200 205

<210> SEQ ID NO 87
<211> LENGTH: 1023
<212> TYPE: DNA
<213> ORGANISM: Escherichia coli

<400> SEQUENCE: 87
atgtttcagc agcaaaaaga ctgggaaaca agagaaaacg cgtttgctgc ttttaccatg 60
ggaccgctga ctgatttctg gcgtcagcgt gatgaagcag agtttactgg tgtggatgac 120
attccggtgc gctttgtccg ttttcgcgca cagcaccatg accgggtggt agtcatctgc 180
ccggggcgta ttgagagcta cgtaaaatat gcggaactgg cctatgacct gttccatttg 240
gggtttgatg tcttaatcat cgaccatcgc gggcagggac gttccggtcg cctgttagcc 300
gatccgcatc tcgggcatgt taatcgcttt aatgattatg ttgatgatct ggcggcattc 360
tggcagcagg aggttcagcc cggtccgtgg cgtaaacgct atatactggc acattcgatg 420
ggcggtgcga tctccacatt atttctgcaa cgccatccag gtgtatgtga cgccattgcg 480
ctaactgcgc caatgtttgg gatcgtgatt cgtatgccgt catttatggc acggcagatc 540
ctcaactggg ccgaagcgca tccacgtttc cgtgatggct atgcaatagg caccgggcgc 600
tggcgcgcgt tgccgtttgc tatcaacgta ctgacccaca gcagacagcg atatcgacgt 660
aacttacgct tctatgctga tgacccaacg attcgcgtcg gtgggccgac ctaccattgg 720
gtacgcgaaa gtattctggc tggcgaacag gtgttagccg gtgcgggtga tgacgccacg 780
ccaacgcttc tcttgcaggc tgaagaggaa cgcgtggtgg ataaccgcat gcatgaccgt 840
ttttgtgaac tccgcaccgc cgcgggccat cctgtcgaag gaggacggcc gttggtaatt 900
aaaggtgctt accatgagat cctttttgaa aaggacgcaa tggcctcagt cgcgctccac 960
gccatcgttg atttttcaa caggcataac tcacccagcg gaaaccgctc tacagaggtt 1020
taa 1023

<210> SEQ ID NO 88
<211> LENGTH: 340
<212> TYPE: PRT
<213> ORGANISM: Escherichia coli

<400> SEQUENCE: 88

Met Phe Gln Gln Gln Lys Asp Trp Glu Thr Arg Glu Asn Ala Phe Ala
1 5 10 15

Ala Phe Thr Met Gly Pro Leu Thr Asp Phe Trp Arg Gln Arg Asp Glu
20 25 30

Ala Glu Phe Thr Gly Val Asp Asp Ile Pro Val Arg Phe Val Arg Phe
35 40 45

Arg Ala Gln His His Asp Arg Val Val Val Ile Cys Pro Gly Arg Ile
50 55 60

Glu Ser Tyr Val Lys Tyr Ala Glu Leu Ala Tyr Asp Leu Phe His Leu
65 70 75 80

Gly Phe Asp Val Leu Ile Ile Asp His Arg Gly Gln Gly Arg Ser Gly
85 90 95

Arg Leu Leu Ala Asp Pro His Leu Gly His Val Asn Arg Phe Asn Asp
100 105 110

Tyr Val Asp Asp Leu Ala Ala Phe Trp Gln Gln Glu Val Gln Pro Gly
115 120 125

-continued

```
Pro Trp Arg Lys Arg Tyr Ile Leu Ala His Ser Met Gly Gly Ala Ile
    130                 135                 140

Ser Thr Leu Phe Leu Gln Arg His Pro Gly Val Cys Asp Ala Ile Ala
145                 150                 155                 160

Leu Thr Ala Pro Met Phe Gly Ile Val Ile Arg Met Pro Ser Phe Met
                165                 170                 175

Ala Arg Gln Ile Leu Asn Trp Ala Glu Ala His Pro Arg Phe Arg Asp
            180                 185                 190

Gly Tyr Ala Ile Gly Thr Gly Arg Trp Arg Ala Leu Pro Phe Ala Ile
        195                 200                 205

Asn Val Leu Thr His Ser Arg Gln Arg Tyr Arg Arg Asn Leu Arg Phe
    210                 215                 220

Tyr Ala Asp Asp Pro Thr Ile Arg Val Gly Gly Pro Thr Tyr His Trp
225                 230                 235                 240

Val Arg Glu Ser Ile Leu Ala Gly Glu Gln Val Leu Ala Gly Ala Gly
                245                 250                 255

Asp Asp Ala Thr Pro Thr Leu Leu Leu Gln Ala Glu Glu Glu Arg Val
            260                 265                 270

Val Asp Asn Arg Met His Asp Arg Phe Cys Glu Leu Arg Thr Ala Ala
        275                 280                 285

Gly His Pro Val Glu Gly Gly Arg Pro Leu Val Ile Lys Gly Ala Tyr
    290                 295                 300

His Glu Ile Leu Phe Glu Lys Asp Ala Met Ala Ser Val Ala Leu His
305                 310                 315                 320

Ala Ile Val Asp Phe Phe Asn Arg His Asn Ser Pro Ser Gly Asn Arg
                325                 330                 335

Ser Thr Glu Val
            340


<210> SEQ ID NO 89
<211> LENGTH: 1203
<212> TYPE: DNA
<213> ORGANISM: Artificial Sequence
<220> FEATURE:
<223> OTHER INFORMATION: Vupat1 - nucleotide sequence codon optimized
      for S. elongatus 7942.

<400> SEQUENCE: 89

atggccgcca cacagacccc tagtaaagtt gacgatggtg cactgattac ggtgctctcg      60

attgacgggg ggggtatccg cgggatcatc cctgggattc tcctcgcgtt cctcgagagc     120

gaattgcaaa aactggatgg tgctgatgcc cgtctcgccg actactttga tgtcatcgca     180

ggcacttcta ccggaggctt ggttactgct atgctgaccg cgccaaatga gaataatcgc     240

cccctctacg ctgctaaaga tattaaagat ttctatctcg aacacacccc aaaaatcttt     300

ccgcagtcgt cgagctggaa cctgattgcc accgcgatga agaagggccg cagcctgatg     360

gggccacagt acgacggcaa atacctgcat aaattggtcc gtgaaaaact gggcaatacg     420

aagctcgagc acactctgac caacgtggtc atcccggcgt tcgacatcaa aaatctgcaa     480

cccgccattt tcagtagctt ccaagttaag aaacgcccct acctcaatgc agccctcagc     540

gacatttgta tctcgaccag cgctgcaccc acgtatctgc cagcgcactg ctttgaaaca     600

aagacttcga cggccagttt caagtttgac ttggtggatg ggggcgtcgc tgcgaataac     660

cctgcgttgg tcgccatggc cgaggtctcg aacgaaatcc gcaacgaggg ttcgtgcgct     720

tccctgaagg tgaaaccgct gcagtacaaa aagtttctgg tcatttctct gggaaccggc     780
```

```
tcccagcaac acgaaatgcg atattccgca gataaggcca gcacgtgggg cttggtcgga    840

tggctcagct cgtccggtgg caccccgctg attgacgtct tctctcatgc gagctccgat    900

atggttgatt ttcatattag tagtgtgttt caagcccgcc acgcagaaca aaactacctg    960

cggattcaag acgataccct gacgggtgat ctgggctccg tcgatgttgc cacagagaag   1020

aatttgaacg gtctcgtgca ggtggccgaa gcgttgctga agaagcccgt tagcaaaatc   1080

aatttgcgta cgggtatcca cgaaccggtt gaatctaacg aaacgaatgc tgaagcgttg   1140

aagcggtttg cagcacggtt gtctaaccag cggcgatttc gcaaaagtca gactttcgct   1200

tag                                                                 1203


<210> SEQ ID NO 90
<211> LENGTH: 400
<212> TYPE: PRT
<213> ORGANISM: Synechococcus elongatus PCC 7942

<400> SEQUENCE: 90

Met Ala Ala Thr Gln Thr Pro Ser Lys Val Asp Asp Gly Ala Leu Ile
 1               5                  10                  15

Thr Val Leu Ser Ile Asp Gly Gly Gly Ile Arg Gly Ile Ile Pro Gly
            20                  25                  30

Ile Leu Leu Ala Phe Leu Glu Ser Glu Leu Gln Lys Leu Asp Gly Ala
        35                  40                  45

Asp Ala Arg Leu Ala Asp Tyr Phe Asp Val Ile Ala Gly Thr Ser Thr
    50                  55                  60

Gly Gly Leu Val Thr Ala Met Leu Thr Ala Pro Asn Glu Asn Asn Arg
65                  70                  75                  80

Pro Leu Tyr Ala Ala Lys Asp Ile Lys Asp Phe Tyr Leu Glu His Thr
                85                  90                  95

Pro Lys Ile Phe Pro Gln Ser Ser Ser Trp Asn Leu Ile Ala Thr Ala
            100                 105                 110

Met Lys Lys Gly Arg Ser Leu Met Gly Pro Gln Tyr Asp Gly Lys Tyr
        115                 120                 125

Leu His Lys Leu Val Arg Glu Lys Leu Gly Asn Thr Lys Leu Glu His
    130                 135                 140

Thr Leu Thr Asn Val Val Ile Pro Ala Phe Asp Ile Lys Asn Leu Gln
145                 150                 155                 160

Pro Ala Ile Phe Ser Ser Phe Gln Val Lys Lys Arg Pro Tyr Leu Asn
                165                 170                 175

Ala Ala Leu Ser Asp Ile Cys Ile Ser Thr Ser Ala Ala Pro Thr Tyr
            180                 185                 190

Leu Pro Ala His Cys Phe Glu Thr Lys Thr Ser Thr Ala Ser Phe Lys
        195                 200                 205

Phe Asp Leu Val Asp Gly Gly Val Ala Ala Asn Asn Pro Ala Leu Val
    210                 215                 220

Ala Met Ala Glu Val Ser Asn Glu Ile Arg Asn Glu Gly Ser Cys Ala
225                 230                 235                 240

Ser Leu Lys Val Lys Pro Leu Gln Tyr Lys Lys Phe Leu Val Ile Ser
                245                 250                 255

Leu Gly Thr Gly Ser Gln Gln His Glu Met Arg Tyr Ser Ala Asp Lys
            260                 265                 270

Ala Ser Thr Trp Gly Leu Val Gly Trp Leu Ser Ser Ser Gly Gly Thr
        275                 280                 285

Pro Leu Ile Asp Val Phe Ser His Ala Ser Ser Asp Met Val Asp Phe
```

```
    290                 295                 300

His Ile Ser Ser Val Phe Gln Ala Arg His Ala Glu Gln Asn Tyr Leu
305                 310                 315                 320

Arg Ile Gln Asp Asp Thr Leu Thr Gly Asp Leu Gly Ser Val Asp Val
                325                 330                 335

Ala Thr Glu Lys Asn Leu Asn Gly Leu Val Gln Val Ala Glu Ala Leu
            340                 345                 350

Leu Lys Lys Pro Val Ser Lys Ile Asn Leu Arg Thr Gly Ile His Glu
        355                 360                 365

Pro Val Glu Ser Asn Glu Thr Asn Ala Glu Ala Leu Lys Arg Phe Ala
    370                 375                 380

Ala Arg Leu Ser Asn Gln Arg Arg Phe Arg Lys Ser Gln Thr Phe Ala
385                 390                 395                 400
```

<210> SEQ ID NO 91
<211> LENGTH: 861
<212> TYPE: DNA
<213> ORGANISM: Escherichia coli

<400> SEQUENCE: 91

```
atgagtcagg cgctaaaaaa tttactgaca ttgttaaatc tggaaaaaat tgaggaagga      60

ctctttcgcg gccagagtga agatttaggt ttacgccagg tgtttggcgg ccaggtcgtg     120

ggtcaggcct tgtatgctgc aaaagagacc gtccctgaag agcggctggt acattcgttt     180

cacagctact ttcttcgccc tggcgatagt aagaagccga ttatttatga tgtcgaaacg     240

ctgcgtgacg gtaacagctt cagcgcccgc cgggttgctg ctattcaaaa cggcaaaccg     300

atttttata tgactgcctc tttccaggca ccagaagcgg gtttcgaaca tcaaaaaaca     360

atgccgtccg cgccagcgcc tgatggcctc ccttcggaaa cgcaaatcgc ccaatcgctg     420

gcgcacctgc tgccgccagt gctgaaagat aaattcatct gcgatcgtcc gctggaagtc     480

cgtccggtgg agtttcataa cccactgaaa ggtcacgtcg cagaaccaca tcgtcaggtg     540

tggatccgcg caaatggtag cgtgccggat gacctgcgcg ttcatcagta tctgctcggt     600

tacgcttctg atcttaactt cctgccggta gctctacagc cgcacggcat cggttttctc     660

gaaccgggga ttcagattgc caccattgac cattccatgt ggttccatcg cccgtttaat     720

ttgaatgaat ggctgctgta tagcgtggag agcacctcgg cgtccagcgc acgtggcttt     780

gtgcgcggtg agttttatac ccaagacggc gtactggttg cctcgaccgt tcaggaaggg     840

gtgatgcgta atcacaatta a                                               861
```

<210> SEQ ID NO 92
<211> LENGTH: 286
<212> TYPE: PRT
<213> ORGANISM: Escherichia coli

<400> SEQUENCE: 92

```
Met Ser Gln Ala Leu Lys Asn Leu Leu Thr Leu Leu Asn Leu Glu Lys
 1               5                  10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
```

```
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285


<210> SEQ ID NO 93
<211> LENGTH: 552
<212> TYPE: DNA
<213> ORGANISM: Escherichia coli

<400> SEQUENCE: 93

atggctgata cattgctgat tttgggtgat agtttgtctg cgggttaccg catgagcgcc     60

agcgccgcct ggccagccct cctgaatgat aaatggcagt ccaaaacgag cgttgtcaat    120

gcgtctatta gtggcgatac cagtcaacag ggactggctc gcctcccggc cttgctgaaa    180

cagcatcaac cgcgctgggt gctggtcgaa ctcggaggga atgatggtct gcgcggtttt    240

caacctcagc aaaccgagca aacgctccgt caaattctgc aggacgttaa ggcggcgaac    300

gctgagcccc tgctgatgca gattcgcctc cccgccaatt acgggcgtcg ctataacgaa    360

gcgttttcgg cgatttaccc gaagctcgcc aaagaatttg atgtcccact gctccccttt    420

ttcatggaag aagtctatct caaaccacaa tggatgcagg atgatggcat tcatcccaac    480

cgcgacgcgc aaccctttat tgcggattgg atggcgaaac aactccaacc actcgtgaac    540

cacgattcgt ag                                                        552


<210> SEQ ID NO 94
<211> LENGTH: 183
<212> TYPE: PRT
<213> ORGANISM: Escherichia coli

<400> SEQUENCE: 94

Met Ala Asp Thr Leu Leu Ile Leu Gly Asp Ser Leu Ser Ala Gly Tyr
 1               5                  10                  15
```

```
Arg Met Ser Ala Ser Ala Ala Trp Pro Ala Leu Leu Asn Asp Lys Trp
            20                  25                  30

Gln Ser Lys Thr Ser Val Val Asn Ala Ser Ile Ser Gly Asp Thr Ser
        35                  40                  45

Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
    130                 135                 140

Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180
```

<210> SEQ ID NO 95
<211> LENGTH: 1023
<212> TYPE: DNA
<213> ORGANISM: Artificial Sequence
<220> FEATURE:
<223> OTHER INFORMATION: pldB from E. coli - codon optimized for S. elongatus.

<400> SEQUENCE: 95

```
atgttccagc agcagaagga ctgggagacg cgggagaatg catttgcagc gtttaccatg     60

ggtcctctga ccgatttctg gcgtcaacgc gacgaagctg agtttacggg cgtcgatgat    120

attccggtgc gctttgtccg ctttcgagca caacatcacg atcgcgtggt cgttatttgc    180

cccggtcgta tcgaaagcta tgtgaaatat gcagaattgg cgtatgacct gttccatctc    240

gggtttgatg tgctcattat tgaccaccgg ggccaaggtc ggtcgggtcg tctgttggca    300

gatccgcatt tggggcatgt caaccggttt aatgattatg ttgatgacct cgctgctttc    360

tggcaacagg aggttcagcc cggtccatgg cgtaaacgct atatcctggc acattccatg    420

ggcggcgcca ttagtactct gttcctccaa cgccacccgg gcgtctgtga tgctattgct    480

ctcaccgccc caatgttcgg catcgttatc cgcatgccga gtttcatggc ccgacagatt    540

ttgaattggg cggaagcgca cccgcggttt cgtgacggat acgccatcgg tacgggccgt    600

tggcgagcac tgccttttgc catcaacgtc ttgactcaca gccgacagcg ataccggcga    660

aacctgcgct tctacgctga tgacccgacc atccgggttg ggggccccac gtatcactgg    720

gtgcgggaat ctattttggc cggggaacag gtgctggcgg gggccggaga cgatgctacc    780

ccaaccctcc tgctgcaagc cgaggaggag cgcgtcgttg ataaccgcat gcatgatcgc    840

ttctgcgagc tccgcacagc agccggccat cccgtggagg gaggccgccc tttggtgatc    900

aagggggctt accacgaaat cctgttcgaa aaagatgcga tggcttcggt ggccctgcac    960

gcaattgtcg attttttaa tcgccacaat tctcccagcg gcaaccgttc cacagaagtt   1020
```

tag 1023

<210> SEQ ID NO 96
<211> LENGTH: 243
<212> TYPE: DNA
<213> ORGANISM: Synechococcus elongatus PCC 7942

<400> SEQUENCE: 96
atgagccaag aagacatctt cagcaaagtc aaagacattg tggctgagca gctgagtgtg 60
gatgtggctg aagtcaagcc agaatccagc ttccaaaacg atctgggagc ggactcgctg 120
gacaccgtgg aactggtgat ggctctggaa gaggctttcg atatcgaaat ccccgatgaa 180
gccgctgaag gcattgcgac cgttcaagac gccgtcgatt tcatcgctag caaagctgcc 240
tag 243

<210> SEQ ID NO 97
<211> LENGTH: 80
<212> TYPE: PRT
<213> ORGANISM: Synechococcus elongatus PCC 7942

<400> SEQUENCE: 97

Met Ser Gln Glu Asp Ile Phe Ser Lys Val Lys Asp Ile Val Ala Glu
1 5 10 15

Gln Leu Ser Val Asp Val Ala Glu Val Lys Pro Glu Ser Ser Phe Gln
20 25 30

Asn Asp Leu Gly Ala Asp Ser Leu Asp Thr Val Glu Leu Val Met Ala
35 40 45

Leu Glu Glu Ala Phe Asp Ile Glu Ile Pro Asp Glu Ala Ala Glu Gly
50 55 60

Ile Ala Thr Val Gln Asp Ala Val Asp Phe Ile Ala Ser Lys Ala Ala
65 70 75 80

<210> SEQ ID NO 98
<211> LENGTH: 261
<212> TYPE: DNA
<213> ORGANISM: Acinetobacter sp. ADP1

<400> SEQUENCE: 98
atgtcgaacc tggcggatga gatcaaacaa atgatcattg acgtcctcgc tctcgaggat 60
atccaaatcc aggatattga tgaaacggca ccgctgttcg gggatggttt gggcctggat 120
agtattgacg cgctcgaact cggcctggcc ttgaaaaagc gctaccacat ccatttgaat 180
gccgaatctg acgaaactaa gcagcacttt cggtccattc agagcctggt gaccctggtg 240
gaggcccaac agaaagctta g 261

<210> SEQ ID NO 99
<211> LENGTH: 86
<212> TYPE: PRT
<213> ORGANISM: Acinetobacter sp. ADP1

<400> SEQUENCE: 99

Met Ser Asn Leu Ala Asp Glu Ile Lys Gln Met Ile Ile Asp Val Leu
1 5 10 15

Ala Leu Glu Asp Ile Gln Ile Gln Asp Ile Asp Glu Thr Ala Pro Leu
20 25 30

Phe Gly Asp Gly Leu Gly Leu Asp Ser Ile Asp Ala Leu Glu Leu Gly
35 40 45

Leu Ala Leu Lys Lys Arg Tyr His Ile His Leu Asn Ala Glu Ser Asp 50 55 60

Glu Thr Lys Gln His Phe Arg Ser Ile Gln Ser Leu Val Thr Leu Val
65 70 75 80

Glu Ala Gln Gln Lys Ala
85

<210> SEQ ID NO 100
<211> LENGTH: 246
<212> TYPE: DNA
<213> ORGANISM: Acinetobacter sp. ADP1

<400> SEQUENCE: 100
atgttgagtc aggaacacat cctctccaca ctccgcgaat ggatggagga cttgtttgaa 60
atcgagcctg aaaccattca actggattct aacctgtact cggacctgga tgtggatagc 120
attgatgcgg tcgatctgat tgtcaagatc aaagagctca cgggcaaaca ggtgaaaccg 180
gaagacttca agaatgtccg gactgtccat gatgttgtga ccgtgatcca aaacatgacg 240
gcttag 246

<210> SEQ ID NO 101
<211> LENGTH: 81
<212> TYPE: PRT
<213> ORGANISM: Acinetobacter sp. ADP1

<400> SEQUENCE: 101

Met Leu Ser Gln Glu His Ile Leu Ser Thr Leu Arg Glu Trp Met Glu
1 5 10 15

Asp Leu Phe Glu Ile Glu Pro Glu Thr Ile Gln Leu Asp Ser Asn Leu
20 25 30

Tyr Ser Asp Leu Asp Val Asp Ser Ile Asp Ala Val Asp Leu Ile Val
35 40 45

Lys Ile Lys Glu Leu Thr Gly Lys Gln Val Lys Pro Glu Asp Phe Lys
50 55 60

Asn Val Arg Thr Val His Asp Val Val Thr Val Ile Gln Asn Met Thr
65 70 75 80

Ala

<210> SEQ ID NO 102
<211> LENGTH: 345
<212> TYPE: DNA
<213> ORGANISM: Acinetobacter sp. ADP1

<400> SEQUENCE: 102
atggtcgtct acacgtggcc gaaatgtcgt tgcattaact ttcagaaaat ccaatacagc 60
atcaaactga cagcgatcaa aacgcctcga gcaatgcgcc gcattcccgt gtctgatatt 120
gaacaacggg tgaagcaggc cgtggcagaa cagctcggca tcaaagccga agaaatcaag 180
aatgaggctt cgttcatgga tgacttgggt gccgacagtc tggatctcgt cgagctggtg 240
atgagctttg agaatgattt tgatatcacc attccggatg aagactcgaa cgagatcact 300
accgttcaat ccgcgattga ctacgtgacc aagaagctgg gttag 345

<210> SEQ ID NO 103
<211> LENGTH: 114
<212> TYPE: PRT
<213> ORGANISM: Acinetobacter sp. ADP1

<400> SEQUENCE: 103

```
Met Val Val Tyr Thr Trp Pro Lys Cys Arg Cys Ile Asn Phe Gln Lys
 1               5                  10                  15

Ile Gln Tyr Ser Ile Lys Leu Thr Ala Ile Lys Thr Pro Arg Ala Met
            20                  25                  30

Arg Arg Ile Pro Val Ser Asp Ile Glu Gln Arg Val Lys Gln Ala Val
        35                  40                  45

Ala Glu Gln Leu Gly Ile Lys Ala Glu Glu Ile Lys Asn Glu Ala Ser
    50                  55                  60

Phe Met Asp Asp Leu Gly Ala Asp Ser Leu Asp Leu Val Glu Leu Val
65                  70                  75                  80

Met Ser Phe Glu Asn Asp Phe Asp Ile Thr Ile Pro Asp Glu Asp Ser
                85                  90                  95

Asn Glu Ile Thr Thr Val Gln Ser Ala Ile Asp Tyr Val Thr Lys Lys
            100                 105                 110

Leu Gly


<210> SEQ ID NO 104
<211> LENGTH: 246
<212> TYPE: DNA
<213> ORGANISM: Spinacia oleracea

<400> SEQUENCE: 104

gcaaagaagg aaacaattga caaagtgtgc gacattgtaa aggagaaact ggctttagga      60

gctgatgttg tggtcacagc tgattccgag tttagtaaac tcggtgctga ttcattggac     120

acggttgaga tagtgatgaa cctcgaggaa gagttcggta tcaatgtgga tgaagataaa     180

gctcaagata tatcaaccat ccaacaagcc gccgacgtta ttgagagtct tcttgagaag     240

aaatag                                                                246


<210> SEQ ID NO 105
<211> LENGTH: 81
<212> TYPE: PRT
<213> ORGANISM: Spinacia oleracea

<400> SEQUENCE: 105

Ala Lys Lys Glu Thr Ile Asp Lys Val Cys Asp Ile Val Lys Glu Lys
 1               5                  10                  15

Leu Ala Leu Gly Ala Asp Val Val Val Thr Ala Asp Ser Glu Phe Ser
            20                  25                  30

Lys Leu Gly Ala Asp Ser Leu Asp Thr Val Glu Ile Val Met Asn Leu
        35                  40                  45

Glu Glu Glu Phe Gly Ile Asn Val Asp Glu Asp Lys Ala Gln Asp Ile
    50                  55                  60

Ser Thr Ile Gln Gln Ala Ala Asp Val Ile Glu Ser Leu Leu Glu Lys
65                  70                  75                  80

Lys


<210> SEQ ID NO 106
<211> LENGTH: 1953
<212> TYPE: DNA
<213> ORGANISM: Synechococcus elongatus PCC 7942 0918

<400> SEQUENCE: 106

atggtgactg gaaccgccct cgcgcaaccc cgcgccatta cgccccacga acagcagctt      60

ttggccaaac tgaaaagcta tcgcgatatc caaagcttgt cgcaaatttg gggacgtgct     120

gccagtcaat ttggatcgat gccggctttg gttgcacccc atgccaaacc agcgatcacc     180
```

```
ctcagttatc aagaattggc gattcagatc caagcgtttg cagccggact gctcgcgctg    240

ggagtgccta cctccacagc cgatgacttt ccgcctcgct tggcgcagtt tgcggataac    300

agccccgct ggttgattgc tgaccaaggc acgttgctgg caggggctgc caatgcggtg    360

cgcggcgccc aagctgaagt atcggagctg ctctacgtct tagaggacag cggttcgatc    420

ggcttgattg tcgaagacgc ggcgctgctg aagaaactac agcctggttt agcgtcacta    480

tcgctgcagt ttgtgatcgt gctcagcgat gaagtagtcg agatcgacag cctgcgcgtc    540

gttggtttta gtgacgtgct ggagatgggg cgatcgctgc cggcaccgga gccaattttg    600

cagctcgatc gcttagccac tttgatctat acctcgggca ccacaggccc accgaagggc    660

gtgatgcttt ctcacggcaa cctgctgcac caagtcacaa cattaggtgt ggttgtgcag    720

ccgcaacctg gcgacaccgt gctgagtatt ttgccgactt ggcactccta cgagcgagct    780

tgtgaatatt tcctgctctc ccagggctgc acacaggtct acacgacgct gcgcaatgtc    840

aaacaagaca tccggcagta tcggccgcag ttcatggtca gtgtgctgcg cctctgggaa    900

tcgatctacg agggcgtgca gaagcagttt cgcgagcaac cggcgaagaa acgtcgcttg    960

atcgatacct tctttggctt gagtcaacgc tatgttttgg cacggcgccg ctggcaagga   1020

ctggatttgc tggcactgaa ccaatcccca gcccagcgcc tcgctgaggg tgtccggatg   1080

ttggcgctag caccgttgca taagctgggc gatcgcctcg tctacggcaa agtacgagaa   1140

gccacgggtg gccgaattcg gcaggtgatc agtggcggtg gctcactggc actgcacctc   1200

gataccttct tcgaaattgt tggtgttgat ttgctggtgg gttatggctt gacagaaacc   1260

tcaccagtgc tgacggggcg acggccttgg cacaacctac ggggttcggc cggtcagccg   1320

attccaggta cggcgattcg gatcgtcgat cctgaaacga aggaaaaccg acccagtggc   1380

gatcgcggct tggtgctggc gaaagggccg caaatcatgc agggctactt caataaaccc   1440

gaggcgaccg cgaaagcgat cgatgccgaa ggttggtttg acaccggcga cttaggctac   1500

atcgtcggtg aaggcaactt ggtgctaacg gggcgcgcta aggacacgat cgtgctgacc   1560

aatggcgaaa acattgaacc ccagccgatt gaagatgcct gcctacgaag ttcctatatc   1620

agccaaatca tgttggtggg acaagaccgc aagagtttgg gggcgttgat tgtgcccaat   1680

caagaggcga tcgcactctg ggccagcgaa cagggcatca gccaaaccga tctgcaggga   1740

gtggtacaga agctgattcg cgaggaactg aaccgcgaag tgcgcgatcg cccgggctac   1800

cgcatcgacg atcgcattgg accattccgc ctcatcgaag aaccgttcag catggaaaat   1860

ggccagctaa cccaaaccct gaaaatccgt cgcaacgttg tcgcggaaca ctacgcggct   1920

atgatcgacg ggatgtttga atcggcgagt taa                                1953
```

<210> SEQ ID NO 107
<211> LENGTH: 650
<212> TYPE: PRT
<213> ORGANISM: Synechococcus elongatus PCC 7942 0918

<400> SEQUENCE: 107

```
Met Val Thr Gly Thr Ala Leu Ala Gln Pro Arg Ala Ile Thr Pro His
 1               5                   10                  15

Glu Gln Gln Leu Leu Ala Lys Leu Lys Ser Tyr Arg Asp Ile Gln Ser
            20                  25                  30

Leu Ser Gln Ile Trp Gly Arg Ala Ala Ser Gln Phe Gly Ser Met Pro
        35                  40                  45

Ala Leu Val Ala Pro His Ala Lys Pro Ala Ile Thr Leu Ser Tyr Gln
```

```
    50                  55                  60

Glu Leu Ala Ile Gln Ile Gln Ala Phe Ala Ala Gly Leu Leu Ala Leu
65                  70                  75                  80

Gly Val Pro Thr Ser Thr Ala Asp Asp Phe Pro Pro Arg Leu Ala Gln
                85                  90                  95

Phe Ala Asp Asn Ser Pro Arg Trp Leu Ile Ala Asp Gln Gly Thr Leu
            100                 105                 110

Leu Ala Gly Ala Ala Asn Ala Val Arg Gly Ala Gln Ala Glu Val Ser
        115                 120                 125

Glu Leu Leu Tyr Val Leu Glu Asp Ser Gly Ser Ile Gly Leu Ile Val
    130                 135                 140

Glu Asp Ala Ala Leu Leu Lys Lys Leu Gln Pro Gly Leu Ala Ser Leu
145                 150                 155                 160

Ser Leu Gln Phe Val Ile Val Leu Ser Asp Glu Val Val Glu Ile Asp
                165                 170                 175

Ser Leu Arg Val Val Gly Phe Ser Asp Val Leu Glu Met Gly Arg Ser
            180                 185                 190

Leu Pro Ala Pro Glu Pro Ile Leu Gln Leu Asp Arg Leu Ala Thr Leu
        195                 200                 205

Ile Tyr Thr Ser Gly Thr Thr Gly Pro Pro Lys Gly Val Met Leu Ser
    210                 215                 220

His Gly Asn Leu Leu His Gln Val Thr Thr Leu Gly Val Val Val Gln
225                 230                 235                 240

Pro Gln Pro Gly Asp Thr Val Leu Ser Ile Leu Pro Thr Trp His Ser
                245                 250                 255

Tyr Glu Arg Ala Cys Glu Tyr Phe Leu Leu Ser Gln Gly Cys Thr Gln
            260                 265                 270

Val Tyr Thr Thr Leu Arg Asn Val Lys Gln Asp Ile Arg Gln Tyr Arg
        275                 280                 285

Pro Gln Phe Met Val Ser Val Leu Arg Leu Trp Glu Ser Ile Tyr Glu
    290                 295                 300

Gly Val Gln Lys Gln Phe Arg Glu Gln Pro Ala Lys Lys Arg Arg Leu
305                 310                 315                 320

Ile Asp Thr Phe Phe Gly Leu Ser Gln Arg Tyr Val Leu Ala Arg Arg
                325                 330                 335

Arg Trp Gln Gly Leu Asp Leu Leu Ala Leu Asn Gln Ser Pro Ala Gln
            340                 345                 350

Arg Leu Ala Glu Gly Val Arg Met Leu Ala Leu Ala Pro Leu His Lys
        355                 360                 365

Leu Gly Asp Arg Leu Val Tyr Gly Lys Val Arg Glu Ala Thr Gly Gly
    370                 375                 380

Arg Ile Arg Gln Val Ile Ser Gly Gly Gly Ser Leu Ala Leu His Leu
385                 390                 395                 400

Asp Thr Phe Phe Glu Ile Val Gly Val Asp Leu Leu Val Gly Tyr Gly
                405                 410                 415

Leu Thr Glu Thr Ser Pro Val Leu Thr Gly Arg Arg Pro Trp His Asn
            420                 425                 430

Leu Arg Gly Ser Ala Gly Gln Pro Ile Pro Gly Thr Ala Ile Arg Ile
        435                 440                 445

Val Asp Pro Glu Thr Lys Glu Asn Arg Pro Ser Gly Asp Arg Gly Leu
    450                 455                 460

Val Leu Ala Lys Gly Pro Gln Ile Met Gln Gly Tyr Phe Asn Lys Pro
465                 470                 475                 480
```

```
Glu Ala Thr Ala Lys Ala Ile Asp Ala Glu Gly Trp Phe Asp Thr Gly
                485                 490                 495

Asp Leu Gly Tyr Ile Val Gly Glu Gly Asn Leu Val Leu Thr Gly Arg
            500                 505                 510

Ala Lys Asp Thr Ile Val Leu Thr Asn Gly Glu Asn Ile Glu Pro Gln
        515                 520                 525

Pro Ile Glu Asp Ala Cys Leu Arg Ser Ser Tyr Ile Ser Gln Ile Met
    530                 535                 540

Leu Val Gly Gln Asp Arg Lys Ser Leu Gly Ala Leu Ile Val Pro Asn
545                 550                 555                 560

Gln Glu Ala Ile Ala Leu Trp Ala Ser Glu Gln Gly Ile Ser Gln Thr
                565                 570                 575

Asp Leu Gln Gly Val Val Gln Lys Leu Ile Arg Glu Glu Leu Asn Arg
            580                 585                 590

Glu Val Arg Asp Arg Pro Gly Tyr Arg Ile Asp Asp Arg Ile Gly Pro
        595                 600                 605

Phe Arg Leu Ile Glu Glu Pro Phe Ser Met Glu Asn Gly Gln Leu Thr
    610                 615                 620

Gln Thr Leu Lys Ile Arg Arg Asn Val Val Ala Glu His Tyr Ala Ala
625                 630                 635                 640

Met Ile Asp Gly Met Phe Glu Ser Ala Ser
                645                 650
```

<210> SEQ ID NO 108
<211> LENGTH: 1161
<212> TYPE: DNA
<213> ORGANISM: Acinetobacter sp ADP1

<400> SEQUENCE: 108

```
atggcgttta gatttattga ggggattccc acaagtttgg gcgtgttcgg tgtggtaggt     60

tcattgtgta tgtcgcatgc acatgcaatt gaagctgtac agacttctgc aacaattacg    120

cccaccagtc ctgcggcttg cattggtttg gagtcgaatt cagatcgtct ggcttgttat    180

gatgctctgt ttaaagtagc agatacggca aaaacaactc cagttattga acaaaaagct    240

gctttgaacc cttcgccgtc ggtagagcag tctgagctca atcctcaatc tattaaggaa    300

aaaattggta atctttttgc gattgaaggt ccaagaattg atccgaatac atccttactg    360

gataggcgct gggagctctc cgaaaaatca aaattaggta catggaatat tcgtggttat    420

aaacctgtct atttattacc tatttttttgg acatctaaaa agaatgaatt tccttcgagt    480

ccaaatcctg aaaatacagt gcatgaaaat cagaatttaa cttcggctga atccaagttt    540

caattatctt taaaaaccaa agcctgggaa aatatttttg gcaataacgg agatttatgg    600

ctagggtata cccagtcttc tcgttggcag gtttacaatg cagacgagtc acgtccgttt    660

cgtgaaacca attatgaacc tgaggcaagc ctaattttcc gaaccaatta tgagttcttg    720

ggattaaacg gccgactttt gggggtaact ttaaatcacc agtcaaatgg tcgttctgat    780

ccattatcaa gaagctggaa tcgtgtcatc tttaatatag gattagagcg agataatttt    840

gcgctggtac tcagaccatg gattcgtatt caagaagaag ccaagaacga caataatccc    900

gatatcgagg attatgtagg acgtggtgat ttaactgctt tttatcgctg gaaagataat    960

gatttttctt taatgctgcg tcattcatta aaagatggtg ataaatcgca tggtgcggtg   1020

cagtttgatt gggctttccc aatttcaggt aagcttcgtg gaaattttca gttatttaat   1080

ggttacggtg aaagcctgat tgattataac catcgtgcaa cttatgttgg tttgggcgtt   1140
```

-continued tcactgatga actggtattg a 1161

<210> SEQ ID NO 109
<211> LENGTH: 386
<212> TYPE: PRT
<213> ORGANISM: Acinetobacter sp ADP1

<400> SEQUENCE: 109

Met Ala Phe Arg Phe Ile Glu Gly Ile Pro Thr Ser Leu Gly Val Phe
1 5 10 15

Gly Val Val Gly Ser Leu Cys Met Ser His Ala His Ala Ile Glu Ala
20 25 30

Val Gln Thr Ser Ala Thr Ile Thr Pro Thr Ser Pro Ala Ala Cys Ile
35 40 45

Gly Leu Glu Ser Asn Ser Asp Arg Leu Ala Cys Tyr Asp Ala Leu Phe
50 55 60

Lys Val Ala Asp Thr Ala Lys Thr Thr Pro Val Ile Glu Gln Lys Ala
65 70 75 80

Ala Leu Asn Pro Ser Pro Ser Val Glu Gln Ser Glu Leu Asn Pro Gln
85 90 95

Ser Ile Lys Glu Lys Ile Gly Asn Leu Phe Ala Ile Glu Gly Pro Arg
100 105 110

Ile Asp Pro Asn Thr Ser Leu Leu Asp Arg Arg Trp Glu Leu Ser Glu
115 120 125

Lys Ser Lys Leu Gly Thr Trp Asn Ile Arg Gly Tyr Lys Pro Val Tyr
130 135 140

Leu Leu Pro Ile Phe Trp Thr Ser Lys Lys Asn Glu Phe Pro Ser Ser
145 150 155 160

Pro Asn Pro Glu Asn Thr Val His Glu Asn Gln Asn Leu Thr Ser Ala
165 170 175

Glu Ser Lys Phe Gln Leu Ser Leu Lys Thr Lys Ala Trp Glu Asn Ile
180 185 190

Phe Gly Asn Asn Gly Asp Leu Trp Leu Gly Tyr Thr Gln Ser Ser Arg
195 200 205

Trp Gln Val Tyr Asn Ala Asp Glu Ser Arg Pro Phe Arg Glu Thr Asn
210 215 220

Tyr Glu Pro Glu Ala Ser Leu Ile Phe Arg Thr Asn Tyr Glu Phe Leu
225 230 235 240

Gly Leu Asn Gly Arg Leu Leu Gly Val Thr Leu Asn His Gln Ser Asn
245 250 255

Gly Arg Ser Asp Pro Leu Ser Arg Ser Trp Asn Arg Val Ile Phe Asn
260 265 270

Ile Gly Leu Glu Arg Asp Asn Phe Ala Leu Val Leu Arg Pro Trp Ile
275 280 285

Arg Ile Gln Glu Glu Ala Lys Asn Asp Asn Asn Pro Asp Ile Glu Asp
290 295 300

Tyr Val Gly Arg Gly Asp Leu Thr Ala Phe Tyr Arg Trp Lys Asp Asn
305 310 315 320

Asp Phe Ser Leu Met Leu Arg His Ser Leu Lys Asp Gly Asp Lys Ser
325 330 335

His Gly Ala Val Gln Phe Asp Trp Ala Phe Pro Ile Ser Gly Lys Leu
340 345 350

Arg Gly Asn Phe Gln Leu Phe Asn Gly Tyr Gly Glu Ser Leu Ile Asp
355 360 365

Tyr Asn His Arg Ala Thr Tyr Val Gly Leu Gly Val Ser Leu Met Asn
    370                 375                 380

Trp Tyr
385

<210> SEQ ID NO 110
<211> LENGTH: 870
<212> TYPE: DNA
<213> ORGANISM: Escherichia coli

<400> SEQUENCE: 110
atgcggactc tgcagggctg gttgttgccg gtgtttatgt tgcctatggc agtatatgca 60
caagaggcaa cggtgaaaga ggtgcatgac gcgccagcgg tgcgtggcag tattatcgcc 120
aatatgctgc aggagcatga caatccgttc acgctctatc cttatgacac caactacctc 180
atttacaccc aaaccagcga tctgaataaa gaagcgattg ccagttacga ctgggcggaa 240
aatgcgcgta aggatgaagt aaagtttcag ttgagcctgg catttccgct gtggcgtggg 300
attttaggcc cgaactcggt gttgggtgcg tcttatacgc aaaaatcctg gtggcaactg 360
tccaatagcg aagagtcttc accgtttcgt gaaaccaact acgaaccgca attgttcctc 420
ggttttgcca ccgattaccg ttttgcaggt tggacgctgc gcgatgtgga gatggggtat 480
aaccacgact ctaacgggcg ttccgacccg acctcccgca gctggaaccg cctttatact 540
cgcctgatgg cagaaaacgg taactggctg gtagaagtga agccgtggta tgtggtgggt 600
aatactgacg ataacccgga tatcaccaaa tatatgggtt actaccagct taaaatcggc 660
tatcacctcg gtgatgcggt gctcagtgcg aaaggacagt acaactggaa caccggctac 720
ggcggcgcgg agttaggctt aagttacccg atcaccaaac atgtgcgcct ttatactcag 780
gtttacagcg gctatggcga atcgctcatc gactataact tcaaccagac ccgtgtcggt 840
gtgggggtta tgctaaacga tttgttttga 870

<210> SEQ ID NO 111
<211> LENGTH: 289
<212> TYPE: PRT
<213> ORGANISM: Escherichia coli

<400> SEQUENCE: 111

Met Arg Thr Leu Gln Gly Trp Leu Leu Pro Val Phe Met Leu Pro Met
1               5                   10                  15

Ala Val Tyr Ala Gln Glu Ala Thr Val Lys Glu Val His Asp Ala Pro
            20                  25                  30

Ala Val Arg Gly Ser Ile Ile Ala Asn Met Leu Gln Glu His Asp Asn
        35                  40                  45

Pro Phe Thr Leu Tyr Pro Tyr Asp Thr Asn Tyr Leu Ile Tyr Thr Gln
    50                  55                  60

Thr Ser Asp Leu Asn Lys Glu Ala Ile Ala Ser Tyr Asp Trp Ala Glu
65                  70                  75                  80

Asn Ala Arg Lys Asp Glu Val Lys Phe Gln Leu Ser Leu Ala Phe Pro
                85                  90                  95

Leu Trp Arg Gly Ile Leu Gly Pro Asn Ser Val Leu Gly Ala Ser Tyr
            100                 105                 110

Thr Gln Lys Ser Trp Trp Gln Leu Ser Asn Ser Glu Glu Ser Ser Pro
        115                 120                 125

Phe Arg Glu Thr Asn Tyr Glu Pro Gln Leu Phe Leu Gly Phe Ala Thr
    130                 135                 140

```
Asp Tyr Arg Phe Ala Gly Trp Thr Leu Arg Asp Val Glu Met Gly Tyr
145                 150                 155                 160

Asn His Asp Ser Asn Gly Arg Ser Asp Pro Thr Ser Arg Ser Trp Asn
                165                 170                 175

Arg Leu Tyr Thr Arg Leu Met Ala Glu Asn Gly Asn Trp Leu Val Glu
            180                 185                 190

Val Lys Pro Trp Tyr Val Val Gly Asn Thr Asp Asp Asn Pro Asp Ile
        195                 200                 205

Thr Lys Tyr Met Gly Tyr Tyr Gln Leu Lys Ile Gly Tyr His Leu Gly
    210                 215                 220

Asp Ala Val Leu Ser Ala Lys Gly Gln Tyr Asn Trp Asn Thr Gly Tyr
225                 230                 235                 240

Gly Gly Ala Glu Leu Gly Leu Ser Tyr Pro Ile Thr Lys His Val Arg
                245                 250                 255

Leu Tyr Thr Gln Val Tyr Ser Gly Tyr Gly Glu Ser Leu Ile Asp Tyr
            260                 265                 270

Asn Phe Asn Gln Thr Arg Val Gly Val Gly Val Met Leu Asn Asp Leu
        275                 280                 285

Phe


<210> SEQ ID NO 112
<211> LENGTH: 1188
<212> TYPE: DNA
<213> ORGANISM: Streptomyces coelicolor A3(2)

<400> SEQUENCE: 112

atgaccgtcg ttgaaccgac tcccggtgcc gaccgggtca gcatccaacg gctgcgtcgc     60

cgtttggaaa ggctgatcgg tgtcgccgcc accgaaggga acgaactcgt cgcgctgcgc    120

aacggcgacg agatcttccc cgccatgctg gggcgatcc gggcggccga gcacacgatc    180

gacatgatga cgttcgtgta ctggcgcggg cagatagccc gcgacttcgc cgccgctctc    240

gccgaccggg cccggtcggg agtacgggtc cggctgctgc tggacggctt cggcgccaag    300

gagatcgaac aggacctgct ggacgctatg gaggccgcgg gagtacagat cgcctggttc    360

cgtaaaccgc tgtggctgtc gccgttcaag cagaaccacc gctgccaccg caaggccctc    420

gtcattgacg agcacactgc cttcaccgga ggcgtcggca tcgccgagga gtggtgcggc    480

gacgcccgcg gccccggcga gtggcgcgac acccacgtcc aggtgcgcgg cccggccgtg    540

gacggcgtcg ccgccgcctt cgcccagaac tgggccgagt gccacgacga gttgtacgac    600

gaccgggacc ggttctccga tcacacccag cccggcacat ccatcgtcca ggtggtgcgc    660

ggttcggcca gcttcggttg gcaggacatg cagaccctca tccgcgtcat gctcacctcc    720

gcggagcacc gcttccgcct ggcgaccgcc tacttcgccc cggatacata cttcatcgac    780

ctgctctgcg ccaccgcccg gcgcggtgtc acggtggaga tcctgctccc cggcccgcat    840

acggaccagc gggcctgcca actggccggc cagtaccact acacccgttt gctggacgcc    900

ggggtgtcaa ttcgcgagta ccagccgacc atgatgcacg ccaagatcat caccgtggac    960

gggctggccg ccctgatcgg gtccaccaac ttcaaccggc gctccatgga ccacgacgag   1020

gagatcatgc tcgccgtcct ggaccaggag ttcaccaacg gcctggaccg ggacttcgac   1080

gccgacctgg aacgcagcac cgccatcgag ccgacccgct ggaagcgccg cgccaccctg   1140

cgacgcctcc gggagacggc cgtcctgccc ctgcgccggt tcctgtga                1188
```

<210> SEQ ID NO 113
<211> LENGTH: 395
<212> TYPE: PRT
<213> ORGANISM: Streptomyces coelicolor A3(2)

<400> SEQUENCE: 113

```
Met Thr Val Val Glu Pro Thr Pro Gly Ala Asp Arg Val Ser Ile Gln
 1               5                  10                  15

Arg Leu Arg Arg Arg Leu Glu Arg Leu Ile Gly Val Ala Ala Thr Glu
            20                  25                  30

Gly Asn Glu Leu Val Ala Leu Arg Asn Gly Asp Glu Ile Phe Pro Ala
        35                  40                  45

Met Leu Gly Ala Ile Arg Ala Ala Glu His Thr Ile Asp Met Met Thr
    50                  55                  60

Phe Val Tyr Trp Arg Gly Gln Ile Ala Arg Asp Phe Ala Ala Ala Leu
65                  70                  75                  80

Ala Asp Arg Ala Arg Ser Gly Val Arg Val Arg Leu Leu Leu Asp Gly
                85                  90                  95

Phe Gly Ala Lys Glu Ile Glu Gln Asp Leu Leu Asp Ala Met Glu Ala
            100                 105                 110

Ala Gly Val Gln Ile Ala Trp Phe Arg Lys Pro Leu Trp Leu Ser Pro
        115                 120                 125

Phe Lys Gln Asn His Arg Cys His Arg Lys Ala Leu Val Ile Asp Glu
    130                 135                 140

His Thr Ala Phe Thr Gly Gly Val Gly Ile Ala Glu Glu Trp Cys Gly
145                 150                 155                 160

Asp Ala Arg Gly Pro Gly Glu Trp Arg Asp Thr His Val Gln Val Arg
                165                 170                 175

Gly Pro Ala Val Asp Gly Val Ala Ala Ala Phe Ala Gln Asn Trp Ala
            180                 185                 190

Glu Cys His Asp Glu Leu Tyr Asp Asp Arg Asp Arg Phe Ser Asp His
        195                 200                 205

Thr Gln Pro Gly Thr Ser Ile Val Gln Val Val Arg Gly Ser Ala Ser
    210                 215                 220

Phe Gly Trp Gln Asp Met Gln Thr Leu Ile Arg Val Met Leu Thr Ser
225                 230                 235                 240

Ala Glu His Arg Phe Arg Leu Ala Thr Ala Tyr Phe Ala Pro Asp Thr
                245                 250                 255

Tyr Phe Ile Asp Leu Leu Cys Ala Thr Ala Arg Arg Gly Val Thr Val
            260                 265                 270

Glu Ile Leu Leu Pro Gly Pro His Thr Asp Gln Arg Ala Cys Gln Leu
        275                 280                 285

Ala Gly Gln Tyr His Tyr Thr Arg Leu Leu Asp Ala Gly Val Ser Ile
    290                 295                 300

Arg Glu Tyr Gln Pro Thr Met Met His Ala Lys Ile Ile Thr Val Asp
305                 310                 315                 320

Gly Leu Ala Ala Leu Ile Gly Ser Thr Asn Phe Asn Arg Arg Ser Met
                325                 330                 335

Asp His Asp Glu Glu Ile Met Leu Ala Val Leu Asp Gln Glu Phe Thr
            340                 345                 350

Asn Gly Leu Asp Arg Asp Phe Asp Ala Asp Leu Glu Arg Ser Thr Ala
        355                 360                 365

Ile Glu Pro Thr Arg Trp Lys Arg Arg Ala Thr Leu Arg Arg Leu Arg
    370                 375                 380
```

Glu Thr Ala Val Leu Pro Leu Arg Arg Phe Leu
385 390 395

<210> SEQ ID NO 114
<211> LENGTH: 658
<212> TYPE: DNA
<213> ORGANISM: Arabidopsis thaliana

<400> SEQUENCE: 114
attcgtcttc taccttcttc taactcactt cattttcacc aaaaccaaca aatatattct 60
tctcactttc cgagctttcc agttcaacta tggcggctcc gatcatactt ttctctttcc 120
ttttattctt ctctgtctct gtctcggcac ttaacgtcgg tgttcagctc atacatccct 180
ccatttcctt gactaaagaa tgtagccgga aatgtgaatc agagttttgt tcagtgcctc 240
catttctgag gtatgggaag tactgtggac tactttacag tggatgtcct ggtgagagac 300
cttgtgatgg tcttgattct tgttgcatga aacatgatgc ttgtgtccaa tccaagaata 360
atgattatct aagccaagag tgtagtcaga agttcattaa ctgcatgaac aatttcagcc 420
agaagaagca accgacgttc aaaggtaaca aatgcgacgc tgatgaagtg attgatgtca 480
tctccattgt catggaagct gctcttatcg ccggcaaagt cctcaagaaa ccctaactat 540
ttatatatat ttttctatat ttctagttac aattgtttcc ctttttttcc ccctcaggac 600
atttgtctta atttatcaaa atactattaa gtaatactat agcttttttt tttttgtc 658

<210> SEQ ID NO 115
<211> LENGTH: 148
<212> TYPE: PRT
<213> ORGANISM: Arabidopsis thaliana

<400> SEQUENCE: 115

Met Ala Ala Pro Ile Ile Leu Phe Ser Phe Leu Leu Phe Phe Ser Val
1 5 10 15

Ser Val Ser Ala Leu Asn Val Gly Val Gln Leu Ile His Pro Ser Ile
20 25 30

Ser Leu Thr Lys Glu Cys Ser Arg Lys Cys Glu Ser Glu Phe Cys Ser
35 40 45

Val Pro Pro Phe Leu Arg Tyr Gly Lys Tyr Cys Gly Leu Leu Tyr Ser
50 55 60

Gly Cys Pro Gly Glu Arg Pro Cys Asp Gly Leu Asp Ser Cys Cys Met
65 70 75 80

Lys His Asp Ala Cys Val Gln Ser Lys Asn Asn Asp Tyr Leu Ser Gln
85 90 95

Glu Cys Ser Gln Lys Phe Ile Asn Cys Met Asn Asn Phe Ser Gln Lys
100 105 110

Lys Gln Pro Thr Phe Lys Gly Asn Lys Cys Asp Ala Asp Glu Val Ile
115 120 125

Asp Val Ile Ser Ile Val Met Glu Ala Ala Leu Ile Ala Gly Lys Val
130 135 140

Leu Lys Lys Pro
145

<210> SEQ ID NO 116
<211> LENGTH: 1074
<212> TYPE: DNA
<213> ORGANISM: Arabidopsis thaliana

<400> SEQUENCE: 116

```
atggagtatc aggggcttca aaattgggac ggtcttttag acccattgga cgacaatctc      60

cggcgagaga ttctccggta cggtcaattt gtcgaatcgg cttatcaagc atttgatttc     120

gatccttcct ctccaaccta cgggacatgc cggtttccga ggagcacgtt gttagagcga     180

tccggtttac ccaactccgg ttatcgacta acgaagaacc ttcgtgccac gtcaggtatt     240

aacttgccac gttggattga gaaagcgcca agctggatgg ctacacaatc tagctggatt     300

ggttacgtgg cagtttgcca ggacaaagaa gagatctcgc ggcttgggcg tagagacgtc     360

gtcatctcct tccgtggaac cgccacgtgt ctcgagtggt tagagaacct tcgcgccacg     420

ctgactcatc tccctaatgg gcctactgga gcaaatctaa acgggtctaa ctctgggccc     480

atggttgaga gcgggttttt aagcttgtat acttcaggtg ttcacagttt gagagacatg     540

gtaagagaag agatcgcaag gctactccaa tcttacggcg acgagccgtt aagtgtaacg     600

ataaccggtc acagcctcgg cgctgcgatc gcgacactag cagcttacga tatcaaaacg     660

acgtttaaac gtgcgcctat ggttaccgta atatctttcg gaggtccacg tgtcggaaac     720

agatgctttc ggaaactcct tgagaagcaa ggcacgaagg ttctaagaat cgtgaactcc     780

gacgacgtca tcaccaaagt tcctggagtt gttttagaaa acagagagca agataacgtt     840

aagatgacag cgtcgataat gccgagctgg atacagagac gcgtggagga gacgccgtgg     900

gtttacgctg aaatcggtaa ggagcttcgg ctgagtagcc gtgactcgcc gcacttgagc     960

agcatcaatg tggccacgtg tcatgagctg aaaacgtatt tacatttggt agacgggttt    1020

gtgagctcca cgtgtccatt cagagaaaca gctcggagag ttctccatag atga          1074
```

```
<210> SEQ ID NO 117
<211> LENGTH: 357
<212> TYPE: PRT
<213> ORGANISM: Arabidopsis thaliana

<400> SEQUENCE: 117

Met Glu Tyr Gln Gly Leu Gln Asn Trp Asp Gly Leu Leu Asp Pro Leu
 1               5                  10                  15

Asp Asp Asn Leu Arg Arg Glu Ile Leu Arg Tyr Gly Gln Phe Val Glu
            20                  25                  30

Ser Ala Tyr Gln Ala Phe Asp Phe Asp Pro Ser Ser Pro Thr Tyr Gly
        35                  40                  45

Thr Cys Arg Phe Pro Arg Ser Thr Leu Leu Glu Arg Ser Gly Leu Pro
    50                  55                  60

Asn Ser Gly Tyr Arg Leu Thr Lys Asn Leu Arg Ala Thr Ser Gly Ile
65                  70                  75                  80

Asn Leu Pro Arg Trp Ile Glu Lys Ala Pro Ser Trp Met Ala Thr Gln
                85                  90                  95

Ser Ser Trp Ile Gly Tyr Val Ala Val Cys Gln Asp Lys Glu Glu Ile
            100                 105                 110

Ser Arg Leu Gly Arg Arg Asp Val Val Ile Ser Phe Arg Gly Thr Ala
        115                 120                 125

Thr Cys Leu Glu Trp Leu Glu Asn Leu Arg Ala Thr Leu Thr His Leu
    130                 135                 140

Pro Asn Gly Pro Thr Gly Ala Asn Leu Asn Gly Ser Asn Ser Gly Pro
145                 150                 155                 160

Met Val Glu Ser Gly Phe Leu Ser Leu Tyr Thr Ser Gly Val His Ser
                165                 170                 175

Leu Arg Asp Met Val Arg Glu Glu Ile Ala Arg Leu Leu Gln Ser Tyr
            180                 185                 190
```

Gly Asp Glu Pro Leu Ser Val Thr Ile Thr Gly His Ser Leu Gly Ala
195 200 205

Ala Ile Ala Thr Leu Ala Ala Tyr Asp Ile Lys Thr Thr Phe Lys Arg
210 215 220

Ala Pro Met Val Thr Val Ile Ser Phe Gly Gly Pro Arg Val Gly Asn
225 230 235 240

Arg Cys Phe Arg Lys Leu Leu Glu Lys Gln Gly Thr Lys Val Leu Arg
245 250 255

Ile Val Asn Ser Asp Asp Val Ile Thr Lys Val Pro Gly Val Val Leu
260 265 270

Glu Asn Arg Glu Gln Asp Asn Val Lys Met Thr Ala Ser Ile Met Pro
275 280 285

Ser Trp Ile Gln Arg Arg Val Glu Glu Thr Pro Trp Val Tyr Ala Glu
290 295 300

Ile Gly Lys Glu Leu Arg Leu Ser Ser Arg Asp Ser Pro His Leu Ser
305 310 315 320

Ser Ile Asn Val Ala Thr Cys His Glu Leu Lys Thr Tyr Leu His Leu
325 330 335

Val Asp Gly Phe Val Ser Ser Thr Cys Pro Phe Arg Glu Thr Ala Arg
340 345 350

Arg Val Leu His Arg
355

<210> SEQ ID NO 118
<211> LENGTH: 1416
<212> TYPE: DNA
<213> ORGANISM: Arabidopsis thaliana

<400> SEQUENCE: 118
atggcggcca aagtcttcac tcagaaccct atctattctc aatctctagt tagagacaaa 60
actcctcaac agaaacacaa tcttgaccat ttctctatat cccagcacac ctctaaaaga 120
ctcgttgtct cttcttctac aatgtcccct ccgatttcat cttctccact ctctcttcct 180
tcttcttctt cttctcaggc cattcctcct tctcgagcac ctgcagtgac tctaccgttg 240
tctcgggttt ggagagagat acaagggagc aataactggg aaaatctcat tgaacctcta 300
agccctattc tccaacaaga gatcactcgc tacgggaact tactctccgc ttcttacaaa 360
gggtttgatc taaaccctaa ctccaaacgt tacttgagtt gcaagtatgg aaaaaagaac 420
ttgcttaaag aatccggaat ccatgaccct gatggctacc aagtcaccaa gtatatctac 480
gccacaccag acatcaacct caaccctatc aagaacgagc ctaaccgtgc acgttggatc 540
ggttatgtag cggtttcttc tgatgaatcg gtgaaacgtt tgggaaggag ggatattttg 600
gtgacgtttc gtggcactgt caccaaccat gagtggttag ctaacctaaa gagctctttg 660
actccggcta ggcttgatcc tcataaccct cgtcctgatg tcaaggtcga atccgggttc 720
ttaggtttat acacatccgg tgagagcgag agcaaattcg ggctagaaag ctgccgtgag 780
cagcttctct ccgagatctc gaggcttatg aacaagcaca aaggcgagga aataagcata 840
acacttgcgg gacatagtat ggggagttct ctagctcagc ttctagctta cgacatagcg 900
gaactcggta tgaaccagag aagggacgaa aaacctgttc cggtgaccgt gttttcgttt 960
gctggtccta gagttggtaa cttggggttc aaaaaacggt gtgaggagct aggagttaaa 1020
gtcttgagga tcacgaatgt aaacgatccg atcaccaaac ttccaggttt cttatttaat 1080
gagaatttca gatctttagg tggtgtttac gagcttcctt ggagctgttc ttgctacact 1140

```
cacgtgggag tcgaactcac cctcgatttc ttcgatgttc aaaacatttc ttgtgtccat   1200

gacctcgaga cttacatcac tctagtaaac cgtccgagat gctcgaaatt ggcggttaat   1260

gaagacaatt ttggcggcga gtttttgaac agaacaagtg aactgatgtt cagtaaggga   1320

cgacgtcaag cgttgcattt tacaaacgca gcgaccaatg cggcatatct actttgttct   1380

atatccaacc atatgttgta ttataatata ttttag                             1416


<210> SEQ ID NO 119
<211> LENGTH: 471
<212> TYPE: PRT
<213> ORGANISM: Arabidopsis thaliana

<400> SEQUENCE: 119

Met Ala Ala Lys Val Phe Thr Gln Asn Pro Ile Tyr Ser Gln Ser Leu
1               5                   10                  15

Val Arg Asp Lys Thr Pro Gln Gln Lys His Asn Leu Asp His Phe Ser
            20                  25                  30

Ile Ser Gln His Thr Ser Lys Arg Leu Val Val Ser Ser Ser Thr Met
        35                  40                  45

Ser Pro Pro Ile Ser Ser Ser Pro Leu Ser Leu Pro Ser Ser Ser Ser
    50                  55                  60

Ser Gln Ala Ile Pro Pro Ser Arg Ala Pro Ala Val Thr Leu Pro Leu
65                  70                  75                  80

Ser Arg Val Trp Arg Glu Ile Gln Gly Ser Asn Asn Trp Glu Asn Leu
                85                  90                  95

Ile Glu Pro Leu Ser Pro Ile Leu Gln Gln Glu Ile Thr Arg Tyr Gly
            100                 105                 110

Asn Leu Leu Ser Ala Ser Tyr Lys Gly Phe Asp Leu Asn Pro Asn Ser
        115                 120                 125

Lys Arg Tyr Leu Ser Cys Lys Tyr Gly Lys Lys Asn Leu Leu Lys Glu
    130                 135                 140

Ser Gly Ile His Asp Pro Asp Gly Tyr Gln Val Thr Lys Tyr Ile Tyr
145                 150                 155                 160

Ala Thr Pro Asp Ile Asn Leu Asn Pro Ile Lys Asn Glu Pro Asn Arg
                165                 170                 175

Ala Arg Trp Ile Gly Tyr Val Ala Val Ser Ser Asp Glu Ser Val Lys
            180                 185                 190

Arg Leu Gly Arg Arg Asp Ile Leu Val Thr Phe Arg Gly Thr Val Thr
        195                 200                 205

Asn His Glu Trp Leu Ala Asn Leu Lys Ser Ser Leu Thr Pro Ala Arg
    210                 215                 220

Leu Asp Pro His Asn Pro Arg Pro Asp Val Lys Val Glu Ser Gly Phe
225                 230                 235                 240

Leu Gly Leu Tyr Thr Ser Gly Glu Ser Glu Ser Lys Phe Gly Leu Glu
                245                 250                 255

Ser Cys Arg Glu Gln Leu Leu Ser Glu Ile Ser Arg Leu Met Asn Lys
            260                 265                 270

His Lys Gly Glu Glu Ile Ser Ile Thr Leu Ala Gly His Ser Met Gly
        275                 280                 285

Ser Ser Leu Ala Gln Leu Leu Ala Tyr Asp Ile Ala Glu Leu Gly Met
    290                 295                 300

Asn Gln Arg Arg Asp Glu Lys Pro Val Pro Val Thr Val Phe Ser Phe
305                 310                 315                 320
```

```
Ala Gly Pro Arg Val Gly Asn Leu Gly Phe Lys Lys Arg Cys Glu Glu
                325                 330                 335

Leu Gly Val Lys Val Leu Arg Ile Thr Asn Val Asn Asp Pro Ile Thr
            340                 345                 350

Lys Leu Pro Gly Phe Leu Phe Asn Glu Asn Phe Arg Ser Leu Gly Gly
        355                 360                 365

Val Tyr Glu Leu Pro Trp Ser Cys Ser Cys Tyr Thr His Val Gly Val
    370                 375                 380

Glu Leu Thr Leu Asp Phe Phe Asp Val Gln Asn Ile Ser Cys Val His
385                 390                 395                 400

Asp Leu Glu Thr Tyr Ile Thr Leu Val Asn Arg Pro Arg Cys Ser Lys
                405                 410                 415

Leu Ala Val Asn Glu Asp Asn Phe Gly Gly Glu Phe Leu Asn Arg Thr
            420                 425                 430

Ser Glu Leu Met Phe Ser Lys Gly Arg Arg Gln Ala Leu His Phe Thr
        435                 440                 445

Asn Ala Ala Thr Asn Ala Ala Tyr Leu Leu Cys Ser Ile Ser Asn His
    450                 455                 460

Met Leu Tyr Tyr Asn Ile Phe
465                 470


<210> SEQ ID NO 120
<211> LENGTH: 1285
<212> TYPE: DNA
<213> ORGANISM: Arabidopsis thaliana

<400> SEQUENCE: 120

aatcgccctc caagaaaaac aaaccgccat cgtgcggatc actcgtaacc atcctcagcc     60

ttgatggtgg tggagtcaga ggaatcatcg ccggagtaat ccttgccttt ctcgaaaaac    120

aacttcagga actcgatgga gaagaggcga ggcttgcgga ttacttcgac gtgatagctg    180

gaactagcac cggtggtctt gtgacggcga tgttgactgt accggacgag accggtcgac    240

ctcatttcgc ggctaaagac attgtgccgt tttaccttga acattgtccc aagatatttc    300

cccagcccac aggcgtgctt gctctgttac cgaagcttcc aaagcttctg tctggtccaa    360

agtacagcgg aaagtatctg cgaaatcttc tgagtaagct tcttggagag acaagacttc    420

accagaccct cacaaacatt gttataccta ccttcgatat caagaaactt caacccacta    480

ttttctcctc ttaccagctg ttggttgacc ctagcttgga tgtcaaggta tcagacatat    540

gcatcggcac ttcagctgct cccactttct ttcctcccca ttacttttcc aacgaagaca    600

gtcaaggcaa taagacggag tttaatctcg ttgatggcgc ggttactgct aataacccga    660

ctttggtggc catgacagct gtgtctaagc agattgtgaa gaataatcct gatatgggta    720

agctcaagcc gttaggtttc gaccggtttc tcgttatatc gataggaaca ggatcaacaa    780

aaagggaaga gaagtacagc gcaaaaaagg ctgcaaaatg ggggatcata tcttggttat    840

atgacgatgg atctactccg atattagaca ttaccatgga atcaagccgc gacatgatcc    900

attatcacag ctctgttgtg tttaaagccc tacaatctga agacaagtac ctccgaatcg    960

atgatgatac attggaagga gatgtaagca ctatggatct agcgacaaag tctaacttgg   1020

agaatcttca aaagattgga gagaagatgc tgacaaacag agtcatgcaa atgaacatcg   1080

acactggtgt atatgaacct gttgctgaaa atattaccaa tgatgaacag ctaaagaggt   1140

atgcaaaaat tctctcggac gaaaggaaat taaggagact aagaagcgac acaatgatta   1200

aagattcatc aaatgaatca caagagataa aataaaagga aatcattcgt gcttttgtgt   1260
```

gaaattgttt gttgcatatg tttta 1285

<210> SEQ ID NO 121
<211> LENGTH: 410
<212> TYPE: PRT
<213> ORGANISM: Arabidopsis thaliana

<400> SEQUENCE: 121

```
Ser Pro Ser Lys Lys Asn Lys Pro Pro Ser Cys Gly Ser Leu Val Thr
1               5                   10                  15

Ile Leu Ser Leu Asp Gly Gly Gly Val Arg Gly Ile Ile Ala Gly Val
            20                  25                  30

Ile Leu Ala Phe Leu Glu Lys Gln Leu Gln Glu Leu Asp Gly Glu Glu
        35                  40                  45

Ala Arg Leu Ala Asp Tyr Phe Asp Val Ile Ala Gly Thr Ser Thr Gly
    50                  55                  60

Gly Leu Val Thr Ala Met Leu Thr Val Pro Asp Glu Thr Gly Arg Pro
65                  70                  75                  80

His Phe Ala Ala Lys Asp Ile Val Pro Phe Tyr Leu Glu His Cys Pro
                85                  90                  95

Lys Ile Phe Pro Gln Pro Thr Gly Val Leu Ala Leu Leu Pro Lys Leu
            100                 105                 110

Pro Lys Leu Leu Ser Gly Pro Lys Tyr Ser Gly Lys Tyr Leu Arg Asn
        115                 120                 125

Leu Leu Ser Lys Leu Leu Gly Glu Thr Arg Leu His Gln Thr Leu Thr
    130                 135                 140

Asn Ile Val Ile Pro Thr Phe Asp Ile Lys Lys Leu Gln Pro Thr Ile
145                 150                 155                 160

Phe Ser Ser Tyr Gln Leu Leu Val Asp Pro Ser Leu Asp Val Lys Val
                165                 170                 175

Ser Asp Ile Cys Ile Gly Thr Ser Ala Ala Pro Thr Phe Phe Pro Pro
            180                 185                 190

His Tyr Phe Ser Asn Glu Asp Ser Gln Gly Asn Lys Thr Glu Phe Asn
        195                 200                 205

Leu Val Asp Gly Ala Val Thr Ala Asn Asn Pro Thr Leu Val Ala Met
    210                 215                 220

Thr Ala Val Ser Lys Gln Ile Val Lys Asn Asn Pro Asp Met Gly Lys
225                 230                 235                 240

Leu Lys Pro Leu Gly Phe Asp Arg Phe Leu Val Ile Ser Ile Gly Thr
                245                 250                 255

Gly Ser Thr Lys Arg Glu Glu Lys Tyr Ser Ala Lys Lys Ala Ala Lys
            260                 265                 270

Trp Gly Ile Ile Ser Trp Leu Tyr Asp Asp Gly Ser Thr Pro Ile Leu
        275                 280                 285

Asp Ile Thr Met Glu Ser Ser Arg Asp Met Ile His Tyr His Ser Ser
    290                 295                 300

Val Val Phe Lys Ala Leu Gln Ser Glu Asp Lys Tyr Leu Arg Ile Asp
305                 310                 315                 320

Asp Asp Thr Leu Glu Gly Asp Val Ser Thr Met Asp Leu Ala Thr Lys
                325                 330                 335

Ser Asn Leu Glu Asn Leu Gln Lys Ile Gly Glu Lys Met Leu Thr Asn
            340                 345                 350

Arg Val Met Gln Met Asn Ile Asp Thr Gly Val Tyr Glu Pro Val Ala
        355                 360                 365
```

```
Glu Asn Ile Thr Asn Asp Glu Gln Leu Lys Arg Tyr Ala Lys Ile Leu
    370                 375                 380

Ser Asp Glu Arg Lys Leu Arg Arg Leu Arg Ser Asp Thr Met Ile Lys
385                 390                 395                 400

Asp Ser Ser Asn Glu Ser Gln Glu Ile Lys
                405                 410


<210> SEQ ID NO 122
<211> LENGTH: 2061
<212> TYPE: DNA
<213> ORGANISM: Anabaena variabilis ATCC 29413

<400> SEQUENCE: 122

gtgataaatc tagcaaatac acaaacagtc ttaaaatttg atgggataga tgattatata      60

gattttggca aaaacgatat tggtggtgtt tttgctcaag ggagttcatg ttttacggtt     120

tcaggatgga taaatcctca taaattaaca gaaaaatcca ctagctatgg aacgcggaat     180

gtatttttg ctcgttcttc agatcgatac agtgataatt ttgaattcgg tatcagtgag     240

acagggagtt tagatatctt cattgatgaa accattagca agggtatcag aacttttggt     300

aatggagaat taactatagg acaatggcac tttttcgcca ttgtttttaa tagcggtcaa     360

atcacagtat atcttgatga tcatgaatac aatgactctc tgagaggttc atctttaaac     420

aaagcaacaa gctctgtaac tttgggtgca accttacaca agcaagtcta ttttacagga     480

caattagcaa acatcagcgt ctggaattat ccatgtactc aggtacaaat taagacccat     540

cattgtgggc taatagtcgg ggatgaacca ggattagtgg cttactggaa attagatgaa     600

ggccaaggaa caacagttaa aaacaaagct ggaaaatctt atcaaggaaa ttttcggggt     660

aatcctagct gggatttagc gcaaattcca tttgcagcac cattatccag tcaagacgat     720

atccaggagg atgtccaatt tgagatagga attattgccg aaacaagtat ttcaacatta     780

actacagatt tattggcagc aacagtaccg ctagttagta acaacgaaga ccaaacaata     840

gaaattcaat atccagaaat aaatagcgaa aaatcagaga ttattgcaaa cttgatcaat     900

ctcccatcac atgaagaagc aagcaaaaca gaccaaactg aagttcttgt aaatagccaa     960

caattacaaa cattcattca ggcagaatcg ccagaaacca tgaatacaaa atcccgtccc    1020

agatataaaa tactttccat tgatggtggt ggtattcggg gcattattcc tgcattactc    1080

ttagcagaaa ttgaacgacg gacacaagag cctatattta gtttatttga cttaattgct    1140

ggtacttcaa gcggcggaat tttagcactg ggactaacta aaccccgatt aaattcatct    1200

gaagaattgc ccttagctga atacaccgct gaagaccttg tacaattatt tcttgagtat    1260

ggagtagaaa tattttatga gccattattt gaaagactac ttggcccgtt agaagatata    1320

tttctccagc caaaatatcc ttccacaagc aaagaagaaa tcttaaggca atatttgggt    1380

aaaactcctc tagtaaataa tcttaaagaa gtttttgtca ctagttacga tatcgagcag    1440

cgaattccgg tatttttac aaaccaacta gaaaaacagc aaatagaatc taagaattct    1500

cataatttat gtggtaatgt atccctctta gatgccgcat tagccactag tgctaccccg    1560

acttattttg ctcctcatcg tatcgtcagc cccgaaaata gtgcgatcgc ttatacttta    1620

attgacgggg gagtatttgc taataaccca gcccatttag ctattttaga agcgcaaatt    1680

agtagtaaac gcaaagccca aacagtcctt aatcaagaag atattttagt agtttcttta    1740

ggtacaggtt cgccaacaag tgcttatcct tataaagaag tcaagaattg gggactttta    1800

caatggggaa gaccactttt aaatattgtg tttgacggtg gtagcggtgt ggtatctgga    1860
```

```
gaattagaac agttgtttga acctagcgat aaagaagcta aaagttttta ttatcgcttt   1920

caaacattgt tagatgcaga gttagaagca atagataata cgaaactaca aaatactcgt   1980

cagctacaag ctatagccca caaactgatt tctgaaaaaa gtcaacaaat cgatgaactt   2040

tgtgagcttt tgttgggcta a                                             2061


<210> SEQ ID NO 123
<211> LENGTH: 686
<212> TYPE: PRT
<213> ORGANISM: Anabaena variabilis ATCC 29413

<400> SEQUENCE: 123

Met Ile Asn Leu Ala Asn Thr Gln Thr Val Leu Lys Phe Asp Gly Ile
 1               5                  10                  15

Asp Asp Tyr Ile Asp Phe Gly Lys Asn Asp Ile Gly Gly Val Phe Ala
            20                  25                  30

Gln Gly Ser Ser Cys Phe Thr Val Ser Gly Trp Ile Asn Pro His Lys
        35                  40                  45

Leu Thr Glu Lys Ser Thr Ser Tyr Gly Thr Arg Asn Val Phe Phe Ala
    50                  55                  60

Arg Ser Ser Asp Arg Tyr Ser Asp Asn Phe Glu Phe Gly Ile Ser Glu
65                  70                  75                  80

Thr Gly Ser Leu Asp Ile Phe Ile Asp Glu Thr Ile Ser Lys Gly Ile
                85                  90                  95

Arg Thr Phe Gly Asn Gly Glu Leu Thr Ile Gly Gln Trp His Phe Phe
            100                 105                 110

Ala Ile Val Phe Asn Ser Gly Gln Ile Thr Val Tyr Leu Asp Asp His
        115                 120                 125

Glu Tyr Asn Asp Ser Leu Arg Gly Ser Ser Leu Asn Lys Ala Thr Ser
    130                 135                 140

Ser Val Thr Leu Gly Ala Thr Leu His Lys Gln Val Tyr Phe Thr Gly
145                 150                 155                 160

Gln Leu Ala Asn Ile Ser Val Trp Asn Tyr Pro Cys Thr Gln Val Gln
                165                 170                 175

Ile Lys Thr His His Cys Gly Leu Ile Val Gly Asp Glu Pro Gly Leu
            180                 185                 190

Val Ala Tyr Trp Lys Leu Asp Glu Gly Gln Gly Thr Thr Val Lys Asn
        195                 200                 205

Lys Ala Gly Lys Ser Tyr Gln Gly Asn Phe Arg Gly Asn Pro Ser Trp
    210                 215                 220

Asp Leu Ala Gln Ile Pro Phe Ala Ala Pro Leu Ser Ser Gln Asp Asp
225                 230                 235                 240

Ile Gln Glu Asp Val Gln Phe Glu Ile Gly Ile Ile Ala Glu Thr Ser
                245                 250                 255

Ile Ser Thr Leu Thr Thr Asp Leu Leu Ala Ala Thr Val Pro Leu Val
            260                 265                 270

Ser Asn Asn Glu Asp Gln Thr Ile Glu Ile Gln Tyr Pro Glu Ile Asn
        275                 280                 285

Ser Glu Lys Ser Glu Ile Ile Ala Asn Leu Ile Asn Leu Pro Ser His
    290                 295                 300

Glu Glu Ala Ser Lys Thr Asp Gln Thr Glu Val Leu Val Asn Ser Gln
305                 310                 315                 320

Gln Leu Gln Thr Phe Ile Gln Ala Glu Ser Pro Glu Thr Met Asn Thr
                325                 330                 335
```

-continued

```
Lys Ser Arg Pro Arg Tyr Lys Ile Leu Ser Ile Asp Gly Gly Gly Ile
            340                 345                 350

Arg Gly Ile Ile Pro Ala Leu Leu Leu Ala Glu Ile Glu Arg Arg Thr
        355                 360                 365

Gln Glu Pro Ile Phe Ser Leu Phe Asp Leu Ile Ala Gly Thr Ser Ser
    370                 375                 380

Gly Gly Ile Leu Ala Leu Gly Leu Thr Lys Pro Arg Leu Asn Ser Ser
385                 390                 395                 400

Glu Glu Leu Pro Leu Ala Glu Tyr Thr Ala Glu Asp Leu Val Gln Leu
                405                 410                 415

Phe Leu Glu Tyr Gly Val Glu Ile Phe Tyr Glu Pro Leu Phe Glu Arg
            420                 425                 430

Leu Leu Gly Pro Leu Glu Asp Ile Phe Leu Gln Pro Lys Tyr Pro Ser
        435                 440                 445

Thr Ser Lys Glu Glu Ile Leu Arg Gln Tyr Leu Gly Lys Thr Pro Leu
    450                 455                 460

Val Asn Asn Leu Lys Glu Val Phe Val Thr Ser Tyr Asp Ile Glu Gln
465                 470                 475                 480

Arg Ile Pro Val Phe Phe Thr Asn Gln Leu Glu Lys Gln Gln Ile Glu
                485                 490                 495

Ser Lys Asn Ser His Asn Leu Cys Gly Asn Val Ser Leu Leu Asp Ala
            500                 505                 510

Ala Leu Ala Thr Ser Ala Thr Pro Thr Tyr Phe Ala Pro His Arg Ile
        515                 520                 525

Val Ser Pro Glu Asn Ser Ala Ile Ala Tyr Thr Leu Ile Asp Gly Gly
    530                 535                 540

Val Phe Ala Asn Asn Pro Ala His Leu Ala Ile Leu Glu Ala Gln Ile
545                 550                 555                 560

Ser Ser Lys Arg Lys Ala Gln Thr Val Leu Asn Gln Glu Asp Ile Leu
                565                 570                 575

Val Val Ser Leu Gly Thr Gly Ser Pro Thr Ser Ala Tyr Pro Tyr Lys
            580                 585                 590

Glu Val Lys Asn Trp Gly Leu Leu Gln Trp Gly Arg Pro Leu Leu Asn
        595                 600                 605

Ile Val Phe Asp Gly Gly Ser Gly Val Val Ser Gly Glu Leu Glu Gln
    610                 615                 620

Leu Phe Glu Pro Ser Asp Lys Glu Ala Lys Ser Phe Tyr Tyr Arg Phe
625                 630                 635                 640

Gln Thr Leu Leu Asp Ala Glu Leu Glu Ala Ile Asp Asn Thr Lys Leu
                645                 650                 655

Gln Asn Thr Arg Gln Leu Gln Ala Ile Ala His Lys Leu Ile Ser Glu
            660                 665                 670

Lys Ser Gln Gln Ile Asp Glu Leu Cys Glu Leu Leu Leu Gly
        675                 680                 685
```

<210> SEQ ID NO 124
<211> LENGTH: 1995
<212> TYPE: DNA
<213> ORGANISM: Saccharomyces cerevisiae S288c

<400> SEQUENCE: 124

```
atgaagttgc agagtttgtt ggtttctgct gcagttttga cttctctaac agagaacgtt      60

aacgcttggt caccaaataa cagttacgtc cctgcgaacg taacctgtga tgatgatatt     120
```

```
aacttagtca gagaagcatc tggtttgtca gataacgaaa cagaatggct gaaaaaaaga    180
gatgcataca ccaaggaggc tttgcattct tttttgaata gggccacttc gaatttcagt    240
gacacttcct tgctatccac tctttttggt agcaactctt ccaatatgcc taagattgcc    300
gtcgcctgtt ctggtggtgg ttaccgtgcc atgttgtctg gtgctggtat gcttgctgct    360
atggacaatc gtactgatgg cgcaaatgag catggtcttg gtgggctgct gcaaggtgca    420
acttacttgg caggtctgtc gggtggtaac tggttaacaa gtactttggc ttggaacaac    480
tggacgtctg tgcaagctat cgtggataat acaacagaat ctaactcaat ttgggacatc    540
tctcattcaa ttcttacccc agacggcatt aacatcttta agactgggag tagatgggac    600
gacatatcag atgacgttca ggataaaaaa gacgccggtt tcaacatctc tttggcggat    660
gtttggggcc gtgctcttgc gtacaatttt tggccaagct tacaccgtgg tggtgtaggg    720
tacacatggt caactttaag ggaagctgat gtcttcaaga atggagaaat gcccttccct    780
atcactgttg cagacggtag atacccaggt accaccgtga taaacttgaa tgccactctt    840
ttcgaattta atccctttga aatgggttca tgggacccca ctttgaacgc atttacggat    900
gtgaagtatt taggtaccaa cgttacaaac ggtaaaccag ttaataaagg ccaatgcatt    960
gccgggtttg ataacactgg tttcataaca gccacttcat ctacgttgtt taaccaattt   1020
ttactaagat tgaattctac cgatttacct tcatttattg ctaacttagc caccgatttc   1080
ctggaagatt tatccgacaa tagtgacgat attgcaattt acgccccaaa tccattcaag   1140
gaagctaatt ttcttcaaaa gaacgcaacc tccagtatta tcgaatcaga atatctattt   1200
ttggttgatg gtggtgaaga taaccaaaat attcctttag ttccattgtt gcaaaaggaa   1260
cgtgaactag atgttatttt tgcattagac aattctgctg atactgacga ctattggcca   1320
gatggtgctt cattagttaa cacttatcag cgtcaatttg gcagccaagg tctcaatttg   1380
tctttcccat atgttccaga tgtgaacaca tttgtcaact tggggttgaa caaaaagcca   1440
accttttttg gttgtgatgc aagaaatttg acagacttgg agtacattcc accattaatt   1500
gtttacattc caaattcaag acattcattt aatggtaacc aaagtacttt taagatgtca   1560
tactccgatt cagaacgtct tggtatgatt aagaatgggt ttgaagctgc cacaatgggt   1620
aattttactg atgattctga tttcttgggc tgtgttggtt gcgccattat cagacgtaag   1680
caacaaaact tgaatgctac attgccctct gaatgcagcc agtgttttac caactactgc   1740
tggaacggta ctattgacag caggtcagtc tcaggtgtag gaaatgatga ttattcttct   1800
tctgcttcct tgtctgcctc cgccgctgct gcctctgcct ctgcctctgc ctctgcttcc   1860
gcctctgcct ctgcttctgg gtcttccact cataagaaaa atgcgggcaa tgctttggtg   1920
aattattcta acttaaacac taacactttt attggtgtct taagtgtcat tagtgccgtc   1980
ttcggtctaa tttag                                                    1995
```

<210> SEQ ID NO 125
<211> LENGTH: 664
<212> TYPE: PRT
<213> ORGANISM: Saccharomyces cerevisiae S288c

<400> SEQUENCE: 125

```
Met Lys Leu Gln Ser Leu Leu Val Ser Ala Ala Val Leu Thr Ser Leu
 1               5                  10                  15

Thr Glu Asn Val Asn Ala Trp Ser Pro Asn Asn Ser Tyr Val Pro Ala
            20                  25                  30

Asn Val Thr Cys Asp Asp Asp Ile Asn Leu Val Arg Glu Ala Ser Gly
```

-continued

```
        35                  40                  45

Leu Ser Asp Asn Glu Thr Glu Trp Leu Lys Lys Arg Asp Ala Tyr Thr
    50                  55                  60

Lys Glu Ala Leu His Ser Phe Leu Asn Arg Ala Thr Ser Asn Phe Ser
65                  70                  75                  80

Asp Thr Ser Leu Leu Ser Thr Leu Phe Gly Ser Asn Ser Ser Asn Met
                85                  90                  95

Pro Lys Ile Ala Val Ala Cys Ser Gly Gly Gly Tyr Arg Ala Met Leu
            100                 105                 110

Ser Gly Ala Gly Met Leu Ala Ala Met Asp Asn Arg Thr Asp Gly Ala
        115                 120                 125

Asn Glu His Gly Leu Gly Gly Leu Leu Gln Gly Ala Thr Tyr Leu Ala
    130                 135                 140

Gly Leu Ser Gly Gly Asn Trp Leu Thr Ser Thr Leu Ala Trp Asn Asn
145                 150                 155                 160

Trp Thr Ser Val Gln Ala Ile Val Asp Asn Thr Thr Glu Ser Asn Ser
                165                 170                 175

Ile Trp Asp Ile Ser His Ser Ile Leu Thr Pro Asp Gly Ile Asn Ile
            180                 185                 190

Phe Lys Thr Gly Ser Arg Trp Asp Asp Ile Ser Asp Asp Val Gln Asp
        195                 200                 205

Lys Lys Asp Ala Gly Phe Asn Ile Ser Leu Ala Asp Val Trp Gly Arg
    210                 215                 220

Ala Leu Ala Tyr Asn Phe Trp Pro Ser Leu His Arg Gly Gly Val Gly
225                 230                 235                 240

Tyr Thr Trp Ser Thr Leu Arg Glu Ala Asp Val Phe Lys Asn Gly Glu
                245                 250                 255

Met Pro Phe Pro Ile Thr Val Ala Asp Gly Arg Tyr Pro Gly Thr Thr
            260                 265                 270

Val Ile Asn Leu Asn Ala Thr Leu Phe Glu Phe Asn Pro Phe Glu Met
        275                 280                 285

Gly Ser Trp Asp Pro Thr Leu Asn Ala Phe Thr Asp Val Lys Tyr Leu
    290                 295                 300

Gly Thr Asn Val Thr Asn Gly Lys Pro Val Asn Lys Gly Gln Cys Ile
305                 310                 315                 320

Ala Gly Phe Asp Asn Thr Gly Phe Ile Thr Ala Thr Ser Ser Thr Leu
                325                 330                 335

Phe Asn Gln Phe Leu Leu Arg Leu Asn Ser Thr Asp Leu Pro Ser Phe
            340                 345                 350

Ile Ala Asn Leu Ala Thr Asp Phe Leu Glu Asp Leu Ser Asp Asn Ser
        355                 360                 365

Asp Asp Ile Ala Ile Tyr Ala Pro Asn Pro Phe Lys Glu Ala Asn Phe
    370                 375                 380

Leu Gln Lys Asn Ala Thr Ser Ser Ile Ile Glu Ser Glu Tyr Leu Phe
385                 390                 395                 400

Leu Val Asp Gly Gly Glu Asp Asn Gln Asn Ile Pro Leu Val Pro Leu
                405                 410                 415

Leu Gln Lys Glu Arg Glu Leu Asp Val Ile Phe Ala Leu Asp Asn Ser
            420                 425                 430

Ala Asp Thr Asp Asp Tyr Trp Pro Asp Gly Ala Ser Leu Val Asn Thr
        435                 440                 445

Tyr Gln Arg Gln Phe Gly Ser Gln Gly Leu Asn Leu Ser Phe Pro Tyr
    450                 455                 460
```

```
Val Pro Asp Val Asn Thr Phe Val Asn Leu Gly Leu Asn Lys Lys Pro
465                 470                 475                 480

Thr Phe Phe Gly Cys Asp Ala Arg Asn Leu Thr Asp Leu Glu Tyr Ile
                485                 490                 495

Pro Pro Leu Ile Val Tyr Ile Pro Asn Ser Arg His Ser Phe Asn Gly
            500                 505                 510

Asn Gln Ser Thr Phe Lys Met Ser Tyr Ser Asp Ser Glu Arg Leu Gly
        515                 520                 525

Met Ile Lys Asn Gly Phe Glu Ala Ala Thr Met Gly Asn Phe Thr Asp
    530                 535                 540

Asp Ser Asp Phe Leu Gly Cys Val Gly Cys Ala Ile Ile Arg Arg Lys
545                 550                 555                 560

Gln Gln Asn Leu Asn Ala Thr Leu Pro Ser Glu Cys Ser Gln Cys Phe
                565                 570                 575

Thr Asn Tyr Cys Trp Asn Gly Thr Ile Asp Ser Arg Ser Val Ser Gly
            580                 585                 590

Val Gly Asn Asp Asp Tyr Ser Ser Ser Ala Ser Leu Ser Ala Ser Ala
        595                 600                 605

Ala Ala Ala Ser Ala Ser Ala Ser Ala Ser Ala Ser Ala Ser Ala Ser
    610                 615                 620

Ala Ser Gly Ser Ser Thr His Lys Lys Asn Ala Gly Asn Ala Leu Val
625                 630                 635                 640

Asn Tyr Ser Asn Leu Asn Thr Asn Thr Phe Ile Gly Val Leu Ser Val
                645                 650                 655

Ile Ser Ala Val Phe Gly Leu Ile
            660
```

<210> SEQ ID NO 126
<211> LENGTH: 2121
<212> TYPE: DNA
<213> ORGANISM: Saccharomyces cerevisiae S288c

<400> SEQUENCE: 126

```
atgcaattac ggaacatatt acaggctagc tcgctaattt ctggactttc gctcgctgca      60

gattcgtcgt ccactactgg tgatggttat gctccatcaa taattccttg tcccagtgat     120

gatacctctt tagttagaaa cgcgtctggc ttatctaccg ctgaaactga ttggttaaag     180

aaaagagatg cgtacactaa agaagcttta cattccttct taagcagagc tacttctaac     240

ttcagtgaca cttctttgct atccactctt ttcagtagta actcttccaa tgtacccaaa     300

attggtattg catgctctgg tggtggttat cgtgccatgt tgggtggtgc tggtatgatt     360

gctgctatgg acaatcgtac tgatggtgct aacgagcatg gtcttggtgg tttactacaa     420

agttccacgt atctatcggg tttgtccggt ggtaactggt tgactggtac tttggcatgg     480

aacaattgga cctctgtaca ggaaattgta gaccatatga gtgagagcga ttccatctgg     540

aatatcacga aatccattgt gaaccctggt ggctctaatt tgacctacac aattgaaaga     600

tgggagtcca ttgtacaaga agtgcaggct aagtctgatg caggcttcaa tatatctttg     660

tcggatttgt gggcccgtgc actttcttac aacttctttc caagcttgcc agatgctggc     720

tccgctttga cttggtcctc tttgagagat gttgatgtgt tcaaaaacgg tgaaatgcct     780

ttaccaatta ctgttgcaga tggtagatac ccaggtacca ccgtgataaa cttgaatgcc     840

actcttttcg agttcactcc atttgaaatg ggttcttggg atccttcttt gaacgctttt     900

acggatgtga aatatctagg taccaacgtt acaaatggta aaccggtcaa caaggatcaa     960
```

-continued

```
tgcgtttctg gttacgataa tgctggattt gtaattgcca catccgccag tttattcaac   1020

gaattttccc tggaagcttc cacttcgacc tattataaaa tgattaatag ttttgccaac   1080

aagtacgtta acaacctatc ccaagatgac gatgatattg caatttacgc tgcaaatcca   1140

ttcaaggata cagaatttgt tgaccgcaat tacacttcca gtattgttga tgccgatgat   1200

ttgtttttag ttgatggtgg tgaggacggc caaaatttgc cgttggttcc actaatcaag   1260

aaggaacgtg acttggatgt ggtgttcgca ttggatatat ccgacaatac tgatgaatca   1320

tggccaagtg gtgtgtgcat gacgaacact tatgagcgcc agtattctaa gcaaggtaaa   1380

ggaatggctt tcccatatgt tccagacgtt aacaccttcc ttaacttggg cttaactaat   1440

aagccaacgt tttttggttg tgatgcaaaa aatttgacgg acttggagta tattccacct   1500

ttagttgtat atatcccaaa cacaaaacat tcattcaatg gtaaccaaag tactttgaag   1560

atgaactaca atgttacaga acgtcttgga atgatcagaa atggttttga agctgctaca   1620

atgggcaact ttacggatga ctctaacttt ttaggttgca taggttgtgc catcattaga   1680

cgtaagcaag aaagcctaaa tgccaccttg ccccctgaat gtaccaaatg ttttgcggat   1740

tactgctgga acggcacact aagtacctca gctaatcctg aactatcggg aaatagtacg   1800

tatcaaagcg gtgctattgc ctctgcaatc tctgaggcta ctgacggtat tccaataacg   1860

gctctcttag gttcatcaac ctccggaaat actacatcaa actcaacaac ctcgacttca   1920

tcaaatgtca cttctaactc aaactcttcg tcaaatacaa ctttaaactc aaattcttca   1980

tcctcttcaa tttcttcctc tacagctcgt tcttcttcct ctacggcaaa caaagcgaat   2040

gctgcggcta tttcctatgc gaacactaat actctaatga gtttgttagg tgccataaca   2100

gcattatttg gactaattta g                                             2121
```

<210> SEQ ID NO 127
<211> LENGTH: 706
<212> TYPE: PRT
<213> ORGANISM: Saccharomyces cerevisiae S288c

<400> SEQUENCE: 127

```
Met Gln Leu Arg Asn Ile Leu Gln Ala Ser Ser Leu Ile Ser Gly Leu
1               5                   10                  15

Ser Leu Ala Ala Asp Ser Ser Ser Thr Thr Gly Asp Gly Tyr Ala Pro
            20                  25                  30

Ser Ile Ile Pro Cys Pro Ser Asp Asp Thr Ser Leu Val Arg Asn Ala
        35                  40                  45

Ser Gly Leu Ser Thr Ala Glu Thr Asp Trp Leu Lys Lys Arg Asp Ala
    50                  55                  60

Tyr Thr Lys Glu Ala Leu His Ser Phe Leu Ser Arg Ala Thr Ser Asn
65                  70                  75                  80

Phe Ser Asp Thr Ser Leu Leu Ser Thr Leu Phe Ser Ser Asn Ser Ser
                85                  90                  95

Asn Val Pro Lys Ile Gly Ile Ala Cys Ser Gly Gly Gly Tyr Arg Ala
            100                 105                 110

Met Leu Gly Gly Ala Gly Met Ile Ala Ala Met Asp Asn Arg Thr Asp
        115                 120                 125

Gly Ala Asn Glu His Gly Leu Gly Gly Leu Leu Gln Ser Ser Thr Tyr
    130                 135                 140

Leu Ser Gly Leu Ser Gly Gly Asn Trp Leu Thr Gly Thr Leu Ala Trp
145                 150                 155                 160
```

```
Asn Asn Trp Thr Ser Val Gln Glu Ile Val Asp His Met Ser Glu Ser
                165                 170                 175

Asp Ser Ile Trp Asn Ile Thr Lys Ser Ile Val Asn Pro Gly Gly Ser
            180                 185                 190

Asn Leu Thr Tyr Thr Ile Glu Arg Trp Glu Ser Ile Val Gln Glu Val
        195                 200                 205

Gln Ala Lys Ser Asp Ala Gly Phe Asn Ile Ser Leu Ser Asp Leu Trp
    210                 215                 220

Ala Arg Ala Leu Ser Tyr Asn Phe Phe Pro Ser Leu Pro Asp Ala Gly
225                 230                 235                 240

Ser Ala Leu Thr Trp Ser Ser Leu Arg Asp Val Asp Val Phe Lys Asn
                245                 250                 255

Gly Glu Met Pro Leu Pro Ile Thr Val Ala Asp Gly Arg Tyr Pro Gly
            260                 265                 270

Thr Thr Val Ile Asn Leu Asn Ala Thr Leu Phe Glu Phe Thr Pro Phe
        275                 280                 285

Glu Met Gly Ser Trp Asp Pro Ser Leu Asn Ala Phe Thr Asp Val Lys
    290                 295                 300

Tyr Leu Gly Thr Asn Val Thr Asn Gly Lys Pro Val Asn Lys Asp Gln
305                 310                 315                 320

Cys Val Ser Gly Tyr Asp Asn Ala Gly Phe Val Ile Ala Thr Ser Ala
                325                 330                 335

Ser Leu Phe Asn Glu Phe Ser Leu Glu Ala Ser Thr Ser Thr Tyr Tyr
            340                 345                 350

Lys Met Ile Asn Ser Phe Ala Asn Lys Tyr Val Asn Asn Leu Ser Gln
        355                 360                 365

Asp Asp Asp Asp Ile Ala Ile Tyr Ala Ala Asn Pro Phe Lys Asp Thr
    370                 375                 380

Glu Phe Val Asp Arg Asn Tyr Thr Ser Ser Ile Val Asp Ala Asp Asp
385                 390                 395                 400

Leu Phe Leu Val Asp Gly Gly Glu Asp Gly Gln Asn Leu Pro Leu Val
                405                 410                 415

Pro Leu Ile Lys Lys Glu Arg Asp Leu Asp Val Val Phe Ala Leu Asp
            420                 425                 430

Ile Ser Asp Asn Thr Asp Glu Ser Trp Pro Ser Gly Val Cys Met Thr
        435                 440                 445

Asn Thr Tyr Glu Arg Gln Tyr Ser Lys Gln Gly Lys Gly Met Ala Phe
    450                 455                 460

Pro Tyr Val Pro Asp Val Asn Thr Phe Leu Asn Leu Gly Leu Thr Asn
465                 470                 475                 480

Lys Pro Thr Phe Phe Gly Cys Asp Ala Lys Asn Leu Thr Asp Leu Glu
                485                 490                 495

Tyr Ile Pro Pro Leu Val Val Tyr Ile Pro Asn Thr Lys His Ser Phe
            500                 505                 510

Asn Gly Asn Gln Ser Thr Leu Lys Met Asn Tyr Asn Val Thr Glu Arg
        515                 520                 525

Leu Gly Met Ile Arg Asn Gly Phe Glu Ala Ala Thr Met Gly Asn Phe
    530                 535                 540

Thr Asp Asp Ser Asn Phe Leu Gly Cys Ile Gly Cys Ala Ile Ile Arg
545                 550                 555                 560

Arg Lys Gln Glu Ser Leu Asn Ala Thr Leu Pro Pro Glu Cys Thr Lys
                565                 570                 575

Cys Phe Ala Asp Tyr Cys Trp Asn Gly Thr Leu Ser Thr Ser Ala Asn
```

```
            580                 585                 590

Pro Glu Leu Ser Gly Asn Ser Thr Tyr Gln Ser Gly Ala Ile Ala Ser
        595                 600                 605

Ala Ile Ser Glu Ala Thr Asp Gly Ile Pro Ile Thr Ala Leu Leu Gly
    610                 615                 620

Ser Ser Thr Ser Gly Asn Thr Thr Ser Asn Ser Thr Thr Ser Thr Ser
625                 630                 635                 640

Ser Asn Val Thr Ser Asn Ser Asn Ser Ser Ser Asn Thr Thr Leu Asn
                645                 650                 655

Ser Asn Ser Ser Ser Ser Ser Ile Ser Ser Ser Thr Ala Arg Ser Ser
            660                 665                 670

Ser Ser Thr Ala Asn Lys Ala Asn Ala Ala Ala Ile Ser Tyr Ala Asn
        675                 680                 685

Thr Asn Thr Leu Met Ser Leu Leu Gly Ala Ile Thr Ala Leu Phe Gly
    690                 695                 700

Leu Ile
705
```

<210> SEQ ID NO 128
<211> LENGTH: 636
<212> TYPE: DNA
<213> ORGANISM: Acinetobacter sp. ADP1

<400> SEQUENCE: 128

```
atgcaactgt ataacatgtt tttagacggg aaatgggcaa aatggttctt gattggttca     60

tttagcgtaa taccttttac agtttcggca aaaaccattc ttatcttagg cgacagtctg    120

agtgcgggtt atggcattaa ccccgaacag ggctgggtcg ctttattaca aaaacgtctg    180

gatcaacaat ttcccaagca gcataaagtc attaatgcca gtgtaagtgg ggaaaccacc    240

agtggtgctt tagctcgttt acccaaacta cttactactt atcgacctaa tgtggtggtc    300

attgagcttg gtggtaatga tgcattaaga ggacaaccgc ctcaaatgat tcaaagtaat    360

ctggaaaaat taatccagca cagccaaaag gcaaaatcta aagtcgtggt gtttggaatg    420

aaaataccac caaattatgg cactgcctat agtcaggcat ttgaaaataa ttataaggta    480

gtgagtcaaa catatcaggt taagttgttg ccattttttc ttgatggtgt ggctggacac    540

aaaagtctaa tgcaaaatga ccagatccat ccaaatgcca aagcccagtc aatcttgcta    600

aataacgcat acccatatat taaaggcgct ttataa                              636
```

<210> SEQ ID NO 129
<211> LENGTH: 211
<212> TYPE: PRT
<213> ORGANISM: Acinetobacter sp. ADP1

<400> SEQUENCE: 129

```
Met Gln Leu Tyr Asn Met Phe Leu Asp Gly Lys Trp Ala Lys Trp Phe
 1               5                  10                  15

Leu Ile Gly Ser Phe Ser Val Ile Pro Phe Thr Val Ser Ala Lys Thr
            20                  25                  30

Ile Leu Ile Leu Gly Asp Ser Leu Ser Ala Gly Tyr Gly Ile Asn Pro
        35                  40                  45

Glu Gln Gly Trp Val Ala Leu Leu Gln Lys Arg Leu Asp Gln Gln Phe
    50                  55                  60

Pro Lys Gln His Lys Val Ile Asn Ala Ser Val Ser Gly Glu Thr Thr
65                  70                  75                  80
```

-continued

```
Ser Gly Ala Leu Ala Arg Leu Pro Lys Leu Leu Thr Thr Tyr Arg Pro
                85                  90                  95

Asn Val Val Val Ile Glu Leu Gly Gly Asn Asp Ala Leu Arg Gly Gln
            100                 105                 110

Pro Pro Gln Met Ile Gln Ser Asn Leu Glu Lys Leu Ile Gln His Ser
        115                 120                 125

Gln Lys Ala Lys Ser Lys Val Val Val Phe Gly Met Lys Ile Pro Pro
    130                 135                 140

Asn Tyr Gly Thr Ala Tyr Ser Gln Ala Phe Glu Asn Asn Tyr Lys Val
145                 150                 155                 160

Val Ser Gln Thr Tyr Gln Val Lys Leu Leu Pro Phe Phe Leu Asp Gly
                165                 170                 175

Val Ala Gly His Lys Ser Leu Met Gln Asn Asp Gln Ile His Pro Asn
            180                 185                 190

Ala Lys Ala Gln Ser Ile Leu Leu Asn Asn Ala Tyr Pro Tyr Ile Lys
        195                 200                 205

Gly Ala Leu
    210
```

<210> SEQ ID NO 130
<211> LENGTH: 1029
<212> TYPE: DNA
<213> ORGANISM: Acinetobacter sp. ADP1

<400> SEQUENCE: 130

```
atgtcagata tcccgtttct gaatccgaca atactacaac agcttgattt acctgtacct     60

agtcgtgatc aaaccccttt agtgttgcct cagttaaatc tcaatcattc ttttgagcct    120

tcacgtgatt tattggccta tcgaaagtta tatggtttag atctactggc tggtgattac    180

tggcaaggct atattcagat gcccttgttt cgtttacatg tacaagtttt tacgccagaa    240

agagaaattc cattaggaac ggtgtgctta ttacatggct atcttgaaca tagtggtatt    300

tatcaaccga tcatccgtga aatactggat caaggtttta gtgtggtcac ttatgatctg    360

cctggacatg gattaagtga tggatcaccc gctaatattc agaattttga tcattatcaa    420

caggttttaa tggcggttta ccagtatgtt aaaaatgcag atcagttgcc taaaccttgg    480

ttaggaattg gtcaaagtac aggtggcgca atctggatgc atcatttgtt ggaatatgca    540

gagaaacgac aagatccgat tgttgatcgg gtattactat tgtcaccact catacgccca    600

gcaaaaacgg catggtggca taattctgtg ggtttaggca ttattcgaag aattcgtcgt    660

caagttccaa gacattttag acgtaataat cataatcctg agtttttacg ttttatccgt    720

cttaaagatc cgttacaacc acgcatgatg ggaatggact ggatacttgc gatgtcaaaa    780

tggatgtttg aaatggaaca gcgaccagcc tgtcgtatac cagtatggct tgcacaaggg    840

gcattagatc agactgtaga ttggcgttat aacattgaat ttattcgacg taaatttcgc    900

ttacaaacct tgttgatgtt agaagaagga tctcatcaac tcatcaatga gcgcgctgat    960

attcgtgctg ctttgacagg acttattcca gcatttttac atgctcgtcc aaaacatcat   1020

tattattaa                                                           1029
```

<210> SEQ ID NO 131
<211> LENGTH: 342
<212> TYPE: PRT
<213> ORGANISM: Acinetobacter sp. ADP1

<400> SEQUENCE: 131

-continued

```
Met Ser Asp Ile Pro Phe Leu Asn Pro Thr Ile Leu Gln Gln Leu Asp
1               5                   10                  15

Leu Pro Val Pro Ser Arg Asp Gln Thr Pro Leu Val Leu Pro Gln Leu
            20                  25                  30

Asn Leu Asn His Ser Phe Glu Pro Ser Arg Asp Leu Leu Ala Tyr Arg
        35                  40                  45

Lys Leu Tyr Gly Leu Asp Leu Leu Ala Gly Asp Tyr Trp Gln Gly Tyr
    50                  55                  60

Ile Gln Met Pro Leu Phe Arg Leu His Val Gln Val Phe Thr Pro Glu
65                  70                  75                  80

Arg Glu Ile Pro Leu Gly Thr Val Cys Leu Leu His Gly Tyr Leu Glu
                85                  90                  95

His Ser Gly Ile Tyr Gln Pro Ile Ile Arg Glu Ile Leu Asp Gln Gly
            100                 105                 110

Phe Ser Val Val Thr Tyr Asp Leu Pro Gly His Gly Leu Ser Asp Gly
        115                 120                 125

Ser Pro Ala Asn Ile Gln Asn Phe Asp His Tyr Gln Gln Val Leu Met
    130                 135                 140

Ala Val Tyr Gln Tyr Val Lys Asn Ala Asp Gln Leu Pro Lys Pro Trp
145                 150                 155                 160

Leu Gly Ile Gly Gln Ser Thr Gly Gly Ala Ile Trp Met His His Leu
                165                 170                 175

Leu Glu Tyr Ala Glu Lys Arg Gln Asp Pro Ile Val Asp Arg Val Leu
            180                 185                 190

Leu Leu Ser Pro Leu Ile Arg Pro Ala Lys Thr Ala Trp Trp His Asn
        195                 200                 205

Ser Val Gly Leu Gly Ile Ile Arg Arg Ile Arg Arg Gln Val Pro Arg
    210                 215                 220

His Phe Arg Arg Asn Asn His Asn Pro Glu Phe Leu Arg Phe Ile Arg
225                 230                 235                 240

Leu Lys Asp Pro Leu Gln Pro Arg Met Met Gly Met Asp Trp Ile Leu
                245                 250                 255

Ala Met Ser Lys Trp Met Phe Glu Met Glu Gln Arg Pro Ala Cys Arg
            260                 265                 270

Ile Pro Val Trp Leu Ala Gln Gly Ala Leu Asp Gln Thr Val Asp Trp
        275                 280                 285

Arg Tyr Asn Ile Glu Phe Ile Arg Arg Lys Phe Arg Leu Gln Thr Leu
    290                 295                 300

Leu Met Leu Glu Glu Gly Ser His Gln Leu Ile Asn Glu Arg Ala Asp
305                 310                 315                 320

Ile Arg Ala Ala Leu Thr Gly Leu Ile Pro Ala Phe Leu His Ala Arg
                325                 330                 335

Pro Lys His His Tyr Tyr
            340
```

<210> SEQ ID NO 132
<211> LENGTH: 840
<212> TYPE: DNA
<213> ORGANISM: Rhodococcus jostii RHA1

<400> SEQUENCE: 132

```
atgcagcatc gagaatcatc cttcgccggc gtcggcggaa ttcccatcgt ctacgacgtg      60

tggctccccg agcggcgccc gcgcggcgtg ctggttctgt gccacggctt cggcgagcat     120

gcccggcggt acgaccatgt gatcgaacgg ctcggggaac tcgacctcgc gatctacgcg     180
```

```
cccgaccacc gtgggcacgg gcggtcgggc ggcaaacggg tccatctgaa ggactggacc    240

gagttcaccg acgacctgca ccagttgttc ggcatcgcgt cgacggactg gcccggcacc    300

gaccggtttc tcctcgggca cagcatgggc ggttccatcg cgctgaccta cgcactcgac    360

caccagcagg acctgaaggc actcatgctg tccgggcctg cggtcgacgt gacgagcggc    420

acgccgcgca tcgtggtgga gatcggcaag ctggtgggtc gcttccttcc cggagtgccc    480

gtcgagtcgc tcgacgcgaa gttggtctcc cgcgatcctg cggtcgtgtc ggcctacgag    540

gaggatcccc tcgtccacca cgggaaggtg cctgccggga ttgcgcgcgg gatgatcctc    600

gccgccgaac ggttgccgga acgtctgccg tcgctgacga ttcccctgct tctccagcac    660

ggccaggacg acggactcgc gagtgtgcac ggcacggaac tgatcgcgga gtacgtcggt    720

tcggaggatc tcacggtgga gatctacgaa aacctgttcc acgaggtgtt caacgaaccg    780

gagaacgagg aggtactcga cgacctcgtc gagtggttgc ggccgcgcgt gcaggcctga    840


<210> SEQ ID NO 133
<211> LENGTH: 279
<212> TYPE: PRT
<213> ORGANISM: Rhodococcus jostii RHA1

<400> SEQUENCE: 133

Met Gln His Arg Glu Ser Ser Phe Ala Gly Val Gly Gly Ile Pro Ile
 1               5                  10                  15

Val Tyr Asp Val Trp Leu Pro Glu Arg Arg Pro Arg Gly Val Leu Val
            20                  25                  30

Leu Cys His Gly Phe Gly Glu His Ala Arg Arg Tyr Asp His Val Ile
        35                  40                  45

Glu Arg Leu Gly Glu Leu Asp Leu Ala Ile Tyr Ala Pro Asp His Arg
    50                  55                  60

Gly His Gly Arg Ser Gly Gly Lys Arg Val His Leu Lys Asp Trp Thr
65                  70                  75                  80

Glu Phe Thr Asp Asp Leu His Gln Leu Phe Gly Ile Ala Ser Thr Asp
                85                  90                  95

Trp Pro Gly Thr Asp Arg Phe Leu Leu Gly His Ser Met Gly Gly Ser
            100                 105                 110

Ile Ala Leu Thr Tyr Ala Leu Asp His Gln Gln Asp Leu Lys Ala Leu
        115                 120                 125

Met Leu Ser Gly Pro Ala Val Asp Val Thr Ser Gly Thr Pro Arg Ile
    130                 135                 140

Val Val Glu Ile Gly Lys Leu Val Gly Arg Phe Leu Pro Gly Val Pro
145                 150                 155                 160

Val Glu Ser Leu Asp Ala Lys Leu Val Ser Arg Asp Pro Ala Val Val
                165                 170                 175

Ser Ala Tyr Glu Glu Asp Pro Leu Val His His Gly Lys Val Pro Ala
            180                 185                 190

Gly Ile Ala Arg Gly Met Ile Leu Ala Ala Glu Arg Leu Pro Glu Arg
        195                 200                 205

Leu Pro Ser Leu Thr Ile Pro Leu Leu Leu Gln His Gly Gln Asp Asp
    210                 215                 220

Gly Leu Ala Ser Val His Gly Thr Glu Leu Ile Ala Glu Tyr Val Gly
225                 230                 235                 240

Ser Glu Asp Leu Thr Val Glu Ile Tyr Glu Asn Leu Phe His Glu Val
                245                 250                 255
```

-continued

```
Phe Asn Glu Pro Glu Asn Glu Glu Val Leu Asp Asp Leu Val Glu Trp
            260                 265                 270

Leu Arg Pro Arg Val Gln Ala
        275
```

```
<210> SEQ ID NO 134
<211> LENGTH: 2546
<212> TYPE: DNA
<213> ORGANISM: Artificial Sequence
<220> FEATURE:
<223> OTHER INFORMATION: Codon optimized SDP1

<400> SEQUENCE: 134

catatggaca tcagtaatga ggcaagcgtt gaccccttta gtattgggcc gtcttcgatc      60
atgggccgaa ccatcgcttt tcgagttctc ttctgtcgca gcatgagtca actgcgccgg     120
gatttgttcc gctttttgct ccactggttt ctgcgcttta aactgacggt gagtccattc     180
gtctcctggt tccacccgcg caatccacaa ggcattctcg cggttgtcac catcattgcc     240
tttgtcttga aacgctatac gaatgtgaag atcaaagccg agatggcgta ccgtcggaag     300
ttttggcgga acatgatgcg gacagcattg acttacgaag agtgggccca tgcagctaaa     360
atgctggaga aggagacgcc gaagatgaat gagagcgatc tctatgacga agaattggtt     420
aaaaacaaac tgcaagagct gcggcatcgc cgtcaagaag gatcgctgcg cgatatcatg     480
ttttgcatgc gagcggacct ggtccgcaat ctgggcaaca tgtgtaacag tgagctgcat     540
aaagggcgac tccaagtgcc ccgccacatc aaagaatata tcgatgaagt tagtacccag     600
ctgcgcatgg tttgcaattc ggatagcgag gagctgagct tggaagagaa actctcgttc     660
atgcacgaaa cacgtcatgc gtttggtcgc actgctttgt tgctgtccgg gggtgcgtcc     720
ctgggtgcat tccatgtcgg agtggtccga acgctggtgg agcacaagct gctgccccga     780
atcattgcgg gctccagcgt tggtagcatc atctgcgcag ttgtcgcttc ccggagttgg     840
ccggagctgc agtcgttttt tgaaaacagc ctccatagtt tgcagttttt cgatcagctc     900
ggaggagtgt tctccatcgt gaagcgcgtt atgacgcagg gtgccctcca tgacattcgg     960
caattgcaat gtatgttgcg aaacctcacc tcgaacctca ctttccagga ggcttatgac    1020
atgacaggtc gaatcttggg aattaccgtg tgttcgcctc gcaagcacga accgccacgt    1080
tgtctcaatt acctgacctc gccccatgtc gtcatctgga gtgccgtcac ggcgagttgt    1140
gcgtttcctg gcttgttcga ggcacaggag ttgatggcga aagaccgcag cggcgaaatt    1200
gttccgtacc atcctccgtt taatctcgat ccagaggtgg ggacgaaaag ctcgagcggc    1260
cggcgctggc gcgatgggag cctcgaagtc gatctgccca tgatgcagtt gaaggaactc    1320
tttaacgtca atcacttcat cgtgagccag gccaatcctc atattgcacc cctgctccga    1380
ctcaaggatc tggtgcgcgc atacggtggc cgttttgccg caaaattggc tcatttggtc    1440
gagatggaag tgaaacaccg gtgcaaccag gtgttggaac tcggcttccc cctgggcggc    1500
ctcgccaaac tgtttgccca agaatgggaa ggtgatgtca cggttgtcat gccggcgacc    1560
ctggctcagt atagcaagat cattcaaaat ccgacccatg tggaactcca aaaggccgcc    1620
aatcaagggc gtcgttgcac ttgggagaag ctgtctgcga tcaagagtaa ctgcggtatt    1680
gaactggccc tggatgatag cgtggcgatt ctcaatcaca tgcgccgcct gaagaagtcc    1740
gccgaacgag ccgccactgc gacctcgtcc agccaccacg gcttggcctc caccacgcgc    1800
tttaatgctt cgcggcgcat ccccagttgg aatgtcctgg cccgtgagaa ctctacgggt    1860
tctctcgatg acctggtcac tgacaacaat ctccacgcgt ccagtggtcg caacctgtcg    1920
```

```
gattctgaaa cagagtcggt cgaactgtcg tcctggactc ggacgggggg cccactgatg   1980

cgcactgcta gtgctaataa gttcattgat ttcgtgcagt ctctcgatat tgacatcgca   2040

ttggtgcgtg gtttttcgtc gagcccgaac tcgcctgccg tgcctcctgg cgggagcttc   2100

acacccagtc cccggagcat tgctgcgcat tctgacattg agtctaactc gaacagcaat   2160

aatctgggaa cctccacatc cagtattact gtgacagagg gtgatctcct gcaacccgaa   2220

cgtacctcta atggcttcgt tctcaacgtt gtgaaacggg aaaacttggg catgcctagc   2280

attggcaacc aaaacaccga actgccggaa agcgttcaac tggacattcc tgaaaaagag   2340

atggattgca gcagcgtgag cgagcatgaa gaagacgaca atgataacga ggaagaacat   2400

aacggaagtt cgttggtcac cgtttcttcg gaggacagtg gtctgcagga acccgtgtct   2460

gggtccgtga ttgatgctta ggaagagcaa atcgataagc tcttcgttac tatccatacg   2520

atgttcccga ttacgcttag agatct                                        2546
```

<210> SEQ ID NO 135
<211> LENGTH: 825
<212> TYPE: PRT
<213> ORGANISM: Arabidopsis thaliana

<400> SEQUENCE: 135

```
Met Asp Ile Ser Asn Glu Ala Ser Val Asp Pro Phe Ser Ile Gly Pro
1               5                   10                  15

Ser Ser Ile Met Gly Arg Thr Ile Ala Phe Arg Val Leu Phe Cys Arg
            20                  25                  30

Ser Met Ser Gln Leu Arg Arg Asp Leu Phe Arg Phe Leu Leu His Trp
        35                  40                  45

Phe Leu Arg Phe Lys Leu Thr Val Ser Pro Phe Val Ser Trp Phe His
    50                  55                  60

Pro Arg Asn Pro Gln Gly Ile Leu Ala Val Val Thr Ile Ile Ala Phe
65                  70                  75                  80

Val Leu Lys Arg Tyr Thr Asn Val Lys Ile Lys Ala Glu Met Ala Tyr
                85                  90                  95

Arg Arg Lys Phe Trp Arg Asn Met Met Arg Thr Ala Leu Thr Tyr Glu
            100                 105                 110

Glu Trp Ala His Ala Ala Lys Met Leu Glu Lys Glu Thr Pro Lys Met
        115                 120                 125

Asn Glu Ser Asp Leu Tyr Asp Glu Glu Leu Val Lys Asn Lys Leu Gln
    130                 135                 140

Glu Leu Arg His Arg Arg Gln Glu Gly Ser Leu Arg Asp Ile Met Phe
145                 150                 155                 160

Cys Met Arg Ala Asp Leu Val Arg Asn Leu Gly Asn Met Cys Asn Ser
                165                 170                 175

Glu Leu His Lys Gly Arg Leu Gln Val Pro Arg His Ile Lys Glu Tyr
            180                 185                 190

Ile Asp Glu Val Ser Thr Gln Leu Arg Met Val Cys Asn Ser Asp Ser
        195                 200                 205

Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Gly Ala Ser Leu
225                 230                 235                 240

Gly Ala Phe His Val Gly Val Val Arg Thr Leu Val Glu His Lys Leu
                245                 250                 255
```

```
Leu Pro Arg Ile Ile Ala Gly Ser Ser Val Gly Ser Ile Ile Cys Ala
            260                 265                 270

Val Val Ala Ser Arg Ser Trp Pro Glu Leu Gln Ser Phe Phe Glu Asn
        275                 280                 285

Ser Leu His Ser Leu Gln Phe Phe Asp Gln Leu Gly Gly Val Phe Ser
    290                 295                 300

Ile Val Lys Arg Val Met Thr Gln Gly Ala Leu His Asp Ile Arg Gln
305                 310                 315                 320

Leu Gln Cys Met Leu Arg Asn Leu Thr Ser Asn Leu Thr Phe Gln Glu
                325                 330                 335

Ala Tyr Asp Met Thr Gly Arg Ile Leu Gly Ile Thr Val Cys Ser Pro
            340                 345                 350

Arg Lys His Glu Pro Pro Arg Cys Leu Asn Tyr Leu Thr Ser Pro His
        355                 360                 365

Val Val Ile Trp Ser Ala Val Thr Ala Ser Cys Ala Phe Pro Gly Leu
    370                 375                 380

Phe Glu Ala Gln Glu Leu Met Ala Lys Asp Arg Ser Gly Glu Ile Val
385                 390                 395                 400

Pro Tyr His Pro Pro Phe Asn Leu Asp Pro Glu Val Gly Thr Lys Ser
                405                 410                 415

Ser Ser Gly Arg Arg Trp Arg Asp Gly Ser Leu Glu Val Asp Leu Pro
            420                 425                 430

Met Met Gln Leu Lys Glu Leu Phe Asn Val Asn His Phe Ile Val Ser
        435                 440                 445

Gln Ala Asn Pro His Ile Ala Pro Leu Leu Arg Leu Lys Asp Leu Val
    450                 455                 460

Arg Ala Tyr Gly Gly Arg Phe Ala Ala Lys Leu Ala His Leu Val Glu
465                 470                 475                 480

Met Glu Val Lys His Arg Cys Asn Gln Val Leu Glu Leu Gly Phe Pro
                485                 490                 495

Leu Gly Gly Leu Ala Lys Leu Phe Ala Gln Glu Trp Glu Gly Asp Val
            500                 505                 510

Thr Val Val Met Pro Ala Thr Leu Ala Gln Tyr Ser Lys Ile Ile Gln
        515                 520                 525

Asn Pro Thr His Val Glu Leu Gln Lys Ala Ala Asn Gln Gly Arg Arg
    530                 535                 540

Cys Thr Trp Glu Lys Leu Ser Ala Ile Lys Ser Asn Cys Gly Ile Glu
545                 550                 555                 560

Leu Ala Leu Asp Asp Ser Val Ala Ile Leu Asn His Met Arg Arg Leu
                565                 570                 575

Lys Lys Ser Ala Glu Arg Ala Ala Thr Ala Thr Ser Ser Ser His His
            580                 585                 590

Gly Leu Ala Ser Thr Thr Arg Phe Asn Ala Ser Arg Arg Ile Pro Ser
        595                 600                 605

Trp Asn Val Leu Ala Arg Glu Asn Ser Thr Gly Ser Leu Asp Asp Leu
    610                 615                 620

Val Thr Asp Asn Asn Leu His Ala Ser Ser Gly Arg Asn Leu Ser Asp
625                 630                 635                 640

Ser Glu Thr Glu Ser Val Glu Leu Ser Ser Trp Thr Arg Thr Gly Gly
                645                 650                 655

Pro Leu Met Arg Thr Ala Ser Ala Asn Lys Phe Ile Asp Phe Val Gln
            660                 665                 670

Ser Leu Asp Ile Asp Ile Ala Leu Val Arg Gly Phe Ser Ser Ser Pro
```

-continued

```
        675                 680                 685

Asn Ser Pro Ala Val Pro Pro Gly Gly Ser Phe Thr Pro Ser Pro Arg
    690                 695                 700

Ser Ile Ala Ala His Ser Asp Ile Glu Ser Asn Ser Asn Ser Asn Asn
705                 710                 715                 720

Leu Gly Thr Ser Thr Ser Ser Ile Thr Val Thr Glu Gly Asp Leu Leu
                725                 730                 735

Gln Pro Glu Arg Thr Ser Asn Gly Phe Val Leu Asn Val Val Lys Arg
            740                 745                 750

Glu Asn Leu Gly Met Pro Ser Ile Gly Asn Gln Asn Thr Glu Leu Pro
        755                 760                 765

Glu Ser Val Gln Leu Asp Ile Pro Glu Lys Glu Met Asp Cys Ser Ser
    770                 775                 780

Val Ser Glu His Glu Glu Asp Asp Asn Asp Asn Glu Glu Glu His Asn
785                 790                 795                 800

Gly Ser Ser Leu Val Thr Val Ser Ser Glu Asp Ser Gly Leu Gln Glu
                805                 810                 815

Pro Val Ser Gly Ser Val Ile Asp Ala
            820                 825


<210> SEQ ID NO 136
<211> LENGTH: 1506
<212> TYPE: DNA
<213> ORGANISM: Acinetobacter sp. ADP1

<400> SEQUENCE: 136

atgttaggca taaaaaagtc agatatgaat ccttatcaag ctcatcgcat aaaaaaatta     60

aaataccagc ttgaaaatgc cgaaagctat gaagagtgga aatctaccgc attgcaactc    120

gatgaagaaa cgggtttgca agaatggaaa tatgataact gttctgccta ttttgatgct    180

gagctgatct cataccgact caatttatta cgtaaatatc gcctgcaaca gcgcgtcatg    240

gattctgtat atctgttaca ggagggatta acgcatgata ttgccaacat tggacatcca    300

atgctttttg cagccactta tgttggaacc aagcaaatta tcgaggacta tattgaggaa    360

gtatctttat cactcgcatt tattgcggca agtcaatgtc agaccttaac ggtggcagag    420

aaactcaaat tctttaaaaa ttgtcaaaag acctatggac agccagcact catgttttca    480

ggtggtgcta ctttgggttt gtttcatagt ggagtatgta aaactctgat ccagcaagat    540

ttgatgccga gagtgttatc aggctcaagt gctggtgcga ttatggctgg tatgcttggt    600

acttcaactg catcagaatt tcagaaaatt ttattaggcg aaaacttttt tagtgaggct    660

tttcattttc gtggtgtcag agacctgctt aaaggaaatg gcggttttgc ggatgtgaaa    720

tatctgaaaa agtttttgat tgaaaatctg ggcgacttaa ccttttcaga agcgtatgaa    780

agatctggat tgcatattaa tgttgctgtt gctccttatg atggctcgca aaatgcaaga    840

atcttaaatg cgtacactgc acctaatctt ttggtctgga gtgctgtgtt ggcttcatgt    900

gcagtgcctg ttttatttcc gcctgtacgt ctgaccagta aaaaacgtga cggtagccat    960

acgccttata tggccaatac taaatgggta gatggcagcg ttagaagtga ttttccacag   1020

gaaaaaatgg cgcgtttata taatttgaat tatacgattg ccagtcaagt caatccgcat   1080

gtggttcctt ttatgcagag cgatgcatca cgctatcgaa aggatattct gagttggccg   1140

caacgtattt tacgtcgtca aggtaaagtg atttcattag gcatcatgga ttttacccgt   1200

gaacgattag gcaatgttcc gccagtcaga cgcttgcttg atcatggtta tggcatagtg   1260
```

-continued

```
gggcagaggt attatggtga cgtcaatatc attgcgccgt tcaatctgcg gcagtatgca   1320

tatatgctgc aaaaccctcg accacactta tttaagttac ttcaacagca gggagagcgt   1380

gccacatggc caaaaatttc tgccattgaa acacatgctc ggattggtaa aacgattcag   1440

cactgtatcg aggtactgga ttatcaaaaa aatcgatata tacaagctga aaaagccagt   1500

gcttaa                                                              1506


<210> SEQ ID NO 137
<211> LENGTH: 501
<212> TYPE: PRT
<213> ORGANISM: Acinetobacter sp. ADP1

<400> SEQUENCE: 137

Met Leu Gly Ile Lys Lys Ser Asp Met Asn Pro Tyr Gln Ala His Arg
 1               5                  10                  15

Ile Lys Lys Leu Lys Tyr Gln Leu Glu Asn Ala Glu Ser Tyr Glu Glu
            20                  25                  30

Trp Lys Ser Thr Ala Leu Gln Leu Asp Glu Glu Thr Gly Leu Gln Glu
        35                  40                  45

Trp Lys Tyr Asp Asn Cys Ser Ala Tyr Phe Asp Ala Glu Leu Ile Ser
    50                  55                  60

Tyr Arg Leu Asn Leu Leu Arg Lys Tyr Arg Leu Gln Gln Arg Val Met
65                  70                  75                  80

Asp Ser Val Tyr Leu Leu Gln Glu Gly Leu Thr His Asp Ile Ala Asn
                85                  90                  95

Ile Gly His Pro Met Leu Phe Ala Ala Thr Tyr Val Gly Thr Lys Gln
            100                 105                 110

Ile Ile Glu Asp Tyr Ile Glu Glu Val Ser Leu Ser Leu Ala Phe Ile
        115                 120                 125

Ala Ala Ser Gln Cys Gln Thr Leu Thr Val Ala Glu Lys Leu Lys Phe
    130                 135                 140

Phe Lys Asn Cys Gln Lys Thr Tyr Gly Gln Pro Ala Leu Met Phe Ser
145                 150                 155                 160

Gly Gly Ala Thr Leu Gly Leu Phe His Ser Gly Val Cys Lys Thr Leu
                165                 170                 175

Ile Gln Gln Asp Leu Met Pro Arg Val Leu Ser Gly Ser Ser Ala Gly
            180                 185                 190

Ala Ile Met Ala Gly Met Leu Gly Thr Ser Thr Ala Ser Glu Phe Gln
        195                 200                 205

Lys Ile Leu Leu Gly Glu Asn Phe Phe Ser Glu Ala Phe His Phe Arg
    210                 215                 220

Gly Val Arg Asp Leu Leu Lys Gly Asn Gly Gly Phe Ala Asp Val Lys
225                 230                 235                 240

Tyr Leu Lys Lys Phe Leu Ile Glu Asn Leu Gly Asp Leu Thr Phe Ser
                245                 250                 255

Glu Ala Tyr Glu Arg Ser Gly Leu His Ile Asn Val Ala Val Ala Pro
            260                 265                 270

Tyr Asp Gly Ser Gln Asn Ala Arg Ile Leu Asn Ala Tyr Thr Ala Pro
        275                 280                 285

Asn Leu Leu Val Trp Ser Ala Val Leu Ala Ser Cys Ala Val Pro Val
    290                 295                 300

Leu Phe Pro Pro Val Arg Leu Thr Ser Lys Lys Arg Asp Gly Ser His
305                 310                 315                 320

Thr Pro Tyr Met Ala Asn Thr Lys Trp Val Asp Gly Ser Val Arg Ser
```

-continued

```
            325                 330                 335

Asp Phe Pro Gln Glu Lys Met Ala Arg Leu Tyr Asn Leu Asn Tyr Thr
            340                 345                 350

Ile Ala Ser Gln Val Asn Pro His Val Val Pro Phe Met Gln Ser Asp
        355                 360                 365

Ala Ser Arg Tyr Arg Lys Asp Ile Leu Ser Trp Pro Gln Arg Ile Leu
    370                 375                 380

Arg Arg Gln Gly Lys Val Ile Ser Leu Gly Ile Met Asp Phe Thr Arg
385                 390                 395                 400

Glu Arg Leu Gly Asn Val Pro Pro Val Arg Arg Leu Leu Asp His Gly
                405                 410                 415

Tyr Gly Ile Val Gly Gln Arg Tyr Tyr Gly Asp Val Asn Ile Ile Ala
            420                 425                 430

Pro Phe Asn Leu Arg Gln Tyr Ala Tyr Met Leu Gln Asn Pro Arg Pro
        435                 440                 445

His Leu Phe Lys Leu Leu Gln Gln Gln Gly Glu Arg Ala Thr Trp Pro
    450                 455                 460

Lys Ile Ser Ala Ile Glu Thr His Ala Arg Ile Gly Lys Thr Ile Gln
465                 470                 475                 480

His Cys Ile Glu Val Leu Asp Tyr Gln Lys Asn Arg Tyr Ile Gln Ala
                485                 490                 495

Glu Lys Ala Ser Ala
            500
```

<210> SEQ ID NO 138
<211> LENGTH: 2733
<212> TYPE: DNA
<213> ORGANISM: Saccharomyces cerevisiae S288c

<400> SEQUENCE: 138

```
atgagcagca aaatatcaga tcttacatct acacaaaata agcccctcct tgttacgcaa     60

caactaatcg aaaaatatta cgaacagatc ctgggcactt cccagaacat aattcctatt    120

ttaaatccga agaacaagtt tattaggccc agtaaggata attcagatgt tgaaagggtg    180

gaggaggatg ctggtaaaag actgcaaact ggcaagaaca aaactacgaa caaagtaaat    240

ttcaacctgg atactggaaa cgaggataaa cttgacgatg accaagagac agtaacagaa    300

aatgaaaata atgatatcga gatggttgag acagacgaag gcgaagatga aaggcaaggg    360

tcatctttag ccagtaaatg caaatcattt ctttacaacg tttttgtggg aaactatgaa    420

agagacattc ttattgacaa agtctgttca caaaagcaac atgcgatgtc atttgaagaa    480

tggtgttctg cgggcgccag attggatgac ctcactggga aaacagaatg gaagcagaaa    540

ttggaaagtc ccttgtatga ttacaagcta ataaaagatt taacatctag aatgcgtgag    600

gagcgcttga ataggaatta cgctcaattg ttgtacatca ttaggacgaa ttgggtacga    660

aacctgggaa atatggggaa tgtaaaccta tataggcact cccatgtagg caccaaatat    720

ttaattgacg agtatatgat ggagtctagg ttagcgctag aatctttaat ggagtctgat    780

cttgatgata gttacctttt gggtatactg caacaaacga gaagaaatat tggtcgtacc    840

gctttagttc tcagtggggg tggaactttt ggtcttttcc acatcggtgt ccttggtact    900

ctatttgaat tggatttatt acccagagtg attagtggta gcagtgctgg tgcaattgta    960

gcaagcatat tatctgtcca tcacaaagaa gaaattccgg ttttactaaa tcatattttg   1020

gataaagaat tcaacatttt caaagacgat aaacagaaaa gtgaaagcga gaatttgtta   1080
```

ataaaaatat ctaggttctt caaaaacggt acgtggtttg ataacaagca tctggtaaat 1140
acaatgatag aatttttggg agatttgaca tttagggaag cttacaatag aacgggtaaa 1200
attttgaata taaccgtttc gccggcatct ttatttgaac aaccgcgctt gctgaataat 1260
ttgactgcac caaacgtcct gatttggtcc gccgtatgtg catcatgttc actaccggga 1320
attttcccct cgagcccact ttacgaaaaa gatccaaaaa cgggagaaag gaaaccatgg 1380
actggtagta gttcggtcaa atttgtcgat ggttctgtgg acaatgactt gcccatttct 1440
cgtctttctg aaatgtttaa tgtagaccat attatcgcat gccaggtgaa tattcacgta 1500
tttccctttt tgaaactatc actatcctgt gttggcgggg aaattgagga cgaatttagt 1560
gcaagattaa agcaaaactt atcaagtata tacaatttta tggccaatga agctattcat 1620
attctagaaa ttggaagtga gatgggaatt gccaaaaacg cgcttacaaa actgagatcg 1680
gtattatctc aacaatattc tggtgacatc actattttgc ccgacatgtg tatgcttttt 1740
agaataaagg agctgttgtc aaacccaaca aaagaatttt tattaaggga aatcaccaat 1800
ggtgcaaaag ctacgtggcc caaggtttcc attattcaaa atcactgtgg ccaggaattt 1860
gctctggata aggcgatttc ttatatcaaa ggtaggatga ttgtcacctc ctctttaaaa 1920 accccccttcc aatttgctga ttcagtcatt ggattaatta aagctccaga gcaaacgtca 1980
gatgagtcca aaaacccaga aaattcaaca ttgctaacta ggactccaac caagggtgac 2040
aatcatattt ccaatgtttt agatgacaac ttattagaat cagaatcgac aaactctttg 2100
ctattgttac gtgagaatgc aagcacatat gggcggtcac cttccgggtt tagaccgcgg 2160
tattccatta cgtccgcttc tctcaatccg cgtcaccaaa gaaggaaatc agatactatt 2220
tcaacttcaa ggcgaccagc caaatccttt tcattttcag ttgcttctcc cacatcaagg 2280
atgttgaggc aatccagcaa aatcaatgga cacccaccgc caattctgca gaaaaaaaca 2340
agtatgggcc ggctaatgtt tcctatggat gccaagacct atgacccgga aagccatgaa 2400
cttatcccac attctgccag cattgaaaca cctgccatgg tagacaagaa attgcatttt 2460
ggccgaaaga gtagatactt gaggcatatg aacaaaaaat gggtcagcag tagcaacata 2520
ttatacacag attcggataa agaagaccat cctacattga gactgataag taacttcgat 2580
tcagacgcaa tgattcatag tgatttagcg ggcaatttca ggcgtcatag cattgatgga 2640
agaccccctt ctcaagctac aaagagctca ccgtttcgat cgaggccttc ttcttcaacg 2700
cagcacaaaa gcaccaccag ttttactcaa taa 2733

<210> SEQ ID NO 139
<211> LENGTH: 910
<212> TYPE: PRT
<213> ORGANISM: Saccharomyces cerevisiae S288c

<400> SEQUENCE: 139

Met Ser Ser Lys Ile Ser Asp Leu Thr Ser Thr Gln Asn Lys Pro Leu
1 5 10 15

Leu Val Thr Gln Gln Leu Ile Glu Lys Tyr Tyr Glu Gln Ile Leu Gly
20 25 30

Thr Ser Gln Asn Ile Ile Pro Ile Leu Asn Pro Lys Asn Lys Phe Ile
35 40 45

Arg Pro Ser Lys Asp Asn Ser Asp Val Glu Arg Val Glu Glu Asp Ala
50 55 60

Gly Lys Arg Leu Gln Thr Gly Lys Asn Lys Thr Thr Asn Lys Val Asn
65 70 75 80

-continued

```
Phe Asn Leu Asp Thr Gly Asn Glu Asp Lys Leu Asp Asp Asp Gln Glu
                85                  90                  95

Thr Val Thr Glu Asn Glu Asn Asn Asp Ile Glu Met Val Glu Thr Asp
            100                 105                 110

Glu Gly Glu Asp Glu Arg Gln Gly Ser Ser Leu Ala Ser Lys Cys Lys
        115                 120                 125

Ser Phe Leu Tyr Asn Val Phe Val Gly Asn Tyr Glu Arg Asp Ile Leu
    130                 135                 140

Ile Asp Lys Val Cys Ser Gln Lys Gln His Ala Met Ser Phe Glu Glu
145                 150                 155                 160

Trp Cys Ser Ala Gly Ala Arg Leu Asp Asp Leu Thr Gly Lys Thr Glu
                165                 170                 175

Trp Lys Gln Lys Leu Glu Ser Pro Leu Tyr Asp Tyr Lys Leu Ile Lys
            180                 185                 190

Asp Leu Thr Ser Arg Met Arg Glu Glu Arg Leu Asn Arg Asn Tyr Ala
        195                 200                 205

Gln Leu Leu Tyr Ile Ile Arg Thr Asn Trp Val Arg Asn Leu Gly Asn
    210                 215                 220

Met Gly Asn Val Asn Leu Tyr Arg His Ser His Val Gly Thr Lys Tyr
225                 230                 235                 240

Leu Ile Asp Glu Tyr Met Met Glu Ser Arg Leu Ala Leu Glu Ser Leu
                245                 250                 255

Met Glu Ser Asp Leu Asp Asp Ser Tyr Leu Leu Gly Ile Leu Gln Gln
            260                 265                 270

Thr Arg Arg Asn Ile Gly Arg Thr Ala Leu Val Leu Ser Gly Gly Gly
        275                 280                 285

Thr Phe Gly Leu Phe His Ile Gly Val Leu Gly Thr Leu Phe Glu Leu
    290                 295                 300

Asp Leu Leu Pro Arg Val Ile Ser Gly Ser Ser Ala Gly Ala Ile Val
305                 310                 315                 320

Ala Ser Ile Leu Ser Val His His Lys Glu Glu Ile Pro Val Leu Leu
                325                 330                 335

Asn His Ile Leu Asp Lys Glu Phe Asn Ile Phe Lys Asp Asp Lys Gln
            340                 345                 350

Lys Ser Glu Ser Glu Asn Leu Leu Ile Lys Ile Ser Arg Phe Phe Lys
        355                 360                 365

Asn Gly Thr Trp Phe Asp Asn Lys His Leu Val Asn Thr Met Ile Glu
    370                 375                 380

Phe Leu Gly Asp Leu Thr Phe Arg Glu Ala Tyr Asn Arg Thr Gly Lys
385                 390                 395                 400

Ile Leu Asn Ile Thr Val Ser Pro Ala Ser Leu Phe Glu Gln Pro Arg
                405                 410                 415

Leu Leu Asn Asn Leu Thr Ala Pro Asn Val Leu Ile Trp Ser Ala Val
            420                 425                 430

Cys Ala Ser Cys Ser Leu Pro Gly Ile Phe Pro Ser Ser Pro Leu Tyr
        435                 440                 445

Glu Lys Asp Pro Lys Thr Gly Glu Arg Lys Pro Trp Thr Gly Ser Ser
    450                 455                 460

Ser Val Lys Phe Val Asp Gly Ser Val Asp Asn Asp Leu Pro Ile Ser
465                 470                 475                 480

Arg Leu Ser Glu Met Phe Asn Val Asp His Ile Ile Ala Cys Gln Val
                485                 490                 495

Asn Ile His Val Phe Pro Phe Leu Lys Leu Ser Leu Ser Cys Val Gly
```

-continued

```
            500                 505                 510

Gly Glu Ile Glu Asp Glu Phe Ser Ala Arg Leu Lys Gln Asn Leu Ser
        515                 520                 525

Ser Ile Tyr Asn Phe Met Ala Asn Glu Ala Ile His Ile Leu Glu Ile
    530                 535                 540

Gly Ser Glu Met Gly Ile Ala Lys Asn Ala Leu Thr Lys Leu Arg Ser
545                 550                 555                 560

Val Leu Ser Gln Gln Tyr Ser Gly Asp Ile Thr Ile Leu Pro Asp Met
                565                 570                 575

Cys Met Leu Phe Arg Ile Lys Glu Leu Leu Ser Asn Pro Thr Lys Glu
            580                 585                 590

Phe Leu Leu Arg Glu Ile Thr Asn Gly Ala Lys Ala Thr Trp Pro Lys
        595                 600                 605

Val Ser Ile Ile Gln Asn His Cys Gly Gln Glu Phe Ala Leu Asp Lys
    610                 615                 620

Ala Ile Ser Tyr Ile Lys Gly Arg Met Ile Val Thr Ser Ser Leu Lys
625                 630                 635                 640

Thr Pro Phe Gln Phe Ala Asp Ser Val Ile Gly Leu Ile Lys Ala Pro
                645                 650                 655

Glu Gln Thr Ser Asp Glu Ser Lys Asn Pro Glu Asn Ser Thr Leu Leu
            660                 665                 670

Thr Arg Thr Pro Thr Lys Gly Asp Asn His Ile Ser Asn Val Leu Asp
        675                 680                 685

Asp Asn Leu Leu Glu Ser Glu Ser Thr Asn Ser Leu Leu Leu Leu Arg
    690                 695                 700

Glu Asn Ala Ser Thr Tyr Gly Arg Ser Pro Ser Gly Phe Arg Pro Arg
705                 710                 715                 720

Tyr Ser Ile Thr Ser Ala Ser Leu Asn Pro Arg His Gln Arg Arg Lys
                725                 730                 735

Ser Asp Thr Ile Ser Thr Ser Arg Arg Pro Ala Lys Ser Phe Ser Phe
            740                 745                 750

Ser Val Ala Ser Pro Thr Ser Arg Met Leu Arg Gln Ser Ser Lys Ile
        755                 760                 765

Asn Gly His Pro Pro Pro Ile Leu Gln Lys Lys Thr Ser Met Gly Arg
    770                 775                 780

Leu Met Phe Pro Met Asp Ala Lys Thr Tyr Asp Pro Glu Ser His Glu
785                 790                 795                 800

Leu Ile Pro His Ser Ala Ser Ile Glu Thr Pro Ala Met Val Asp Lys
                805                 810                 815

Lys Leu His Phe Gly Arg Lys Ser Arg Tyr Leu Arg His Met Asn Lys
            820                 825                 830

Lys Trp Val Ser Ser Ser Asn Ile Leu Tyr Thr Asp Ser Asp Lys Glu
        835                 840                 845

Asp His Pro Thr Leu Arg Leu Ile Ser Asn Phe Asp Ser Asp Ala Met
    850                 855                 860

Ile His Ser Asp Leu Ala Gly Asn Phe Arg Arg His Ser Ile Asp Gly
865                 870                 875                 880

Arg Pro Pro Ser Gln Ala Thr Lys Ser Ser Pro Phe Arg Ser Arg Pro
                885                 890                 895

Ser Ser Ser Thr Gln His Lys Ser Thr Thr Ser Phe Thr Gln
            900                 905                 910
```

<210> SEQ ID NO 140

<211> LENGTH: 1413
<212> TYPE: DNA
<213> ORGANISM: Rhodococcus jostii RHA1

<400> SEQUENCE: 140

```
atgatcggat cgagagcacg acgacgtcga atgctgctgg tgggagcgat ggtggtgggc     60
gcacagctcg ccgtcgccgc gccgtcggtc ggggctcccg ccgacgacgg aacgccggtg    120
gacgtgcagc cggctactac cgtccccgcc tggcccgagg ccgaccgggg gttctacgaa    180
ccaccggcgg acgtggtcgc ggcggccgag ccgggcgaaa tcatcgccgc ccgcgaagtg    240
cacctggcga acctgtcggt gcttccggtg aacgtcgacg cgtggcagct gtcgtatcgc    300
tccaccaact cgcgggacga gccgatcccg gcggtcgcga cggtcgtcaa gccgcggggc    360
acgatcgacg gcgtccgcaa tctgctctcg ctccagccgg aggaagactc cctcggcaag    420
tactgcgccg cttcgtacgc actgcagcag tggtccgtgc ccgcgccgct gaccggtcag    480
atcgtcgcgc cgctgcagtt cctcgaggcg caggccgccc tcgcccaggg atgggccgtc    540
gtgatgccgg atcaccaggg cccgaacgcc gcgtatgcgg ccgggcccct cgcgggccgc    600
atcaccctgg acgggatccg ggcggcggag aacttcggcc cactgggcct gacaggcagg    660
cagactccgg tcgggttgat gggctattcc ggaggcgcga tcgcgacggg tcacgccgcc    720
gaactccacg cgagctacgc accggacctg aacatcgtcg gtgcggccga aggcggcatc    780
ccggccgatc tcggcgccct cgtcgatctc gccgacaaca acctgggcgc gggaatcgtg    840
ctgggcggcg tgttcggcgt gagccgtgat tatcccgagc tcgcggagta tctcgacaca    900
catctgaatc cactcggcaa gcagctcctg accgccaaga gcaacctctg cgtgagctac    960
cagtcggcgc tcctgccgtt cgcgaacctg cggggcctgt tcgacagccc gagcggtgac   1020
ccgctgcgcg atccggtggt cgagtcggta ctcgaccgga cgaagatggg tcaccgggtc   1080
ccggacgtcc cgatgttcat gtaccaggcg aacccggact ggctggtgcc ggtcgggccc   1140
gtcgacacac tcgtcgacac ctactgccag gacccggacg cccgggtgac ctacacccgc   1200
gaccacgcca gcgagcacct gtccctcgaa ccggtcgcgg cggcgagcgc cctgatgtgg   1260
ctgcgggacc ggttcgccgg ggtcccggcc gagaccggat gcagcaccca cgacgtcgga   1320
tcgatggccc tcgaccaggc gacgtggccg gtgtggtcgt cgatcgtcgg cgacacgatc   1380
acgagcctgc tcggtcagcc gatcggcacg tga                                1413
```

<210> SEQ ID NO 141
<211> LENGTH: 470
<212> TYPE: PRT
<213> ORGANISM: Rhodococcus jostii RHA1

<400> SEQUENCE: 141

```
Met Ile Gly Ser Arg Ala Arg Arg Arg Arg Met Leu Leu Val Gly Ala
1               5                   10                  15

Met Val Val Gly Ala Gln Leu Ala Val Ala Ala Pro Ser Val Gly Ala
            20                  25                  30

Pro Ala Asp Asp Gly Thr Pro Val Asp Val Gln Pro Ala Thr Thr Val
        35                  40                  45

Pro Ala Trp Pro Glu Ala Asp Arg Gly Phe Tyr Glu Pro Pro Ala Asp
    50                  55                  60

Val Val Ala Ala Ala Glu Pro Gly Glu Ile Ile Ala Ala Arg Glu Val
65                  70                  75                  80

His Leu Ala Asn Leu Ser Val Leu Pro Val Asn Val Asp Ala Trp Gln
                85                  90                  95
```

Leu Ser Tyr Arg Ser Thr Asn Ser Arg Asp Glu Pro Ile Pro Ala Val
100 105 110

Ala Thr Val Val Lys Pro Arg Gly Thr Ile Asp Gly Val Arg Asn Leu
115 120 125

Leu Ser Leu Gln Pro Glu Glu Asp Ser Leu Gly Lys Tyr Cys Ala Ala
130 135 140

Ser Tyr Ala Leu Gln Gln Trp Ser Val Pro Ala Pro Leu Thr Gly Gln
145 150 155 160

Ile Val Ala Pro Leu Gln Phe Leu Glu Ala Gln Ala Ala Leu Ala Gln
165 170 175

Gly Trp Ala Val Val Met Pro Asp His Gln Gly Pro Asn Ala Ala Tyr
180 185 190

Ala Ala Gly Pro Leu Ala Gly Arg Ile Thr Leu Asp Gly Ile Arg Ala
195 200 205

Ala Glu Asn Phe Gly Pro Leu Gly Leu Thr Gly Arg Gln Thr Pro Val
210 215 220

Gly Leu Met Gly Tyr Ser Gly Gly Ala Ile Ala Thr Gly His Ala Ala
225 230 235 240

Glu Leu His Ala Ser Tyr Ala Pro Asp Leu Asn Ile Val Gly Ala Ala
245 250 255

Glu Gly Gly Ile Pro Ala Asp Leu Gly Ala Leu Val Asp Leu Ala Asp
260 265 270

Asn Asn Leu Gly Ala Gly Ile Val Leu Gly Gly Val Phe Gly Val Ser
275 280 285

Arg Asp Tyr Pro Glu Leu Ala Glu Tyr Leu Asp Thr His Leu Asn Pro
290 295 300

Leu Gly Lys Gln Leu Leu Thr Ala Lys Ser Asn Leu Cys Val Ser Tyr
305 310 315 320

Gln Ser Ala Leu Leu Pro Phe Ala Asn Leu Arg Gly Leu Phe Asp Ser
325 330 335

Pro Ser Gly Asp Pro Leu Arg Asp Pro Val Val Glu Ser Val Leu Asp
340 345 350

Arg Thr Lys Met Gly His Arg Val Pro Asp Val Pro Met Phe Met Tyr
355 360 365

Gln Ala Asn Pro Asp Trp Leu Val Pro Val Gly Pro Val Asp Thr Leu
370 375 380

Val Asp Thr Tyr Cys Gln Asp Pro Asp Ala Arg Val Thr Tyr Thr Arg
385 390 395 400

Asp His Ala Ser Glu His Leu Ser Leu Glu Pro Val Ala Ala Ala Ser
405 410 415

Ala Leu Met Trp Leu Arg Asp Arg Phe Ala Gly Val Pro Ala Glu Thr
420 425 430

Gly Cys Ser Thr His Asp Val Gly Ser Met Ala Leu Asp Gln Ala Thr
435 440 445

Trp Pro Val Trp Ser Ser Ile Val Gly Asp Thr Ile Thr Ser Leu Leu
450 455 460

Gly Gln Pro Ile Gly Thr
465 470

<210> SEQ ID NO 142
<211> LENGTH: 2103
<212> TYPE: DNA
<213> ORGANISM: Saccharomyces cerevisiae S288c

<400> SEQUENCE: 142

```
atggttgctc aatataccgt tccagttggg aaagccgcca atgagcatga aactgctcca      60
agaagaaatt atcaatgccg cgagaagccg ctcgtcagac cgcctaacac aaagtgttcc     120
actgtttatg agtttgttct agagtgcttt cagaagaaca aaaattcaaa tgctatgggt     180
tggagggatg ttaaggaaat tcatgaagaa tccaaatcgg ttatgaaaaa agttgatggc     240
aaggagactt cagtggaaaa gaaatggatg tattatgaac tatcgcatta tcattataat     300
tcatttgacc aattgaccga tatcatgcat gaaattggtc gtgggttggt gaaaatagga     360
ttaaagccta atgatgatga caaattacat ctttacgcag ccacttctca caagtggatg     420
aagatgttct taggagcgca gtctcaaggt attcctgtcg tcactgccta cgatactttg     480
ggagagaaag ggctaattca ttctttggtg caaacggggt ctaaggccat tttaccgat      540
aactctttat taccatcctt gatcaaacca gtgcaagccg ctcaagacgt aaaatacata     600
attcatttcg attccatcag ttctgaggac aggaggcaaa gtggtaagat ctatcaatct     660
gctcatgatg ccatcaacag aattaaagaa gttagacctg atatcaagac ctttagcttt     720
gacgacatct tgaagctagg taaagaatcc tgtaacgaaa tcgatgttca tccacctggc     780
aaggatgatc tttgttgcat catgtatacg tctggttcta caggtgagcc aaagggtgtt     840
gtcttgaaac attcaaatgt tgtcgcaggt gttggtggtg caagtttgaa tgttttgaag     900
tttgtgggca ataccgaccg tgttatctgt tttttgccac tagctcatat ttttgaattg     960
gttttcgaac tattgtcctt ttattggggg gcctgcattg gttatgccac cgtaaaaact    1020
ttaactagca gctctgtgag aaattgtcaa ggtgatttgc aagaattcaa gcccacaatc    1080
atggttggtg tcgccgctgt ttgggaaaca gtgagaaaag ggatcttaaa ccaaattgat    1140
aatttgccct tcctcaccaa gaaaatcttc tggaccgcgt ataataccaa gttgaacatg    1200
caacgtctcc acatccctgg tggcggcgcc ttaggaaact tggttttcaa aaaaatcaga    1260
actgccacag gtggccaatt aagatatttg ttaaacggtg gttctccaat cagtcgggat    1320
gctcaggaat tcatcacaaa tttaatctgc cctatgctta ttggttacgg tttaaccgag    1380
acatgcgcta gtaccaccat cttggatcct gctaattttg aactcggcgt cgctggtgac    1440
ctaacaggtt gtgttaccgt caaactagtt gatgttgaag aattaggtta ttttgctaaa    1500
aacaaccaag gtgaagtttg gatcacaggt gccaatgtca cgcctgaata ttataagaat    1560
gaggaagaaa cttctcaagc tttaacaagc gatggttggt tcaagaccgg tgacatcggt    1620
gaatgggaag caaatggcca tttgaaaata attgacagga agaaaaactt ggtcaaaaca    1680
atgaacggtg aatatatcgc actcgagaaa ttagagtccg tttacagatc taacgaatat    1740
gttgctaaca tttgtgttta tgccgaccaa tctaagacta agccagttgg tattattgta    1800
ccaaatcatg ctccattaac gaagcttgct aaaaagttgg gaattatgga acaaaaagac    1860
agttcaatta atatcgaaaa ttatttggag gatgcaaaat tgattaaagc tgtttattct    1920
gatcttttga agacaggtaa agaccaaggt ttggttggca ttgaattact agcaggcata    1980
gtgttctttg acggcgaatg gactccacaa aacggttttg ttacgtccgc tcagaaattg    2040
aaaagaaaag acattttgaa tgctgtcaaa gataaagttg acgccgttta tagttcgtct    2100
taa                                                                  2103
```

<210> SEQ ID NO 143
<211> LENGTH: 700
<212> TYPE: PRT
<213> ORGANISM: Saccharomyces cerevisiae S288c

<400> SEQUENCE: 143

Met Val Ala Gln Tyr Thr Val Pro Val Gly Lys Ala Ala Asn Glu His
1 5 10 15

Glu Thr Ala Pro Arg Arg Asn Tyr Gln Cys Arg Glu Lys Pro Leu Val
20 25 30

Arg Pro Pro Asn Thr Lys Cys Ser Thr Val Tyr Glu Phe Val Leu Glu
35 40 45

Cys Phe Gln Lys Asn Lys Asn Ser Asn Ala Met Gly Trp Arg Asp Val
50 55 60

Lys Glu Ile His Glu Glu Ser Lys Ser Val Met Lys Lys Val Asp Gly
65 70 75 80

Lys Glu Thr Ser Val Glu Lys Lys Trp Met Tyr Tyr Glu Leu Ser His
85 90 95

Tyr His Tyr Asn Ser Phe Asp Gln Leu Thr Asp Ile Met His Glu Ile
100 105 110

Gly Arg Gly Leu Val Lys Ile Gly Leu Lys Pro Asn Asp Asp Asp Lys
115 120 125

Leu His Leu Tyr Ala Ala Thr Ser His Lys Trp Met Lys Met Phe Leu
130 135 140

Gly Ala Gln Ser Gln Gly Ile Pro Val Val Thr Ala Tyr Asp Thr Leu
145 150 155 160

Gly Glu Lys Gly Leu Ile His Ser Leu Val Gln Thr Gly Ser Lys Ala
165 170 175

Ile Phe Thr Asp Asn Ser Leu Leu Pro Ser Leu Ile Lys Pro Val Gln
180 185 190

Ala Ala Gln Asp Val Lys Tyr Ile Ile His Phe Asp Ser Ile Ser Ser
195 200 205

Glu Asp Arg Arg Gln Ser Gly Lys Ile Tyr Gln Ser Ala His Asp Ala
210 215 220

Ile Asn Arg Ile Lys Glu Val Arg Pro Asp Ile Lys Thr Phe Ser Phe
225 230 235 240

Asp Asp Ile Leu Lys Leu Gly Lys Glu Ser Cys Asn Glu Ile Asp Val
245 250 255

His Pro Pro Gly Lys Asp Asp Leu Cys Cys Ile Met Tyr Thr Ser Gly
260 265 270

Ser Thr Gly Glu Pro Lys Gly Val Val Leu Lys His Ser Asn Val Val
275 280 285

Ala Gly Val Gly Gly Ala Ser Leu Asn Val Leu Lys Phe Val Gly Asn
290 295 300

Thr Asp Arg Val Ile Cys Phe Leu Pro Leu Ala His Ile Phe Glu Leu
305 310 315 320

Val Phe Glu Leu Leu Ser Phe Tyr Trp Gly Ala Cys Ile Gly Tyr Ala
325 330 335

Thr Val Lys Thr Leu Thr Ser Ser Ser Val Arg Asn Cys Gln Gly Asp
340 345 350

Leu Gln Glu Phe Lys Pro Thr Ile Met Val Gly Val Ala Ala Val Trp
355 360 365

Glu Thr Val Arg Lys Gly Ile Leu Asn Gln Ile Asp Asn Leu Pro Phe
370 375 380

Leu Thr Lys Lys Ile Phe Trp Thr Ala Tyr Asn Thr Lys Leu Asn Met
385 390 395 400

Gln Arg Leu His Ile Pro Gly Gly Gly Ala Leu Gly Asn Leu Val Phe

-continued

```
                405                 410                 415

Lys Lys Ile Arg Thr Ala Thr Gly Gly Gln Leu Arg Tyr Leu Leu Asn
            420                 425                 430

Gly Gly Ser Pro Ile Ser Arg Asp Ala Gln Glu Phe Ile Thr Asn Leu
        435                 440                 445

Ile Cys Pro Met Leu Ile Gly Tyr Gly Leu Thr Glu Thr Cys Ala Ser
    450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
                485                 490                 495

Tyr Phe Ala Lys Asn Asn Gln Gly Glu Val Trp Ile Thr Gly Ala Asn
            500                 505                 510

Val Thr Pro Glu Tyr Tyr Lys Asn Glu Glu Glu Thr Ser Gln Ala Leu
        515                 520                 525

Thr Ser Asp Gly Trp Phe Lys Thr Gly Asp Ile Gly Glu Trp Glu Ala
    530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
                565                 570                 575

Ser Asn Glu Tyr Val Ala Asn Ile Cys Val Tyr Ala Asp Gln Ser Lys
            580                 585                 590

Thr Lys Pro Val Gly Ile Ile Val Pro Asn His Ala Pro Leu Thr Lys
        595                 600                 605

Leu Ala Lys Lys Leu Gly Ile Met Glu Gln Lys Asp Ser Ser Ile Asn
    610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
                645                 650                 655

Leu Ala Gly Ile Val Phe Phe Asp Gly Glu Trp Thr Pro Gln Asn Gly
            660                 665                 670

Phe Val Thr Ser Ala Gln Lys Leu Lys Arg Lys Asp Ile Leu Asn Ala
        675                 680                 685

Val Lys Asp Lys Val Asp Ala Val Tyr Ser Ser Ser
    690                 695                 700
```

<210> SEQ ID NO 144
<211> LENGTH: 2235
<212> TYPE: DNA
<213> ORGANISM: Saccharomyces cerevisiae S288c

<400> SEQUENCE: 144

```
atggccgctc cagattatgc acttaccgat ttaattgaat cggatcctcg tttcgaaagt      60

ttgaagacaa gattagccgg ttacaccaaa ggctctgatg aatatattga agagctatac     120

tctcaattac cactgaccag ctatcccagg tacaaaacat ttttaaagaa acaggcggtt     180

gccatttcga atccggataa tgaagctggt tttagctcga tttataggag ttctctttct     240

tctgaaaatc tagtgagctg tgtggataaa aacttaagaa ctgcatacga tcacttcatg     300

ttttctgcaa ggagatggcc tcaacgtgac tgtttaggtt caaggccaat tgataaagcc     360

acaggcacct gggaggaaac attccgtttc gagtcgtact ccacggtatc taaaagatgt     420

cataatatcg gaagtggtat attgtctttg gtaaacacga aaaggaaacg tcctttggaa     480
```

-continued gccaatgatt ttgttgttgc tatcttatca cacaacaacc ctgaatggat cctaacagat 540
ttggcctgtc aggcctattc tctaactaac acggctttgt acgaaacatt aggtccaaac 600
acctccgagt acatattgaa tttaaccgag gcccccattc tgatttttgc aaaatcaaat 660
atgtatcatg tattgaagat ggtgcctgat atgaaatttg ttaatacttt ggtttgtatg 720
gatgaattaa ctcatgacga gctccgtatg ctaaatgaat cgttgctacc cgttaagtgc 780
aactctctca atgaaaaaat cacatttttt tcattggagc aggtagaaca agttggttgc 840
tttaacaaaa ttcctgcaat tccacctacc ccagattcct tgtatactat ttcgtttact 900
tctggtacta caggtttacc taaaggtgtg gaaatgtctc acagaaacat tgcgtctggg 960
atagcatttg ctttttctac cttcagaata ccgccagata aaagaaacca acagttatat 1020
gatatgtgtt ttttgccatt ggctcatatt tttgaaagaa tggttattgc gtatgatcta 1080
gccatcgggt ttggaatagg cttcttacat aaaccagacc caactgtatt ggtagaggat 1140
ttgaagattt tgaaacctta cgcggttgcc ctggttccta gaatattaac acggtttgaa 1200
gccggtataa aaaacgcttt ggataaatcg actgtccaga ggaacgtagc aaatactata 1260
ttggattcta aatcggccag atttaccgca agaggtggtc cagataaatc gattatgaat 1320
tttctagttt atcatcgcgt attgattgat aaaatcagag actctttagg tttgtccaat 1380
aactcgttta taattaccgg atcagctccc atatctaaag ataccttact atttttaaga 1440
agtgccttgg atattggtat aagacagggc tacggcttaa ctgaaacttt tgctggtgtc 1500
tgtttaagcg aaccgtttga aaaagatgtc ggatcttgtg gtgccatagg tatttctgca 1560
gaatgtagat tgaagtctgt tccagaaatg ggttaccatg ccgacaagga tttaaaaggt 1620
gaactgcaaa ttcgtggccc acaggttttt gaaagatatt ttaaaaatcc gaatgaaact 1680
tcaaaagccg ttgaccaaga tggttggttt tccacgggag atgttgcatt tatcgatgga 1740
aaaggtcgca tcagcgtcat tgatcgagtc aagaactttt tcaagctagc acatggtgaa 1800
tatattgctc cagagaaaat cgaaaatatt tatttatcat catgccccta tatcacgcaa 1860
atatttgtct ttggagatcc tttaaagaca tttttagttg gcatcgttgg tgttgatgtt 1920
gatgcagcgc aaccgatttt agctgcaaag cacccagagg tgaaaacgtg gactaaggaa 1980
gtgctagtag aaaacttaaa tcgtaataaa aagctaagga aggaattttt aaacaaaatt 2040
aataaatgca ccgatgggct acaaggattc gaaaaattgc ataacatcaa agtcggactt 2100
gagcctttaa ctctcgagga tgatgttgtg acgccaactt ttaaaataaa gcgtgccaaa 2160
gcatcaaaat tcttcaaaga tacattagac caactatacg ccgaaggttc actagtcaag 2220
acagaaaagc tttag 2235

<210> SEQ ID NO 145
<211> LENGTH: 744
<212> TYPE: PRT
<213> ORGANISM: Saccharomyces cerevisiae S288c

<400> SEQUENCE: 145

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn

-continued

```
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220

Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
            260                 265                 270

Glu Gln Val Glu Gln Val Gly Cys Phe Asn Lys Ile Pro Ala Ile Pro
        275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
        355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480
```

Ser Ala Leu Asp Ile Gly Ile Arg Gln Gly Tyr Gly Leu Thr Glu Thr
485 490 495

Phe Ala Gly Val Cys Leu Ser Glu Pro Phe Glu Lys Asp Val Gly Ser
500 505 510

Cys Gly Ala Ile Gly Ile Ser Ala Glu Cys Arg Leu Lys Ser Val Pro
515 520 525

Glu Met Gly Tyr His Ala Asp Lys Asp Leu Lys Gly Glu Leu Gln Ile
530 535 540

Arg Gly Pro Gln Val Phe Glu Arg Tyr Phe Lys Asn Pro Asn Glu Thr
545 550 555 560

Ser Lys Ala Val Asp Gln Asp Gly Trp Phe Ser Thr Gly Asp Val Ala
565 570 575

Phe Ile Asp Gly Lys Gly Arg Ile Ser Val Ile Asp Arg Val Lys Asn
580 585 590

Phe Phe Lys Leu Ala His Gly Glu Tyr Ile Ala Pro Glu Lys Ile Glu
595 600 605

Asn Ile Tyr Leu Ser Ser Cys Pro Tyr Ile Thr Gln Ile Phe Val Phe
610 615 620

Gly Asp Pro Leu Lys Thr Phe Leu Val Gly Ile Val Gly Val Asp Val
625 630 635 640

Asp Ala Ala Gln Pro Ile Leu Ala Ala Lys His Pro Glu Val Lys Thr
645 650 655

Trp Thr Lys Glu Val Leu Val Glu Asn Leu Asn Arg Asn Lys Lys Leu
660 665 670

Arg Lys Glu Phe Leu Asn Lys Ile Asn Lys Cys Thr Asp Gly Leu Gln
675 680 685

Gly Phe Glu Lys Leu His Asn Ile Lys Val Gly Leu Glu Pro Leu Thr
690 695 700

Leu Glu Asp Asp Val Val Thr Pro Thr Phe Lys Ile Lys Arg Ala Lys
705 710 715 720

Ala Ser Lys Phe Phe Lys Asp Thr Leu Asp Gln Leu Tyr Ala Glu Gly
725 730 735

Ser Leu Val Lys Thr Glu Lys Leu
740

<210> SEQ ID NO 146
<211> LENGTH: 2081
<212> TYPE: DNA
<213> ORGANISM: Artificial Sequence
<220> FEATURE:
<223> OTHER INFORMATION: S. cerevisiae FadD homolog (Faa3p) - codon optimized

<400> SEQUENCE: 146
atgtctgaac aacactcggt ggccgtcggt aaagccgcta acgaacatga aactgccccc 60
cgacgtaacg tgcgcgtgaa aaaacgcccc ttgattcgcc ctctcaatag cagcgcgtcg 120
acgttgtatg agtttgccct ggaatgcttt aacaaggggg gcaaacgcga tggcatggcg 180
tggcgagacg tcatcgagat tcacgaaacg aagaagacta tcgtgcgtaa ggtcgacgga 240
aaggataaaa gcattgaaaa gacctggctg tactacgaaa tgagcccgta caaaatgatg 300
acgtatcagg aactcatttg ggtgatgcat gatatgggtc gcgggctcgc caagattggc 360
atcaagccca acggtgaaca caaatttcat attttcgcgt cgacctccca caaatggatg 420
aaaatctttc tcggctgcat ctcgcaaggc attcctgtgg tcaccgctta tgataccctc 480

-continued

```
ggcgaaagtg gtctcattca ttctatggtg gaaacagaga gtgctgctat ctttacagat    540

aaccaattgc tggcgaaaat gatcgtgcct ctgcagtctg ctaaagatat caagtttctc    600

attcacaacg agccaatcga ccccaatgat cgacgccaga atggaaaact ctataaagct    660

gctaaggacg cgatcaacaa gattcgcgag gttcggcctg atatcaagat ttactcgttc    720

gaagaagtgg ttaaaatcgg caagaagagt aaagatgaag tgaaactgca tccgcccgaa    780

cccaaggatc tcgcgtgtat catgtacacc agtggatcta tcagcgcgcc caaaggggtg    840

gtcctgaccc attataatat cgtcagtggg attgcaggcg ttgggcataa cgtctttggc    900

tggatcggct ccaccgatcg tgtcctgagc tttttgcctc tcgcacacat tttcgaactc    960

gtttttgaat tcgaagcgtt ctactggaat ggtattctgg gatacggcag cgtgaaaacc   1020

ttgacgaata cgagcacccg caactgtaaa ggtgatctgg tggagtttaa accgaccatc   1080

atgattggtg ttgcggccgt ttgggagacg gtccgcaaag cgatcctgga gaaaatcagt   1140

gatttgacac cggtgctgca gaagattttc tggtcggctt acagcatgaa agagaaaagt   1200

gtgccatgca cgggattttt gtctcgtatg gtctttaaaa aggttcgaca agctaccggt   1260

ggtcacctca agtatattat gaatggcggc tccgctatct ctattgacgc ccaaaaattc   1320

tttagtatcg tcttgtgccc gatgatcatt ggttatggct tgactgaaac agtggcaaac   1380

gcctgtgttc tcgagccgga ccattttgag tatggcatcg ttggggacct ggtggggtcg   1440

gtcacggcaa aattggttga cgtgaaggat ctggggtact atgccaaaaa taatcagggg   1500

gaactcctgt tgaagggagc gcccgtctgc agcgaatact acaagaatcc gattgagaca   1560

gctgtgagct tcacatacga cggttggttt cgtaccggcg atatcgtcga gtggacgcca   1620

aagggtcagc tcaaaattat tgatcggcgc aagaacctgg tcaagacttt gaatggcgag   1680

tatattgcgc tggaaaagct ggagagcgtt taccgctcga acagttacgt caagaatatc   1740

tgtgtgtacg ccgatgagtc ccgagtgaaa cccgttggta ttgtggtccc aaaccctgga   1800

ccgctgtcta agtttgctgt caagctgcgc attatgaaga agggggaaga cattgagaat   1860

tatattcacg ataaggcgct ccggaacgca gtgttcaaag agatgatcgc cactgcaaaa   1920

tcgcagggcc tggtcggcat tgagctgttg tgtggtatcg ttttcttcga cgaggaatgg   1980

actcccgaaa atggcttcgt gactagcgcc caaaagttga aacggcgcga gattttggca   2040

gccgtcaaat ccgaggttga acgcgtctat aaagaaaata g                       2081
```

<210> SEQ ID NO 147
<211> LENGTH: 694
<212> TYPE: PRT
<213> ORGANISM: Saccharomyces cerevisiae S288c

<400> SEQUENCE: 147

```
Met Ser Glu Gln His Ser Val Ala Val Gly Lys Ala Ala Asn Glu His
 1               5                  10                  15

Glu Thr Ala Pro Arg Arg Asn Val Arg Val Lys Lys Arg Pro Leu Ile
            20                  25                  30

Arg Pro Leu Asn Ser Ser Ala Ser Thr Leu Tyr Glu Phe Ala Leu Glu
        35                  40                  45

Cys Phe Asn Lys Gly Gly Lys Arg Asp Gly Met Ala Trp Arg Asp Val
    50                  55                  60

Ile Glu Ile His Glu Thr Lys Lys Thr Ile Val Arg Lys Val Asp Gly
65                  70                  75                  80

Lys Asp Lys Ser Ile Glu Lys Thr Trp Leu Tyr Tyr Glu Met Ser Pro
                85                  90                  95
```

-continued

```
Tyr Lys Met Met Thr Tyr Gln Glu Leu Ile Trp Val Met His Asp Met
            100                 105                 110

Gly Arg Gly Leu Ala Lys Ile Gly Ile Lys Pro Asn Gly Glu His Lys
        115                 120                 125

Phe His Ile Phe Ala Ser Thr Ser His Lys Trp Met Lys Ile Phe Leu
    130                 135                 140

Gly Cys Ile Ser Gln Gly Ile Pro Val Val Thr Ala Tyr Asp Thr Leu
145                 150                 155                 160

Gly Glu Ser Gly Leu Ile His Ser Met Val Glu Thr Glu Ser Ala Ala
                165                 170                 175

Ile Phe Thr Asp Asn Gln Leu Leu Ala Lys Met Ile Val Pro Leu Gln
            180                 185                 190

Ser Ala Lys Asp Ile Lys Phe Leu Ile His Asn Glu Pro Ile Asp Pro
        195                 200                 205

Asn Asp Arg Arg Gln Asn Gly Lys Leu Tyr Lys Ala Ala Lys Asp Ala
    210                 215                 220

Ile Asn Lys Ile Arg Glu Val Arg Pro Asp Ile Lys Ile Tyr Ser Phe
225                 230                 235                 240

Glu Glu Val Val Lys Ile Gly Lys Lys Ser Lys Asp Glu Val Lys Leu
                245                 250                 255

His Pro Pro Glu Pro Lys Asp Leu Ala Cys Ile Met Tyr Thr Ser Gly
            260                 265                 270

Ser Ile Ser Ala Pro Lys Gly Val Val Leu Thr His Tyr Asn Ile Val
        275                 280                 285

Ser Gly Ile Ala Gly Val Gly His Asn Val Phe Gly Trp Ile Gly Ser
    290                 295                 300

Thr Asp Arg Val Leu Ser Phe Leu Pro Leu Ala His Ile Phe Glu Leu
305                 310                 315                 320

Val Phe Glu Phe Glu Ala Phe Tyr Trp Asn Gly Ile Leu Gly Tyr Gly
                325                 330                 335

Ser Val Lys Thr Leu Thr Asn Thr Ser Thr Arg Asn Cys Lys Gly Asp
            340                 345                 350

Leu Val Glu Phe Lys Pro Thr Ile Met Ile Gly Val Ala Ala Val Trp
        355                 360                 365

Glu Thr Val Arg Lys Ala Ile Leu Glu Lys Ile Ser Asp Leu Thr Pro
    370                 375                 380

Val Leu Gln Lys Ile Phe Trp Ser Ala Tyr Ser Met Lys Glu Lys Ser
385                 390                 395                 400

Val Pro Cys Thr Gly Phe Leu Ser Arg Met Val Phe Lys Lys Val Arg
                405                 410                 415

Gln Ala Thr Gly Gly His Leu Lys Tyr Ile Met Asn Gly Gly Ser Ala
            420                 425                 430

Ile Ser Ile Asp Ala Gln Lys Phe Phe Ser Ile Val Leu Cys Pro Met
        435                 440                 445

Ile Ile Gly Tyr Gly Leu Thr Glu Thr Val Ala Asn Ala Cys Val Leu
    450                 455                 460

Glu Pro Asp His Phe Glu Tyr Gly Ile Val Gly Asp Leu Val Gly Ser
465                 470                 475                 480

Val Thr Ala Lys Leu Val Asp Val Lys Asp Leu Gly Tyr Tyr Ala Lys
                485                 490                 495

Asn Asn Gln Gly Glu Leu Leu Leu Lys Gly Ala Pro Val Cys Ser Glu
            500                 505                 510
```

-continued

```
Tyr Tyr Lys Asn Pro Ile Glu Thr Ala Val Ser Phe Thr Tyr Asp Gly
        515                 520                 525

Trp Phe Arg Thr Gly Asp Ile Val Glu Trp Thr Pro Lys Gly Gln Leu
    530                 535                 540

Lys Ile Ile Asp Arg Arg Lys Asn Leu Val Lys Thr Leu Asn Gly Glu
545                 550                 555                 560

Tyr Ile Ala Leu Glu Lys Leu Glu Ser Val Tyr Arg Ser Asn Ser Tyr
                565                 570                 575

Val Lys Asn Ile Cys Val Tyr Ala Asp Glu Ser Arg Val Lys Pro Val
            580                 585                 590

Gly Ile Val Val Pro Asn Pro Gly Pro Leu Ser Lys Phe Ala Val Lys
        595                 600                 605

Leu Arg Ile Met Lys Lys Gly Glu Asp Ile Glu Asn Tyr Ile His Asp
    610                 615                 620

Lys Ala Leu Arg Asn Ala Val Phe Lys Glu Met Ile Ala Thr Ala Lys
625                 630                 635                 640

Ser Gln Gly Leu Val Gly Ile Glu Leu Leu Cys Gly Ile Val Phe Phe
                645                 650                 655

Asp Glu Glu Trp Thr Pro Glu Asn Gly Phe Val Thr Ser Ala Gln Lys
            660                 665                 670

Leu Lys Arg Arg Glu Ile Leu Ala Ala Val Lys Ser Glu Val Glu Arg
        675                 680                 685

Val Tyr Lys Glu Asn Ser
    690


<210> SEQ ID NO 148
<211> LENGTH: 1752
<212> TYPE: DNA
<213> ORGANISM: Escherichia coli

<400> SEQUENCE: 148

atgttaacgg catgtatatc atttggggtt gcgatgacga cgaacacgca ttttagaggt     60

gaagaattga aaaaagtgtg gctcaatcgg tatccggcgg atgtcccaac tgaaatcaac    120

cctgatcgat atcagtccct cgtggacatg tttgaacaga gcgtggcacg ctacgccgat    180

cagcccgcct tcgtgaatat gggcgaggtt atgacgtttc ggaaattgga agaacgctct    240

cgggcgtttg cggcttattt gcagcagggc ctgggcctga agaaaggtga tcgggtcgcc    300

ttgatgatgc ccaacctctt gcaatacccg gtcgccctgt ttggaatcct gcgtgctggc    360

atgattgtcg tgaatgtgaa tcctctctac acccctcgtg aactcgaaca ccagctgaac    420

gatagtggcg cttccgctat tgttatcgtg tctaatttcg ctcatacgct ggagaaggtc    480

gtggacaaga cagccgttca acacgtcatt ctgacccgca tgggtgatca actgagtacg    540

gcaaaaggta cggtcgtcaa ttttgtcgtc aaatatatca aacgtctggt ccccaagtac    600

catctgccag acgcgatttc cttccggagt gctttgcata acggatatcg aatgcaatac    660

gtgaaacccg aactggtgcc tgaggacctc gcatttctgc agtacacagg tggcaccacc    720

ggggtggcca agggtgctat gctgacacat cgaaatatgc tcgccaacct cgagcaggtc    780

aacgccacct acggtccgct gttgcaccca ggcaaggagc tggttgtgac ggctttgccc    840

ctgtatcata tttttgctct gacgatcaac tgcctgctgt ttattgagtt gggtggtcag    900

aacctcctga tcaccaatcc acgcgatatt ccgggcctcg ttaaagaact cgcgaaatac    960

ccctttactg cgatcacggg tgttaatact ctctttaacg cgctgctcaa caataaggag   1020

ttccaacagt tggacttcag cagcctgcat ctctctgccg gcggtggcat gcctgtgcaa   1080
```

```
caagttgttg cggagcgatg ggtgaaattg acggggcagt atctgttgga ggggtacggg   1140

ttgaccgaat gcgcacctct ggtgtcggtg aacccctacg atattgacta ccacagcgga   1200

tcgatcggcc tgccggtgcc gtcgacagaa gcgaaactgg ttgacgacga tgataacgag   1260

gtgcccccag gccaaccggg ggagttgtgt gttaagggac cgcaagtcat gctcgggtac   1320

tggcagcggc cggatgccac tgatgaaatt atcaagaatg gttggctcca caccggggac   1380

attgcagtta tggatgaaga gggattcctg cgcatcgtcg atcgcaaaaa agacatgatc   1440

ctcgtgtccg gctttaatgt ctatccaaat gaaatcgagg atgtcgttat gcagcaccct   1500

ggggtgcagg aggttgccgc tgttggcgtg cctagcggga gtagcggcga agcggtcaaa   1560

attttcgttg tcaagaagga ccccagtttg accgaagagt cgttggtcac gttctgtcgc   1620

cgccaactga ctggatataa agtccccaaa ctcgtcgaat ttcgggatga attgcccaag   1680

tcgaacgtcg gcaagatcct ccgccgcgag ttgcgcgatg aagcacgcgg taaggttgac   1740

aataaggctt ag                                                        1752


<210> SEQ ID NO 149
<211> LENGTH: 583
<212> TYPE: PRT
<213> ORGANISM: Escherichia coli

<400> SEQUENCE: 149

Met Leu Thr Ala Cys Ile Ser Phe Gly Val Ala Met Thr Thr Asn Thr
 1               5                  10                  15

His Phe Arg Gly Glu Glu Leu Lys Lys Val Trp Leu Asn Arg Tyr Pro
            20                  25                  30

Ala Asp Val Pro Thr Glu Ile Asn Pro Asp Arg Tyr Gln Ser Leu Val
        35                  40                  45

Asp Met Phe Glu Gln Ser Val Ala Arg Tyr Ala Asp Gln Pro Ala Phe
    50                  55                  60

Val Asn Met Gly Glu Val Met Thr Phe Arg Lys Leu Glu Glu Arg Ser
65                  70                  75                  80

Arg Ala Phe Ala Ala Tyr Leu Gln Gln Gly Leu Gly Leu Lys Lys Gly
                85                  90                  95

Asp Arg Val Ala Leu Met Met Pro Asn Leu Leu Gln Tyr Pro Val Ala
            100                 105                 110

Leu Phe Gly Ile Leu Arg Ala Gly Met Ile Val Val Asn Val Asn Pro
        115                 120                 125

Leu Tyr Thr Pro Arg Glu Leu Glu His Gln Leu Asn Asp Ser Gly Ala
    130                 135                 140

Ser Ala Ile Val Ile Val Ser Asn Phe Ala His Thr Leu Glu Lys Val
145                 150                 155                 160

Val Asp Lys Thr Ala Val Gln His Val Ile Leu Thr Arg Met Gly Asp
                165                 170                 175

Gln Leu Ser Thr Ala Lys Gly Thr Val Val Asn Phe Val Val Lys Tyr
            180                 185                 190

Ile Lys Arg Leu Val Pro Lys Tyr His Leu Pro Asp Ala Ile Ser Phe
        195                 200                 205

Arg Ser Ala Leu His Asn Gly Tyr Arg Met Gln Tyr Val Lys Pro Glu
    210                 215                 220

Leu Val Pro Glu Asp Leu Ala Phe Leu Gln Tyr Thr Gly Gly Thr Thr
225                 230                 235                 240

Gly Val Ala Lys Gly Ala Met Leu Thr His Arg Asn Met Leu Ala Asn
```

```
                245                 250                 255

Leu Glu Gln Val Asn Ala Thr Tyr Gly Pro Leu Leu His Pro Gly Lys
            260                 265                 270

Glu Leu Val Val Thr Ala Leu Pro Leu Tyr His Ile Phe Ala Leu Thr
        275                 280                 285

Ile Asn Cys Leu Leu Phe Ile Glu Leu Gly Gly Gln Asn Leu Leu Ile
    290                 295                 300

Thr Asn Pro Arg Asp Ile Pro Gly Leu Val Lys Glu Leu Ala Lys Tyr
305                 310                 315                 320

Pro Phe Thr Ala Ile Thr Gly Val Asn Thr Leu Phe Asn Ala Leu Leu
                325                 330                 335

Asn Asn Lys Glu Phe Gln Gln Leu Asp Phe Ser Ser Leu His Leu Ser
            340                 345                 350

Ala Gly Gly Gly Met Pro Val Gln Gln Val Val Ala Glu Arg Trp Val
        355                 360                 365

Lys Leu Thr Gly Gln Tyr Leu Leu Glu Gly Tyr Gly Leu Thr Glu Cys
    370                 375                 380

Ala Pro Leu Val Ser Val Asn Pro Tyr Asp Ile Asp Tyr His Ser Gly
385                 390                 395                 400

Ser Ile Gly Leu Pro Val Pro Ser Thr Glu Ala Lys Leu Val Asp Asp
                405                 410                 415

Asp Asp Asn Glu Val Pro Pro Gly Gln Pro Gly Glu Leu Cys Val Lys
            420                 425                 430

Gly Pro Gln Val Met Leu Gly Tyr Trp Gln Arg Pro Asp Ala Thr Asp
        435                 440                 445

Glu Ile Ile Lys Asn Gly Trp Leu His Thr Gly Asp Ile Ala Val Met
    450                 455                 460

Asp Glu Glu Gly Phe Leu Arg Ile Val Asp Arg Lys Lys Asp Met Ile
465                 470                 475                 480

Leu Val Ser Gly Phe Asn Val Tyr Pro Asn Glu Ile Glu Asp Val Val
                485                 490                 495

Met Gln His Pro Gly Val Gln Glu Val Ala Ala Val Gly Val Pro Ser
            500                 505                 510

Gly Ser Ser Gly Glu Ala Val Lys Ile Phe Val Val Lys Lys Asp Pro
        515                 520                 525

Ser Leu Thr Glu Glu Ser Leu Val Thr Phe Cys Arg Arg Gln Leu Thr
    530                 535                 540

Gly Tyr Lys Val Pro Lys Leu Val Glu Phe Arg Asp Glu Leu Pro Lys
545                 550                 555                 560

Ser Asn Val Gly Lys Ile Leu Arg Arg Glu Leu Arg Asp Glu Ala Arg
                565                 570                 575

Gly Lys Val Asp Asn Lys Ala
            580


<210> SEQ ID NO 150
<211> LENGTH: 1474
<212> TYPE: DNA
<213> ORGANISM: Cuphea hookeriana

<400> SEQUENCE: 150

ctggatacca ttttccctgc gaaaaaacat ggtggctgct gcagcaagtt ccgcattctt     60

ccctgttcca gccccgggag cctcccctaa acccgggaag ttcggaaatt ggccctcgag    120

cttgagccct tccttcaagc ccaagtcaat ccccaatggc ggatttcagg ttaaggcaaa    180
```

-continued

```
tgacagcgcc catccaaagg ctaacggttc tgcagttagt ctaaagtctg gcagcctcaa    240

cactcaggag gacacttcgt cgtcccctcc tcctcggact ttccttcacc agttgcctga    300

ttggagtagg cttctgactg caatcacgac cgtgttcgtg aaatctaaga ggcctgacat    360

gcatgatcgg aaatccaaga ggcctgacat gctggtggac tcgtttgggt tggagagtac    420

tgttcaggat gggctcgtgt tccgacagag tttttcgatt aggtcttatg aaataggcac    480

tgatcgaacg gcctctatag agacacttat gaaccacttg caggaaacat ctctcaatca    540

ttgtaagagt accggtattc tccttgacgg cttcggtcgt actcttgaga tgtgtaaaag    600

ggacctcatt tgggtggtaa taaaaatgca gatcaaggtg aatcgctatc cagcttgggg    660

cgatactgtc gagatcaata cccggttctc ccggttgggg aaaatcggta tgggtcgcga    720

ttggctaata agtgattgca acacaggaga aattcttgta agagctacga gcgcgtatgc    780

catgatgaat caaaagacga gaagactctc aaaacttcca tacgaggttc accaggagat    840

agtgcctctt tttgtcgact ctcctgtcat tgaagacagt gatctgaaag tgcataagtt    900

taaagtgaag actggtgatt ccattcaaaa gggtctaact ccggggtgga atgacttgga    960

tgtcaatcag cacgtaagca acgtgaagta cattgggtgg attctcgaga gtatgccaac   1020

agaagttttg gagacccagg agctatgctc tctcgccctt gaatataggc gggaatgcgg   1080

aagggacagt gtgctggagt ccgtgaccgc tatggatccc tcaaaagttg gagtccgttc   1140

tcagtaccag caccttctgc ggcttgagga tgggactgct atcgtgaacg gtgcaactga   1200

gtggcggccg aagaatgcag gagctaacgg ggcgatatca acgggaaaga cttcaaatgg   1260

aaactcggtc tcttagaagt gtctcggaac ccttccgaga tgtgcatttc ttttctcctt   1320

ttcattttgt ggtgagctga aagaagagca tgtcgttgca atcagtaaat tgtgtagttc   1380

gtttttcgct ttgcttcgct cctttgtata ataatatggt cagtcgtctt tgtatcattt   1440

catgttttca gtttatttac gccatataat tttt                               1474
```

```
<210> SEQ ID NO 151
<211> LENGTH: 987
<212> TYPE: DNA
<213> ORGANISM: Artificial Sequence
<220> FEATURE:
<223> OTHER INFORMATION: Codon optimized polynucleotide encoding mature
      form of C8/C10FatB

<400> SEQUENCE: 151

atgctgccag attggagccg actcttgacc gccatcacca cagtctttgt taagtctaaa     60

cggcccgaca tgcacgatcg aaaaagcaag cgcccccgata tgctggtgga cagctttggc    120

ttggaatcta ccgtgcagga tgggttggtc tttcgacaga gtttctcgat tcgcagttat    180

gaaattggca ctgatcgtac ggcaagcatt gagactctga tgaaccactt gcaagagaca    240

agcttgaacc attgcaaatc gacagggatt ctcctcgatg gcttcggtcg tacgctggaa    300

atgtgcaagc gcgatctgat ttgggttgtg atcaaaaatgc agattaaggt taaccgttat    360

cccgcatggg gtgatacggt ggaaattaac acgcggttct cccgcctggg aaaaatcggc    420

atgggacgcg attggctgat ctccgattgc aacacgggcg agatcctcgt gcgcgctact    480

tcggcctacg ccatgatgaa tcaaaaaacc cggcgcctca gtaagctgcc ctacgaggtg    540

caccaagaaa ttgttccgtt gtttgtggat agccctgtca tcgaggattc ggatctgaag    600

gtccataaat tcaaagttaa aacgggagac tcgatccaaa agggcttgac gccgggttgg    660

aatgacctgg acgtcaatca gcatgtttcg aacgtgaaat acatcggctg gattctggag    720
```

```
tccatgccaa ccgaagtgtt ggaaacccag gagttgtgtt cgctcgctct cgaataccgg    780

cgcgaatgtg gccgtgatag tgttctcgag agtgtcaccg ccatggaccc tagcaaagtc    840

ggggtgcgct ctcagtatca acacctgttg cgcttggaag acggcacagc gatcgtgaat    900

ggtgcgaccg agtggcgtcc gaagaacgcc ggtgcgaatg gtgcaatttc gactgggaag    960

accagcaatg gtaatagtgt cagttag                                        987


<210> SEQ ID NO 152
<211> LENGTH: 415
<212> TYPE: PRT
<213> ORGANISM: Cuphea hookeriana

<400> SEQUENCE: 152

Met Val Ala Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
    210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
```

```
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415


<210> SEQ ID NO 153
<211> LENGTH: 328
<212> TYPE: PRT
<213> ORGANISM: Cuphea hookeriana

<400> SEQUENCE: 153

Met Leu Pro Asp Trp Ser Arg Leu Leu Thr Ala Ile Thr Thr Val Phe
 1               5                  10                  15

Val Lys Ser Lys Arg Pro Asp Met His Asp Arg Lys Ser Lys Arg Pro
            20                  25                  30

Asp Met Leu Val Asp Ser Phe Gly Leu Glu Ser Thr Val Gln Asp Gly
        35                  40                  45

Leu Val Phe Arg Gln Ser Phe Ser Ile Arg Ser Tyr Glu Ile Gly Thr
    50                  55                  60

Asp Arg Thr Ala Ser Ile Glu Thr Leu Met Asn His Leu Gln Glu Thr
65                  70                  75                  80

Ser Leu Asn His Cys Lys Ser Thr Gly Ile Leu Leu Asp Gly Phe Gly
                85                  90                  95

Arg Thr Leu Glu Met Cys Lys Arg Asp Leu Ile Trp Val Val Ile Lys
            100                 105                 110

Met Gln Ile Lys Val Asn Arg Tyr Pro Ala Trp Gly Asp Thr Val Glu
        115                 120                 125

Ile Asn Thr Arg Phe Ser Arg Leu Gly Lys Ile Gly Met Gly Arg Asp
    130                 135                 140

Trp Leu Ile Ser Asp Cys Asn Thr Gly Glu Ile Leu Val Arg Ala Thr
145                 150                 155                 160

Ser Ala Tyr Ala Met Met Asn Gln Lys Thr Arg Arg Leu Ser Lys Leu
                165                 170                 175

Pro Tyr Glu Val His Gln Glu Ile Val Pro Leu Phe Val Asp Ser Pro
            180                 185                 190

Val Ile Glu Asp Ser Asp Leu Lys Val His Lys Phe Lys Val Lys Thr
        195                 200                 205

Gly Asp Ser Ile Gln Lys Gly Leu Thr Pro Gly Trp Asn Asp Leu Asp
    210                 215                 220

Val Asn Gln His Val Ser Asn Val Lys Tyr Ile Gly Trp Ile Leu Glu
225                 230                 235                 240

Ser Met Pro Thr Glu Val Leu Glu Thr Gln Glu Leu Cys Ser Leu Ala
                245                 250                 255

Leu Glu Tyr Arg Arg Glu Cys Gly Arg Asp Ser Val Leu Glu Ser Val
            260                 265                 270

Thr Ala Met Asp Pro Ser Lys Val Gly Val Arg Ser Gln Tyr Gln His
        275                 280                 285
```

-continued

```
Leu Leu Arg Leu Glu Asp Gly Thr Ala Ile Val Asn Gly Ala Thr Glu
    290                 295                 300

Trp Arg Pro Lys Asn Ala Gly Ala Asn Gly Ala Ile Ser Thr Gly Lys
305                 310                 315                 320

Thr Ser Asn Gly Asn Ser Val Ser
                325
```

<210> SEQ ID NO 154
<211> LENGTH: 1561
<212> TYPE: DNA
<213> ORGANISM: Umbellularia californica

<400> SEQUENCE: 154

```
agagagagag agagagagag agctaaatta aaaaaaaaac ccagaagtgg gaaatcttcc      60

ccatgaaata acggatcctc ttgctactgc tactactact actacaaact gtagccattt     120

atataattct atataatttt caacatggcc accacctctt tagcttccgc tttctgctcg     180

atgaaagctg taatgttggc tcgtgatggc cggggcatga aacccaggag cagtgatttg     240

cagctgaggg cgggaaatgc gccaacctct ttgaagatga tcaatgggac caagttcagt     300

tacacggaga gcttgaaaag gttgcctgac tggagcatgc tctttgcagt gatcacaacc     360

atcttttcgg ctgctgagaa gcagtggacc aatctagagt ggaagccgaa gccgaagcta     420

ccccagttgc ttgatgacca ttttggactg catgggttag ttttcaggcg cacctttgcc     480

atcagatctt atgaggtggg acctgaccgc tccacatcta tactggctgt tatgaatcac     540

atgcaggagg ctacacttaa tcatgcgaag agtgtgggaa ttctaggaga tggattcggg     600

acgacgctag agatgagtaa gagagatctg atgtgggttg tgagacgcac gcatgttgct     660

gtggaacggt accctacttg gggtgatact gtagaagtag agtgctggat tggtgcatct     720

ggaaataatg gcatgcgacg tgatttcctt gtccgggact gcaaaacagg cgaaattctt     780

acaagatgta ccagcctttc ggtgctgatg aatacaagga caaggaggtt gtccacaatc     840

cctgacgaag ttagagggga gatagggcct gcattcattg ataatgtggc tgtcaaggac     900

gatgaaatta agaaactaca gaagctcaat gacagcactg cagattacat ccaaggaggt     960

ttgactcctc gatggaatga tttggatgtc aatcagcatg tgaacaacct caaatacgtt    1020

gcctgggttt ttgagaccgt cccagactcc atctttgaga gtcatcatat ttccagcttc    1080

actcttgaat acaggagaga gtgcacgagg gatagcgtgc tgcggtccct gaccactgtc    1140

tctggtggct cgtcggaggc tgggttagtg tgcgatcact tgctccagct tgaaggtggg    1200

tctgaggtat tgagggcaag aacagagtgg aggcctaagc ttaccgatag tttcagaggg    1260

attagtgtga tacccgcaga accgagggtg taactaatga aagaagcatc tgttgaagtt    1320

tctcccatgc tgttcgtgag gatacttttt agaagctgca gtttgcattg cttgtgcaga    1380

atcatggtct gtggttttag atgtatataa aaaatagtcc tgtagtcatg aaacttaata    1440

tcagaaaaat aactcaatgg gtcaaggtta tcgaagtagt catttaagct ttgaaatatg    1500

ttttgtattc ctcggcttaa tctgtaagct ctttctcttg caataaagtt cgcctttcaa    1560

t                                                                    1561
```

<210> SEQ ID NO 155
<211> LENGTH: 975
<212> TYPE: DNA
<213> ORGANISM: Artificial Sequence
<220> FEATURE:
<223> OTHER INFORMATION: Codon optimized polynucleotide encoding mature
form of C12FatB1 from Umbellularia californica

<400> SEQUENCE: 155

```
atgctgccgg attggagtat gttgttcgcg gtcattacca ccatcttctc ggccgcggaa      60

aagcagtgga ctaatctcga atggaagccc aagcctaaat tgccgcaact gttggatgat     120

cactttggtc tgcatggcct ggtcttccga cgaactttcg ccatccgctc ttacgaggtc     180

ggtccagatc gatcgacgtc cattctggcg gtgatgaacc acatgcagga agctacactg     240

aatcacgcca agagtgtcgg catcctgggc gatggttttg gtacgacgct cgagatgagt     300

aagcgcgatt tgatgtgggt ggtccgccgc acacatgtgg ccgtcgaacg ctatcctacg     360

tggggtgaca cggtcgaagt cgagtgttgg atcggagcca gcggcaataa tgggatgcgg     420

cgcgattttc tcgtgcggga ttgtaagacc ggtgaaattc tgacacgttg caccagcctc     480

tccgtcctga tgaacacgcg gactcgccgc ctgtcgacta tcccggatga agtgcgcggc     540

gaaattgggc ccgcatttat cgacaatgtt gctgtcaagg atgacgagat taaaaaactg     600

caaaaactca acgatagcac tgccgattac attcaaggcg gactcacgcc gcgttggaac     660

gacctcgacg ttaaccagca cgtgaacaac ctcaaatacg tggcatgggt cttcgaaacc     720

gttccagaca gcatcttcga atctcatcat atcagctcgt tcacgttgga gtatcgtcgt     780

gagtgcaccc gggattccgt gttgcgatct ctgaccaccg tttccggggg cagcagcgag     840

gctggactcg tttgcgacca cctgctgcaa ttggaaggcg gctcggaggt gctgcgagca     900

cggaccgaat ggcgcccgaa attgacggat agctttcggg gcattagtgt tatccccgcc     960

gagccccgcg tttag                                                      975
```

<210> SEQ ID NO 156
<211> LENGTH: 382
<212> TYPE: PRT
<213> ORGANISM: Umbellularia californica

<400> SEQUENCE: 156

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
```

```
                180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380


<210> SEQ ID NO 157
<211> LENGTH: 324
<212> TYPE: PRT
<213> ORGANISM: Umbellularia californica

<400> SEQUENCE: 157

Met Leu Pro Asp Trp Ser Met Leu Phe Ala Val Ile Thr Thr Ile Phe
 1               5                  10                  15

Ser Ala Ala Glu Lys Gln Trp Thr Asn Leu Glu Trp Lys Pro Lys Pro
            20                  25                  30

Lys Leu Pro Gln Leu Leu Asp Asp His Phe Gly Leu His Gly Leu Val
        35                  40                  45

Phe Arg Arg Thr Phe Ala Ile Arg Ser Tyr Glu Val Gly Pro Asp Arg
    50                  55                  60

Ser Thr Ser Ile Leu Ala Val Met Asn His Met Gln Glu Ala Thr Leu
65                  70                  75                  80

Asn His Ala Lys Ser Val Gly Ile Leu Gly Asp Gly Phe Gly Thr Thr
                85                  90                  95

Leu Glu Met Ser Lys Arg Asp Leu Met Trp Val Val Arg Arg Thr His
            100                 105                 110

Val Ala Val Glu Arg Tyr Pro Thr Trp Gly Asp Thr Val Glu Val Glu
        115                 120                 125

Cys Trp Ile Gly Ala Ser Gly Asn Asn Gly Met Arg Arg Asp Phe Leu
    130                 135                 140

Val Arg Asp Cys Lys Thr Gly Glu Ile Leu Thr Arg Cys Thr Ser Leu
145                 150                 155                 160

Ser Val Leu Met Asn Thr Arg Thr Arg Arg Leu Ser Thr Ile Pro Asp
                165                 170                 175
```

```
Glu Val Arg Gly Glu Ile Gly Pro Ala Phe Ile Asp Asn Val Ala Val
            180                 185                 190

Lys Asp Asp Glu Ile Lys Lys Leu Gln Lys Leu Asn Asp Ser Thr Ala
        195                 200                 205

Asp Tyr Ile Gln Gly Gly Leu Thr Pro Arg Trp Asn Asp Leu Asp Val
    210                 215                 220

Asn Gln His Val Asn Asn Leu Lys Tyr Val Ala Trp Val Phe Glu Thr
225                 230                 235                 240

Val Pro Asp Ser Ile Phe Glu Ser His His Ile Ser Ser Phe Thr Leu
                245                 250                 255

Glu Tyr Arg Arg Glu Cys Thr Arg Asp Ser Val Leu Arg Ser Leu Thr
            260                 265                 270

Thr Val Ser Gly Gly Ser Ser Glu Ala Gly Leu Val Cys Asp His Leu
        275                 280                 285

Leu Gln Leu Glu Gly Gly Ser Glu Val Leu Arg Ala Arg Thr Glu Trp
    290                 295                 300

Arg Pro Lys Leu Thr Asp Ser Phe Arg Gly Ile Ser Val Ile Pro Ala
305                 310                 315                 320

Glu Pro Arg Val
```

<210> SEQ ID NO 158
<211> LENGTH: 1430
<212> TYPE: DNA
<213> ORGANISM: Cinnamomum camphora

<400> SEQUENCE: 158

```
tcaacatggc caccacctct ttagcttctg ctttctgctc gatgaaagct gtaatgttgg     60

ctcgtgatgg caggggcatg aaacccagga gcagtgattt gcagctgagg gcgggaaatg    120

cacaaacctc tttgaagatg atcaatggga ccaagttcag ttacacagag agcttgaaaa    180

agttgcctga ctggagcatg ctctttgcag tgatcacgac catcttttcg gctgctgaga    240

agcagtggac caatctagag tggaagccga agccgaatcc accccagttg cttgatgacc    300

attttgggcc gcatgggtta gttttcaggc gcacctttgc catcagatcg tatgaggtgg    360

gacctgaccg ctccacatct atagtggctg ttatgaatca cttgcaggag gctgcactta    420

atcatgcgaa gagtgtggga attctaggag atggattcgg tacgacgcta gagatgagta    480

agagagatct gatatgggtt gtgaaacgca cgcatgttgc tgtggaacgg taccctgctt    540

ggggtgatac tgttgaagta gagtgctggg ttggtgcatc gggaaataat ggcaggcgcc    600

atgatttcct tgtccgggac tgcaaaacag gcgaaattct tacaagatgt accagtcttt    660

cggtgatgat gaatacaagg acaaggaggt tgtccaaaat ccctgaagaa gttagagggg    720

agatagggcc tgcattcatt gataatgtgg ctgtcaagga cgaggaaatt aagaaaccac    780

agaagctcaa tgacagcact gcagattaca tccaaggagg attgactcct cgatggaatg    840

atttggatat caatcagcac gttaacaaca tcaaatacgt tgactggatt cttgagactg    900

tcccagactc aatctttgag agtcatcata tttccagctt cactattgaa tacaggagag    960

agtgcacgat ggatagcgtg ctgcagtccc tgaccactgt ctccggtggc tcgtcggaag   1020

ctgggttagt gtgcgagcac ttgctccagc ttgaaggtgg gtctgaggta ttgagggcaa   1080

aaacagagtg gaggcctaag cttaccgata gtttcagagg gattagtgtg atacccgcag   1140

aatcgagtgt ctaactaacg aaagaagcat ctgatgaagt ttctcctgtg ctgttgttcg   1200

tgaggatgct ttttagaagc tgcagtttgc attgcttgtg cagaatcatg gcctgtggtt   1260
```

ttagatatat atccaaaatt gtcctatagt caagaaactt aatatcagaa aaataactca 1320
atgagtcaag gttatcgaag tagtcatgta agctttgaaa tatgttgtgt attcctcggc 1380
tttatgtaat ctgtaagctc tttctcttgc aataaatttc gcctttcaat 1430

<210> SEQ ID NO 159
<211> LENGTH: 975
<212> TYPE: DNA
<213> ORGANISM: Artificial Sequence
<220> FEATURE:
<223> OTHER INFORMATION: Codon optimized polynucleotide encoding mature form of C14FatB1 from Cinnamomum camphora

<400> SEQUENCE: 159
atgttgcccg attggagcat gttgttcgca gtcatcacca ccattttcag cgcagcggag 60
aagcaatgga ccaatttgga gtggaaacca aagccgaatc cccctcagct gctggatgat 120
cattttggac cccacgggtt ggtctttcgc cgaacgtttg ccatccgcag ctatgaagtg 180
ggcccggatc gctcgacgag cattgttgct gttatgaatc acctgcaaga agcggctctg 240
aatcatgcta agagcgtggg tatcttgggc gacggtttcg ggacaactct ggagatgtcg 300
aagcgcgatc tgatctgggt ggtcaaacgt acccatgtgg ctgttgaacg gtacccggcc 360
tggggagata ctgtggaggt tgagtgctgg gttggcgcaa gcggcaataa cggccgccga 420
catgatttcc tcgtgcgcga ctgtaaaacc ggcgaaattt tgacccgatg cacctcgctc 480
agtgtcatga tgaacacgcg cactcgtcgg ctgtccaaaa tccccgagga agtccgtggc 540
gagatcggac cggcgttcat tgacaacgtg gcagtgaagg acgaagaaat taaaaagccg 600
cagaagctga acgattccac agcggattac atccagggtg gtctgacgcc ccggtggaac 660
gacctcgaca ttaaccagca cgtcaataac attaagtacg tggattggat cttggaaaca 720
gtgccggatt cgatttttga gtcgcatcat atcagcagtt ttacgatcga atatcgccgc 780
gaatgtacga tggatagcgt gttgcagagc ctcacgacag tctctggggg gagtagtgag 840
gccggtctgg tctgcgaaca cctgctccaa ctcgaaggcg gttctgaagt gctccgtgcc 900
aaaactgagt ggcgccctaa actcactgac tcgtttcggg gtatttccgt cattccagcc 960
gagtccagtg tttag 975

<210> SEQ ID NO 160
<211> LENGTH: 382
<212> TYPE: PRT
<213> ORGANISM: Cinnamomum camphora

<400> SEQUENCE: 160

Met Ala Thr Thr Ser Leu Ala Ser Ala Phe Cys Ser Met Lys Ala Val
1 5 10 15

Met Leu Ala Arg Asp Gly Arg Gly Met Lys Pro Arg Ser Ser Asp Leu
20 25 30

Gln Leu Arg Ala Gly Asn Ala Gln Thr Ser Leu Lys Met Ile Asn Gly
35 40 45

Thr Lys Phe Ser Tyr Thr Glu Ser Leu Lys Lys Leu Pro Asp Trp Ser
50 55 60

Met Leu Phe Ala Val Ile Thr Thr Ile Phe Ser Ala Ala Glu Lys Gln
65 70 75 80

Trp Thr Asn Leu Glu Trp Lys Pro Lys Pro Asn Pro Pro Gln Leu Leu
85 90 95

Asp Asp His Phe Gly Pro His Gly Leu Val Phe Arg Arg Thr Phe Ala
100 105 110

```
Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
        355                 360                 365

Ser Phe Arg Gly Ile Ser Val Ile Pro Ala Glu Ser Ser Val
    370                 375                 380


<210> SEQ ID NO 161
<211> LENGTH: 324
<212> TYPE: PRT
<213> ORGANISM: Cinnamomum camphora

<400> SEQUENCE: 161

Met Leu Pro Asp Trp Ser Met Leu Phe Ala Val Ile Thr Thr Ile Phe
 1               5                  10                  15

Ser Ala Ala Glu Lys Gln Trp Thr Asn Leu Glu Trp Lys Pro Lys Pro
            20                  25                  30

Asn Pro Pro Gln Leu Leu Asp Asp His Phe Gly Pro His Gly Leu Val
        35                  40                  45

Phe Arg Arg Thr Phe Ala Ile Arg Ser Tyr Glu Val Gly Pro Asp Arg
    50                  55                  60

Ser Thr Ser Ile Val Ala Val Met Asn His Leu Gln Glu Ala Ala Leu
65                  70                  75                  80

Asn His Ala Lys Ser Val Gly Ile Leu Gly Asp Gly Phe Gly Thr Thr
                85                  90                  95

Leu Glu Met Ser Lys Arg Asp Leu Ile Trp Val Val Lys Arg Thr His
```

```
            100                 105                 110

Val Ala Val Glu Arg Tyr Pro Ala Trp Gly Asp Thr Val Glu Val Glu
        115                 120                 125

Cys Trp Val Gly Ala Ser Gly Asn Asn Gly Arg Arg His Asp Phe Leu
    130                 135                 140

Val Arg Asp Cys Lys Thr Gly Glu Ile Leu Thr Arg Cys Thr Ser Leu
145                 150                 155                 160

Ser Val Met Met Asn Thr Arg Thr Arg Arg Leu Ser Lys Ile Pro Glu
                165                 170                 175

Glu Val Arg Gly Glu Ile Gly Pro Ala Phe Ile Asp Asn Val Ala Val
            180                 185                 190

Lys Asp Glu Glu Ile Lys Lys Pro Gln Lys Leu Asn Asp Ser Thr Ala
        195                 200                 205

Asp Tyr Ile Gln Gly Gly Leu Thr Pro Arg Trp Asn Asp Leu Asp Ile
    210                 215                 220

Asn Gln His Val Asn Asn Ile Lys Tyr Val Asp Trp Ile Leu Glu Thr
225                 230                 235                 240

Val Pro Asp Ser Ile Phe Glu Ser His His Ile Ser Ser Phe Thr Ile
                245                 250                 255

Glu Tyr Arg Arg Glu Cys Thr Met Asp Ser Val Leu Gln Ser Leu Thr
            260                 265                 270

Thr Val Ser Gly Gly Ser Ser Glu Ala Gly Leu Val Cys Glu His Leu
        275                 280                 285

Leu Gln Leu Glu Gly Gly Ser Glu Val Leu Arg Ala Lys Thr Glu Trp
    290                 295                 300

Arg Pro Lys Leu Thr Asp Ser Phe Arg Gly Ile Ser Val Ile Pro Ala
305                 310                 315                 320

Glu Ser Ser Val


<210> SEQ ID NO 162
<211> LENGTH: 1744
<212> TYPE: DNA
<213> ORGANISM: Cuphea hookeriana

<400> SEQUENCE: 162

ctttgatcgg tcgatccttt cctctcgctc ataatttacc cattagtccc ctttgccttc      60

tttaaaccct cctttccttt ctcttccctt cttcctctct gggaagttta aagcttttgc     120

ctttctcccc cccacaacct ctttcccgca tttgttgagc tgttttttttg tcgccattcg    180

tcctctcctc ttcagttcaa cagaaatggt ggctaccgct gcaagttctg cattcttccc     240

cctcccatcc gccgacacct catcgagacc cggaaagctc ggcaataagc catcgagctt     300

gagccccctc aagcccaaat cgaccccccaa tggcggtttg caggttaagg caaatgccag    360

tgcccctcct aagatcaatg gttccccggt cggtctaaag tcgggcggtc tcaagactca     420

ggaagacgct cattcggccc ctcctccgcg aacttttatc aaccagttgc ctgattggag     480

tatgcttctt gctgcaatca cgactgtctt cttggctgca gagaagcaat ggatgatgct     540

tgattggaaa cctaagaggc ctgacatgct tgtggacccg tttggattgg gaagtattgt     600

tcaggatggg cttgtgttca ggcagaattt ttcgattagg tcctatgaaa taggcgccga     660

tcgcactgcg tctatagaga cggtgatgaa ccatttgcag gaaacagctc tcaatcatgt     720

taagattgct gggctttcta atgacggctt tggtcgtact cctgagatgt ataaaaggga     780

ccttatttgg gttgttgcga aaatgcaagt catggttaac cgctatccta cttggggtga     840
```

```
cacggttgaa gtgaatactt gggttgccaa gtcagggaaa aatggtatgc gtcgtgactg    900

gctcataagt gattgcaata ctggagagat tcttacaaga gcatcaagcg tgtgggtcat    960

gatgaatcaa aagacaagaa gattgtcaaa aattccagat gaggttcgaa atgagataga   1020

gcctcatttt gtggactctc ctcccgtcat tgaagacgat gaccggaaac ttcccaagct   1080

ggatgagaag actgctgact ccatccgcaa gggtctaact ccgaggtgga atgacttgga   1140

tgtcaatcaa cacgtcaaca acgtgaagta catcgggtgg attcttgaga gtactccacc   1200

agaagttctg gagacccagg agttatgttc ccttactctg gaatacaggc gggaatgtgg   1260

aagggagagc gtgctggagt ccctcactgc tatggatccc tctggagggg gttatgggtc   1320

ccagtttcag caccttctgc ggcttgagga tggaggtgag atcgtgaagg ggagaactga   1380

gtggcggccc aagaatggtg taatcaatgg ggtggtacca accggggagt cctcacctgg   1440

agactactct tagaagggag ccctgacccc tttggagttg tgatttcttt attgtcggac   1500

gagctaagtg aagggcaggt aagatagtag caatcggtag attgtgtagt ttgtttgctg   1560

ctttttcacg atggctctcg tgtataatat catggtctgt cttctttgta tcctcttctt   1620

cgcatgttcc gggttgattc atacattata ttctttctat ttgtttgaag gcgagtagcg   1680

ggttgtaatt atttattttg tcattacaat gtcgtttaac ttttcaaatg aaactactta   1740

tgtg                                                                1744
```

<210> SEQ ID NO 163
<211> LENGTH: 990
<212> TYPE: DNA
<213> ORGANISM: Artificial Sequence
<220> FEATURE:
<223> OTHER INFORMATION: Codon optimized polynucleotide encoding mature form of C16FatB1 from Cuphea hookeriana

<400> SEQUENCE: 163

```
atgctgcctg actggtcgat gctgttggct gcaattacta ccgtcttcct ggcggctgaa     60

aaacaatgga tgatgttgga ctggaagccc aaacgacccg atatgctcgt cgatccgttc    120

gggttgggca gcatcgttca agacggtctg gtgtttcgcc aaaatttttc cattcgatct    180

tatgaaatcg gcgctgaccg gacagcatcc atcgaaacgg tcatgaacca tctccaagag    240

accgccctga atcacgtgaa gattgccgga ctctccaatg atggattcgg ccggaccccg    300

gaaatgtaca aacgcgatct gatctgggtg gtcgccaaga tgcaggtcat ggtcaatcgg    360

tacccgacct gggggggacac ggttgaggtc aacacttggg tggcgaaatc gggtaagaac    420

ggcatgcgcc gcgactggct cattagcgac tgcaatacgg gcgagatcct cacgcgtgcc    480

agttctgtgt gggtcatgat gaaccagaaa actcgacgct tgagcaagat tccagatgaa    540

gttcgtaatg agattgaacc tcattttgtt gactcgcccc ccgtgatcga ggatgatgat    600

cggaagctcc ccaagctgga cgaaaaaacg gcggatagca tccgcaaagg cctgacacca    660

cggtggaacg atctggatgt caatcaacac gtgaacaacg tgaaatacat cgggtggatt    720

ctcgaatcta ccccccccaga agttctcgag actcaggagc tgtgcagctt gacgttggag    780

taccgccgag aatgtggccg tgagtcggtg ctggagagtc tgaccgcaat ggacccgtcg    840

ggcggtggtt atggcagtca gtttcagcat ttgctgcgct tggaggatgg tggggaaatt    900

gtgaaaggtc ggactgaatg gcgccccaag aatggagtga ttaatggtgt tgtccctaca    960

ggcgaaagta gccccgggga ttatagttag                                    990
```

<210> SEQ ID NO 164

<211> LENGTH: 415
<212> TYPE: PRT
<213> ORGANISM: Cuphea hookeriana

<400> SEQUENCE: 164

```
Met Val Ala Thr Ala Ala Ser Ser Ala Phe Phe Pro Leu Pro Ser Ala
 1               5                  10                  15

Asp Thr Ser Ser Arg Pro Gly Lys Leu Gly Asn Lys Pro Ser Ser Leu
            20                  25                  30

Ser Pro Leu Lys Pro Lys Ser Thr Pro Asn Gly Gly Leu Gln Val Lys
        35                  40                  45

Ala Asn Ala Ser Ala Pro Pro Lys Ile Asn Gly Ser Pro Val Gly Leu
    50                  55                  60

Lys Ser Gly Gly Leu Lys Thr Gln Glu Asp Ala His Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Ser Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ile Ala Gly
                165                 170                 175

Leu Ser Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg Asn Glu Ile Glu
            260                 265                 270

Pro His Phe Val Asp Ser Pro Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Arg Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Met Asp Pro Ser Gly Gly
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Asn Gly Val Ile
```

```
385                 390                 395                 400

Asn Gly Val Val Pro Thr Gly Glu Ser Ser Pro Gly Asp Tyr Ser
                405                 410                 415


<210> SEQ ID NO 165
<211> LENGTH: 329
<212> TYPE: PRT
<213> ORGANISM: Cuphea hookeriana

<400> SEQUENCE: 165

Met Leu Pro Asp Trp Ser Met Leu Leu Ala Ala Ile Thr Thr Val Phe
 1               5                  10                  15

Leu Ala Ala Glu Lys Gln Trp Met Met Leu Asp Trp Lys Pro Lys Arg
            20                  25                  30

Pro Asp Met Leu Val Asp Pro Phe Gly Leu Gly Ser Ile Val Gln Asp
        35                  40                  45

Gly Leu Val Phe Arg Gln Asn Phe Ser Ile Arg Ser Tyr Glu Ile Gly
    50                  55                  60

Ala Asp Arg Thr Ala Ser Ile Glu Thr Val Met Asn His Leu Gln Glu
65                  70                  75                  80

Thr Ala Leu Asn His Val Lys Ile Ala Gly Leu Ser Asn Asp Gly Phe
                85                  90                  95

Gly Arg Thr Pro Glu Met Tyr Lys Arg Asp Leu Ile Trp Val Val Ala
            100                 105                 110

Lys Met Gln Val Met Val Asn Arg Tyr Pro Thr Trp Gly Asp Thr Val
        115                 120                 125

Glu Val Asn Thr Trp Val Ala Lys Ser Gly Lys Asn Gly Met Arg Arg
    130                 135                 140

Asp Trp Leu Ile Ser Asp Cys Asn Thr Gly Glu Ile Leu Thr Arg Ala
145                 150                 155                 160

Ser Ser Val Trp Val Met Met Asn Gln Lys Thr Arg Arg Leu Ser Lys
                165                 170                 175

Ile Pro Asp Glu Val Arg Asn Glu Ile Glu Pro His Phe Val Asp Ser
            180                 185                 190

Pro Pro Val Ile Glu Asp Asp Asp Arg Lys Leu Pro Lys Leu Asp Glu
        195                 200                 205

Lys Thr Ala Asp Ser Ile Arg Lys Gly Leu Thr Pro Arg Trp Asn Asp
    210                 215                 220

Leu Asp Val Asn Gln His Val Asn Asn Val Lys Tyr Ile Gly Trp Ile
225                 230                 235                 240

Leu Glu Ser Thr Pro Pro Glu Val Leu Glu Thr Gln Glu Leu Cys Ser
                245                 250                 255

Leu Thr Leu Glu Tyr Arg Arg Glu Cys Gly Arg Glu Ser Val Leu Glu
            260                 265                 270

Ser Leu Thr Ala Met Asp Pro Ser Gly Gly Gly Tyr Gly Ser Gln Phe
        275                 280                 285

Gln His Leu Leu Arg Leu Glu Asp Gly Gly Glu Ile Val Lys Gly Arg
    290                 295                 300

Thr Glu Trp Arg Pro Lys Asn Gly Val Ile Asn Gly Val Val Pro Thr
305                 310                 315                 320

Gly Glu Ser Ser Pro Gly Asp Tyr Ser
                325
```